US008569583B2

(12) United States Patent
Donovan et al.

(10) Patent No.: US 8,569,583 B2
(45) Date of Patent: Oct. 29, 2013

(54) **SECRETED INSECTICIDAL PROTEIN AND GENE COMPOSITIONS FROM *BACILLUS THURINGIENSIS* AND USES THEREFOR**

(75) Inventors: Judith Donovan, Manchester, MO (US); William Donovan, Manchester, MO (US); James Engleman, Ephrata, PA (US); Thomas Malvar, North Stonington, CT (US); John Pitkin, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 13/171,519

(22) Filed: Jun. 29, 2011

(65) Prior Publication Data

US 2011/0283417 A1 Nov. 17, 2011

Related U.S. Application Data

(62) Division of application No. 10/581,763, filed as application No. PCT/US2004/042611 on Dec. 14, 2004, now abandoned.

(60) Provisional application No. 60/529,917, filed on Dec. 16, 2003.

(51) Int. Cl.
*A01H 5/00* (2006.01)
*A01H 5/10* (2006.01)
*C12N 15/82* (2006.01)
*C12N 15/32* (2006.01)
*C07K 14/325* (2006.01)

(52) U.S. Cl.
USPC ........ 800/302; 536/23.71; 514/4.5; 424/93.2; 435/418; 435/320.1; 800/279

(58) Field of Classification Search
None
See application file for complete search history.

(56) References Cited

U.S. PATENT DOCUMENTS

| 6,177,615 | B1 | 1/2001 | Baum |
| 7,355,099 | B2 * | 4/2008 | Carozzi et al. ................ 800/302 |
| 2004/0197916 | A1 | 10/2004 | Carozzi et al. |

FOREIGN PATENT DOCUMENTS

| CN | 1134981 A | 6/1996 |
| EP | 1708561 | 11/2010 |
| WO | 01/87940 | 11/2001 |
| WO | 02/22662 | 3/2002 |
| WO | 2004/074462 | 9/2004 |

OTHER PUBLICATIONS de Maagd et al, 1999, Appl. Environ. Microbiol. 65:4369-4374.*
Tounsi et al, 2003, J. Appl. Microbiol. 95:23-28.*
Aronson et al, 2001, FEMS Microbiol. Lett. 195:1-8.*
de Maagd et al, 2001, Trends Genet. 17:193-199.*
Guo et al (2004, Proc. Natl. Acad. Sci. USA 101: 9205-9210).*
Translation of Office Action issued on Aug. 24, 2010 regarding Chinese Patent Application No. 200480037707.4.

* cited by examiner

*Primary Examiner* — Anne Kubelik
(74) *Attorney, Agent, or Firm* — Thompson Coburn LLP; J. Wendy Davis

(57) ABSTRACT

The present invention relates to the isolation and characterization of nucleotide sequences encoding novel insecticidal proteins secreted into the extracellular space from *Bacillus thuringiensis* and related strains. The proteins are isolated from culture supernatants of *Bacillus thuringiensis* and related strains and display insecticidal activity against lepidopteran insects including European corn borer (ECB), tobacco budworm (TBW) and diamondback moth (DBM). Insecticidal proteins encoded by nucleotide sequences that hybridize under stringent conditions to the isolated and characterized nucleotide sequences are disclosed. Methods are disclosed for making and using transgenic cells and plants comprising the novel nucleotide sequence of the invention.

16 Claims, No Drawings

SECRETED INSECTICIDAL PROTEIN AND GENE COMPOSITIONS FROM *BACILLUS THURINGIENSIS* AND USES THEREFOR

BACKGROUND OF INVENTION

The present invention relates to a new family of genes encoding lepidopteran-toxic proteins and insecticidal fragments thereof. In particular, the present invention is directed to exemplary proteins designated herein as TIC900, TIC402, TIC403, TIC404, TIC961, TIC962, TIC963, TIC965 and TIC966, and insecticidal fragments thereof, each encoded by exemplary nucleotide coding sequences designated herein respectively as tic900, tic402, tic403, tic404, tic434, tic961, tic962, tic963, tic965, and tic966, as well as to nucleotide sequence homologs that (1) encode insecticidal proteins and (2) hybridize to the tic900, tic402, tic403, tic404, tic434, tic961, tic962, tic963, tic965, and tic966 coding sequences under stringent hybridization conditions. The present invention also relates to host cells transformed with one or more nucleotide sequences of the present invention or transformed with variants of the nucleotide sequences set forth herein, genes related by identity and/or similarity to the sequences set forth herein, and/or homologs thereof, particularly those sequences that have been modified for improved expression in plants. In a preferred embodiment, the transformed host cells are plant cells.

Almost all field crops, plants, and commercial farming areas are susceptible to attack by one or more insect pests. Particularly problematic are Coleopteran and Lepidoptern pests. For example, vegetable and cole crops such as artichokes, kohlrabi, arugula, leeks, asparagus, lentils, beans, lettuce (e.g., head, leaf, romaine), beets, bok choy, malanga, broccoli, melons (e.g., muskmelon, watermelon, crenshaw, honeydew, cantaloupe), brussels sprouts, cabbage, cardoni, carrots, napa, cauliflower, okra, onions, celery, parsley, chick peas, parsnips, chicory, peas, chinese cabbage, peppers, collards, potatoes, cucumber, pumpkins, cucurbits, radishes, dry bulb onions, rutabaga, eggplant, salsify, escarole, shallots, endive, soybean, garlic, spinach, green onions, squash, greens, sugar beets, sweet potatoes, turnip, swiss chard, horseradish, tomatoes, kale, turnips, and a variety of spices are sensitive to infestation by one or more of the following insect pests: alfalfa looper, armyworm, beet armyworm, artichoke plume moth, cabbage budworm, cabbage looper, cabbage webworm, corn earworm, celery leafeater, cross-striped cabbageworm, european corn borer, diamondback moth, green cloverworm, imported cabbageworm, melonworm, omnivorous leafroller, pickleworm, rindworm complex, saltmarsh caterpillar, soybean looper, tobacco budworm, tomato fruitworm, tomato hornworm, tomato pinworm, velvetbean caterpillar, and yellowstriped armyworm. Likewise, pasture and hay crops such as alfalfa, pasture grasses and silage are often attacked by such pests as armyworm, beef armyworm, alfalfa caterpillar, European skipper, a variety of loopers and webworms, as well as yellowstriped armyworms.

Fruit and vine crops such as apples, apricots, cherries, nectarines, peaches, pears, plums, prunes, quince almonds, chestnuts, filberts, pecans, pistachios, walnuts, citrus, blackberries, blueberries, boysenberries, cranberries, currants, loganberries, raspberries, strawberries, grapes, avocados, bananas, kiwi, persimmons, pomegranate, pineapple, and tropical fruits are often susceptible to attack and defoliation by achema sphinx moth, amorbia, armyworm, citrus cutworm, banana skipper, blackheaded fireworm, blueberry leafroller, cankerworm, cherry fruitworm, citrus cutworm, cranberry girdler, eastern tent caterpillar, fall webworm, fall webworm, filbert leafroller, filbert webworm, fruit tree leafroller, grape berry moth, grape leaffolder, grapeleaf skeletonizer, green fruitworm, gummosos-batrachedra commosae, gypsy moth, hickory shuckworm, hornworms, loopers, navel orangeworm, obliquebanded leafroller, omnivorous leafroller. omnivorous looper, orange tortrix, orangedog, oriental fruit moth, pandemis leafroller, peach twig borer, pecan nut casebearer, redbanded leafroller, redhumped caterpillar, roughskinned cutworm, saltmarsh caterpillar, spanworm, tent caterpillar, thecla-thecla basillides, tobacco budworm, tortrix moth, tufted apple budmoth, variegated leafroller, walnut caterpillar, western tent caterpillar, and yellowstriped armyworm.

Field crops such as canola/rape seed, evening primrose, meadow foam, corn (field, sweet, popcorn), cotton, hops, jojoba, peanuts, rice, safflower, small grains (barley, oats, rye, wheat, etc.), sorghum, soybeans, sunflowers, and tobacco are often targets for infestation by insects including armyworm, asian and other corn borers, banded sunflower moth, beet armyworm, bollworm, cabbage looper, corn rootworm (including southern and western varieties), cotton leaf perforator, diamondback moth, european corn borer, green cloverworm, headmoth, headworm, imported cabbageworm, loopers (including Anacamptodes spp.), obliquebanded leafroller, omnivorous leaftier, podworm, podworm, saltmarsh caterpillar, southwestern corn borer, soybean looper, spotted cutworm, sunflower moth, tobacco budworm, tobacco hornworm, and velvetbean caterpillar.

Bedding plants, flowers, ornamentals, vegetables and container stock are frequently fed upon by a host of insect pests such as armyworm, azalea moth, beet armyworm, diamondback moth, ello moth (hornworm), Florida fern caterpillar, Io moth, loopers, oleander moth, omnivorous leafroller, omnivorous looper, and tobacco budworm.

Forests, fruit, ornamental, and nut-bearing trees, as well as shrubs and other nursery stock are often susceptible to attack from diverse insects such as bagworm, blackheaded budworm, browntail moth, california oakworm, douglas fir tussock moth, elm spanworm, fall webworm, fruittree leafroller, greenstriped mapleworm, gypsy moth, jack pine budworm, mimosa webworm, pine butterfly, redhumped caterpillar, saddleback caterpillar, saddle prominent caterpillar, spring and fall cankerworm, spruce budworm, tent caterpillar, tortrix, and western tussock moth. Likewise, pests such as armyworm, sod webworm, and tropical sod webworm often attack turf grasses.

Because crops of commercial interest are often the target of insect attack, environmentally-sensitive methods for controlling or eradicating insect infestation are desirable in many instances. This is particularly true for farmers, nurserymen, growers, and commercial and residential areas which seek to control insect populations using eco-friendly compositions.

*Bacillus thuringiensis* is a gram-positive bacterium that produces proteinaceous crystalline inclusions during sporulation. These *B. thuringiensis* crystal proteins are often highly toxic to specific insects. Insecticidal activities have been identified for crystal proteins from various *B. thuringiensis* strains against insect larvae from the insect orders Lepidoptera (caterpillars), Coleoptera (beetles) and Diptera (mosquitoes, flies).

Individual *B. thuringiensis* crystal proteins, also called delta-endotoxins or parasporal crystals or toxin proteins, can differ extensively in their structures and insecticidal activities. These insecticidal proteins are encoded by genes typically located on large plasmids, greater than 30 mega Daltons (mDa) in size, that are found in *B. thuringiensis* strains. A number of these *B. thuringiensis* toxin genes have been cloned and the insecticidal crystal protein products characterized for their specific insecticidal properties. Hofte et al. (1989) and Schnepf et al. (1998) provide reviews of *B. thuringiensis* toxin genes and crystal proteins.

The insecticidal properties of *B. thuringiensis* have been long recognized, and *B. thuringiensis* strains have been incorporated in commercial biological insecticide products for over forty years. Commercial *B. thuringiensis* insecticide formulations typically contain dried sporulated *B. thuringiensis* fermentation cultures whose crystal proteins are toxic to various insect species.

Traditional commercial *B. thuringiensis* bio-insecticide products are derived from "wild-type" *B. thuringiensis* strains, i.e., purified cultures of *B. thuringiensis* strains isolated from natural sources. Newer commercial *B. thuringiensis* bio-insecticide products are based on genetically altered *B. thuringiensis* strains, such as the transconjugant *B. thuringiensis* strains described in U.S. Pat. Nos. 5,080,897 and 4,935,353.

A characteristic of crystal proteins is their ability to coalesce to form crystals inside the *B. thuringiensis* mother cell. Upon lysis of the mother cell the proteins are released as crystals into the external environment. In addition, *B. thuringiensis* also produces non-crystal proteins that, in contrast to crystal proteins, are secreted by *B. thuringiensis* cells as soluble proteins into the culture medium. Secreted non-crystal proteins of *B. thuringiensis* include phospholipases, proteases, and β-lactamase that have little, if any, insecticidal activity. However, three secreted non-crystal proteins of *B. thuringiensis* designated Vip1, Vip2 and Vip3 have been reported to be toxic to coleopteran or lepidopteran insects (Estruch et al., 1996; U.S. Pat. No. 5,866,326; WO94/21795; WO96/10083). A non-crystal protein of *B. thuringiensis* designated CryV is reported to be toxic to lepidopteran insects (Kostichka et al., 1996). A large number of *Bacillus thuringiensis* isolates producing extracellular secreted insecticidal toxin proteins have been identified by a number of different investigators. Such isolates have all been shown to produce one or more of these VIP or CryV toxin proteins or closely related homologs. Coleopteran inhibitory secreted BT proteins such as TIC901, TIC1201, TIC407, and TIC417 have been previously disclosed but appear to be unrelated to the proteins of the present invention (U.S. Provisional Patent Application No. 60/485,483 filed Jul. 7, 2003; PCT/US04/21692 filed Jul. 6, 2004).

The inventors herein disclose a new class of extracellular secreted insecticidal protein toxins that do not exhibit homology to the known VIP or CryV classes of proteins. None of the one hundred thirty-seven known insect-toxic proteins of *B. thuringiensis* (Crickmore et al., 1998), more or less, are substantially related to the proteins of the present invention. In fact, no significant homology was found between the sequences of the proteins of the present invention and any of the thousands of protein sequences contained in the National Center for Genome Resources (GenBank), Santa Fe, N. Mex.

SUMMARY OF INVENTION

In one embodiment, the present invention relates to an isolated and purified insecticidal protein, exhibiting an amino acid sequence substantially as set forth in SEQ ID NO:4, (TIC900), SEQ ID NO:6 (TIC402), SEQ ID NO:8 (TIC403), SEQ ID NO:10 (TIC404), SEQ ID NO:30 (TIC434), SEQ ID NO:12 (TIC961), SEQ ID NO:14 (TIC962), SEQ ID NO:16 (TIC963), SEQ ID NO:18 (TIC965), and SEQ ID NO:20 (TIC966), or related amino acid sequences and homologs thereof. Insecticidal activity of TIC900 and related proteins have been demonstrated in bioassays with lepidopteran insects including European corn borer (ECB), tobacco budworm (TBW) and Diamondback Moth (DBM), as shown herein.

In another embodiment, the present invention relates to an isolated and purified nucleotide sequence, i.e. a coding sequence, comprising a nucleotide sequence as set forth in SEQ ID NO:3 (tic900), SEQ ID NO:5 (tic402), SEQ ID NO:7 (tic403), SEQ ID NO:9 (tic404), SEQ ID NO:29 (tic434), SEQ ID NO:11 (tic961), SEQ ID NO:13 (tic962), SEQ ID NO:15 (tic963), SEQ ID NO:17 (tic965), or SEQ ID NO: 19 (tic966), or related sequences or homologs thereof. The native tic900 coding sequence as set forth in SEQ ID NO:3 encodes the TIC900 protein exhibiting the amino acid sequence as set forth in SEQ ID NO:4. Organisms producing TIC900 or related proteins exhibit insecticidal activity and/or insect-resistance properties. The native tic402 coding sequence as set forth in SEQ ID NO:5 encodes the TIC402 protein exhibiting the amino acid sequence as set forth in SEQ ID NO:6. The native tic403 coding sequence as set forth in SEQ ID NO:7 encodes the TIC403 protein exhibiting the amino acid sequence as set forth in SEQ ID NO:8. The native tic404 coding sequence as set forth in SEQ ID NO:9 encodes the TIC404 protein exhibiting the amino acid sequence as set forth in SEQ ID NO:10. The native tic434 coding sequence as set forth in SEQ ID NO:29 encodes the TIC434 protein exhibiting the amino acid sequence as set forth in SEQ ID NO:30. The native tic961 coding sequence as set forth in SEQ ID NO:11 encodes the TIC961 protein exhibiting the amino acid sequence as set forth in SEQ ID NO:12. The native tic962 coding sequence as set forth in SEQ ID NO:13 encodes the TIC962 protein exhibiting the amino acid sequence as set forth in SEQ ID NO:14. The native tic963 coding sequence as set forth in SEQ ID NO:15 encodes the TIC963 protein exhibiting the amino acid sequence as set forth in SEQ ID NO:16. The native tic965 coding sequence as set forth in SEQ ID NO:17 encodes the TIC965 protein exhibiting the amino acid sequence as set forth in SEQ ID NO:18. The native tic966 coding sequence as set forth in SEQ ID NO:19 encodes the TIC966 protein exhibiting the amino acid sequence as set forth in SEQ ID NO:20. TIC900 or related proteins and nucleotide sequences derived from Bt strains that encode these proteins are described herein as homologs of each other, i.e., insecticidal proteins or insecticidal fragments thereof encoded by nucleotide sequences that hybridize to each or any of the sequences disclosed herein either under specific hybridization conditions or under stringent hybridization conditions, and are specifically intended to be included within the scope of the present invention.

In a further embodiment, the present invention relates to a biologically pure culture of a *Bacillus thuringiensis* bacterium transformed with a plasmid vector containing a nucleotide sequence as set forth in SEQ ID NO:3 (tic900), SEQ ID NO:5 (tic402), SEQ ID NO:7 (tic403), SEQ ID NO:9 (tic404), SEQ ID NO:29 (tic434), SEQ ID NO:11 (tic961), SEQ ID NO:13 (tic962), SEQ ID NO:15 (tic963), SEQ ID NO:17 (tic965), or SEQ ID NO: 19 (tic966), or a related sequence or homolog that produces an insecticidal protein and secretes the protein into the extracellular space surrounding the bacterial strain during fermentation. An exemplary strain SIC9002 has been deposited in the Northern Regional Research Laboratory of Agricultural Research Service Center Collection (NRRL), USDA, 1815 North University Street, Peoria, Ill. 61604, pursuant to the Budapest Treaty on the International Recognition of the Deposit of Microorganism for the Purposes of Patent Procedure on Apr. 25, 2000 and has been assigned the accession No. NRRL B-30582. One plasmid containing the tic900 nucleotide sequence is set forth herein as pBD1.

In a further embodiment, the invention also relates to a biologically pure culture of a *B. thuringiensis* bacterium designated as strain EG5438 exhibiting insecticidal activity against lepidopteran insects. *B. thuringiensis* strain EG5438 represents a wild type *B. thuringiensis* strain from which a tic900 coding sequence was isolated. The strain has been deposited in the NRRL, USDA, pursuant to the Budapest Treaty on May 3, 2000 and has been assigned the accession No. NRRL B-30584.

In a further embodiment, the present invention provides a nucleotide sequence as set forth in SEQ ID NO:3 encoding a TIC900 amino acid sequence (SEQ ID NO:4), and an oligonucleotide portion that can be labeled and used as a hybridization probe for identifying additional related genes encoding related insecticidal proteins or homologues thereof. Other related nucleotide sequences specifically exemplified herein comprise sequences as set forth in SEQ ID NO:5, SEQ ID NO:7, SEQ ID NO:9, SEQ ID NO:29, SEQ ID NO:11, SEQ ID NO:13, SEQ ID NO:15, SEQ ID NO:17, and SEQ ID NO:19, each of which encode insecticidal protein toxins as set forth in SEQ ID NO:6, SEQ ID NO:8, SEQ ID NO:10, SEQ ID NO:30, SEQ ID NO:12, SEQ ID NO:14, SEQ ID NO:16, SEQ ID NO:18, and SEQ ID NO:20, respectively.

In yet a further embodiment, the invention provides plant cells and plants that have been transformed with a nucleotide sequence encoding a TIC900 or related protein as set forth in SEQ ID NO:4 or insecticidal fragment thereof, or a TIC900 protein homolog thereof, selected from the group consisting of SEQ ID NO:6, SEQ ID NO:8, SEQ ID NO:10, SEQ ID NO:30, SEQ ID NO:12, SEQ ID NO:14, SEQ ID NO:16, SEQ ID NO:18, and SEQ ID NO:20. The nucleotide sequence can be translated and expressed by plant cells and in plant tissues at levels sufficient to inhibit or kill lepidopteran insect pests that come into contact with the transgenic plant expressing said protein, particularly when said pests ingest parts of said transgenic plant. Both monocot and dicot plants are within the scope of the invention. Modification of the sequence may be required in order to affect the maximum level of expression and to enhance the ability of the plant containing the sequence to produce insecticidal levels of the TIC900 or related protein. Transformation of plants with the nucleotide sequences disclosed herein may result in increased frequency of transformants that express the transgene, i.e., tic900 or its homolog, as well as the generation of a greater percentage of transformation events exhibiting morphologically normal physiology.

In yet a further embodiment, the present invention also provides a method for producing a transgenic plant that exhibits increased expression levels of a nucleotide sequence encoding a TIC900 protein or insecticidal fragment thereof or its homolog and thereafter increased levels of the insecticidal TIC900 protein or its homolog. Thus the plants transformed with the nucleotide sequences disclosed herein exhibit improved and increased levels of lepidopteran pest resistance abilities in comparison to a plant lacking a nucleotide sequence encoding a TIC900, an insecticidal fragment of a TIC900, or one of its homologs.

In accomplishing the foregoing, a method for expressing a nucleotide sequence encoding a TIC900 protein or its homolog in a plant is provided comprising the steps of a) inserting into the genome of a plant cell a nucleic acid sequence comprising in the 5' to 3' direction, a plant functional promoter operably linked to a structural DNA sequence optimized for plant expression that causes production of an RNA sequence encoding all of or an insecticidal fragment of a TIC900 polypeptide sequence as set forth in SEQ ID NO:4, or its homolog selected from the group consisting of SEQ ID NO:6, SEQ ID NO:8, SEQ ID NO:10, SEQ ID NO:30, SEQ ID NO:12, SEQ ID NO:14, SEQ ID NO:16, SEQ ID NO:18, and SEQ ID NO:20, or a sequence having at least from about 80%, or from at least about 85%, or from at least about 90%, or from at least about 95%, or from at least about 99% sequence identity to the amino acid sequence as set forth in SEQ ID NO:4, or a sequence encoding an insecticidal protein that hybridizes to any of these sequences under either specific or stringent hybridization conditions, and a 3' non-translated DNA sequence that functions in the cells of the plant to cause transcription termination and polyadenylation; b) obtaining transformed plant cells containing the nucleic acid sequence; and c) generating from the transformed plant cells genetically transformed plants that express the nucleotide sequence encoding the TIC900 or a related protein, wherein the transformed plants are morphologically normal and exhibit elevated or improved levels of lepidopteran pest resistance compared to a plant not transformed to express said protein.

Another embodiment of the present invention is the provision for antibodies that bind specifically to epitopes presented only by the TIC900 protein or its homologs. Antibodies can be used for identifying the presence of a TIC900 protein or a homolog, for purifying the protein or homolog, for identifying a nucleotide sequence from which a TIC900 protein or a homolog is being expressed, and for use in kits designed to allow the detection of a TIC900 protein or a homolog or the detection of a nucleotide sequence expressing the protein or homolog.

The inventors contemplate that the protein compositions disclosed herein will find particular utility as insecticides for topical and/or systemic application to field crops, grasses, fruits and vegetables, and ornamental plants. In a preferred embodiment, the bioinsecticide composition comprises an oil flowable suspension of bacterial cells which expresses a novel insecticidal protein disclosed herein. Preferably the cells are *B. thuringiensis* EG5438 or SIC9002 cells, however, any such bacterial host cell expressing the novel nucleic acid segments disclosed herein and producing a crystal protein is contemplated to be useful, such as *B. megaterium, B. subtilis, E. coli*, or *Pseudomonas* spp.

A particular advantage of the present invention comprises an improvement in insect resistance management (IRM). The ability to combine two or more insecticidal agents, each toxic to the same insect pest species, into a single composition, and each agent exhibiting a mode of action different from the other insecticidal agents with which it is combined, present a means for more effectively controlling a particular insect pest species by substantially reducing the likelihood that resistance to the insecticidal composition will develop in a population. The TIC900 protein an insecticidal fragment thereof, or any homolog thereof, of the present invention can be combined with any number of known insecticidal agents to achieve the level of resistance management in a particular composition, preferably by expression of the combination of insecticidal agents in plants. In particular TIC900 or related insecticidal protein compositions can be combined with a Cry1 or Cry2 amino acid sequence or a variant thereof to achieve control of various lepidopteran plant pest species, or with other appropriate Cry proteins, and with various insecticidal compositions derived from *Xenorhabdus* and *Photorhabdus* bacterium species that have been shown to exhibit insecticidal bioactivity directed to lepidopteran plant pest species. Preferably the in planta use of these compositions would be directed to enhanced expression of the proteins in the parts of the plant that exhibit the greatest vulnerability to lepidopteran insect predation. For protection of maize species against European corn borer (ECB), it would be preferable to achieve the highest levels of expression in the leaves and stems of the plant. For tobacco species susceptible to budworm, it would be preferable to achieve the highest levels of expression in the sprouting parts of the plant, i.e., within the bud systems of the plant. For protection of a cruciferous vegetable species against diamondback moth (DBM), it would be preferable to achieve the highest levels of expression in the leaves and stems of the plant.

The insecticidal proteins of the present invention can also be combined with insecticidal and/or fungicidal toxins expressed in planta to achieve a recombinant plant that exhibits multiple levels of resistance to infestation by pests that are not beneficial to plants. For example, a protein of the present invention can be expressed along with a protein that exhibits coleopteran insect control, and/or along with a protein or other agent that exhibits antifungal activity, to achieve a recombinant transgenic plant that exhibits improved resistance to lepidopteran insect pests, coleopteran insect pests, and fungal pests. Other permutations of levels of resistance are known to those of skill in the art, such as means for resistance to piercing and sucking insect infestation, and nematode infestation, etc. The insecticidal proteins of the present invention can also be combined with one or more nucleotide sequences expressed as one or more dsRNA's for use in suppression of one or more genes (1) in the target pest as a means for achieving a plant that exhibits multiple layers of resistance to infestation by a particular pest, (2) in the plant as a means for achieving desired plant traits, or (3) in various combinations to achieve the desired properties of (1) or (2) collectively.

Chimeric proteins consisting of all or a part of one or more proteins of the present invention fused to other proteins that are useful in plant protection from infestation or otherwise are contemplated herein. For example, domains of the proteins of the present invention have been found to exhibit a low level of similarity to other Bt toxins, such as Cry3Aa toxin domain I, Cry1Ca toxin domain II, and Cry1Ja toxin domain III (in particular, Domains I, II, and III of the toxin portion of the TIC900 protein, respectively). The proteins of the present invention can be fused to the protoxin domains of any of the Cry1 proteins known in the art, resulting in crystal toxin protein formation when expressed in Bt or other *Bacillus* strains of bacteria. Furthermore, the domains identified herein within the amino acid sequence of the proteins of the present invention can be exchanged with other similar domains from insecticidal Bt toxin proteins to achieve improved insecticidal activity and/or host ranges that have not previously been observed with Cry1 toxin domain exchanges (Malvar et al. U.S. Pat. No. 6,017,534; Galizzi et al, PCT/EP90/0114, WO 91/01087).

Another embodiment comprises an isolated polynucleotide that encodes a *Bacillus thuringiensis* insecticidal toxin or insecticidal fragment thereof, active against an insect pest, wherein the toxin or insecticidal fragment has a molecular weight between approximately 65,000 Daltons and approximately 70,000 Daltons. In addition, the nucleotide sequence encoding the toxin, or the complement thereof, hybridizes under specific or stringent hybridization conditions to SEQ ID NO:3. The toxin preferably exhibits biological activity in controlling or killing a lepidopteran insect pest, preferably European corn borer (ECB), tobacco budworm (TBW) and/or diamondback moth (DBM). In one embodiment the nucleotide sequence encoding the toxin is optimized for expression in plants, yet encodes substantially the toxin or an insecticidal fragment thereof, i.e., encodes the same or substantially the same amino acid sequence as present in the native amino acid sequence.

Another embodiment of the present invention provides for host cells transformed to contain a polynucleotide encoding an insecticidal protein of the present invention or an insecticidal fragment thereof. Preferably the nucleotide sequences of the present invention are modified to improve expression of the proteins of the present invention in a preferred host cell. The host cell of the present invention is selected from the group consisting of a bacterial cell, a fungal cell, and a plant cell. Expression in a plant cell can comprise expression to achieve accumulation of the insecticidal protein in the cytoplasm, or can result in the insecticidal protein being accumulated into a subcellular organelle such as a plastid, chloroplast, or mitochondria. Alternatively the insecticidal protein of the present invention or insecticidal fragments thereof could be localized to the protein secretion machinery of the particular host cell and result in an accumulation of the protein product outside of the cell and into the extracellular spaces surrounding the cell.

An additional embodiment of the present invention provides a method for controlling infestation of a plant by a lepidopteran insect species. Preferably a pesticidal amount of an insecticidal protein of the present invention or insecticidal fragment thereof is provided for consumption by the insect pest in the diet of the insect. The diet can consist of a plant part that the insect normally feeds upon, such as a plant tissue or plant cell. The insecticidal protein or insecticidal fragment thereof can be provided in a composition that is applied to the surface of the plant tissue, plant part, or plant cell or more preferably can be produced by the protein synthesis machinery of the cell and, as described above, accumulated within the plant cell or secreted outside of the plant cell, so long as the amount of the protein toxin provided is an insecticidal amount sufficient to inhibit the insect pest from further feeding, or to inhibit the further growth and development of the insect pest, or to cause mortality to the insect pest. The insecticidal toxin or fragment thereof is derived from a nucleotide sequence that is encoded in *Bacillus thuringiensis* by a nucleotide sequence that hybridizes under stringent conditions to the nucleotide sequence substantially complementary to SEQ ID NO:3.

The present invention also provides a method for detecting a first nucleotide sequence that hybridizes to a second nucleotide sequence as set forth in SEQ ID NO:3, wherein the first nucleotide sequence encodes an insecticidal protein or insecticidal fragment thereof and hybridizes under specific or stringent hybridization conditions to the second nucleotide sequence. Other exemplary second nucleotide sequences are SEQ ID NO:5, SEQ ID NO:7, SEQ ID NO:9, SEQ ID NO:29, SEQ ID NO:11, SEQ ID NO:13, SEQ ID NO:15, SEQ ID NO:17, and SEQ ID NO:19.

It is also contemplated that the proteins of the present invention would be useful when expressed in planta to provide an improved level of protection from insect infestation to plants expressing the proteins or insecticidal fragments thereof. Therefore it is envisioned that one or more nucleotide sequences encoding a TIC900 insecticidal protein or insecticidal fragment thereof or homolog thereof, or combinations thereof, whether expressed individually or as chimeras or as fusions, would be introduced into the plant cell, either into the genome, into the chloroplast or mitochondrial DNA, or into an organelle as a stable and autonomously replicating extra-chromosomal element, for expression of the said TIC900 protein or insecticidal fragment thereof or homolog thereof. Preferably the sequence is a non-naturally occurring nucleotide sequence that encodes the insecticidal protein or insecticidal fragment thereof. Plant cells transformed with such sequences are provided for herein. Plants grown from the transformed plant cells are provided by the instant inventions. Seeds and progeny of the seeds from the transformed plants of the present invention are also provided so long as the seeds contain at least the sequences encoding the insecticidal proteins or insecticidal protein fragments thereof. The nucleotide sequences envisioned are at least from about 60 to about 85% identical to the nucleotide sequences of the present invention as isolated from *B. thuringiensis.*

Exemplary sequences of the present invention include at least, in addition to those related to SEQ ID NO:5 and SEQ ID NO:4: (1) the nucleotide sequence as set forth in SEQ ID NO:5, and the amino acid sequence encoded by SEQ ID NO:5 as set forth in SEQ ID NO:6, also referred to herein as insecticidal protein TIC402; (2) the nucleotide sequence as set forth in SEQ ID NO:7, and the amino acid sequence encoded by SEQ ID NO:7 as set forth in SEQ ID NO:8, also referred to herein as insecticidal protein TIC403; (3) the nucleotide sequence as set forth in SEQ ID NO:9, and the amino acid sequence encoded by SEQ ID NO:9 as set forth in SEQ ID NO:10, also referred to herein as insecticidal protein TIC404; (4) the nucleotide sequence as set forth in SEQ ID NO:29, and the amino acid sequence encoded by SEQ ID NO:29 as set forth in SEQ ID NO:30, also referred to herein as insecticidal protein TIC434; (5) the nucleotide sequence as set forth in SEQ ID NO:11, and the amino acid sequence encoded by SEQ ID NO:11 as set forth in SEQ ID NO:12, also referred to herein as insecticidal protein TIC961; (6) the nucleotide sequence as set forth in SEQ ID NO:13, and the amino acid sequence encoded by SEQ ID NO:13 as set forth in SEQ ID NO:14, also referred to herein as insecticidal protein TIC962; (7) the nucleotide sequence as set forth in SEQ ID NO:15, and the amino acid sequence encoded by SEQ ID NO:15 as set forth in SEQ ID NO:16, also referred to herein as insecticidal protein TIC963; (8) the nucleotide sequence as set forth in SEQ ID NO:17, and the amino acid sequence encoded by SEQ ID NO:17 as set forth in SEQ ID NO:18, also referred to herein as insecticidal protein TIC965; and (9) the nucleotide sequence as set forth in SEQ ID NO:19, and the amino acid sequence encoded by SEQ ID NO:19 as set forth in SEQ ID NO:20, also referred to herein as insecticidal protein TIC966. Each of these proteins and the native B.t. nucleotide sequences encoding these proteins are related to TIC900 as defined herein. For example, and respectively, SEQ ID NO:5 is a nucleotide sequence encoding a TIC402 insecticidal protein as set forth in SEQ ID NO:6. SEQ ID NO:5 as shown herein is identifiable by hybridization to SEQ ID NO:3 under stringent conditions. SEQ ID NO:5 encodes a protein that exhibits lepidopteran toxic biological activity, exhibiting toxicity to European corn borer (ECB), tobacco budworm (TBW) and/or diamondback moth (DBM). SEQ ID NO:7, SEQ ID NO:9, SEQ ID NO:29, SEQ ID NO:11, SEQ ID NO:13, SEQ ID NO:15, SEQ ID NO:17, and SEQ ID NO:19 are each capable of hybridizing to each other under stringent conditions, and each sequence can be identified by hybridization to SEQ ID NO:3 under stringent conditions, and each sequence can be identified by amplification using the oligonucleotide primers as set forth in SEQ ID NO:21 and SEQ ID NO:22. The primers as set forth in SEQ ID NO:21 and SEQ ID NO:22 are diagnostic for identifying the presence of a nucleotide sequence encoding a TIC900 or related insecticidal protein in a sample. These oligonucleotides, when used together under defined amplification conditions and in the presence of a suitable nucleotide sequence substrate, produce an amplicon that is diagnostic for the presence of a TIC900 coding sequence or a homolog thereof. This particular reaction is useful for detecting the presence of a B.t. gene encoding an insecticidal protein corresponding to a TIC900 or related protein in a sample, and greatly simplifies the search for and identification of such related sequences.

Kits for detecting the presence of the nucleotide sequences of the present invention are also contemplated. Such kits contain one or more nucleotide sequences each for use as a probe for detecting the presence of a nucleotide sequence encoding an insecticidal protein of the present invention or fragment thereof. Such kits could also or alternatively contain antibody specific for binding to one or more peptides of the proteins of the present invention, as well as reagents for use with the probe or antibody, and the kits would also contain control samples for use in ensuring that the nucleotides or peptides identified with the probe and or antibody and reagents were functioning according to the manufacturers" instructions. All of the reagents necessary for carrying out the methods of identification of either nucleotide sequences or peptides would be packaged together in a kit along with instructions for use. An exemplary kit could contain a TIC900 or related nucleotide sequence encoding an insecticidal protein along with a sample of the exemplary nucleotide sequence amplification primers as set forth in SEQ ID NO:21 and SEQ ID NO:22, together with the necessary reagents necessary for carrying out an amplification reaction, all packaged together in the kit.

A plant or plant tissue transformed to contain (a) a nucleotide sequence encoding one or more of the proteins of the present invention, (2) all or an insecticidally active portion of one or more of the proteins of the present invention, or (3) a chimera containing all or any portion of one or more proteins of the present invention can be detected using any number of means well known in the art including but not limited to nucleotide sequence based detection methods and/or protein based detection methods. Agronomically and commercially important products and/or compositions of matter derived from such transformed plants or plant tissues include but are not limited to animal feed, commodities, and corn, soy, cotton, canola, wheat, oat, rice, sugar-cane, chick-pea, and cowpea products and by-products that are intended for use as food for human consumption or for use in compositions that are intended for human consumption including but not limited to flours, meals, syrups, oil, starch, popcorn, cakes, cereals containing the fruits and seeds of these crops and by-products, and the like are intended to be within the scope of the present invention if these products and compositions of matter contain detectable amounts of the nucleotide sequences encoding the proteins or derivatives of the proteins as set forth herein.

Plants or plant parts suspected of containing a protein or nucleotide encoding a protein of the present invention in a biological sample can be detected using the method comprising the steps of contacting a sample suspected of containing said nucleotide with a polynucleotide probe that hybridizes under stringent hybridization conditions with said nucleotide and that does not hybridize under stringent hybridization conditions with a nucleotide from a control plant, subjecting said sample and said probe to said stringent hybridization conditions, and detecting the hybridization of said probe to the nucleotide.

One embodiment of the present invention comprises a biological sample derived from a transgenic plant, tissue, or seed, wherein the sample comprises a nucleotide sequence which is or is complementary to a sequence encoding a protein of the present invention, and wherein said sequence is detectable in said sample using a nucleic acid amplification or nucleic acid hybridization method. The sample can consist of a sample that is selected from the group consisting of an extract obtainable from the transgenic plant containing the nucleotide sequence, and the extract can contain any nucleotide sequence encoding one or more of the proteins of the present invention, or the complement thereof. The biological sample is preferably selected from the group consisting of a flour such as corn flour, a meal such as corn meal, a syrup such as corn syrup, an oil such as corn oil, cotton oil, linseed oil, soybean or canola oil, safflower oil, sunflower oil, peanut oil, and the like, a starch such as corn starch, and any cereal that can be manufactured in whole or in part to contain grain or grain by-products. The nucleotide sequence is detectable in the extract using a nucleic acid amplification or nucleic acid hybridization method.

BRIEF DESCRIPTION OF THE SEQUENCES

SEQ ID NO:1 represents an amino acid sequence deduced by Edmund degradation of a 14 kDa cyanogen bromide fragment of a TIC900 protein and corresponds to amino acid positions 397-414 as set forth in SEQ ID NO:4.

SEQ ID NO:2 represents the nucleotide sequence of a hybridization probe designated as WD470 designed based upon the amino acid sequence as set forth in SEQ ID NO:1, for use in detecting nucleotide sequences encoding TIC900 and related proteins.

SEQ ID NO:3 represents a native *Bacillus thuringiensis* nucleotide sequence consisting of 1803 consecutive nucleotides encoding a TIC900 insecticidal protein consisting of 601 amino acid as set forth in SEQ ID NO:4.

SEQ ID NO:4 represents the TIC900 amino acid sequence deduced from the nucleotide sequence as set forth in SEQ ID NO:3.

SEQ ID NO:5 represents a tic900 homologous nucleotide sequence encoding a native *Bacillus thuringiensis* TIC900 related protein, designated herein as TIC402.

SEQ ID NO:6 represents the TIC402 amino acid sequence deduced from the nucleotide sequence as set forth in SEQ ID NO:5.

SEQ ID NO:7 represents a tic900 homologous nucleotide sequence encoding a native *Bacillus thuringiensis* TIC900 related protein, designated herein as TIC403.

SEQ ID NO:8 represents the TIC403 amino acid sequence deduced from the nucleotide sequence as set forth in SEQ ID NO:7.

SEQ ID NO:9 represents a tic900 homologous nucleotide sequence encoding a native *Bacillus thuringiensis* TIC900 related protein, designated herein as TIC404.

SEQ ID NO:10 represents the TIC404 amino acid sequence deduced from the nucleotide sequence as set forth in SEQ ID NO:9.

SEQ ID NO:11 represents a tic900 homologous nucleotide sequence encoding a native *Bacillus thuringiensis* TIC900 related protein, designated herein as TIC961.

SEQ ID NO:12 represents the TIC961 amino acid sequence deduced from the nucleotide sequence as set forth in SEQ ID NO:11.

SEQ ID NO:13 represents a tic900 homologous nucleotide sequence encoding a native *Bacillus thuringiensis* TIC900 related protein, designated herein as TIC962.

SEQ ID NO:14 represents the TIC962 amino acid sequence deduced from the nucleotide sequence as set forth in SEQ ID NO:13.

SEQ ID NO:15 represents a tic900 homologous nucleotide sequence encoding a native *Bacillus thuringiensis* TIC900 related protein, designated herein as TIC963.

SEQ ID NO:16 represents the TIC963 amino acid sequence deduced from the nucleotide sequence as set forth in SEQ ID NO:15.

SEQ ID NO:17 represents a tic900 homologous nucleotide sequence encoding a native *Bacillus thuringiensis* TIC900 related protein, designated herein as TIC965.

SEQ ID NO:18 represents the TIC965 amino acid sequence deduced from the nucleotide sequence as set forth in SEQ ID NO:17.

SEQ ID NO:19 represents a tic900 homologous nucleotide sequence encoding a native *Bacillus thuringiensis* TIC900 related protein, designated herein as TIC966.

SEQ ID NO:20 represents the TIC966 amino acid sequence deduced from the nucleotide sequence as set forth in SEQ ID NO:19.

SEQ ID NO:21 represents a 5' end sequence primer used as a probe that binds specifically to TIC900 homologous sequences.

SEQ ID NO:22 represents a 3' end sequence primer used as a probe that binds specifically to TIC900 homologous sequences.

SEQ ID NO:23 represents a tic109 nucleotide sequence encoding a TIC109 chimeric protein consisting of a nucleotide sequence encoding a TIC900 insecticidal protein domain linked in frame to a nucleotide sequence encoding a Cry1Ac protoxin domain fragment.

SEQ ID NO:24 represents a TIC109 chimeric protein amino acid sequence consisting of a TIC900 insecticidal amino acid sequence (1-603) linked to a Cry1Ac protoxin domain fragment amino acid sequence (606-1168).

SEQ ID NO:25 represents a tic110 nucleotide sequence encoding a TIC110 chimeric protein consisting of a nucleotide sequence encoding a Cry1F toxin domain I fragment (nucleotides 1-723) linked in frame to a nucleotide sequence encoding a TIC900 toxin fragment domain II-III (nucleotides 724-1809) linked in frame to a nucleotide sequence encoding a Cry1Ac protoxin domain fragment (nucleotides 1810-3510).

SEQ ID NO:26 represents a TIC110 chimeric protein amino acid sequence consisting of a Cry 1F toxin domain I fragment (amino acids 1-233) linked to a TIC900 toxin domain II-III fragment (amino acids 234-603) linked to a Cry1Ac protoxin domain fragment (amino acids 604-1170).

SEQ ID NO:27 represents a tic111 nucleotide sequence encoding a TIC111 chimeric protein consisting of a nucleotide sequence encoding a Cry1Ac toxin domain I fragment (nucleotides 1-705) linked in frame to a nucleotide sequence encoding a TIC900 toxin domain II-III fragment (nucleotides 706-1815) linked in frame to a nucleotide sequence encoding a Cry1Ac protoxin domain fragment (nucleotides 1822-3516).

SEQ ID NO:28 represents a TIC111 chimeric protein amino acid sequence consisting of a Cry1Ac toxin domain I fragment (amino acids 1-235) linked to a TIC900 toxin domain II-III fragment (amino acids 236-605) linked to a Cry1Ac protoxin domain fragment (amino acids 608-1172).

SEQ ID NO:29 represents a *B. thuringiensis* strain EG4611 about 7.5 kb nucleotide sequence containing a TIC434 coding sequence, said coding sequence being from about nucleotide position 425 through about nucleotide position 2238.

SEQ ID NO:30 represents a TIC434 amino acid sequence.

SEQ ID NO:31 represents a chimeric sequence encoding a TIC435 amino acid sequence corresponding to a TIC434 amino acid sequence fused in frame to a sequence encoding a Cry1 protoxin amino acid sequence; said TIC434 amino acid sequence coding region corresponding to about nucleotide position 1 through about nucleotide position 1825, and said Cry1 protoxin amino acid sequence coding region corresponding to about nucleotide position 1826 through about nucleotide position 3525.

SEQ ID NO:32 represents a chimeric TIC435 amino acid sequence.

DETAILED DESCRIPTION

The following detailed description of the invention is provided to aid those skilled in the art in practicing the present invention. Even so, the detailed description should not be construed to unduly limit the present invention as modifications and variations in the embodiments discussed herein may be made by those of ordinary skill in the art without departing from the spirit or scope of the present inventive discovery.

In accordance with the present invention, a new genus of nucleotide sequences encoding insecticidal proteins derived from *Bacillus thuringiensis* and related *Bacillus* strains has been discovered. As defined elsewhere herein, these nucleotide sequences all hybridize to each other under stringent conditions. The proteins encoded by these nucleotide sequences each exhibit lepidopteran species inhibitory biological activity, and so are considered to be insecticidal proteins. Each of the proteins encoded by these nucleotide sequences can be expressed in plants alone or in combinations with each other or with other lepidopteran inhibitory insecticidal agents such as proteins, crystal proteins, toxins, and/or pest specific double stranded RNA's designed to suppress genes within one or more target pests, and the like to achieve a means of insect resistance management in the field that has not feasible before by merely using the known lepidopteran insecticidal proteins derived from *Bacillus thuringiensis* strains, such as Cry1 proteins and various lepidopteran inhibitory insecticidal proteins derived from *Bacillus laterosporous* species and *Bacillus sphaericus* species. The proteins of the present invention can also be used in plants in combination with other types of insecticidal toxins for achieving plants transformed to contain at least one means for controlling one or more of each of the common plant pests selected from the groups consisting of lepidopteran insect pests, coleopteran insect pests, piercing and sucking insect pests, and the like. The proteins of the present invention are also contemplated for use in formulations, either alone or in combinations with other insecticidal agents, as insecticides for topical and/or systemic application to field crops, grasses, fruits and vegetables, and ornamental plants. In a preferred embodiment, the bio-insecticide composition comprises an oil flowable suspension of bacterial cells that expresses one or more of a novel insecticidal protein disclosed herein. Preferably the cells are *B. thuringiensis* EG5438 or SIC9002 cells, however, any such bacterial host cell expressing the novel nucleic acid segments disclosed herein and producing a crystal protein The insecticidal proteins of the present invention may also be used in compositions for controlling insect infestation of plants either alone or in combination with other insecticidal proteins or agents, and may also be used alone or in combination with gene suppression methodologies. As used herein "gene suppression" means any of the well-known methods for suppressing expression of protein from a gene including post transcriptional gene suppression and transcriptional suppression.

As used herein an "pest resistance" trait is a characteristic of a transgenic plant is resistant to attack from a plant pest such as a virus, a nematode, a larval insect or an adult insect that typically is capable of inflicting crop yield loss in a progenitor plant. Such pest resistance can arise from a natural mutation or more typically from incorporation of recombinant DNA that confers pest resistance. To impart insect resistance to a transgenic plant such recombinant DNA can, for example, encode an insect lethal protein such as a delta endotoxin of *Bacillus thuringiensis* bacteria, e.g. as is used in commercially available varieties of cotton and corn, encode an insecticidal toxin protein disclosed herein such as a TIC900 or related protein or insecticidal fragment thereof, or be transcribed to a double-stranded RNA targeted for suppression of an essential gene in the insect, or any combination of these insecticidal agents. To illustrate that the production of transgenic plants with pest resistance is a capability of those of ordinary skill in the art reference is made to U.S. Pat. Nos. 5,250,515; 5,880,275 and 6,555,655 which disclose plants expressing an endotoxin of *Bacillus thuringiensis* bacteria. See also U.S. Pat. No. 6,506,599 (Fire et al.) and U.S. Patent Application Publication 2003/0061626 A1 (Plaetinck et al.) and U.S. Patent Application Publication 2003/0150017 A1 (Mesa et al.) which disclose control of invertebrates by permitting the pest to feed on transgenic plants which produce double-stranded RNA for suppressing a target gene in the pest. See also U.S. Pat. No. 5,986,175 (Mica et al.) that discloses the control of viral pests by transgenic plants which express viral replicase. All of the above-described patents and applications disclosing materials and methods for pest control in plants are incorporated herein by reference.

Surprisingly, the proteins of the present invention appear to be unrelated to any of the *Bacillus thuringiensis* insecticidal proteins heretofore discovered in the art. The proteins of the present invention are shown herein to be excreted into the extracellular space surrounding the *Bacillus* species from which they are derived. These proteins are shown herein to be significantly smaller than the previously known Cry proteins in the art, and are expressed during the vegetative stage of growth of the isolated and purified bacterial cell cultures. This is unlike the expression of Cry proteins which are expressed generally in the sporulation phase of growth and which form various crystalline bodies within the forespore of the cell.

As will become apparent to those of skill in the art, the inventors herein disclose the isolation and purification of a nucleotide sequence, tic900, encoding a precursor TIC900 protein (TIC900p) that is subsequently processed to release a mature TIC900 protein (TIC900m) that exhibits lepidopteran species inhibitory biological activity. The inventors herein disclose the use of the tic900 sequence as a means for identifying a multitude of other homologs and related sequences, which each also encode insecticidal proteins related to TIC900.

Nucleotide sequences disclosed herein and encoding TIC900 and related proteins were derived from various strains of *Bacillus thuringiensis*, i.e., the strain EG5438 contained at least one gene designated herein as tic900. The strain EG5438 was deposited under the provisions of the Budapest Treaty with the permanent collection of the NRRL on May 3, 2002 and was provided with the NRRL accession No. NRRL B-30584. Another strain identified herein to contain a sequence encoding TIC900, a nucleotide sequence identical to the EG5438 tic900 allele, was *B. thuringiensis* strain EG5526.

Nucleotide sequences related to tic900, and amino acid sequences related to TIC900 (including precursor and mature species of TIC900) which are disclosed herein include but are not limited to tic402 and the encoded insecticidal protein TIC402 isolated from and produced at least by B.t. strains EG3879, tic403 and the encoded insecticidal protein TIC403 isolated from and produced at least by B.t. strain EG4332, tic404 and the encoded insecticidal protein TIC404 isolated from and produced at least by B. t. strain EG4971, tic434 and the encoded insecticidal protein TIC434 isolated from and produced at least by B.t. strain EG4611, tic961 and the encoded insecticidal protein TIC961 isolated from and produced at least by B.t. strain EG4090, tic962 and the encoded insecticidal protein TIC962 isolated from and produced at least by B.t. strain EG4293, tic963 and the encoded insecticidal protein TIC963 isolated from and produced at least by B.t. strain EG4611, tic965 and the encoded insecticidal protein TIC965 isolated from and produced at least by B.t. strain EG5023, and tic966 and the encoded insecticidal protein TIC966 isolated from and produced at least by B.t. strain EG4092.

It is intended that the proteins of the present invention be used for agricultural purposes, i.e., for protecting plants from insect pest infestation, and more particularly for protecting plants from lepidopteran insect pest infestation. As exemplified herein, the proteins of the present invention are useful for protecting plants at least from European corn borer (ECB) infestation, at least from tobacco budworm (TBW) infestation and at least from diamondback moth (DBM) infestation. Plant protection can be achieved by topical application of a plant or plant parts such as by applying to the surface of the plant, i.e., the leaves, flowers, stems, stalks, and roots, a composition that contains an insecticidally effective amount of one or more of the proteins of the present invention. Alternatively, and preferably, the plant itself will be transformed to contain a nucleotide sequence modified for improved expression of the protein of the present invention in planta or expression of an insecticidal portion thereof.

The TIC900 protein is an insecticidal compound active against lepidopteran insects such as ECB, TBW and DBM. The TIC900 protein as set forth in SEQ ID NO:4 and related insecticidal proteins may be used as the active ingredient in insecticidal formulations useful for controlling lepidopteran insects. As used herein and with reference to insecticidal proteins that are related to TIC900, it is intended that related insecticidal proteins are those that are identified as homologs of TIC900 or those that are identified as being encoded by a nucleotide sequence that hybridizes under stringent conditions to all or a part of the native *Bacillus thuringiensis* sequence encoding the TIC900 protein or an insecticidal portion thereof. Of course, one skilled in the art will recognize that, due to the redundancy of the genetic code, many other sequences are capable of encoding such related proteins, and those sequences, to the extent that they function to express insecticidal proteins either in *Bacillus* strains or in plant cells, are intended to be encompassed by the present invention, recognizing of course that many such redundant coding sequences will not hybridize under stringent conditions to the native sequence encoding TIC900. Coding sequences are conceivable that function to encode all or an insecticidal portion of a TIC900 or related protein that do not hybridize under stringent conditions. However, such sequences are derived from the native nucleotide sequence on the basis that the native nucleotide sequence is capable of being modified to exhibit a non-native sequence that still encodes the same or substantially the same native amino acid sequence, or that the native amino acid sequence is capable of being used along with a codon table to back-translate, allowing the skilled artisan to arrive at a nucleotide sequence that encodes all or an insecticidal portion of a TIC900 or related protein. All of these sequences are intended to be within the scope of the present invention.

The *B. thuringiensis* strains containing a nucleotide sequence encoding a TIC900 or related protein and substantial equivalents thereof, can be cultured using standard known media and fermentation techniques. Upon completion of the fermentation cycle, the bacteria expressing TIC900 or a homolog thereof can be harvested by first separating the *B. thuringiensis* spores and crystals from the spent fermentation broth by means well known in the art. The recovered *B. thuringiensis* spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art. The proteins in the spent fermentation broth including TIC900 or related proteins of the present invention can be concentrated and formulated into a wettable powder, a liquid concentrate, granules or other formulations by the addition of surfactants, dispersants, inert carriers and other components to facilitate handling and application for particular target pests.

Formulated bait granules containing an attractant and spores and crystals of the *B. thuringiensis* isolates or concentrated spent fermentation media or insecticidal proteins purified from the spores or spent fermentation media, or recombinant microbes comprising the nucleotide sequences encoding TIC900 or related insecticidal proteins obtainable from the *B. thuringiensis* isolates disclosed herein, can be applied to the environment of the pest. The bait may be applied liberally since the toxin does not affect animals or humans. Product may also be formulated as a spray or powder. Pests pick the product up on their feet or abdomen and carry it back to the nest where other pests will be exposed to the toxin. The *B. thuringiensis* isolate or recombinant host expressing a nucleotide sequence or gene encoding a TIC900 or related protein of the present invention may also be incorporated into a bait or food source for the pest.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg or from about 5 to about 100 parts per million of the active component insecticidal protein, i.e., the TIC900 protein, amino acid sequence variant thereof, insecticidal portion or fragment thereof, or homolog thereof. These formulations will be administered at about 50 mg (liquid or dry) to 1 kg or more per hectare. The formulations can be applied to the environment of the lepidopteran pests, e.g., plants, soil, or water by spraying, dusting, sprinkling, or the like, and can also be applied to the surfaces of seeds as a seed treatment or seed coating and can be permeated into the seed coat and/or cotyledon(s).

One skilled in the art would know that to achieve improved expression of a Bt insecticidal protein in a plant, a nucleotide sequence encoding the Bt protein, or an active variant or fragment of the protein, would first need to be prepared. Then the nucleotide sequence encoding the protein or fragment thereof would be placed into an expression cassette that functions in plants to cause the transcription of the coding sequence into a messenger RNA that is subsequently translated in the cells of the plant such that an insecticidally effective amount of the insecticidal protein is produced within the plant tissues. One skilled in the art would also know to transform a plant cell, preferably a corn, cotton, soybean, canola, rice, wheat, oat, grass, forage plant, cruciferous plant, fruit tree, ornamental flower, tomato, potato, carrot, kale, and tobacco plant cell and the like with the nucleotide sequence embedded within the plant functional expression cassette, and to select for cells that contain the sequence and are expressing insecticidally effective amounts of the insecticidal protein, preferably a TIC900 or related protein or insecticidal fragment thereof, and to produce plants from such transformed cells. One skilled in the art would know to use electroporation, infusion, ballistic methods, or *Agrobacterium tumefaciens* mediated methods and the like for introducing the nucleotide sequences of the present invention or modifications thereof into a plant cell.

The term "variant or modified", with reference to nucleotide sequences, is intended to refer to nucleotide sequences which encode the same toxins or which encode equivalent toxins having similar insecticidal activity, the term "equivalent toxin" referring to a toxin exhibiting the same, essentially the same, or improved biological activity against the target pests as the claimed native or referent toxin. A variant or modified nucleotide sequence intended for use in dicot plants would encode substantially the same amino acid sequence as the native coding sequence, i.e., the coding sequence found in nature, but would comprise a total combined GC composition from about 49 to about 58 percent, and would utilize substantially the codon preference and codon usage frequency determined by compiling such preference and usage frequencies from a consortium of coding sequences derived from one or more individual dicot plant species intended to be transformed with the variant or modified nucleotide sequence. A variant or modified nucleotide sequence intended for use in a monocot plant would also encode substantially the same amino acid sequence as the native coding sequence, but would comprise a total combined GC composition from about 52 to about 59 percent, and would also utilize substantially the codon preference and codon usage frequency determined by compiling such preference and usage frequencies from a consortium of coding sequences derived form one or more individual monocot plant species intended to be transformed with the variant or modified nucleotide sequence. Codon usage frequency is intended to refer to the number of times, on average, that a particular codon is used in a coding sequence. For a particular plant species, a codon that is intended to cause the incorporation of a particular amino acid into a nascent amino acid sequence will be utilized on average with some relative fixed frequency. For amino acids that utilize only two codons, this frequency is generally about fifty-fifty, i.e., each codon being used about half the time, unless one of the codons utilizes a substantially greater number of purines or pyrimidines that are not typically representative of the GC content of the particular plant species. For *Bacillus* species, for example, coding sequences generally are from about 60 to about 70 percent AT. Codon usage in *Bacillus* species is biased toward the use of codons that are enriched for the presence of A or T in a particular codon. Therefore, codons that primarily utilize G or C are used in a native and/or naturally occurring *Bacillus* coding sequence with much less frequency than codons that contain A's or T's. Therefore, when producing a variant or modified nucleotide sequence intended for use in a particular plant, monocot or dicot, it is important to ensure that appropriate attention is given to the use of codons that are not particularly enriched with A's and T's where possible, and to avoid the incorporation of suspected polyadenylation sequences (see for example, U.S. Pat. No. 5,500,365).

As used herein, "synthetic coding sequences" or "non-naturally occurring coding sequences" encoding the *B. thuringiensis* TIC900 proteins or homologs or derivatives thereof as insecticidal toxins of the present invention are those prepared in a manner involving any sort of genetic isolation or manipulation. This includes isolation of the coding sequence from its naturally occurring state, manipulation of the coding sequence as by modification of the nucleotide coding sequence (as described herein), chemical synthesis of all or part of a coding sequence using phosphoramidite chemistry and the like, or site-specific mutagenesis (as described herein), truncation of the coding sequence or any other manipulative or isolative method so that the amino acid sequence encoded by the non-naturally occurring coding sequence encodes substantially the same insecticidal protein as the native coding sequence and furthermore exhibits substantially the same or an improved level of insecticidal bioactivity as the native insecticidal toxin protein.

As used herein, the phrase "percentage of sequence identity" is determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. A first nucleotide sequence when observed in the 5' to 3' direction is said to be a "complement" of a second or reference nucleotide sequence observed in the 3' to 5' direction if the first nucleotide sequence exhibits complete complementarity with the second or reference sequence. As used herein, nucleic acid sequence molecules are said to exhibit "complete complementarity" when every nucleotide of one of the sequences read 5' to 3' is complementary to every nucleotide of the other sequence when read 3' to 5'. A nucleotide sequence that is identical at every position when read 5' to 3' in comparison to a reference nucleotide sequence read 5' to 3' is said to be identical to the reference sequence and vice-versa. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

As used herein, "substantial homology", with reference to nucleic acid sequences, refers to nucleotide sequences that hybridize under stringent conditions to the TIC900 coding sequence as set forth in SEQ ID NO:3 or complements thereof. Sequences that hybridize under stringent conditions to SEQ ID NO:3 or complements thereof, in particular from the nucleotide sequence from about nucleotide position 1 to about nucleotide position 1806, and more particularly from about nucleotide position 121 to about nucleotide position 1806, contain one or more linear sequences that are sufficiently identical to one or more linear sequences of SEQ ID NO:3 such that an alignment is able to take place and the two sequences are then able, under stringent conditions, to form hydrogen bonds with corresponding bases on the opposite strand to form a duplex molecule that is sufficiently stable under the stringent conditions for a long enough period of time to be detectable using methods well known in the art. Such homologous sequences are from about 67% identical, to about 70% identical, to about 80% identical, to about 85% identical, to about 90% identical, to about 95% identical, to about 99% identical or greater to the referent nucleotide sequence as set forth in SEQ ID NO:3 or the complement thereof. In addition, nucleotide sequences that encode insecticidal proteins isolatable from *Bacillus thuringiensis* strains and the like, that hybridize under stringent conditions to SEQ ID NO:3 are also envisioned to exhibit substantial homology with referent nucleotide sequences that hybridize under stringent conditions to the tic900 coding sequence as set forth in SEQ ID NO:3 or complements thereof. Such nucleotide sequences are referred to herein as homologs of SEQ ID NO:3 and the like and comprise SEQ ID NO:5, SEQ ID NO:7, SEQ ID NO:9, SEQ ID NO:29, SEQ ID NO:11, SEQ ID NO:13, SEQ ID NO:15, SEQ ID NO:17, and SEQ ID NO:19, and related sequences and homologues thereof.

With reference to polypeptide sequences, the term "substantial homology" refers to polypeptides that are about 70% homologous to, about 80% homologous to, about 86% homologous to, about 90% homologous to, about 95% homologous to, about 99% homologous to, a referent polypeptide sequence. More specifically, the inventors envision substantial homologues to be about 81, 82, 83, 84, 85, 86, 87, 88, 89, 90, 91, 92, 93, 94, 95, 96, 97, 98, and 99 percent homologous to the referent polypeptide sequence as set forth herein in SEQ ID NO:4, SEQ ID NO:6, SEQ ID NO:8, SEQ ID NO:10, SEQ ID NO:30, SEQ ID NO:12, SEQ ID NO:14, SEQ ID NO:16, SEQ ID NO:18, and SEQ ID NO:20.

With reference to the proteins of the instant application, the terms "variant amino acid sequence", or "amino acid sequence variant", or "modified amino acid sequence variant" are intended to refer to amino acid sequences that are substantially equivalent to the amino acid sequences of the present invention. For example, a protein produced by the introduction of a restriction site for convenience of molecular manipulations into a coding sequence of the present invention that results in the addition or subtraction of one or more codons without otherwise (1) disrupting the native coding sequence, (2) disrupting the native open reading frame, and (3) disrupting the insecticidal biological activity of the protein, would constitute (a) a variant amino acid sequence compared to the native insecticidal toxin, (b) an amino acid sequence variant compared to the native insecticidal toxin, or (c) a modified amino acid sequence variant compared to the native insecticidal toxin. One skilled in the art would recognize that there are other types of modifications that can be made to the amino acid sequence of the present invention without disrupting the biological activity of the protein. Insertions, deletions, and substitutions are within the scope of the present disclosure to the extent that the resulting amino acid sequence variant exhibits insecticidal activity no less than that of the native insecticidal protein. Chimeras of the proteins disclosed herein, fusions of the proteins or parts of the proteins disclosed herein, and permuteins of the proteins disclosed herein are specifically contemplated.

The inventors contemplate that the protein compositions disclosed herein will find particular utility as insecticides for topical and/or systemic application to field crops, grasses, fruits and vegetables, and ornamental plants. In a preferred embodiment, the bioinsecticide composition comprises an oil flowable suspension of bacterial cells that expresses a novel insecticidal protein disclosed herein. Preferably the cells are *B. thuringiensis* EG5438 or SIC9002 cells, however, any such bacterial host cell expressing the novel nucleic acid segments disclosed herein and producing a crystal protein is contemplated to be useful, such as *B. megaterium, B. subtilis, E. coli*, or *Pseudomonas* spp.

In another embodiment, the bioinsecticide composition comprises a water dispersible granule. This granule comprises bacterial cells that express a novel insecticidal protein disclosed herein. Preferred bacterial cells are *B. thuringiensis* EG5438 or SIC9002 cells, however, bacteria such as *B. megaterium, B. subtilis, E. coli*, or *Pseudomonas* spp. cells transformed with a DNA segment disclosed herein and expressing the insecticidal protein are also contemplated to be useful.

In a third embodiment, the bioinsecticide composition comprises a wettable powder, dust, pellet, or collodial concentrate. This powder comprises bacterial cells that express a novel insecticidal protein disclosed herein. Preferred bacterial cells are *B. thuringiensis* EG5438 or SIC9002 cells, however, bacteria such as *B. megaterium, B. subtilis, E. coli*, or *Pseudomonas* spp. cells transformed with a DNA segment disclosed herein and expressing the insecticidal protein are also contemplated to be useful. Such dry forms of the insecticidal compositions may be formulated to dissolve immediately upon wetting, or alternatively, dissolve in a controlled-release, sustained-release, or other time-dependent manner.

In a fourth embodiment, the bio-insecticide composition comprises an aqueous suspension of bacterial cells such as those described above that express the insecticidal protein. Such aqueous suspensions may be provided as a concentrated stock solution which is diluted prior to application, or alternatively, as a diluted solution ready-to-apply.

For these methods involving application of bacterial cells, the cellular host containing the insecticidal protein gene(s) may be grown in any convenient nutrient medium, where the DNA construct provides a selective advantage, providing for a selective medium so that substantially all or all of the cells retain the *B. thuringiensis* gene. These cells may then be harvested in accordance with conventional ways. Alternatively, the cells can be treated prior to harvesting.

When the insecticidal compositions comprise intact *B. thuringiensis* cells expressing the protein of interest, such bacteria may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, suspensions, emulsifiable concentrates, or the like. The ingredients may include rheological agents, surfactants, emulsifiers, dispersants, or polymers.

Alternatively, the novel TIC900 or TIC900-derived or related protein or homolog thereof may be prepared by native or recombinant bacterial expression systems in vitro and isolated for subsequent field application. Such protein may be either in crude cell lysates, suspensions, colloids, etc., or alternatively may be purified, refined, buffered, and/or further processed, before formulating in an active biocidal formulation. Likewise, under certain circumstances, it may be desirable to isolate the protein in some crystalline form and/or as spores from bacterial cultures expressing the insecticidal protein and apply solutions, suspensions, or collodial preparations of such crystals and/or spores as the active bioinsecticidal composition.

Regardless of the method of application, the amount of the active component(s) are applied at an insecticidally-effective amount, which will vary depending on such factors as, for example, the specific lepidopteran insects to be controlled, the specific plant or crop to be treated, the environmental conditions, and the method, rate, and quantity of application of the insecticidally-active composition.

The insecticide compositions described may be made by formulating the bacterial cell, crystal and/or spore suspension, or isolated protein component with the desired agriculturally acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, e.g., inert components, dispersants, surfactants, tackifiers, binders, etc. that are ordinarily used in insecticide formulation technology; these are well known to those skilled in insecticide formulation. The formulations may be mixed with one or more solid or liquid adjuvants and prepared by various means, e.g., by homogeneously mixing, blending and/or grinding the insecticidal composition with suitable adjuvants using conventional formulation techniques.

The insecticidal compositions of this invention are applied to the environment of the target lepidopteran insect, typically onto the foliage of the plant or crop to be protected, by conventional methods, preferably by spraying. The strength and duration of insecticidal application will be set with regard to conditions specific to the particular pest(s), crop(s) to be treated and particular environmental conditions. The proportional ratio of active ingredient to carrier will naturally depend on the chemical nature, solubility, and stability of the insecticidal composition, as well as the particular formulation contemplated.

Other application techniques, e.g., dusting, sprinkling, soaking, soil injection, seed coating, seedling coating, spraying, aerating, misting, atomizing, and the like, are also feasible and may be required under certain circumstances such as e.g., insects that cause root or stalk infestation, or for application to delicate vegetation or ornamental plants. These application procedures are also well known to those of skill in the art.

The insecticidal composition of the invention may be employed in the method of the invention singly or in combination with other compounds, including and not limited to other pesticides. The method of the invention may also be used in conjunction with other treatments such as surfactants, detergents, polymers or time-release formulations. The insecticidal compositions of the present invention may be formulated for either systemic or topical use.

The concentration of insecticidal composition that is used for environmental, systemic, or foliar application will vary widely depending upon the nature of the particular formulation, means of application, environmental conditions, and degree of biocidal activity. Typically, the bio-insecticidal composition will be present in the applied formulation at a concentration of at least about 1% by weight and may be up to and including about 99% by weight. Dry formulations of the compositions may be from about 1% to about 99% or more by weight of the composition, while liquid formulations may generally comprise from about 1% to about 99% or more of the active ingredient by weight. Formulations that comprise intact bacterial cells will generally contain from about $10^4$ to about $10^{12}$ cells/mg.

The insecticidal formulation may be administered to a particular plant or target area in one or more applications as needed, with a typical field application rate per hectare ranging on the order of from about 50 g to about 500 g of active ingredient, or of from about 500 g to about 1000 g, or of from about 1000 g to about 5000 g or more of active ingredient.

Modification and changes may be made in the structure of the peptides of the present invention and DNA segments which encode them and still obtain a functional molecule that encodes a protein or peptide with desirable characteristics. In particular embodiments of the invention, amino acid sequence variants of the proteins of the present invention are contemplated to be useful for increasing the insecticidal activity of the protein, and consequently increasing the insecticidal activity and/or expression of the recombinant transgene in a plant cell. The amino acid changes may be achieved by changing the codons of the DNA sequence.

Proteins that are substantially equivalent to the proteins of the instant application are intended to be biologically functionally equivalent. As used herein, the phrase "biological functional equivalents", with respect to the insecticidal proteins of the present invention, are peptides, polypeptides and proteins that contain a sequence or moiety exhibiting sequence similarity to the novel peptides of the present invention, such as a TIC900 or related protein or insecticidal fragment thereof, and that exhibit the same or similar functional properties as that of the polypeptides disclosed herein, including insecticidal activity. Biological equivalents also include peptides, polypeptides and proteins that react with, i.e., specifically bind to antibodies raised against epitopes present on or within TIC900 and related proteins and that exhibit the same or similar binding or reactive activity, including both monoclonal and polyclonal antibodies.

It is also contemplated that the proteins of the present invention could be useful for protecting dicot plants from insect infestation. Such infestations could be the result of lepidopteran, coleopteran, dipteran, or even infestation by mites, mealworms, grubs, or a wide variety of insects that injure the plant by piercing the plant tissues and extracting the nutrients intended for plant growth and development. Modifications to the primary amino acid sequence of the proteins of the present invention could result in a protein that exhibits a host range different from that of the native protein.

The proteins of the present invention, because of their localization into the extracellular space when expressed by *Bacillus* strains, may be useful for targeting other proteins for localization into the extracellular space. For example, the skilled artisan would know to link a first protein that is not normally secreted into the extracellular space to a second protein that is normally secreted into the extracellular space in order to achieve the localization of the first protein into the extracellular space. The proteins of the present invention could be fused by any number of means well known in the art to one or more insecticidal toxins such as crystalline delta-endotoxins to form a chimeric protein that is targeted for secretion into the extracellular space surrounding a particular host cell. It is even envisioned that the secretion event itself could lead to the separation of the two protein parts such that two separate and distinct insecticidal proteins are released into the extracellular space surrounding a particular host cell. The two proteins could either (1) both be toxic to the same insect species but effectuate their insecticidal activity using different modes of action, or (2) each be toxic to different insect species. It is conceivable that any number of insecticidal proteins could be linked end to end to the proteins of the present invention to form multimeric chimeras that are targeted to the extracellular space surrounding a particular host cell. It is preferable, in situations in which it is contemplated that other Bt insecticidal proteins are used, that the insecticidal proteins fused to the proteins of the present invention be less than full length Cry1 proteins, more preferably merely core insecticidal toxin fragments of Cry1 proteins, Cry2A proteins, Cry3 proteins, Cry9 proteins, etc. Such "other" proteins conceivably could be green fluorescent and related proteins and variants, kinases and phosphatases for modulating cell signaling processes, nucleases, lipases, herbicide tolerance proteins expressed from genes such as gox, various epsps homologues, bar and homologues and the like, PhnO, NptII, Aad, and the like. All of these proteins could be used as selectable markers as well, particularly when linked to a gene encoding one or more of the proteins of the present invention, to track the presence of the genes encoding one or more of the proteins of the present invention in a plant or other host cell.

The proteins of the present invention could be targeted for import into a subcellular organelle. For example, a first nucleotide sequence encoding a chloroplast or plastid targeting sequence could be operably linked or fused to a second nucleotide sequence encoding an insecticidal protein of the present invention to produce a chimeric precursor protein that is targeted for insertion into the chloroplast or plastid within a plant cell. Expression of such chimeric proteins would result in the import of the proteins of the present invention into the plant chloroplast or plastid, resulting in the localization of the insecticidal toxin or insecticidal fragment thereof into the chloroplast or plastid. Additionally, a nucleotide sequence encoding one or more proteins of the present invention could be localized to the chloroplast or plastid for expression. The localization of the nucleotide sequences to the plastid or chloroplast could result in the incorporation of the nucleotide sequences into the chloroplast or plastid genome, or could result in the presence of an autonomously replicating nucleic acid sequence encoding the protein of the present invention. In either sense, the proteins of the present invention would be localized to the chloroplast or plastid. As used herein therefore, the phrase "chloroplast or plastid localized" refers to a biological molecule, either polynucleotide or polypeptide, which is positioned within the chloroplast or plastid such that the molecule is isolated from the cellular cytoplasmic milieu, and functions within the chloroplast or plastid cytoplasm to provide the beneficial insecticidal effects claimed in the instant invention. Localization of a biological molecule to the chloroplast or plastid can occur, with reference to polynucleotides, by artificial mechanical means such as electroporation, mechanical microinjection, or by polynucleotide coated microprojectile bombardment, or with reference to polypeptides, by secretory or import means wherein a natural, synthetic, or heterologous plastid or chloroplast targeting peptide sequence is used which functions to target, insert, assist, or localize a linked polypeptide into a chloroplast or plastid. In any event, localization of one or more insecticidal proteins to the chloroplast or plastid necessarily implies that the resulting plant containing cells which contain plastids that contain such insecticidal protein or proteins localized within must also exhibit normal morphological characteristics. It is not known which, if any, insecticidal protein when localized to the chloroplast or plastid, will result in the achievement of a recombinant plant exhibiting normal morphological characteristics exemplified without limitation by an absence of chlorosis, an absence of stunted or stunting of the plant physiology including but not limited to thicker than average stalks, shortened stalks or internodes, inappropriate flowering, infertility, decreased yield, etc.

As used herein, the phrase "operatively linked" or "operably linked" refers to nucleic acid coding segments connected in frame so that the properties of one influence the expression of the other. These phrases and groups of words can also be used to refer to amino acid sequences which exhibit some function when linked to another amino acid sequence, for example, a signal peptide when linked to a protein of interest is referred to as being operably linked to the protein of interest for the purpose of targeting the protein of interest to the secretory apparatus of the host cell in which the protein is produced.

For the purposes of the present invention, the word "gene" refers to a nucleotide sequence that contains an open reading frame encoding a TIC900 protein, or an insecticidal fragment thereof, or an amino acid sequence variant thereof, or a related protein homolog or insecticidal fragment thereof or amino acid sequence variant thereof that is at least operably linked to a promoter sequence and a transcription termination sequence, wherein the promoter and transcription termination sequences are functional in the host cell in which the protein is produced. As used herein, "structural gene" refers to a gene that is expressed to produce a polypeptide. A structural gene of the present invention can contain, in addition to promoter and transcription termination sequences, five prime non-translated sequences, intronic sequences, and enhancer elements that function in plants in particular, and preferably those that are derived from monocotyledonous plants such as maize plants or from dicotyledonous plants such tobacco plants or cruciferous vegetable plants that, when linked together in proper sequence with one or more coding sequences of the present invention result in improved levels of expression in particular plant tissues, and preferably result in enhanced expression in leaves and stem tissues of those plants.

Nucleotide sequence information provided by the present invention allows for the preparation of relatively short DNA sequences, referred to herein as probes or primers, having the ability to specifically hybridize to sequences of the selected polynucleotides disclosed herein. Such nucleic acid probes of an appropriate length are prepared based on a consideration of selected polypeptide sequences encoding the insecticidal polypeptides of the present invention, e.g., a sequence such as that shown in all or a probe specific part of SEQ ID NO:3, all or a probe specific part of SEQ ID NO:5, all or a probe specific part of SEQ ID NO:7, all or a probe specific part of SEQ ID NO:9, all or a probe specific part of SEQ ID NO:29, all or a probe specific part of SEQ ID NO:11, all or a probe specific part of SEQ ID NO:13, all or a probe specific part of SEQ ID NO:15, all or a probe specific part of SEQ ID NO:17, all or a probe specific part of SEQ ID NO:19, and the like. Reference to the phrase "all or a probe specific part of is" intended to refer to a nucleotide sequence probe comprising at least from about 15 to about 50, more or less, contiguous nucleotides selected from the group of nucleotides set forth in a particular referent sequence such as SEQ ID NO:3, SEQ ID NO:5, SEQ ID NO:7, SEQ ID NO:9, SEQ ID NO:29, SEQ ID NO:11, SEQ ID NO:13, SEQ ID NO:15, SEQ ID NO:17, and SEQ ID NO:19. The ability of such nucleic acid probes to specifically hybridize to a nucleotide sequence encoding an insecticidal polypeptide sequence lends to them particular utility in a variety of embodiments. Most importantly, the probes may be used in a variety of assays for detecting the presence of complementary sequences in a given biological sample. By reference to the term "biological sample", it is intended that any sample that contains a referent nucleotide sequence that can be detected by a probe sequence as set forth herein is a sample that contains a biological molecule selected from the group consisting of contiguous nucleotide sequences set forth herein, and therefore the sample is thus referred to as a "biological sample".

In certain embodiments, it is advantageous to use oligonucleotide primers. The sequence of such primers is designed using a polynucleotide of the present invention for use in detecting, amplifying or modifying a defined segment of an insecticidal protein coding sequence from *B. thuringiensis* or from *Bacillus sphaericus* and the like using thermal amplification technology. Segments of nucleotide sequences related to the polynucleotides encoding the insecticidal polypeptides of the present invention may also be isolated and characterized using thermal amplification technology and such primers.

To provide certain of the advantages in accordance with the present invention, a preferred nucleic acid sequence employed for hybridization studies or assays or as a primer includes sequences that are complementary to at least a 14 to 30 or more contiguous stretch of nucleotides of a polynucleotide sequence encoding all or a part of an insecticidal protein of the present invention, such as that shown in SEQ ID NO:2, SEQ ID NO:3, SEQ ID NO:5, SEQ ID NO:7, SEQ ID NO:9, SEQ ID NO:29, SEQ ID NO:11, SEQ ID NO:13, SEQ ID NO:15, SEQ ID NO:17, SEQ ID NO:19, SEQ ID NO:21, and SEQ ID NO:22.

A primer or probe size of at least 14 nucleotides in length helps to ensure that the fragment will be of sufficient length to form a duplex molecule that is both stable and selective. Molecules having complementary sequences over segments greater than 14 bases in length are generally preferred. In order to increase stability and selectivity of the hybrid, and thereby improve the quality and degree of specific hybrid molecules obtained, one will generally prefer to design nucleic acid molecules having tic900-complementary sequences and the like of 14 to 20 nucleotides, or even longer where desired. Such fragments may be readily prepared by, for example, directly synthesizing the fragment by chemical means, by application of nucleic acid reproduction technology, or by excising selected DNA fragments from recombinant sequences localized in plasmids or other vectors containing appropriate inserts and suitable restriction sites.

The present invention also contemplates an expression vector comprising a polynucleotide of the present invention. Thus, in one embodiment an expression vector is an isolated and purified DNA molecule comprising a promoter operatively linked to a coding region that encodes a polypeptide of the present invention, which coding region is operatively linked to a transcription-terminating region, whereby the promoter drives the transcription of the coding region. The coding region may include a segment encoding a *B. thuringiensis* insecticidal toxin of the present invention and a segment encoding a chloroplast or plastid targeting peptide. The DNA molecule comprising the expression vector may also contain a functional intron sequence positioned either upstream of the coding sequence or even within the coding sequence, and may also contain a five prime (5') non-translated leader sequence (i.e., a UTR or 5'-UTR) positioned between the promoter and the point of translational initiation.

As used herein and with reference to promoter elements, the terms "operatively linked" or "operably linked" are intended to indicate that a nucleotide sequence that contains a promoter, i.e. a genetic element that functions in a particular host cell to drive the initiation of transcription, is connected to a coding region in such a way that the transcription of that coding region is controlled and substantially regulated by that promoter. Means for operatively linking a promoter to a coding region are well known in the art. Promoters that function in bacteria are well known in the art. Exemplary and preferred promoters for the *B. thuringiensis* crystal proteins include the sigA, sigE, and sigK gene promoters. Alternatively, native, modified, heterologous, or recombinant promoters derived from *Bacillus thuringiensis* or other *Bacillus* species can be used for achieving expression of the proteins of the present invention in a *Bacillus* species strain.

Where a nucleotide sequence encoding all or an insecticidal part of a protein of the present invention is to be used to transform a plant, a promoter is selected that has the ability to drive expression of the coding sequence in that particular species of a plant. Promoters that function in different plant species are also well known in the art. Promoters useful for expression of polypeptides in plants are those that are inducible, viral, synthetic, or constitutive as described in Odell et al. (Nature 313:810-812, 1985), and/or promoters that are temporally regulated, spatially regulated, and spatio-temporally regulated. Preferred promoters include the enhanced CaMV35S promoters, the GBOX10 promoter, the FMV35S promoter, the rice Actin promoter, and variants and chimeras thereof. For optimum control of ECB species by expression of the proteins of the present invention in plants, for example, it is preferable to achieve the highest levels of expression of these proteins within the leaves and stems of maize plants. Substantial temporal or spatial regulation refers to the expression of a gene within a plant or plant tissue from a plant operable promoter. With reference to temporal regulation, a promoter may be regulated for expression only during specific times during plant cell or tissue or even whole plant growth and development. A promoter that is actively expressing one or more genes only during seed germination would be one example of temporal regulation. Other examples could include promoters that are actively expressing one or more genes only during times when the plant, plant cell or plant tissue is exposed to certain light intensities or during total darkness. Substantial temporal regulation refers to a promoter which is actively expressed at a certain time but which may or may not be completely suppressed at other times, such that expression may still be detected by monitoring for the presence of some indicator such as an enzyme produced from a coding sequence linked to such a promoter, or as measured by the increase or decrease in some gene products such as an mRNA produced at various times throughout plant growth, differentiation, and development and/or in response to various environmental stimuli. Substantial spatial regulation refers to the expression of a gene linked to a promoter from which expression proceeds only during growth and development of certain cells or tissues within a plant. For example, a tapetal promoter is one that is substantially spatially expressed during flower growth and development. Similarly, a leaf specific or leaf enhanced promoter would only be expected to be substantially spatially expressed from within leaf cells or leaf tissues. Substantially spatially regulated also refers to the level of expression from a particular tissue specific promoter in that particular tissue and as related to levels of expression from that or a similar promoter in other tissues, wherein expression may also be detected in tissues other than the particular tissue in which the promoter expression is preferred, but at significantly lower expression levels as measured by the production of an enzyme produced from a coding sequence linked to the promoter or by the appearance of some detectable gene product. Promoters can also be both substantially temporally and substantially spatially regulated together and simultaneously in a coordinately regulated manner. Other promoters specifically intended to be within the scope of the present invention include but are not limited to the ubiquitin promoter, the sugarcane bacilliform DNA virus promoter, the ribulose bis-phosphate carboxylase large subunit promoter, among others.

Preferred intron sequences for achieving optimum expression of non-naturally occurring nucleotide sequences in monocotyledonous plants may also be included in the DNA expression construct. Such an intron is typically placed near the 5' of the mRNA within or immediately downstream of an untranslated sequence. The intron could be obtained from, but not limited to, a set of introns consisting of the maize Heat Shock Protein (HSP) 70 intron (U.S. Pat. No. 5,424,412; 1995), the rice Act1 intron (McElroy et al., Plant Cell 2:163-171, 1990), the Adh intron 1 (Callis et al., Genes & Develop. 1:1183-1200, 1987), or the sucrose synthase intron (Vasil et al., Plant Phys. 91:1575-1579, 1989).

Another element that functions to regulate or to modulate gene expression is the DNA sequence between the transcription initiation site and the start of the coding sequence, termed the untranslated leader sequence (UTL). Compilations of leader sequences have been made to predict optimum or suboptimum sequences and generate "consensus" and preferred leader sequences (Joshi, Nucl. Acids Res. 15:9627-9640, 1987). Preferred leader sequences are contemplated to include those that comprise sequences predicted to direct optimum expression of the linked structural gene, i.e. to include a preferred consensus leader sequence that increases or maintains mRNA stability and prevents inappropriate initiation of translation. The choice of such sequences will be known to those of skill in the art in light of the present disclosure. Sequences that from genes that are highly expressed in plants, and in particular in maize will be most preferred. One particularly useful leader is the petunia HSP70 leader.

Transcription enhancers or duplications of enhancers could be used to increase expression. These enhancers often are found 5' to the start of transcription in a promoter that functions in eukaryotic cells, but can often be inserted in the forward or reverse orientation 5' or 3' to the coding sequence. Examples of enhancers include elements from the CaMV 35S promoter, octopine synthase genes (Ellis et al., EMBO Journal 6:11-16, 1987), the rice actin gene, and promoter from non-plant eukaryotes (e.g., yeast; Ma et al., Nature 334:631-633, 1988).

RNA polymerase transcribes a nuclear genome DNA coding sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of nuclear transcribed messenger RNA (mRNA). For coding sequences introduced into a chloroplast or plastid, or into a chloroplast or plastid genome, mRNA transcription termination is similar to methods well known in the bacterial gene expression art. For example, either in a polycistronic or a monocistronic sequence, transcription can be terminated by stem and loop structures or structures similar to bacterial rho dependent sequences.

Expression constructs will typically include a coding sequence exemplified in the present invention or a derivative thereof along with a 3' end DNA sequence that functions as a signal to terminate transcription and, in constructs intended for expression from the plant nuclear genome, allow for the 3' end polyadenylation of the resultant RNA transcript. The most preferred 3' elements are contemplated to be those from the nopaline synthase gene of *A. tumefaciens* (nos 3' end), the terminator for the T7 transcript from the octopine synthase gene of *A. tumefaciens*, and the pea RUBISCO synthase E9 gene (E9 3') 3' non-translated transcription termination and polyadenylation sequence. These and other 3' end regulatory sequences are well known in the art.

Preferred plant transformation vectors include those derived from a Ti plasmid of *Agrobacterium tumefaciens*, as well as those disclosed, e.g., by Herrera-Estrella (Nature 303: 209-213, 1983), Bevan (Nature 304:184-187, 1983), Klee (Bio/Technol. 3:637-642, 1985).

The present invention discloses isolated and purified nucleotide sequences encoding insecticidal proteins derived from *Bacillus* species, and particularly from *Bacillus thuringiensis* species. In particular, the *B. thuringiensis* strains EG5438, EG3879, EG4332, EG4971, EG4090, EG4293, EG4611, EG5526, EG5023 and EG4092 are each shown herein to produce one or more soluble insecticidal proteins that are localized to culture supernatants (see Table 1).

TABLE 1

TIC900 Related Proteins and Source *B. thuringiensis* Strains

| Source Bt Strain | TIC900 Related Protein |
|---|---|
| EG3879, EG5526 | TIC402, (TIC964)* |
| EG4332 | TIC403 |
| EG4971 | TIC404 |
| EG4611 | TIC434 |
| EG4090 | TIC961 |
| EG4293 | TIC962 |
| EG4611 | TIC963 |
| EG5438# | TIC900 |
| EG5023 | TIC965 |
| EG4092 | TIC966 |

*the amino acid sequence of TIC964, obtained from strain EG5526, was deduced after nucleotide sequence analysis of a gene exhibiting homology to tic900, and was determined to be identical to tic402 obtained from strain EG3879.
signifies that this strain has been deposited under conditions that assure access to the culture to authorized parties during the pendency of this patent application or patents issued therefrom.

The *B. thuringiensis* strains and other bacterial strains described herein may be cultured using conventional growth media and standard fermentation techniques. The *B. thuringiensis* strains harboring one or more tic900 or related genes may be fermented as described herein until the cultured *B. thuringiensis* cells reach the stage of their growth cycle when the TIC900 and/or related proteins are produced.

Subject cultures have been deposited under conditions that assure that access to the culture will be available to authorized parties during the pendency of this patent application or patents issued. However, it should be understood that the availability of a deposit does not constitute a license to practice the subject invention in derogation of patent rights granted by governmental action.

TIC900 and related proteins of the present invention are produced as shown herein and secreted into the growth media during the vegetative phase of growth. Fermentations using the strains of the present invention may be continued through the sporulation stage when crystal proteins, if any, are formed along with the spores. The spores and cell debris can be separated from the supernatant by centrifugation, and the spent culture medium can be used to isolate the insecticidal proteins of the present invention. The inventors herein illustrate the method of ammonium sulfate precipitation as one means for concentrating and collecting all or most of the proteins present in the spent and clarified culture medium. However, one skilled in the art will recognize that there are a number of other means available for purifying and isolating the proteins of the present invention. Gel filtration and size exclusion chromatography are two readily available means for extracting proteins directly from the spent media. Spent media can also be desalted and the filtrate used to extract protein using ion exchange columns. Also, affinity columns, containing antibodies that bind specifically to TIC900 or related proteins can be used to purify the proteins of the present invention directly from the media.

The amino acid sequences of the present invention have been compared to the amino acid sequences present in commercially available protein sequence databases, and no significant homologies or similarities have been identified.

Based on this analysis, the TIC900 protein and related sequences appear to be unique and form the basis for the establishment of a new and separate class of *Bacillus* insecticidal proteins because the proteins of the present invention do not exhibit any relationship to other known insecticidal proteins.

Modification and changes may be made in the structure of the peptides of the present invention and DNA segments that encode them and still obtain a functional molecule that encodes a protein or peptide with desirable characteristics. The biologically functional equivalent peptides, polypeptides, and proteins contemplated herein should possess from about 70% or greater sequence similarity, or from about 80% or greater sequence similarity, or from about 90% or greater sequence similarity, to the sequence of, or corresponding moiety within, the fundamental TIC900 amino acid sequence as set forth in SEQ ID NO:4, or the corresponding moiety within the amino acid sequences as set forth in SEQ ID NO:6, SEQ ID NO:8, SEQ ID NO:10, SEQ ID NO:30, SEQ ID NO:12, SEQ ID NO:14, SEQ ID NO:16, SEQ ID NO:18, and SEQ ID NO:20 and related sequences.

According to the present invention reference to the tic900 gene and encoded protein toxin, includes not only the full length sequences disclosed herein but also fragments of these sequences, natural variants, mutants, and recombinant or genetically engineered derivatives of the tic900 gene comprising SEQ ID NO:3. Such encoded proteins should retain essentially the same as or greater characteristic insecticidal properties than those of the TIC900 protein comprising SEQ ID NO:4. The proteins useful in the present invention may also include fusion proteins that retain the characteristic insecticidal properties essentially the same as or greater than those of the TIC900 protein. In some instances, the fusion protein may contain, in addition to the characteristic insecticidal properties of the proteins specifically exemplified herein, another insecticidal activity contributed by the amino acid sequence of the fusion partner. Alternatively, crystallographic analysis of the TIC900 protein or insecticidal variants thereof may provide a means for determining whether the protein would be a candidate for the construction of a permutein that exhibits the same or preferably greater insecticidal activity than the native TIC900 or related protein, and which preferably exhibits improved characteristics related to expression in a preferred host cell such as a plant cell.

It should be apparent to a person skilled in the art that nucleotide sequences encoding lepidopteran inhibitory toxins can be identified and obtained through several means. The specific sequences exemplified herein may be obtained from the isolates deposited at a culture depository as described above. These sequences, or portions or variants thereof, may also be constructed synthetically, for example, by use of a nucleotide sequence synthesizer. Variations of coding sequences may be readily constructed using standard techniques for making point mutations. Also, fragments of these sequences can be made using commercially available exonucleases or endonucleases according to standard procedures. For example, enzymes such as Bal31 or site-directed mutagenesis may be used to systematically excise nucleotides from the ends of such sequences as exemplified herein or from within the protein coding sequence. Also, nucleotide sequences that encode insecticidally active protein fragments may be obtained using a variety of restriction enzymes, endonucleases, thermal amplification methods, and the like. Proteases such as proteinase K, trypsin, chymotrypsin, pepsin, and the like may be used to directly obtain active fragments of these toxins.

Other toxins and nucleotide sequences encoding such toxins related to the toxins and coding sequences of the present invention can be derived from DNA obtained from *B. thuringiensis, B. laterosporous, B. sphaericus*, and related *Bacillus* species isolates using the teachings provided in the art in combination with the nucleotide sequences disclosed herein. Such toxins and nucleotides sequences that are related to the toxins and coding sequences of the present invention are deemed herein to be equivalent to the toxins and nucleotide sequences of the present invention. By "equivalent" it is meant that a protein exhibits the characteristics of the TIC900 protein, including but not limited to similar insecticidal inhibitory bioactivity, host range of insecticidal bioactivity, exhibits similar antigenic epitopes that cross react with antibodies raised against TIC900 and related proteins, exhibit a similar size relative to TIC900 and related proteins, exhibit similar expression profiles and characteristics, exhibit a propensity for seclusion to the extracellular environment when expressed in *Bacillus thuringiensis* or related bacterial species, and the like. The phrase "exhibit a propensity for seclusion to the extracellular environment" is intended to include TIC900 and related proteins including but not limited to TIC402, TIC403, TIC404, TIC434, TIC961, TIC962, TIC963, TIC965 and TIC966 that are produced by the bacterium or host cell as a precursor protein that contains an amino acid sequence linked to the insecticidal protein that functions to target the insecticidal protein to a bacterial or host cell secretory apparatus and which, upon contact with the secretory apparatus, is proteolytically cleaved by a signal peptidase, releasing the mature or insecticidal protein into the extracellular environment in the case of a gram positive microbe, at least into the periplasm in the case of a gram negative microbe, and into the endoplasmic reticulum or secretory vesicle or into a subcellular organelle such as a mitochondria or chloroplast or plastic in the case of a fungal or plant or other eukaryotic host cell.

There are a number of methods for identifying the presence of and obtaining equivalent insecticidal toxins related to the peptides disclosed herein. For example, antibodies to the insecticidal toxins disclosed and claimed herein can be used to identify and isolate other toxins from a mixture of proteins. Specifically, antibodies may be raised to the portions of the toxins that are most constant within the new class of proteins and most distinct from other *B. thuringiensis* toxins. These antibodies can then be used to specifically identify equivalent toxins with the characteristic activity by immuno-precipitation, enzyme linked immuno-sorbent assay (ELISA), or Western blotting. Antibodies to the toxins disclosed herein, or to equivalent toxins, or fragments of these toxins, can readily be prepared using standard procedures in the art. The nucleotide sequences that encode these toxins can then be obtained from the microorganism or other various sources.

Fragments and equivalents that retain the insecticidal activity of the exemplified toxins would be within the scope of the present invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the present invention.

It is well known in the art that certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the compositions disclosed herein, or corresponding DNA sequences which encode said peptides without appreciable loss of their biological utility or activity. Such substitutions are also known in the art as conservative substitutions.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It is also understood in the art that the substitution of like amino acids can be made effectively on the basis of hydrophilicity. The greatest local average hydrophilicity of a protein, as governed by the hydrophilicity of its adjacent amino acids, correlates with a biological property of the protein (U.S. Pat. No. 4,554,101).

As outlined above, amino acid substitutions are generally therefore based on the relative similarity of the amino acid side-chain substituents, for example, their hydrophobicity, hydrophilicity, charge, size, and the like. Exemplary substitutions which take the various foregoing characteristics into consideration are well known to those of skill in the art and include: arginine and lysine; glutamate and aspartate; serine and threonine; glutamine and asparagine; and valine, leucine and isoleucine.

Peptides, polypeptides, and proteins biologically functionally equivalent to TIC900, TIC402, TIC403, TIC404, TIC434, TIC961, TIC962, TIC963, TIC965 and TIC966 include amino acid sequences containing conservative amino acid changes in the fundamental sequence shown in SEQ ID NO:4, SEQ ID NO:6, SEQ ID NO:8, SEQ ID NO:10, SEQ ID NO:30, SEQ ID NO:12, SEQ ID NO:14, SEQ ID NO:16, SEQ ID NO:18, and SEQ ID NO:20. In such amino acid sequences, one or more amino acids in the fundamental sequence is (are) substituted with another amino acid(s), the charge and polarity of which is similar to that of the native amino acid, i.e. a conservative amino acid substitution, resulting in a silent change.

Substitutes for an amino acid within the fundamental polypeptide sequence can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cyteine, cystine, tyrosine, asparagine, and glutamine; (4) neutral nonpolar (hydrophobic) amino acids such as alanine, leucine, isoleucine, valine, proline, phenylalanine, tryptophan, and methionine.

Conservative amino acid changes within the fundamental polypeptide sequences of the present invention can be made by substituting one amino acid within one of these groups with another amino acid within the same group. Biologically functional equivalents of TIC900 and related sequences can have 10 or fewer conservative amino acid changes, more preferably seven or fewer conservative amino acid changes, and most preferably five or fewer conservative amino acid changes. The encoding nucleotide sequence (gene, plasmid DNA, cDNA, or synthetic DNA) will thus have corresponding base substitutions, permitting it to encode biologically functional equivalent forms of TIC900.

Amino acid sequence variants of TIC900 and related sequences can be made by procedures well known in the art.

A further method for identifying the toxins and genes of the present invention is through the use of oligonucleotide probes. These probes are essentially nucleotide sequences that hybridize under stringent hybridization conditions to the TIC900 coding sequence or a sequence related to a TIC900 coding sequence. As is well known in the art, if a probe molecule and nucleic acid sequence molecule in a sample hybridize by forming a strong enough bond between the two molecules, it can be reasonably assumed that the two molecules exhibit substantial homology. Probe binding is detected using any number of means known in the art including but not limited to fluorescence, luminescence, isotopic, immunological, surface plasmon resonance spectroscopy, and the like. Such probe analysis provides a rapid method for identifying toxin-encoding genes of the present invention. The nucleotide segments that are used as probes according to the invention can be synthesized by use of DNA synthesizers using standard procedures or by other means known in the art. These nucleotide sequences can also be used as PCR primers to amplify nucleotide sequences of the present invention or portions thereof.

The tic900 and related nucleotide coding sequences as set forth herein in SEQ ID NO:3, SEQ ID NO:5, SEQ ID NO:7, SEQ ID NO:9, SEQ ID NO:29, SEQ ID NO:11, SEQ ID NO:13, SEQ ID NO:15, SEQ ID NO:17, and SEQ ID NO:19 may be used as hybridization probes to identify and isolate natural variants of the tic900 and related nucleotide coding sequences from other strains of B. thuringiensis or from other microorganisms. The present invention encompasses nucleotide sequences from microorganisms, where the nucleotide sequences are isolatable by hybridization with all, or part, of the Bacillus nucleotide sequence of the invention. Proteins encoded by such nucleotide sequences can be tested for insecticidal activity. The invention also encompasses the proteins encoded by the nucleotide sequences.

Antibodies to TIC900 or related proteins of the present invention may be produced using standard immunological techniques for production of polyclonal antisera and, if desired, immortalizing the antibody-producing cells of the immunized host for sources of monoclonal antibody production. Techniques for producing antibodies to any substance of interest are well known, e.g., as in Harlow and Lane (1988) and as in Goding (1986). The anti-TIC900 antibodies may be used as probes to identify B. thuringiensis strains or other microorganisms that produce variants of TIC900 or related proteins that are encoded by variations of a tic900 or related gene. The present invention encompasses proteins obtained from organisms wherein the proteins obtained cross-react with antibodies raised against one or more of the proteins of the present invention.

The antibodies produced in the present invention are also useful in immunoassays for determining the amount or presence of a TIC900 or related protein. Such assays are also useful in quality-controlled production of compositions containing TIC900 or related proteins of the present invention. In addition, the antibodies can be used to assess the efficacy of recombinant production of a TIC900 or related protein, as well as for screening expression libraries for the presence of TIC900 or related protein coding sequences. Antibodies are useful also as affinity ligands for purifying and/or isolating TIC900 and related proteins. TIC900 and related antigenic epitopes may be obtained by over expressing full or partial lengths of a sequence encoding all or part of a TIC900 or related protein in a preferred host cell.

The peptides of the present invention are primarily, though not exclusively, intended for use in plants, and in certain preferred embodiments, nucleotide sequences modified for encoding the proteins of the present invention in plants are contained within one or more plasmid vectors. Such vectors may contain a variety of regulatory and other elements intended to allow for optimal expression of the proteins of the present invention in plant cells. These additional elements may include promoters, terminators, and introns as outlined above. Any vector containing the DNA construct and any regulatory or other elements may be selected from the group consisting of a yeast artificial chromosome, bacterial artificial chromosome, a plasmid, or a cosmid, and the like. Further, the expression vectors themselves may be of a variety of forms. These forms may differ for various reasons, and will likely be comprised of varying components depending upon whether they are intended to transform a monocotyledonous plant or a dicotyledonous plant.

Vectors further envisioned to be within the scope of the present invention include those vectors capable of containing a tic900 or related nucleic acid compositions disclosed above, as well as any other DNA constructs which further comprise plant-expressible coding regions for other insecticidal proteins derived from *Bacillus* species.

The nucleotide sequence encoding the TIC900 insecticidal protein (SEQ ID NO:4) or encoding a related polypeptide sequence such as TIC402 (SEQ ID NO:6), TIC403 (SEQ ID NO:8), TIC404 (SEQ ID NO:10), TIC434 (SEQ ID NO:30), TIC961 (SEQ ID NO:12), TIC962 (SEQ ID NO:14), TIC963 (SEQ ID NO:16), TIC965 (SEQ ID NO:18) and TIC966 (SEQ ID NO:20) may be introduced into a variety of microorganism hosts without undue experimentation, using procedures well known to those skilled in the art of transforming suitable hosts under conditions which allow for stable maintenance and expression of the cloned genes (Sambrook et al., 1989, Molecular Cloning: A Laboratory Manual $2^{nd}$ Ed., Cold Spring Harbor Press, New York). Suitable hosts that allow for expression of the TIC900 protein (SEQ ID NO:4) and related sequences include *B. thuringiensis* and other *Bacillus* species such as *Bacillus subtilis* or *Bacillus megaterium*. Genetically altered or engineered microorganisms containing the tic900 gene (SEQ ID NO:3) can also contain nucleotide sequences encoding other toxin proteins present in the same microorganism; these coding sequences could concurrently produce insecticidal proteins different from the TIC900 or related proteins. In particular, it would be preferable to produce two or more different insecticidal proteins in a host cell, wherein each protein is toxic to the same insect species and each protein exhibits a mode of action different from the other(s).

Plant-colonizing or stem-colonizing microorganisms may also be employed as host cells for the production of a TIC900 or related protein. Exemplary microorganism hosts for *B. thuringiensis* toxin genes include the plant-colonizing microbe *Clavibacter xyli* as described by Turner et al. (1993; Endophytes: an alternative genome for crop improvement; International crop science I. International Crop Science Congress, Ames, Iowa, USA, 14-22 Jul. 1992, pp. 555-560).

The toxin-encoding nucleotide sequences obtainable from the isolates of the present invention can be introduced into a wide variety of microbial or plant hosts. Expression of the toxin gene results, directly or indirectly, in the intracellular production and maintenance of the pesticide. With suitable microbial hosts, e.g., *Pseudomonas*, the microbes can be applied to the situs of the pest, where they will proliferate and be ingested by the pest. The result is a control of the pest. Alternatively, the microbe hosting the toxin gene can be treated under conditions that prolong the activity of the toxin and stabilize the cell. The treated cell, which retains the toxic activity, then can be applied to the environment of the target pest.

Where the tic900 toxin gene or a related nucleotide coding sequence is introduced by means of a suitable vector into a microbial host, and the host is applied to the environment in a living state, it is advantageous to use certain host microbes. For example, microorganism hosts can be selected which are known to occupy the pest's habitat. Microorganism hosts may also live symbiotically with a specific species of pest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the habitat of pests. These microorganisms include bacteria, algae, and fungi. Of particular interest are microorganisms, such as bacteria, e.g., genera *Bacillus*, *Escherichia*, *Pseudomonas*, *Erwinia*, *Serratia*, *Klebsiella*, *Salmonella*, *Pasteurella*, *Xanthomonas*, *Streptomyces*, *Rhizobium*, *Rhodopseudomonas*, *Methylophilius*, *Agrobacterium*, *Acetobacter*, *Lactobacillus*, *Arthrobacter*, *Azotobacter*, *Leuconostoc*, and *Alcaligenes*; fungi, e.g., genera *Metarhizium*, *Bavaria*, *Saccharomyces*, *Cryptococcus*, *Kluyveromyces*, *Sporobolomyces*, *Rhodotorula*, and *Aureobasidium*.

A wide variety of means are available for introducing a toxin gene encoding a toxin into a microorganism host under conditions that allow for stable maintenance and expression of the gene. These methods are well known to those skilled in the art and are described, for example, in U.S. Pat. No. 5,135,867.

As mentioned above, *B. thuringiensis* or recombinant cells expressing a TIC900 or related toxin can be treated to prolong the toxin activity and stabilize the cell. The pesticide microcapsule that is formed comprises one or more TIC900 or related toxins within a cellular structure that has been stabilized and will protect the toxin or toxins when the microcapsule is applied to the environment of the target pest. Suitable host cells may include either prokaryotes or eukaryotes, normally being limited to those cells that do not produce substances toxic to higher organisms, such as mammals. However, organisms which produce substances toxic to higher organisms could be used, where the toxic substances are unstable or the level of application sufficiently low as to avoid any possibility of toxicity to a mammalian host. Of particular interest as hosts will be prokaryotes as well as lower eukaryotes such as fungi. The cells of these organisms will usually be intact and be substantially in the proliferative form when treated, rather than in a spore form, although in some instances spores may be employed. Such microcapsules can also contain one or more TIC900 or related proteins along with one or more unrelated insecticidal protein compositions including but not limited to delta endotoxins insecticidal to lepidopteran species such as Cry1, Cry2, and Cry9 proteins, as well as delta endotoxins insecticidal to coleopteran species such as Cry3, Cry22, ET70, ET80/76, ET33/34, PS149B1, ET100/101, and ET29 proteins and the like.

The cells generally will have enhanced structural stability that will enhance resistance to environmental conditions. Where the pesticide is in a proform or precursor form, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of cell treatment retains at least a substantial portion of the bio-availability or bioactivity of the toxin.

TIC900 and related coding sequences as set forth in SEQ ID NO:3, SEQ ID NO:5, SEQ ID NO:7, SEQ ID NO:9, SEQ ID NO:29, SEQ ID NO:11, SEQ ID NO:13, SEQ ID NO:15, SEQ ID NO:17, and SEQ ID NO:19 and the like can be used as the basis for constructing modified nucleotide sequences for incorporation into plant cells. Even more preferable is the synthesis of a non-naturally occurring nucleotide sequence that encodes a TIC900 or related insecticidal protein or its equivalent for expression in a plant cell, the synthesis of the non-naturally occurring nucleotide sequence being based on the amino acid sequence of the native protein without reference to the native nucleotide sequence from which the native amino acid sequence was deduced. Expression of such sequences in plant cells would render a plant comprised of such cells more resistant to lepidopteran species insect attack. Genetic engineering of plants with modified sequences encoding one or more TIC900 or related proteins or a related insecticidal amino acid sequence may be accomplished by introducing the desired DNA containing the coding sequence into plant tissues or cells, using DNA molecules of a variety of forms and origins that are well known to those skilled in plant genetic engineering. Method for introducing nucleotide sequences into plants, plant cells and plant tissues are well known in the art.

DNA containing a modified gene encoding TIC900 or a related insecticidal protein, operatively linked to a plant functional promoter, may be delivered into the plant cells or tissues directly by a number of means including but not limited to *Agrobacterium* mediated transformation, plant viruses, electroporation, microinjection, vacuum infiltration, liposome fusion means, and ballistic methods. The plant promoter may be a constitutive promoter; a temporally, spatially, chemically, photosynthetically, thermally, or artificially inducible promoter; a tissue-specific promoter; or a chimeric or hybrid promoter assembled from parts of other plant functional promoters. For example, the promoter may be a cauliflower mosaic virus (CaMV) 35S promoter or a plant functional derivative thereof.

Native bacterial genes and coding sequences are often poorly expressed in transgenic plant cells. Plant codon usage more closely resembles that of other higher organisms than unicellular organisms, such as bacteria. Several reports have disclosed methods for improving expression of recombinant genes in plants (Murray et al., 1989, Nucleic Acids Research, Vol. 17:477-498; Diehn et al., 1998(b), Plant Physiology, 117:1433-1443; Rocher et al., 1998, Plant Phys. 117:1445-1461). These reports disclose various methods for engineering coding sequences to represent sequences which are more efficiently translated based on plant codon frequency tables, improvements in codon third base position bias, using recombinant sequences which avoid suspect polyadenylation or A/T rich domains or intron splicing consensus sequences. While these methods for synthetic gene construction are notable, synthetic genes of the present invention for expression in particular plants are prepared substantially according to the method of Brown et al. (U.S. Pat. No. 5,689,052).

The work described herein takes advantage of methods of potentiating in planta expression of TIC900 and related insecticidal proteins, which confer resistance to lepidopteran insect pathogens, by incorporation or localization of coding sequences into the nuclear, plastid, or chloroplast genome of susceptible plants. U.S. Pat. No. 5,500,365 and related patents describe methods for synthesizing plant genes to achieve optimum expression levels of the protein for which the synthesized, non-naturally occurring, synthetic, or artificial gene encodes. These methods relate to the modification of native Bt structural gene sequences to produce a coding sequence that is more "plant-like" and therefore more likely to be translated and expressed by the plant, monocot or dicot. However, the method as disclosed in Brown et al. (U.S. Pat. No. 5,689,052) provides for enhanced expression of transgenes, preferably in monocotyledonous plants.

Thus, the amount of a gene coding for a polypeptide of interest, e.g. a TIC900 or related polypeptide, can be increased in plants by transforming those plants using transformation methods mentioned above. In particular, chloroplast or plastid transformation can result in desired coding sequences being present in up to about 10,000 copies per cell in tissues containing these subcellular organelle structures (McBride et al., WO 95/24492).

DNA encoding TIC900 and related proteins can also be introduced into plants by utilizing a direct DNA transfer method into pollen as described (Zhou et al., 1983, Mol. Cell. Biol., 10:4529-4537; Hess, 1987, Hess, Intern Rev. Cytol., 107:367.). Expression of polypeptide coding sequences, i.e., tic900 and the like, can be obtained by injection of the DNA into reproductive organs of a plant as described (Pena et al., 1987, Nature, 325:274). The DNA can also be injected directly into the cells of immature embryos and into rehydrated desiccated embryos as described (Neuhaus et al., 1987, Theor. Appl. Genet., 75:30).

After effecting delivery of exogenous nucleotide sequences encoding TIC900 or related proteins to recipient cells, the next step to obtain a transgenic plant generally concerns identifying the transformed cells for further culturing and plant regeneration, i.e., selection of the transformed cells. As mentioned herein, in order to improve the ability to identify transformants, one may desire to employ a selectable or screenable marker gene as, or in addition to, the expressible gene of interest. In this case, one would then generally assay the potentially transformed cell population by exposing the cells to a selective agent or agents, or one would screen the cells for the desired marker gene trait.

An exemplary embodiment of methods for identifying transformed cells involves exposing the transformed cultures to a selective agent, such as a metabolic inhibitor, an antibiotic, herbicide or the like. Cells that have been transformed and have stably integrated a marker gene conferring resistance to the selective agent used, will grow and divide in culture. Sensitive cells will not be amenable to further culturing. One example of a preferred marker gene confers resistance to the herbicide glyphosate. When this gene is used as a selectable marker, the putatively transformed cell culture is treated with glyphosate. Upon exposure to glyphosate, transgenic cells containing a recombinant GOX enzyme or a recombinant glyphosate insensitive EPSPS enzyme will be available for further culturing while sensitive, or non-transformed cells, will not. (U.S. Pat. No. 5,569,834). Another example of a preferred selectable marker system is the neomycin phosphotransferase (nptII) resistance system by which resistance to the antibiotic kanamycin is conferred, as described in U.S. Pat. No. 5,569,834. Again, after transformation with this system, transformed cells will be available for further culturing upon treatment with kanamycin, while non-transformed cells will not. Yet another preferred selectable marker system involves the use of a gene construct conferring resistance to paromomycin. Use of this type of a selectable marker system is described in U.S. Pat. No. 5,424, 412. Other selectable markers are well known in the art, including but not limited to antibiotic resistance markers such at nptII, tet, aad, and the like, phnO and other various acetylases (U.S. Pat. No. 6,448,476), various esterases (U.S. Pat. No. 6,107,549), barnase (Hartley, 1988), J. Mol. Biol. 202: 913), bacterial enzymes conferring glyphosate oxidase activity upon the transformed cell (gox) (Barry et al., 1992, Inhibitors of amino acid biosynthesis: Strategies for imparting glyphosate tolerance to crop plants. In: Biosynthesis and Molecular Regulation of Amino Acids in Plants. pp. 139-145. Singh, Flores, and Shannon Eds., American Society of Plant Physiologists, Rockville, Md.) and the like.

Transplastonomic selection (selection of plastid or chloroplast transformation events) is simplified by taking advantage of the sensitivity of chloroplasts or plastids to spectinomycin, an inhibitor of plastid or chloroplast protein synthesis, but not of protein synthesis by the nuclear genome encoded cytoplasmic ribosomes. Spectinomycin prevents the accumulation of chloroplast proteins required for photosynthesis so spectinomycin resistant transformed plant cells may be distinguished on the basis of their difference in color: the resistant, transformed cells are green, whereas the sensitive cells are white, due to inhibition of plastid-protein synthesis. Transformation of chloroplasts or plastids with a suitable bacterial aad gene, or with a gene encoding a spectinomycin resistant plastid or chloroplast functional ribosomal RNA provides a means for selection and maintenance of transplastonomic events (Maliga, 1993, Trends in Biotechnology 11:101-106).

It is further contemplated that combinations of screenable and selectable markers will be useful for identification of transformed cells. In some cell or tissue types a selection agent, such as glyphosate or kanamycin, may either not provide enough killing activity to clearly recognize transformed cells or may cause substantial nonselective inhibition of transformants and non-transformants alike, thus causing the selection technique to not be effective. It is proposed that selection with a growth inhibiting compound, such as glyphosate or AMPA (amino-methyl phosphoric acid) at concentrations below those that cause 100% inhibition, followed by screening of growing tissue for expression of a screenable marker gene such as kanamycin would allow one to recover transformants from cell or tissue types that are not amenable to selection alone. It is proposed that combinations of selection and screening may enable one to identify transformants in a wider variety of cell and tissue types.

The development or regeneration of plants from either single plant protoplasts or various explants is well known in the art. This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing a foreign, exogenous gene that encodes a TIC900 or related polypeptide introduced into the plant genome by *Agrobacterium* transformation of leaf explants can be achieved by methods well known in the art (Horsch et al., Science 227:1229-1231; 1985). In this procedure, transformants are cultured in the presence of a selection agent and in a medium that induces the regeneration of shoots in the plant strain being transformed as described (Fraley et al., PNAS, USA 80:4803; 1983). In particular, U.S. Pat. No. 5,349,124 details the creation of genetically transformed lettuce cells and plants resulting therefrom which express hybrid crystal proteins conferring insecticidal activity against Lepidopteran larvae to such plants.

Preferably, the regenerated plants are self-pollinated to provide homozygous transgenic plants, or pollen obtained from the regenerated plants is crossed to seed-grown plants of agronomically important, preferably inbred lines. Conversely, pollen from plants of those important lines is used to pollinate regenerated plants. A transgenic plant of the present invention containing a nucleotide sequence encoding a desired TIC900 or related polypeptide is cultivated using methods well known to one skilled in the art.

A transgenic plant of this invention thus has an increased amount of a coding region encoding a TIC900 or related polypeptide. A preferred transgenic plant is an independent segregant and can transmit that gene and its activity to its progeny. A more preferred transgenic plant is homozygous for that gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for increased expression of the *B. thuringiensis* transgene. To identify a transgenic plant expressing high levels of a TIC900 or related protein from a preferred nucleotide sequence, it is necessary to screen the selected transgenic event, (Ro generation) for insecticidal activity and/or expression of the gene. This can be accomplished by various methods well known to those skilled in the art, including but not limited to: 1) obtaining small tissue samples from the transgenic Ro plant and directly assaying the tissue for activity against susceptible insects, e.g., European corn borer (ECB), tobacco budworm (TBW) and diamondback moth (DBM), in parallel with tissue derived from a non-expressing, negative control plant; 2) analysis of protein extracts by enzyme linked immunoassays (ELISA) specific for the TIC900 or related protein; or 3) reverse transcriptase thermal amplification (also known in the art as rtPCR) to identify events expressing the sequence encoding the TIC900 or related protein.

The following examples further illustrate the characteristics of the nucleotide sequences disclosed herein and the insecticidal activity of the proteins encoded by the disclosed nucleotide sequences. In addition, methods and procedures for practicing the invention are disclosed. However, those of skill in the art should, in light of the present disclosure, appreciate that many changes can be made in the specific embodiments which are disclosed and still obtain a like or similar result without departing from the spirit and scope of the invention.

EXAMPLES

Example 1

Preparation and Bioassay of *B. Thuringiensis* Strain Eg5438 Culture Supernatant

*B. thuringiensis* strain EG5438 was grown in 60 ml of PYG culture medium with shaking overnight at 30° C. PYG medium contained the following: 11.8 g peptone, 23.6 g yeast extract, 4 ml glycerol, 19.4 g $K_2HPO_4$ anhydrous, and 2.2 g $KH_2PO_4$ anhydrous. Deionized water was added to 1 liter, and the medium was autoclaved for 15 min. The *B. thuring-*

*iensis* culture was centrifuged at 11,000×g for 30 min and the supernatant was transferred to a clean flask. The supernatant was chilled to 4° C., and 34 grams of ammonium sulfate plus 1 ml of 1 M NaOH were slowly added to the supernatant while stirring. The mixture was centrifuged and the resulting pellet was dissolved in 2 ml of 20 mM Tris-HCl pH 7.5. The solution was transferred to dialysis tubing (6000 MWCO) and was dialyzed at 4° C. against 20 mM Tris-HCl pH 7.5. This is referred to as the dialyzed supernatant.

The dialyzed supernatant was tested for toxicity to diamondback moth (DBM) larvae as follows. Fifty µl of the dialyzed supernatant was applied topically to 2 ml of insect diet in a cup. A total of thirty-two diet cups were treated with the dialyzed supernatant. As a control sixty-four diet cups were not treated with dialyzed supernatant. One first-instar DBM larva was placed in each diet cup and insect mortality was scored after 7 days. For larvae on the untreated control diets 1 larvae out of 64 (2%) died. For larvae on the diets treated with the dialyzed supernatant 29 out of 32 (90%) died, suggesting that the dialyzed supernatant of strain EG5438 contained one or more factors toxic to DBM larvae.

Example 2

Fractionation of Proteins in the Dialyzed Supernatant and Bioassay of Protein Fractions Proteins in the dialyzed supernatant were initially fractionated by sodium dodecyl-sulfate polyacrylamide gel electrophoresis (SDS-PAGE). Thirty µl of the dialyzed supernatant was mixed with 15 µl of protein solubilization buffer, the mixture was heated to 100° C. for 5 min, and 25 µl of the mixture was applied to a polyacrylamide gel. An electric current was applied to the gel to size-separate proteins into the gel. The proteins were visualized after electrophoresis by staining with Coomassie dye. The dialyzed supernatant contained approximately twenty proteins ranging in size from approximately 20 kDa to about 100 kDa.

Proteins in the dialyzed supernatant were fractionated by DEAE ion-exchange chromatography. Two ml of the dialyzed supernatant was applied to a 1 ml DEAE column. The column was washed with 10 ml of 20 mM Tris-HCl, pH 7.5, followed by washing with 20 ml of a 0 to 1 M NaCl gradient in 20 mM Tris-HCl, pH 7.5. Fractions of 1 ml were collected. Each fraction was dialyzed against 20 mM Tris-HCl, pH 7.5, and individual fractions were tested for toxicity to DBM larvae as described above. Fractions with the highest toxicity were collected and combined and referred to as the DEAE pool.

The DEAE pool was applied to a carboxymethyl cellulose (CM) ion exchange column. The column was washed with 10 ml of 20 mM Tris-HCl, pH 7.5, followed by washing with 20 ml of a 0 to 1 M NaCl gradient in 20 mM Tris-HCl, pH 7.5. One ml fractions were collected and dialyzed against 20 mM Tris-HCl, pH 7.5. These fractions were referred to as the CM fractions. The CM fractions were tested for toxicity to DBM larvae. This analysis showed that CM fractions had the highest toxicity to DBM and contained a protein of approximately 66 kDa. The 66 kDa protein was referred to as the 5438-66 protein, also referred to as secreted TIC900, TIC900s, or mTIC900 (referring to a mature form of the protein identified in the culture supernatant that may be different from any precursor TIC900 protein (pTIC900) not yet released from the cell).

Example 3

Determination of the N-Terminal Sequence of a Fragment of a TIC900 Protein mTIC900 protein was purified from the supernatant of strain EG5438 by DEAE and CM ion exchange chromatography. Attempts to determine the N-terminal sequence of the purified mTIC900 protein by standard methods were not successful. To overcome this difficulty, mTIC900 protein was fragmented by cyanogen bromide treatment (Cordoba et al., J. Biochem. Biophys. Methods 35: 1, 1997). The cyanogen bromide-generated TIC900 fragments were size-separated by SDS-PAGE without Coomassie staining Separated TIC900 fragments were transferred from the SDS-PAGE to a polyvinylidene difluoride (PVDF) membrane by an electro transfer. The PVDF membrane was stained briefly with Coomassie dye and a portion of the membrane containing an approximately 14 kDa fragment of TIC900 protein was excised with a razor blade. The excised PVDF membrane containing the 14 kDa fragment was subjected to automated Edmund sequencing, revealing the amino acid sequence as shown in SEQ ID NO:1, in which the Xaa amino acid residue at position one (1) was indeterminable except that it was presumed to be either a Serine, Tyrosine, Aspartate or Histidine residue, but most likely a Tyrosine residue, Xaa amino acid residue at position 15 was indeterminable except that it was likely a Proline residue, and the Xaa residue at position 18 was also indeterminable except that it was likely an Arginine residue.

Example 4

Cloning tic900 Gene Encoding TIC900 Protein

Based on the sequence obtained from the 14 kDa TIC900 protein fragment (SEQ ID NO:1), a gene-specific oligonucleotide was designed. Due to the degeneracy of the genetic code it is not possible to know the exact sequence of a gene based on the sequence of the protein encoded by the gene. Therefore for amino acids that can be encoded by more than a single codon, it is necessary to guess at the correct codon. The chance of guessing accurately is improved by the fact that the *B. thuringiensis* genome is approximately 68% AT (adenosine and thymidine). Therefore, for amino acids encoded by more than one codon, the codon or codons which contain A's and T's are selected, and for codons that contain substantially G/C, those codons that have a degeneracy in the third base position are selected preferentially based on whether the third base is an A or a T nucleotide. An oligonucleotide designated WD470 (SEQ ID NO:2) was designed which is one of many that could conceivably encode the amino acid set forth in SEQ ID NO:1, taking into consideration the A/T usage in *Bacillus thuringiensis* for codons encoding any given amino acid.

DNA was purified from *B. thuringiensis* strain EG5438 cells by standard procedures. Samples of the EG5438 DNA were subjected to either HindIII or EcoRI restriction enzyme digestion and were size-fractionated by electrophoresis through an agarose gel and subjected to Southern blot analysis using an alkaline phosphatase conjugated WD470 oligonucleotide probe. After incubation for approximately 16 hours at 40° C. the blot was washed, treated with chemiluminescent buffer, and exposed to x-ray film. The WD470 probe specifically hybridized with EG5438 DNA restriction fragments that were approximately 2.5 kb (HindIII) and 3.0 kb (EcoRI) in length, respectively.

A library of EG5438 DNA consisting of about 3.0 kb EcoRI fragments was constructed in a CIP (calf intestine phosphatase) treated EcoRI digested pUC18 plasmid. The library was transformed by electroporation into an *E. coli* XL1BLUE strain and plated to LB-ampicillin. Colonies that arose were blotted to a membrane and probed with the alkaline phosphatase conjugated WD470 oligonucleotide probe. Several positive clones were selected and plasmid DNA was obtained from each. Plasmid DNA's were digested with EcoRI to confirm the presence of a single EcoRI insert consisting of about 3.0 kb. Plasmids were also subjected to hybridization to the alk-phos conjugated WD470 probe to confirm the complementarity of the probe and inserted DNA. A single clone was selected for further analysis and was designated as plasmid pEG1398. The inserted DNA in pEG1398 was subjected to sequence analysis. A sequence containing a partial open reading frame consisting of nucleotide position 1176 through 1803 as set forth in SEQ ID NO:3 was obtained, as well as an additional 24 nucleotides beyond nucleotide 1803 (data not shown) which contained a termination codon immediately after nucleotides at position 1801-1803 as set forth in SEQ ID NO:3.

The complete sequence of an ORF encoding the TIC900 protein was not present within the EcoRI fragment cloned into plasmid pEG1398. Oligonucleotide primers specific for the 5' and 3' ends of the sequence identified therein were designed to enable the synthesis of a labeled probe for use in detecting a larger cloned fragment of EG5438 DNA that likely contained the full length ORF encoding the TIC900 protein. A digoxygenin labeled DNA probe was prepared by amplification using the primers and the inserted DNA in pEG1398 as a template. The DIG-labeled DNA was used to probe a Southern blot of EG5438 DNA that had been resolved in an agarose gel after digestion with various restriction enzymes. A HindIII fragment about 2.5 kb in length was identified as a fragment that could contain the full length ORF encoding the TIC900 protein.

A EG5438 DNA fragment of about 2.5 kb was cloned using a means similar to that described above for the about 3.0 kb EcoRI fragment except that the HindIII fragment was cloned into a pBlueScript KS plasmid and the probe used was a DIG-labeled DNA segment consisting of a part of the open reading frame identified within the 3.0 Kb EcoRI fragment in the plasmid pEG1398. One plasmid containing an approximately 2.5 kb HindIII fragment that hybridized to the DIG-labeled EcoRI fragment present within pEG1398 was selected for further analysis and designated as plasmid p5438-2.5-kb-H3. The recombinant *E. coli* strain harboring p5438-2.5-H3 was designated as 5438 2.5 kb H3. The DNA sequence of the 2.5 kb HindIII insert in the plasmid p5438-2.5-kb-H3 was determined, and translation of this sequence in all six reading frames revealed an open reading frame of 1803 nucleotides, the sequence of which is set forth in SEQ ID NO:3.

The ORF from nucleotide position 1 through nucleotide position 1803 as set forth in SEQ ID NO:3 is predicted to encode a protein of about 68,868 Daltons, which has been designated herein as TIC900. The amino acid sequence of the predicted precursor form of a TIC900 protein (pTIC900) deduced from the open reading frame in SEQ ID NO:3 is shown as set forth in SEQ ID NO:4. Identity and similarity comparison of the amino acid sequence of the deduced TIC900 amino acid sequence (SEQ ID NO:4) with the GenBank protein database revealed that the nearest identity was to a Cry1Ca protein exhibiting about 49% identity.

Example 5

Expression of a Cloned tic900 Gene in Recombinant *B. Thuringiensis*

*B. thuringiensis* insecticidal toxin genes are often poorly expressed in recombinant *E. coli* strains. *B. thuringiensis* strain EG10650 is an acrystalliferous strain that was designed for use as a recipient strain for testing whether cloned Bt genes encode insecticidal proteins. (EG10650, NRRL Accession Number NRRL B-30217, U.S. Pat. No. 6,468,52). The TIC900 coding sequence on the cloned HindIII fragment in plasmid p5438-2.5 kb-H3 was transferred into the HindIII restriction site in the *B. thuringiensis-E. coli* shuttle vector pEG597 (Baum, J. A.; Coyle, D. M.; Gilbert, M. P.; Jany, C. S.; Gawron-Burke, C., 1990 Novel cloning vectors for *Bacillus thuringiensis*; Applied and Environmental Microbiology 56 (11): 3420-3428) resulting in the construction of plasmid pMON74010 which confers chloramphenicol resistance to recipient *Bacillus* cells. Plasmid pMON74010 was transformed by electroporation into the acrystalliferous *B. thuringiensis* strain EG10650 yielding strain SIC9002. Strain EG10650 was grown as a control in PYG medium as described in Example 1. The recombinant strain SIC9002 was grown in PYG medium plus 5 ug/ml chloramphenicol. Culture supernatants were prepared as described in Example 1. Proteins in the culture supernatants were resolved by standard SDS-PAGE analysis and were visualized after staining with Coomassie brilliant blue. The SDS-PAGE analysis results revealed that strains EG10650 and SIC9002 secreted similar numbers and sizes of proteins into their respective culture supernatants with the exception that the culture supernatant of strain SIC9002 contained a protein of approximately 66 kDa which did not appear to be present in the culture supernatant of strain EG10650. This result suggested that the cloned tic900 open reading frame in p5438-2.5 kb-H3 encoded a protein that migrated with a mass of approximately 66 kDa in SDS-PAGE gels. A discrepancy in the size of the amino acid sequence deduced from the ORF as set forth in SEQ ID NO:3 (about 69 kDa) and the observed mass by migration in SDS-PAGE suggests that the secreted form of the protein may in fact be reduced in size by about 2500 to 3000 Da. This is not unexpected since most secreted proteins exhibit some proteolytic reduction in size as they are passed through any secretion machinery. However, there is no apparent type II signal peptide present as judged from an analysis of the primary amino acid sequence of the precursor TIC900 protein (pTIC900).

Example 6

Bioassay of TIC900 Protein Produced from the Cloned tic900 Coding Sequence

Culture supernatants of strains EG10650 and SIC9002 were applied to the surface of insect diet as described herein above. First instar European corn borer (ECB) larvae and tobacco budworm (TBW) eggs were placed on treated diet and were allowed to develop for 1 week. Insect larvae were visually evaluated. ECB larvae and TBW larvae reared on untreated diet or on diet treated with EG10650 supernatant exhibited normal growth. In contrast, ECB larvae and TBW larvae reared on diet treated with SIC9002 supernatant exhibited significant stunting. These results suggested that the protein produced from expression of the cloned tic900 gene inhibited growth of ECB and TBW larvae.

Example 7

Identification of Strains Containing tic900 Homologs

A DIG-labeled probe encompassing the entire open reading frame of the tic900 coding sequence was prepared using the following thermal amplification primers:

SEQ ID NO: 21
5'-gcgctagcatgaattcaaaggaacatgattatctaaaag-3',,
and

SEQ ID NO: 22
5'-cgggctcgagctattcaacaggaataaattcaatttatcc-3',.

Between one and five µg genomic DNA from a collection of Bt strains was digested to completion with HindIII and the resulting fragments were resolved as a smear on an agarose gel. The gel was used in a Southern blot procedure in which the resolved DNA was denatured, transferred to a nylon membrane, fixed, and exposed to the DIG labeled probe described above. Hybridization was carried out in DIG Easy Hybe (Roche) at 42° C. (DIG Easy Hybe at 42° C. is equivalent to a stringent 42° C. hybridization with a hybridization buffer system containing 50% formamide). Moderately stringent washes were performed as follows: 1) one time for 5 minutes and one time for 15 minutes at 25° C. in 2×SSC, 0.1% SDS; and 2) two times for 15 minutes each at 65° C. in 0.5×SSC, 0.1% SDS.

Thirteen strains were identified that contained from between one and three HindIII fragments that hybridized to the tic900 probe. DNA from each of these strains was used as a template for thermal amplification of tic900 homologs. Primers set forth as SEQ ID NO:21 and SEQ ID NO:22 were used to amplify tic900 homologs using the Expand High Fidelity PCR kit (Roche). Thermal amplification reaction conditions consisted of a 50 μL volume comprising 200 μM each dNTP, 300 nM each primer, 0.1-250 ng genomic DNA template, and 2.6 units enzyme mix in 1× reaction buffer (supplied by the manufacturer with the reagents in 10× concentrate).

Thermal amplification cycles consisted of one cycle of 2 minutes at 94° C.; ten cycles of 15 seconds at 94° C., 30 seconds at 60° C., and 2 minutes at 72° C.; followed by twenty five cycles of 15 seconds at 94° C., 30 seconds at 60° C., and 2 minutes at 72° C., increasing each of the last twenty five cycles by 5 seconds per cycle; and a terminal extension phase of 7 minutes at 72° C. at the end of the last cycle.

DNA from nine of the thirteen strains subjected to this thermal amplification reaction produced amplification products (amplicons) that were subsequently cloned and sequenced. The 5' and 3' end sequences of the cloned thermal amplification products were fixed by the sequences of the primers and may not be representative of the sequence of the native gene throughout the sequence established by the amplification primers. Regardless, the amplicon sequences were substantially the same as the full length native sequences expressed for analysis of insecticidal activity. One skilled in the art will realize that the amplicons can be used as probes to fish out the full-length native sequences encoding insecticidal proteins related to the TIC900 protein. The proteins encoded by the open reading frame for each thermal amplification product and the strains from which each thermal amplification product were obtained are indicated in Table 1, as shown above.

Variant amplification primers and multiple amplification conditions were also used to identify tic900 homologs from the CRW-active Bt strain EG3907. The tic900 homolog in EG3907 was mapped by southern blot to facilitate cloning of the open reading frame encoding this protein. The tic900 homolog in EG3907 had a different HindIII restriction pattern than that of the tic900 gene from EG5438. The EG3907 homolog was identified on an approximately 13 kb BamHI/BglII fragment. BamHI/BglII-digested EG3907 DNA was ligated into BamHI-digested phage lambda GEM-11 arms. Southern blots of DNA from an additional 30 Bt strains exhibiting CRW activity in the fermentation broth identified 2 strains, EG3291, EG3388, containing DNA that hybridized to a tic900 probe under stringent conditions. Both of these strains exhibited identical HindIII restriction patterns, but these were different from the restriction pattern containing the tic900 sequence from strain EG5438 as set forth in SEQ ID NO:3, and different from the restriction pattern containing the homolog identified as being present in strain EG3907.

DNA (0.5 μg) from 132 Bt strains was dot-blotted to Nytran membranes and probed with a tic900 DNA probe under stringent conditions. DNA from the fifteen strains exhibiting the strongest tic900 hybridization signals were analyzed further. DNA from each strain was digested to completion with HindIII and subjected to a Southern blot procedure as described above. DNA from several strains that appeared to hybridize in the dot blots did not exhibit strong hybridization signals using the Southern blot method. 14 strains containing sequences homologous to the tic900 gene have been analyzed using HindIII Southern blots. Based on the hybridization profiles that appear using HindIII digestion, at least 4 different tic900 homologs are present in these strains.

The following *Bacillus thuringiensis* strains exhibit HindIII fragments that hybridize to a tic900 probe under stringent or specific hybridization conditions: EG3291, EG3388, EG3879, EG3907, EG4090, EG4092, EG4293, EG4332, EG4577, EG4611, EG4963, EG4971, EG5023, EG5438, and EG5526. These strains also produce extracellular proteins that can be evaluated for insecticidal activity. Depending on the strain selected, the hybridizing HindIII fragments varied in size from about 0.8 kb to about 6.3 kb. The nucleotide sequence of each fragment that hybridized to the tic900 probe was determined, and open reading frames were deduced from these sequences, each set forth herein as SEQ ID NO:5, SEQ ID NO:7, SEQ ID NO:9, SEQ ID NO:29, SEQ ID NO:11, SEQ ID NO:13, SEQ ID NO:15, SEQ ID NO:17, and SEQ ID NO:19. The amino acid sequence of a protein comparable in size to that of TIC900 was deduced from each of these open reading frames, as set forth respectively in SEQ ID NO:6, SEQ ID NO:8, SEQ ID NO:10, SEQ ID NO:30, SEQ ID NO:12, SEQ ID NO:14, SEQ ID NO:16, SEQ ID NO:18, and SEQ ID NO:20. These deduced amino acid sequences were designated respectively as TIC402, TIC403, TIC404, TIC434, TIC961, TIC962, TIC963, TIC965, and TIC966. As set forth in Table 1, these nucleotide sequences were sourced respectively from the following *B. thuringiensis* strains: EG3879 (TIC402), EG4332 (TIC403), EG4971 (TIC404), EG4090 (TIC961), EG4293 (TIC962), EG4611 (TIC963 and TIC434), EG5023 (TIC965), and EG4092 (TIC966). An additional strain was identified that exhibited a sequence that hybridized to the tic900 probe. Strain EG5526 contained a HindIII fragment that was apparently identical in size to the HindIII fragment identified as encoding TIC402 from strain EG3879. DNA sequence analysis revealed that the EG5526 fragment contained an ORF (TIC964) that was identical in sequence to that of the tic402 ORF. Acrystalliferous strains of *B. thuringiensis* containing plasmids encoding these cloned homologs of tic900 were each subjected to insect bioassay and were determined to exhibit insecticidal bioactivity.

There is a high degree of identity between the sequences encoding the proteins of the present invention. In fact, an alignment of the open reading frames including each of the tic genes reveals that none of the ORF's are less than about 97% identical to each other. An alignment of the amino acid sequences encoded by each of the ORF's also indicates that there is a high degree of identity between the proteins of the present invention. TIC962 and TIC963 are the most distantly related, but still very closely related in that they exhibit greater than a 96% identity at the amino acid sequence level. Most changes to the nucleotide sequence for any given change in any ORF in relation to a consensus sequence established based on an alignment of all of the nucleotide sequences indicates that the changes are silent in that they affect only the third base in a codon and result most often in no modification of the encoded amino acid sequence.

Subcultures of B. thuringiensis strains EG5438 containing the native tic900 gene, and SIC9002 containing the cloned tic900 coding sequence were deposited in the permanent collection of the Agricultural Research Service Culture Collection, Northern Regional Research Laboratory (NRRL), U.S. Department of Agriculture (USDA), 1815 North University Street, Peoria, Ill. 61604, USA. B. thuringiensis strain SIC9002 was deposited on Apr. 25, 2002 and provided with the NRRL accession number NRRL B-30582. B. thuringiensis strain EG5438 was deposited on May 3, 2002 and was provided with the NRRL accession number NRRL B-30584.

Example 8

Genes Encoding Chimeric Insecticidal Proteins

This example illustrates that the TIC900 class of proteins exhibit similarities with the Cry1 class of Bt insecticidal proteins and that a chimeric protein can be constructed from all or a part of a TIC900 class protein linked in frame with all or a part of a Cry1 protein and tested for insecticidal activity.

Comparison of any of the TIC900 class of proteins disclosed herein with other Bt insecticidal proteins suggests that these proteins are most closely related to the Cry1 classes of proteins, and in particular to the insecticidal portion of the Cry1 proteins. The TIC900 class of proteins exhibit structural similarities to the Cry1 protein toxin portions in that the Cry1 proteins exhibit a domain structure consisting of a first domain consisting of about the first 200 to about the first 240 amino terminal amino acids which is referred to as domain I, a second domain that consists of about amino acids 240 through about amino acid 400 or so which is referred to as domain II, and a carboxy-terminal domain referred to as domain III consisting of amino acids from about residue 400 or so through the end of the toxin domain. The TIC900 class of proteins appear to exhibit this type of domain structure even though the TIC900 class of proteins generally are not as long as most Cry1 toxin domains. It has previously been shown that Cry1 toxin domains can be fused to heterologous protoxin peptide structures, and that the fusions result in crystal formation, and often also retain insecticidal bioactivity when the resulting crystals are tested in bioassay. A fusion protein (SEQ ID NO:24, TIC109) was constructed in which TIC900 was fused to the Cry1Ac protoxin peptide structure. The fusion protein was expressed from the nucleotide sequence as set forth in SEQ ID NO:23 in pMON74119 in B. thuringiensis strain EG10650 (recombinant strain designated as SIC1047). SEQ ID NO:23 corresponds to a TIC900 coding sequence from nucleotide position 1-1809, and a Cry1Ac protoxin domain coding sequence from nucleotide position 1816-3504. The chimeric protein TIC109 formed in SIC1047 fermentations produced crystalline inclusions, which were tested in bioassay against Tobacco Budworm, Corn Earworm, and Fall Armyworm. The chimeric protein exhibited bioactivity similar to that exhibited by TIC900, but was not biologically active against Fall Armyworm.

TIC110 (SEQ ID NO:26) encoded by the nucleotide sequence as set forth in SEQ ID NO:25 is a Cry1F/TIC900 chimeric insecticidal protein linked to a Cry1Ac protoxin peptide sequence. SEQ ID NO:25 corresponds to a sequence encoding Cry 1F domain I from about nucleotide position 1-723, a sequence encoding TIC900 domains II and III from about nucleotide position 724-1809, and a Cry1Ac coding sequence from about nucleotide position 1810-3510. This protein can be expressed in an acrystalliferous strain of Bt and the crystalline protein inclusions tested in bioassay to determine the biological activity against various lepidopteran pest species.

TIC111 (SEQ ID NO:28) is encoded by the nucleotide sequence as set forth in SEQ ID NO:27. TIC111 corresponds to an insecticidal chimeric protein consisting of a Cry1Ac domain I linked to TIC900 domains II and III, which is linked to a Cry1Ac protoxin domain. TIC111 can be expressed from pMON74122 and the crystalline protein inclusions tested in bioassay to for bioactivity against various lepidopteran pest species.

pMON74122 was transformed into the acrystalliferous Bt strain EG10650 resulting in the transformed host cell SIC1049 expressing the TIC111 protein. TIC111 crystals were collected and tested in bioassay against black cutworm (BCW), Diamondback Moth (DBM), Tobacco Budworm (TBW), Corn Earworm (CEW), and Fall Armyworm (FAW). Insecticidal bioactivity was observed for BCW, DBM and TBW, consistent with the insecticidal bioactivity for TIC900.

In summary, the above detailed description describes the present invention. It will be understood by those skilled in the art that, without departing from the scope and spirit of the present invention and without undue experimentation, the present invention can be performed within a wide range of equivalent parameters. While the present invention has been described in connection with specific embodiments thereof, it will be understood that it is capable of further modifications. The present invention is intended to include any uses, variations, or adaptations of the invention following the principles of the invention in general. Various permutations and combination of the elements provided in all the claims that follow are possible and fall within the scope of this invention.

Reference to the word 'comprising' or 'comprise' or 'comprises' whether in the claim language or in the specification is intended to be defined as a term or terms meaning "includes at least".

All publications and patents mentioned in this specification are herein incorporated by reference as if each individual publication or patent was specially and individually stated to be incorporated by reference.

REFERENCES

Capecchi, Cell, 22(2): 479-488, 1980.
Clapp, Clin. Perinatol., 20(1): 155-168, 1993.
Crickmore et al. Microbiol. Molecular Biol. Rev. 62, pp. 807-813, 1998.
Curiel et al., Hum. Gen. Ther., 3(2):147-154, 1992.
DeBarjac and Frachon, Entomophaga 35, pp. 233-240, 1990.
Diehn et al., In: Genetic Engineering, Ed. J. K. Setlow, Plenum Press, New York, N.Y., 18:83-99, 1996.
Donovan et al. Mol. Gen. Genet. 214, pp. 365-372, 1988.
Eglitis and Anderson, Biotechniques, 6(7): 608-614, 1988.
Estruch et al., Proc. Natl. Acad. Sci. USA 93, pp. 5389-5394, 1996.
Goding, Monoclonal Antibodies: Principles and Practice, $2^{nd}$ eds, Academic Press, NY.
Fraley et al., Proc. Natl. Acad. Sci. U.S.A., 80:4803, 1983.
Fromm et al., Proc. Natl. Acad. Sci. USA, 82(17): 5824-5828, 1985.

Fynan et al., Proc. Natl. Acad. Sci. USA, 90(24): 11478-11482, 1993.
Graham and Van der Eb, Virology, 54(2): 536-539, 1973.
Harlow and Lane, Antibodies: A Laboratory Manual, Cold Spring Harbor Laboratory, Cold Spring Harbor, N.Y., 1988.
Hess, Intern Rev. Cytol., 107: 367, 1987,
Hofte et al. Microbiol. Rev. 53, pp. 242-255, 1989.
Horsch et al., Science, 227:1229-1231, 1985.
Humason, Gretchen L., Animal Tissue Techniques, W. H. Freeman and Company, 1967.
Johnston and Tang, Methods Cell Biol., 43(A): 353-365, 1994.
Kostichka et al. J. Bacteriol. 178, pp. 2141-2144, 1996.
Kyte and Doolittle, J. Mol. Biol., 157: 105-132, 1982.
Lu et al., J. Exp. Med., 178(6): 2089-2096, 1993.
Maliga, Trends in Biotechnology 11:101-106, 1993.
Maniatis et al., Molecular Cloning: A Laboratory Manual, Cold Spring Harbor Laboratory Press, Cold Spring Harbor, N.Y., 1982.
McBride et al., Bio/Technology 13:362-365, 1995.
Murray et al., Nucl. Acids. Res., 17:477-498, 1989.
Neuhaus et al., Theor. Appl. Genet., 75: 30, 1987.
Obukowicz et al. Gene, 45, pp. 327-331, 1986.
Pena et al., Nature, 325:274, 1987.
Perlak et al. in Proc. Natl. Acad. Sci. USA, 88, pp. 3324-3328, 1991.
Sambrook et al., Molecular Cloning—A Laboratory Manual, $2^{nd}$ Ed., Cold Spring Harbor Laboratory, Cold Spring Harbor, N.Y., 1989.
Schnepf et al. Microbiol. Molec. Biol. Rev. 62, pp. 775-806, 1998.
Turner et al. Appl. Environ. Microbiol, 57, pp. 3522-3528, 1991.
Wagner et al., Proc. Natl. Acad. Sci. USA, 89(13): 6099-6103, 1992.
Wong and Neumann, Biochim. Biophys. Res. Commun., 107 (2): 584-587, 1982.
Zhou et al., Methods in Enzymology, 101: 433, 1983.
U.S. Pat. No. 4,554,101.
U.S. Pat. No. 4,695,455.
U.S. Pat. No. 4,695,462.
U.S. Pat. No. 4,935,353.
U.S. Pat. No. 5,349,124.
U.S. Pat. No. 5,424,412.
U.S. Pat. No. 5,500,365.
U.S. Pat. No. 5,569,834.
U.S. Pat. No. 5,080,897.
U.S. Pat. No. 5,135,867.
U.S. Pat. No. 5,689,052.
U.S. Pat. No. 5,866,326.
U.S. Pat. No. 6,063,756.
WO94/21795 WO96/10083.

What is claimed is:

1. A DNA construct comprising a polynucleotide operably linked to a heterologous promoter, wherein said polynucleotide encodes a Bacillus thuringiensis insecticidal toxin protein or insecticidal fragment thereof, active against a lepidopteran insect pest, wherein said insecticidal toxin protein comprises the polypeptide sequence-as set forth in SEQ ID NO:4 (TIC900), SEQ ID NO:8 (TIC403), SEQ ID NO:10 (TIC404), SEQ ID NO:30 (TIC434), SEQ ID NO:12 (TIC961), SEQ ID NO:14 (TIC962), SEQ ID NO:16 (TIC963), SEQ ID NO:18 (TIC965) or SEQ ID NO:20 (TIC966).

2. The DNA construct of claim 1, wherein said lepidopteran insect pest is selected from the group consisting of a Noctuidae, a Tortricidae, Epinotia aporema, Anticarsia gemmatalis, Pseudoplusia includens, European Corn Borer (ECB), a Tobacco Budworm (TBW), Black Cutworm (BCW), and a Diamondback Moth (DBM).

3. The DNA construct of claim 1, wherein said insecticidal toxin protein has a molecular weight between approximately 65 kDa and approximately 70 kDa, and wherein said insecticidal toxin protein is selected from the group consisting of SEQ ID NO:4 (TIC900), SEQ ID NO:8 (TIC403), SEQ ID NO:10 (TIC404), SEQ ID NO:30 (TIC434), SEQ ID NO:12 (TIC961), SEQ ID NO:14 (TIC962), SEQ ID NO:16 (TIC963), SEQ ID NO:18 (TIC965) and SEQ ID NO:20 (TIC966).

4. The DNA construct of claim 1, wherein the sequence of said polynucleotide has been optimized for expression in plants.

5. The DNA construct of claim 4, wherein said sequence of said polynucleotide has been optimized for
    (a) expression in a monocot plant, said optimization comprising one or more of the steps selected from the group consisting of
        (i) removing polyadenylation sequences,
        (ii) adjusting the A and T content of the nucleotide sequence to be from about 40% to about 49% without modifying the amino acid sequence of the protein, and
        (iii) modifying codons in the coding sequence to be consistent with the steps (i) and (ii), or
    (b) expression in a dicot plant, said optimization comprising one or more of the steps selected from the group consisting of
        (i) removing polyadenylation sequences,
        (ii) adjusting the A and T content of the nucleotide sequence to be from about 40% to about 49% without modifying the amino acid sequence of the protein, and
        (iii) modifying codons in the coding sequence to be consistent with the steps (i) and (ii).

6. An insecticidal protein active against Lepidopteran insects, said protein comprising the amino acid sequence as set forth in SEQ ID NO:4 (TIC900), SEQ ID NO:8 (TIC403), SEQ ID NO:10 (TIC404), SEQ ID NO:30 (TIC434), SEQ ID NO:12 (TIC961), SEQ ID NO:14 (TIC962), SEQ ID NO:16 (TIC963), SEQ ID NO:18 (TIC965) or SEQ ID NO:20 (TIC966).

7. A host cell comprising the DNA construct of claim 1.

8. The host cell of claim 7, wherein said host cell is a plant cell.

9. A method for controlling a lepidopteran insect pest, said method comprising contacting said pest with a pesticidal amount of the insecticidal protein of claim 6 or an insecticidal fragment thereof.

10. The host cell of claim 8, said plant cell selected from the group consisting of a corn plant cell, a wheat plant cell, a rice plant cell, an oat plant cell, an onion plant cell, and a grass plant cell; and wherein said dicot plant cell comprises a cotton plant cell, a canola plant cell, a soybean plant cell, a tobacco plant cell, a fruit tree plant cell, a cruciferous plant cell, a pepper plant cell, an ornamental plant cell, a sunflower plant cell, a cucurbit plant cell, and a melon plant cell.

11. A method for expressing a lepidopteran-active toxin protein in a plant, comprising the steps of:
    (a) inserting into the genome of a plant cell a nucleic acid sequence comprising in the 5' to 3' direction an operably linked recombinant, double-stranded DNA molecule, wherein the recombinant, double-stranded DNA molecule comprises:
        (i) a promoter that functions in the plant cell;
        (ii) a nucleotide sequence encoding the insecticidal amino acid sequence as set forth in SEQ ID NO:4, SEQ ID NO:8, SEQ ID NO:30, SEQ ID NO:10, SEQ ID NO:12, SEQ ID NO:14, SEQ ID NO:16, SEQ ID NO:18, or SEQ ID NO:20; and
        (iii) a 3' non-translated nucleotide sequence that functions in the cells of the plant to cause termination of transcription;
    (b) obtaining a transformed plant cell containing the nucleic acid sequence of step (a); and
    (d) generating from said transformed plant cell a plant that expresses the lepidopteran-active toxin protein in the transformed plant.

12. A plasmid vector comprising the DNA construct of claim 1.

13. A transformed plant comprising the DNA construct of claim 1.

14. A seed from the transformed plant of claim 13, wherein said seed comprises said DNA construct.

15. Progeny of the seed of claim 14, wherein said progeny comprise said DNA construct.

16. A biological sample derived from tissues or seed of the transformed plant of claim 13, said sample comprising a detectable amount of said DNA construct.

* * * * *

SEQUENCE LISTING

```
<160> NUMBER OF SEQ ID NOS: 32

<210> SEQ ID NO 1
<211> LENGTH: 18
<212> TYPE: PRT
<213> ORGANISM: Bacillus thuringiensis
<220> FEATURE:
<221> NAME/KEY: MISC_FEATURE
<222> LOCATION: (1)..(1)
<223> OTHER INFORMATION: unknown amino acid
<220> FEATURE:
<221> NAME/KEY: MISC_FEATURE
<222> LOCATION: (15)..(15)
<223> OTHER INFORMATION: unknown amino acid
<220> FEATURE:
<221> NAME/KEY: MISC_FEATURE
<222> LOCATION: (18)..(18)
<223> OTHER INFORMATION: unknown amino acid

<400> SEQUENCE: 1

Xaa Arg Glu Arg Gly Ser Val Asn Ser Phe Asn Glu Leu Pro Xaa Phe
1               5                   10                  15

Asn Xaa

<210> SEQ ID NO 2
<211> LENGTH: 50
<212> TYPE: DNA
<213> ORGANISM: Artificial Sequence
<220> FEATURE:
<223> OTHER INFORMATION: oligonucleotide probe WD470
<220> FEATURE:
<221> NAME/KEY: misc_feature
<222> LOCATION: (1)..(50)
<223> OTHER INFORMATION: oligonucleotide WD470
```

```
<400> SEQUENCE: 2
tatagagaaa gaggatctgt tgattctttt aatgaattac ctccatttaa             50

<210> SEQ ID NO 3
<211> LENGTH: 1803
<212> TYPE: DNA
<213> ORGANISM: Bacillus thuringiensis
<220> FEATURE:
<221> NAME/KEY: CDS
<222> LOCATION: (1)..(1803)
<223> OTHER INFORMATION: TIC900

<400> SEQUENCE: 3 atg aat tca aag gaa cat gat tat cta aaa gtt tgt aat gat tta agt        48
Met Asn Ser Lys Glu His Asp Tyr Leu Lys Val Cys Asn Asp Leu Ser
 1               5                  10                  15 gac gcc aat att aat atg gag cgg ttt gat aag aat gat gca ctg gaa        96
Asp Ala Asn Ile Asn Met Glu Arg Phe Asp Lys Asn Asp Ala Leu Glu
             20                  25                  30 att ggt atg tcc att gta tct gaa ctt att ggt atg att cca ggc gga       144
Ile Gly Met Ser Ile Val Ser Glu Leu Ile Gly Met Ile Pro Gly Gly
         35                  40                  45 aca gct ttg caa ttt gtg ttt aat caa ttg tgg tct cgt tta ggt gat       192
Thr Ala Leu Gln Phe Val Phe Asn Gln Leu Trp Ser Arg Leu Gly Asp
     50                  55                  60 tct gga tgg aat gcg ttc atg gaa cat gtg gag gaa tta att gat act       240
Ser Gly Trp Asn Ala Phe Met Glu His Val Glu Glu Leu Ile Asp Thr
 65                  70                  75                  80 aaa ata gaa ggg tat gca aaa aat aaa gcc tta tct gaa tta gca ggt       288
Lys Ile Glu Gly Tyr Ala Lys Asn Lys Ala Leu Ser Glu Leu Ala Gly
                 85                  90                  95 ata caa aga aac ctt gaa aca tat ata caa tta cgt aat gaa tgg gaa       336
Ile Gln Arg Asn Leu Glu Thr Tyr Ile Gln Leu Arg Asn Glu Trp Glu
            100                 105                 110 aat gat att gaa aac tca aag gct caa ggt aag gta gct aat tac tat       384
Asn Asp Ile Glu Asn Ser Lys Ala Gln Gly Lys Val Ala Asn Tyr Tyr
        115                 120                 125 gaa agt ctt gag cag gcg gtt gaa agg agt atg cct caa ttt gca gtg       432
Glu Ser Leu Glu Gln Ala Val Glu Arg Ser Met Pro Gln Phe Ala Val
    130                 135                 140 ggg aat ttt gaa gta cca ctt tta act gtt tat gtg caa gct gct aat       480
Gly Asn Phe Glu Val Pro Leu Leu Thr Val Tyr Val Gln Ala Ala Asn
145                 150                 155                 160 ctt cat tta tta tta tta aga gat gtt tca gtt tat gga aag cgt tgg       528
Leu His Leu Leu Leu Leu Arg Asp Val Ser Val Tyr Gly Lys Arg Trp
                165                 170                 175 gga tgg tcg gag cag aaa att aaa att tat tat gat aga cag att aag       576
Gly Trp Ser Glu Gln Lys Ile Lys Ile Tyr Tyr Asp Arg Gln Ile Lys
            180                 185                 190 tat acc cat gaa tac aca aat cat tgt gta aat tgg tat aat aaa gga       624
Tyr Thr His Glu Tyr Thr Asn His Cys Val Asn Trp Tyr Asn Lys Gly
        195                 200                 205 ctt gag aga tta aaa aat aaa ggt tct tct tat caa gat tgg tac aat       672
Leu Glu Arg Leu Lys Asn Lys Gly Ser Ser Tyr Gln Asp Trp Tyr Asn
    210                 215                 220 tat aat cgt ttc cgt aga gaa atg act ctt act gtt tta gat atc gtt       720
Tyr Asn Arg Phe Arg Arg Glu Met Thr Leu Thr Val Leu Asp Ile Val
225                 230                 235                 240 gct tta ttc ccg cac tat gat gta caa act tat cca ata aca acc gtt       768
Ala Leu Phe Pro His Tyr Asp Val Gln Thr Tyr Pro Ile Thr Thr Val
                245                 250                 255
```

|     |     |     |     |     |     |     |     |     |     |     |     |     |     |     |     | |
|---|---|---|---|---|---|---|---|---|---|---|---|---|---|---|---|---|
| gct | cag | tta | aca | agg | gaa | gtt | tat | acg | gat | cct | tta | ctt | aat | ttt | aat | 816 |
| Ala | Gln | Leu | Thr | Arg | Glu | Val | Tyr | Thr | Asp | Pro | Leu | Leu | Asn | Phe | Asn | |
|     |     |     | 260 |     |     |     |     | 265 |     |     |     |     | 270 |     |     | |
| cct | aaa | tta | cat | tct | gtg | tct | caa | tta | cct | agt | ttt | agt | gac | atg | gaa | 864 |
| Pro | Lys | Leu | His | Ser | Val | Ser | Gln | Leu | Pro | Ser | Phe | Ser | Asp | Met | Glu | |
|     |     | 275 |     |     |     |     | 280 |     |     |     |     | 285 |     |     |     | |
| aat | gca | aca | att | aga | act | cca | cat | ctg | atg | gaa | ttt | tta | aga | atg | cta | 912 |
| Asn | Ala | Thr | Ile | Arg | Thr | Pro | His | Leu | Met | Glu | Phe | Leu | Arg | Met | Leu | |
|     | 290 |     |     |     |     | 295 |     |     |     |     | 300 |     |     |     |     | |
| aca | att | tat | aca | gat | tgg | tat | agt | gtg | gga | aga | aac | tat | tat | tgg | gga | 960 |
| Thr | Ile | Tyr | Thr | Asp | Trp | Tyr | Ser | Val | Gly | Arg | Asn | Tyr | Tyr | Trp | Gly | |
| 305 |     |     |     |     | 310 |     |     |     |     | 315 |     |     |     |     | 320 | |
| gga | cat | cgc | gtg | acg | tct | tac | cat | gta | gga | gga | gag | aat | ata | aga | tca | 1008 |
| Gly | His | Arg | Val | Thr | Ser | Tyr | His | Val | Gly | Gly | Glu | Asn | Ile | Arg | Ser | |
|     |     |     |     | 325 |     |     |     |     | 330 |     |     |     |     | 335 |     | |
| cct | cta | tat | ggt | aga | gag | gca | aat | caa | gag | gtt | cct | aga | gat | ttt | tat | 1056 |
| Pro | Leu | Tyr | Gly | Arg | Glu | Ala | Asn | Gln | Glu | Val | Pro | Arg | Asp | Phe | Tyr | |
|     |     |     | 340 |     |     |     |     | 345 |     |     |     |     | 350 |     |     | |
| ttt | tat | gga | ccc | gtt | ttt | aag | acg | tta | tca | aag | ccg | act | cta | aga | cca | 1104 |
| Phe | Tyr | Gly | Pro | Val | Phe | Lys | Thr | Leu | Ser | Lys | Pro | Thr | Leu | Arg | Pro | |
|     |     | 355 |     |     |     |     | 360 |     |     |     |     | 365 |     |     |     | |
| tta | cag | cag | cct | gca | cca | gct | cct | cct | ttt | aat | tta | cgt | agc | tta | gag | 1152 |
| Leu | Gln | Gln | Pro | Ala | Pro | Ala | Pro | Pro | Phe | Asn | Leu | Arg | Ser | Leu | Glu | |
|     | 370 |     |     |     |     | 375 |     |     |     |     | 380 |     |     |     |     | |
| gga | gta | gaa | ttc | cac | act | tct | aca | ggt | agt | ttt | atg | tat | cgt | gaa | aga | 1200 |
| Gly | Val | Glu | Phe | His | Thr | Ser | Thr | Gly | Ser | Phe | Met | Tyr | Arg | Glu | Arg | |
| 385 |     |     |     |     | 390 |     |     |     |     | 395 |     |     |     |     | 400 | |
| gga | tcg | gta | gat | tct | ttt | aat | gag | tta | ccg | cct | ttt | aat | cca | gtt | ggg | 1248 |
| Gly | Ser | Val | Asp | Ser | Phe | Asn | Glu | Leu | Pro | Pro | Phe | Asn | Pro | Val | Gly | |
|     |     |     |     | 405 |     |     |     |     | 410 |     |     |     |     | 415 |     | |
| tta | cct | cat | aag | gta | tac | agt | cac | cgt | tta | tgt | cat | gca | acg | ttt | gtt | 1296 |
| Leu | Pro | His | Lys | Val | Tyr | Ser | His | Arg | Leu | Cys | His | Ala | Thr | Phe | Val | |
|     |     |     | 420 |     |     |     |     | 425 |     |     |     |     | 430 |     |     | |
| cgt | aaa | tct | ggg | acc | cct | tat | tta | aca | aca | ggt | gcc | atc | ttt | tct | tgg | 1344 |
| Arg | Lys | Ser | Gly | Thr | Pro | Tyr | Leu | Thr | Thr | Gly | Ala | Ile | Phe | Ser | Trp | |
|     |     | 435 |     |     |     |     | 440 |     |     |     |     | 445 |     |     |     | |
| aca | cat | cgt | agt | gct | gaa | gaa | acc | aat | aca | att | gaa | tca | aat | att | att | 1392 |
| Thr | His | Arg | Ser | Ala | Glu | Glu | Thr | Asn | Thr | Ile | Glu | Ser | Asn | Ile | Ile | |
|     | 450 |     |     |     |     | 455 |     |     |     |     | 460 |     |     |     |     | |
| acg | caa | atc | ccg | tta | gta | aaa | gca | tat | caa | att | gga | tca | ggc | act | act | 1440 |
| Thr | Gln | Ile | Pro | Leu | Val | Lys | Ala | Tyr | Gln | Ile | Gly | Ser | Gly | Thr | Thr | |
| 465 |     |     |     |     | 470 |     |     |     |     | 475 |     |     |     |     | 480 | |
| gta | agg | aaa | gga | cca | gga | ttc | aca | gga | ggg | gat | ata | ctt | cga | aga | aca | 1488 |
| Val | Arg | Lys | Gly | Pro | Gly | Phe | Thr | Gly | Gly | Asp | Ile | Leu | Arg | Arg | Thr | |
|     |     |     |     | 485 |     |     |     |     | 490 |     |     |     |     | 495 |     | |
| ggt | cct | gga | aca | ttt | gga | gat | atg | aga | ata | aat | att | aat | gca | cca | tta | 1536 |
| Gly | Pro | Gly | Thr | Phe | Gly | Asp | Met | Arg | Ile | Asn | Ile | Asn | Ala | Pro | Leu | |
|     |     |     | 500 |     |     |     |     | 505 |     |     |     |     | 510 |     |     | |
| tct | gaa | aga | tat | cgt | gta | agg | att | cgt | tat | gct | tct | acg | aca | gat | tta | 1584 |
| Ser | Glu | Arg | Tyr | Arg | Val | Arg | Ile | Arg | Tyr | Ala | Ser | Thr | Thr | Asp | Leu | |
|     |     | 515 |     |     |     |     | 520 |     |     |     |     | 525 |     |     |     | |
| caa | ttt | gtc | acg | agt | att | aat | ggg | gcc | acc | att | aat | att | ggt | aac | ttc | 1632 |
| Gln | Phe | Val | Thr | Ser | Ile | Asn | Gly | Ala | Thr | Ile | Asn | Ile | Gly | Asn | Phe | |
|     | 530 |     |     |     |     | 535 |     |     |     |     | 540 |     |     |     |     | |
| cca | aaa | act | att | aat | aat | cta | aat | act | tta | ggt | tct | gag | ggc | tat | aga | 1680 |
| Pro | Lys | Thr | Ile | Asn | Asn | Leu | Asn | Thr | Leu | Gly | Ser | Glu | Gly | Tyr | Arg | |
| 545 |     |     |     |     | 550 |     |     |     |     | 555 |     |     |     |     | 560 | |
| aca | gta | tcg | ttt | agt | act | cca | ttt | agt | ttc | tca | aat | gca | caa | agc | ata | 1728 |
| Thr | Val | Ser | Phe | Ser | Thr | Pro | Phe | Ser | Phe | Ser | Asn | Ala | Gln | Ser | Ile | |
|     |     |     | 565 |     |     |     |     | 570 |     |     |     |     | 575 |     |     | |

```
ttt aga tta ggt ata caa gca ttt tct gga gtt caa gaa gtt tat gtg      1776
Phe Arg Leu Gly Ile Gln Ala Phe Ser Gly Val Gln Glu Val Tyr Val
        580                 585                 590 gat aaa att gaa ttt att cct gtt gaa                                  1803
Asp Lys Ile Glu Phe Ile Pro Val Glu
        595                 600

<210> SEQ ID NO 4
<211> LENGTH: 601
<212> TYPE: PRT
<213> ORGANISM: Bacillus thuringiensis

<400> SEQUENCE: 4

Met Asn Ser Lys Glu His Asp Tyr Leu Lys Val Cys Asn Asp Leu Ser
1               5                   10                  15

Asp Ala Asn Ile Asn Met Glu Arg Phe Asp Lys Asn Asp Ala Leu Glu
            20                  25                  30

Ile Gly Met Ser Ile Val Ser Glu Leu Ile Gly Met Ile Pro Gly Gly
        35                  40                  45

Thr Ala Leu Gln Phe Val Phe Asn Gln Leu Trp Ser Arg Leu Gly Asp
    50                  55                  60

Ser Gly Trp Asn Ala Phe Met Glu His Val Glu Glu Leu Ile Asp Thr
65                  70                  75                  80

Lys Ile Glu Gly Tyr Ala Lys Asn Lys Ala Leu Ser Glu Leu Ala Gly
                85                  90                  95

Ile Gln Arg Asn Leu Glu Thr Tyr Ile Gln Leu Arg Asn Glu Trp Glu
            100                 105                 110

Asn Asp Ile Glu Asn Ser Lys Ala Gln Gly Lys Val Ala Asn Tyr Tyr
        115                 120                 125

Glu Ser Leu Glu Gln Ala Val Glu Arg Ser Met Pro Gln Phe Ala Val
    130                 135                 140

Gly Asn Phe Glu Val Pro Leu Leu Thr Val Tyr Val Gln Ala Ala Asn
145                 150                 155                 160

Leu His Leu Leu Leu Leu Arg Asp Val Ser Val Tyr Gly Lys Arg Trp
                165                 170                 175

Gly Trp Ser Glu Gln Lys Ile Lys Ile Tyr Tyr Asp Arg Gln Ile Lys
            180                 185                 190

Tyr Thr His Glu Tyr Thr Asn His Cys Val Asn Trp Tyr Asn Lys Gly
        195                 200                 205

Leu Glu Arg Leu Lys Asn Lys Gly Ser Ser Tyr Gln Asp Trp Tyr Asn
    210                 215                 220

Tyr Asn Arg Phe Arg Arg Glu Met Thr Leu Thr Val Leu Asp Ile Val
225                 230                 235                 240

Ala Leu Phe Pro His Tyr Asp Val Gln Thr Tyr Pro Ile Thr Thr Val
                245                 250                 255

Ala Gln Leu Thr Arg Glu Val Tyr Thr Asp Pro Leu Leu Asn Phe Asn
            260                 265                 270

Pro Lys Leu His Ser Val Ser Gln Leu Pro Ser Phe Ser Asp Met Glu
        275                 280                 285

Asn Ala Thr Ile Arg Thr Pro His Leu Met Glu Phe Leu Arg Met Leu
    290                 295                 300

Thr Ile Tyr Thr Asp Trp Tyr Ser Val Gly Arg Asn Tyr Tyr Trp Gly
305                 310                 315                 320

Gly His Arg Val Thr Ser Tyr His Val Gly Gly Glu Asn Ile Arg Ser
                325                 330                 335
```

-continued

```
Pro Leu Tyr Gly Arg Glu Ala Asn Gln Glu Val Pro Arg Asp Phe Tyr
            340                 345                 350

Phe Tyr Gly Pro Val Phe Lys Thr Leu Ser Lys Pro Thr Leu Arg Pro
        355                 360                 365

Leu Gln Gln Pro Ala Pro Ala Pro Pro Phe Asn Leu Arg Ser Leu Glu
    370                 375                 380

Gly Val Glu Phe His Thr Ser Thr Gly Ser Phe Met Tyr Arg Glu Arg
385                 390                 395                 400

Gly Ser Val Asp Ser Phe Asn Glu Leu Pro Pro Phe Asn Pro Val Gly
                405                 410                 415

Leu Pro His Lys Val Tyr Ser His Arg Leu Cys His Ala Thr Phe Val
            420                 425                 430

Arg Lys Ser Gly Thr Pro Tyr Leu Thr Thr Gly Ala Ile Phe Ser Trp
        435                 440                 445

Thr His Arg Ser Ala Glu Glu Thr Asn Thr Ile Glu Ser Asn Ile Ile
    450                 455                 460

Thr Gln Ile Pro Leu Val Lys Ala Tyr Gln Ile Gly Ser Gly Thr Thr
465                 470                 475                 480

Val Arg Lys Gly Pro Gly Phe Thr Gly Gly Asp Ile Leu Arg Arg Thr
                485                 490                 495

Gly Pro Gly Thr Phe Gly Asp Met Arg Ile Asn Ile Asn Ala Pro Leu
            500                 505                 510

Ser Glu Arg Tyr Arg Val Arg Ile Arg Tyr Ala Ser Thr Thr Asp Leu
        515                 520                 525

Gln Phe Val Thr Ser Ile Asn Gly Ala Thr Ile Asn Ile Gly Asn Phe
    530                 535                 540

Pro Lys Thr Ile Asn Asn Leu Asn Thr Leu Gly Ser Glu Gly Tyr Arg
545                 550                 555                 560

Thr Val Ser Phe Ser Thr Pro Phe Ser Phe Ser Asn Ala Gln Ser Ile
                565                 570                 575

Phe Arg Leu Gly Ile Gln Ala Phe Ser Gly Val Gln Glu Val Tyr Val
            580                 585                 590

Asp Lys Ile Glu Phe Ile Pro Val Glu
        595                 600
```

<210> SEQ ID NO 5
<211> LENGTH: 1803
<212> TYPE: DNA
<213> ORGANISM: Bacillus thuringiensis
<220> FEATURE:
<221> NAME/KEY: CDS
<222> LOCATION: (1)..(1803)
<223> OTHER INFORMATION: TIC402

<400> SEQUENCE: 5

```
atg aat tca aag gaa cat gat tat cta aaa gtt tgt aat gat tta agt      48
Met Asn Ser Lys Glu His Asp Tyr Leu Lys Val Cys Asn Asp Leu Ser
1               5                   10                  15 gac gcc aat att aat atg gaa cgg ttt gat aag aat gat gca ctg gaa      96
Asp Ala Asn Ile Asn Met Glu Arg Phe Asp Lys Asn Asp Ala Leu Glu
            20                  25                  30 att ggt atg tcc att gta tct gaa ctt att ggt atg att cca ggc gga     144
Ile Gly Met Ser Ile Val Ser Glu Leu Ile Gly Met Ile Pro Gly Gly
        35                  40                  45 aca gct ttg caa ttt gtg ttt aat caa ttg tgg tct cgt tta ggt gat     192
Thr Ala Leu Gln Phe Val Phe Asn Gln Leu Trp Ser Arg Leu Gly Asp
    50                  55                  60 tct gga tgg aat gcg ttc atg gaa cat gtg gag gaa tta att gat act     240
```

-continued

| | | | | | | | | | | | | | | | |
|---|---|---|---|---|---|---|---|---|---|---|---|---|---|---|---|
| Ser | Gly | Trp | Asn | Ala | Phe | Met | Glu | His | Val | Glu | Glu | Leu | Ile | Asp | Thr |
| 65 | | | | 70 | | | | 75 | | | | 80 | | | |

| aaa | ata | gaa | ggg | tat | gca | aaa | aat | aaa | gcc | tta | tct | gaa | tta | gca | ggt | 288 |
|---|---|---|---|---|---|---|---|---|---|---|---|---|---|---|---|---|
| Lys | Ile | Glu | Gly | Tyr | Ala | Lys | Asn | Lys | Ala | Leu | Ser | Glu | Leu | Ala | Gly | |
| | | | | 85 | | | | 90 | | | | 95 | | | | |

| ata | caa | aga | aac | ctt | gaa | aca | tat | ata | caa | tta | cgt | aat | gaa | tgg | gaa | 336 |
|---|---|---|---|---|---|---|---|---|---|---|---|---|---|---|---|---|
| Ile | Gln | Arg | Asn | Leu | Glu | Thr | Tyr | Ile | Gln | Leu | Arg | Asn | Glu | Trp | Glu | |
| | | | 100 | | | | | 105 | | | | 110 | | | | |

| aat | gat | att | gaa | aac | tca | aag | gct | caa | ggt | aag | gta | gct | aat | tac | tat | 384 |
|---|---|---|---|---|---|---|---|---|---|---|---|---|---|---|---|---|
| Asn | Asp | Ile | Glu | Asn | Ser | Lys | Ala | Gln | Gly | Lys | Val | Ala | Asn | Tyr | Tyr | |
| | | | 115 | | | | 120 | | | | | 125 | | | | |

| gaa | agt | ctt | gag | cag | gcg | gtt | gaa | agg | agt | atg | cct | caa | ttt | gca | gtg | 432 |
|---|---|---|---|---|---|---|---|---|---|---|---|---|---|---|---|---|
| Glu | Ser | Leu | Glu | Gln | Ala | Val | Glu | Arg | Ser | Met | Pro | Gln | Phe | Ala | Val | |
| | 130 | | | | | 135 | | | | | 140 | | | | | |

| gag | aat | ttt | gaa | gta | cca | ctt | tta | act | gtc | tat | gtg | caa | gct | gct | aat | 480 |
|---|---|---|---|---|---|---|---|---|---|---|---|---|---|---|---|---|
| Glu | Asn | Phe | Glu | Val | Pro | Leu | Leu | Thr | Val | Tyr | Val | Gln | Ala | Ala | Asn | |
| 145 | | | | | 150 | | | | | 155 | | | | | 160 | |

| ctt | cat | tta | tta | tta | tta | aga | gat | gtt | tca | gtt | tat | gga | aag | tgt | tgg | 528 |
|---|---|---|---|---|---|---|---|---|---|---|---|---|---|---|---|---|
| Leu | His | Leu | Leu | Leu | Leu | Arg | Asp | Val | Ser | Val | Tyr | Gly | Lys | Cys | Trp | |
| | | | | 165 | | | | | 170 | | | | | 175 | | |

| gga | tgg | tcg | gag | cag | aaa | att | aaa | att | tat | tat | gat | aaa | cag | att | aag | 576 |
|---|---|---|---|---|---|---|---|---|---|---|---|---|---|---|---|---|
| Gly | Trp | Ser | Glu | Gln | Lys | Ile | Lys | Ile | Tyr | Tyr | Asp | Lys | Gln | Ile | Lys | |
| | | | 180 | | | | | 185 | | | | | 190 | | | |

| tat | acc | cat | gaa | tac | aca | aat | cat | tgt | gta | aat | tgg | tat | aat | aaa | gga | 624 |
|---|---|---|---|---|---|---|---|---|---|---|---|---|---|---|---|---|
| Tyr | Thr | His | Glu | Tyr | Thr | Asn | His | Cys | Val | Asn | Trp | Tyr | Asn | Lys | Gly | |
| | | | 195 | | | | | 200 | | | | | 205 | | | |

| ctt | gag | aga | tta | aaa | aat | aaa | ggt | tct | tct | tat | caa | gat | tgg | tac | aat | 672 |
|---|---|---|---|---|---|---|---|---|---|---|---|---|---|---|---|---|
| Leu | Glu | Arg | Leu | Lys | Asn | Lys | Gly | Ser | Ser | Tyr | Gln | Asp | Trp | Tyr | Asn | |
| | 210 | | | | | 215 | | | | | 220 | | | | | |

| tat | aat | cgt | ttc | cgt | aga | gaa | atg | act | ctt | act | gtt | tta | gat | atc | gtt | 720 |
|---|---|---|---|---|---|---|---|---|---|---|---|---|---|---|---|---|
| Tyr | Asn | Arg | Phe | Arg | Arg | Glu | Met | Thr | Leu | Thr | Val | Leu | Asp | Ile | Val | |
| 225 | | | | | 230 | | | | | 235 | | | | | 240 | |

| gct | tta | ttc | ccg | cac | tat | gat | gta | caa | act | tat | cca | ata | aca | acc | gtt | 768 |
|---|---|---|---|---|---|---|---|---|---|---|---|---|---|---|---|---|
| Ala | Leu | Phe | Pro | His | Tyr | Asp | Val | Gln | Thr | Tyr | Pro | Ile | Thr | Thr | Val | |
| | | | | 245 | | | | | 250 | | | | | 255 | | |

| gct | cag | cta | aca | agg | gaa | gtt | tat | acg | gat | cct | tta | ctt | aat | ttt | aat | 816 |
|---|---|---|---|---|---|---|---|---|---|---|---|---|---|---|---|---|
| Ala | Gln | Leu | Thr | Arg | Glu | Val | Tyr | Thr | Asp | Pro | Leu | Leu | Asn | Phe | Asn | |
| | | | 260 | | | | | 265 | | | | | 270 | | | |

| cct | aaa | tta | cat | tct | gtg | tct | caa | tta | cct | agt | ttt | agt | gac | atg | gaa | 864 |
|---|---|---|---|---|---|---|---|---|---|---|---|---|---|---|---|---|
| Pro | Lys | Leu | His | Ser | Val | Ser | Gln | Leu | Pro | Ser | Phe | Ser | Asp | Met | Glu | |
| | | | 275 | | | | | 280 | | | | | 285 | | | |

| aat | gca | aca | att | aga | act | cca | cat | ctg | atg | gaa | ttt | tta | aga | atg | cta | 912 |
|---|---|---|---|---|---|---|---|---|---|---|---|---|---|---|---|---|
| Asn | Ala | Thr | Ile | Arg | Thr | Pro | His | Leu | Met | Glu | Phe | Leu | Arg | Met | Leu | |
| | | 290 | | | | | 295 | | | | | 300 | | | | |

| aca | att | tat | aca | gat | tgg | tat | agt | gtg | gga | aga | aac | tat | tat | tgg | gga | 960 |
|---|---|---|---|---|---|---|---|---|---|---|---|---|---|---|---|---|
| Thr | Ile | Tyr | Thr | Asp | Trp | Tyr | Ser | Val | Gly | Arg | Asn | Tyr | Tyr | Trp | Gly | |
| 305 | | | | | 310 | | | | | 315 | | | | | 320 | |

| gga | cat | cgc | gtg | acg | tct | tac | cat | gta | gga | gga | gag | aat | ata | aga | tca | 1008 |
|---|---|---|---|---|---|---|---|---|---|---|---|---|---|---|---|---|
| Gly | His | Arg | Val | Thr | Ser | Tyr | His | Val | Gly | Gly | Glu | Asn | Ile | Arg | Ser | |
| | | | | 325 | | | | | 330 | | | | | 335 | | |

| cct | cta | tat | ggt | aga | gag | gca | aat | caa | gag | gtt | cct | aga | gat | ttt | tat | 1056 |
|---|---|---|---|---|---|---|---|---|---|---|---|---|---|---|---|---|
| Pro | Leu | Tyr | Gly | Arg | Glu | Ala | Asn | Gln | Glu | Val | Pro | Arg | Asp | Phe | Tyr | |
| | | | 340 | | | | | 345 | | | | | 350 | | | |

| ttt | tat | gga | ccc | gtt | ttt | aag | acg | tta | tca | aag | ccg | act | cta | aga | cca | 1104 |
|---|---|---|---|---|---|---|---|---|---|---|---|---|---|---|---|---|
| Phe | Tyr | Gly | Pro | Val | Phe | Lys | Thr | Leu | Ser | Lys | Pro | Thr | Leu | Arg | Pro | |
| | | 355 | | | | | 360 | | | | | 365 | | | | |

| tta | cag | cag | cct | gca | cca | gct | cct | cct | ttt | aat | tta | cgt | agc | tta | gag | 1152 |
|---|---|---|---|---|---|---|---|---|---|---|---|---|---|---|---|---|
| Leu | Gln | Gln | Pro | Ala | Pro | Ala | Pro | Pro | Phe | Asn | Leu | Arg | Ser | Leu | Glu | |
| | 370 | | | | | 375 | | | | | 380 | | | | | |

| gga | gta | gaa | ttc | cac | act | cct | aca | ggt | agt | ttt | atg | tat | cgt | gaa | aga | 1200 |

```
                                                                            -continued Gly Val Glu Phe His Thr Pro Thr Gly Ser Phe Met Tyr Arg Glu Arg
385                 390                 395                 400 gga tcg gta gat tct ttt aat gag ttg ccg cct ttt aat cca gtt ggg      1248
Gly Ser Val Asp Ser Phe Asn Glu Leu Pro Pro Phe Asn Pro Val Gly
                405                 410                 415 tta cct cat aag gta tac agt cac cgt tta tgt cat gca acg ttt gtt      1296
Leu Pro His Lys Val Tyr Ser His Arg Leu Cys His Ala Thr Phe Val
            420                 425                 430 cgt aaa tct ggg acc cct tat tta aca aca ggt gcc atc ttt tct tgg      1344
Arg Lys Ser Gly Thr Pro Tyr Leu Thr Thr Gly Ala Ile Phe Ser Trp
        435                 440                 445 aca cat cgt agt gct gaa gaa acc aat aca att gaa tca aat att att      1392
Thr His Arg Ser Ala Glu Glu Thr Asn Thr Ile Glu Ser Asn Ile Ile
    450                 455                 460 acg caa atc ccg tta gta aaa gca tat caa att ggg tca ggc act act      1440
Thr Gln Ile Pro Leu Val Lys Ala Tyr Gln Ile Gly Ser Gly Thr Thr
465                 470                 475                 480 gta agg aaa gga cca gga ttc aca gga ggg gat ata ctt cga aga aca      1488
Val Arg Lys Gly Pro Gly Phe Thr Gly Gly Asp Ile Leu Arg Arg Thr
                485                 490                 495 ggt cct gga aca ttt gga gat atg aga ata aat att aat gca cca tta      1536
Gly Pro Gly Thr Phe Gly Asp Met Arg Ile Asn Ile Asn Ala Pro Leu
            500                 505                 510 tct caa aga tat cgt gta agg att cgt tat gct tct acg aca gat tta      1584
Ser Gln Arg Tyr Arg Val Arg Ile Arg Tyr Ala Ser Thr Thr Asp Leu
        515                 520                 525 caa ttt gtc acg agt att aat ggg acc acc att aat att ggt aac ttc      1632
Gln Phe Val Thr Ser Ile Asn Gly Thr Thr Ile Asn Ile Gly Asn Phe
    530                 535                 540 ccg aaa act att aat aat cta aat act tta ggt tct gag ggc tat aga      1680
Pro Lys Thr Ile Asn Asn Leu Asn Thr Leu Gly Ser Glu Gly Tyr Arg
545                 550                 555                 560 aca gta tcg ttt agt act cca ttt agt ttc tca aat gca caa agc ata      1728
Thr Val Ser Phe Ser Thr Pro Phe Ser Phe Ser Asn Ala Gln Ser Ile
                565                 570                 575 ttt aga tta ggt ata caa gca ttt tct gga gtt caa gaa gtt tat gtg      1776
Phe Arg Leu Gly Ile Gln Ala Phe Ser Gly Val Gln Glu Val Tyr Val
            580                 585                 590 gat aaa att gaa ttt att cct gtt gaa                                  1803
Asp Lys Ile Glu Phe Ile Pro Val Glu
        595                 600

<210> SEQ ID NO 6
<211> LENGTH: 601
<212> TYPE: PRT
<213> ORGANISM: Bacillus thuringiensis

<400> SEQUENCE: 6

Met Asn Ser Lys Glu His Asp Tyr Leu Lys Val Cys Asn Asp Leu Ser
1               5                   10                  15

Asp Ala Asn Ile Asn Met Glu Arg Phe Asp Lys Asn Asp Ala Leu Glu
            20                  25                  30

Ile Gly Met Ser Ile Val Ser Glu Leu Ile Gly Met Ile Pro Gly Gly
        35                  40                  45

Thr Ala Leu Gln Phe Val Phe Asn Gln Leu Trp Ser Arg Leu Gly Asp
    50                  55                  60

Ser Gly Trp Asn Ala Phe Met Glu His Val Glu Glu Leu Ile Asp Thr
65                  70                  75                  80

Lys Ile Glu Gly Tyr Ala Lys Asn Lys Ala Leu Ser Glu Leu Ala Gly
                85                  90                  95
```

-continued

```
Ile Gln Arg Asn Leu Glu Thr Tyr Ile Gln Leu Arg Asn Glu Trp Glu
            100                 105                 110

Asn Asp Ile Glu Asn Ser Lys Ala Gln Gly Lys Val Ala Asn Tyr Tyr
            115                 120                 125

Glu Ser Leu Glu Gln Ala Val Glu Arg Ser Met Pro Gln Phe Ala Val
            130                 135                 140

Glu Asn Phe Glu Val Pro Leu Leu Thr Val Tyr Val Gln Ala Ala Asn
145                 150                 155                 160

Leu His Leu Leu Leu Arg Asp Val Ser Val Tyr Gly Lys Cys Trp
                165                 170                 175

Gly Trp Ser Glu Gln Lys Ile Lys Ile Tyr Tyr Asp Lys Gln Ile Lys
                180                 185                 190

Tyr Thr His Glu Tyr Thr Asn His Cys Val Asn Trp Tyr Asn Lys Gly
                195                 200                 205

Leu Glu Arg Leu Lys Asn Lys Gly Ser Ser Tyr Gln Asp Trp Tyr Asn
            210                 215                 220

Tyr Asn Arg Phe Arg Arg Glu Met Thr Leu Thr Val Leu Asp Ile Val
225                 230                 235                 240

Ala Leu Phe Pro His Tyr Asp Val Gln Thr Tyr Pro Ile Thr Thr Val
                245                 250                 255

Ala Gln Leu Thr Arg Glu Val Tyr Thr Asp Pro Leu Leu Asn Phe Asn
                260                 265                 270

Pro Lys Leu His Ser Val Ser Gln Leu Pro Ser Phe Ser Asp Met Glu
                275                 280                 285

Asn Ala Thr Ile Arg Thr Pro His Leu Met Glu Phe Leu Arg Met Leu
            290                 295                 300

Thr Ile Tyr Thr Asp Trp Tyr Ser Val Gly Arg Asn Tyr Tyr Trp Gly
305                 310                 315                 320

Gly His Arg Val Thr Ser Tyr His Val Gly Gly Glu Asn Ile Arg Ser
                325                 330                 335

Pro Leu Tyr Gly Arg Glu Ala Asn Gln Glu Val Pro Arg Asp Phe Tyr
            340                 345                 350

Phe Tyr Gly Pro Val Phe Lys Thr Leu Ser Lys Pro Thr Leu Arg Pro
            355                 360                 365

Leu Gln Gln Pro Ala Pro Ala Pro Pro Phe Asn Leu Arg Ser Leu Glu
            370                 375                 380

Gly Val Glu Phe His Thr Pro Thr Gly Ser Phe Met Tyr Arg Glu Arg
385                 390                 395                 400

Gly Ser Val Asp Ser Phe Asn Glu Leu Pro Pro Phe Asn Pro Val Gly
                405                 410                 415

Leu Pro His Lys Val Tyr Ser His Arg Leu Cys His Ala Thr Phe Val
                420                 425                 430

Arg Lys Ser Gly Thr Pro Tyr Leu Thr Thr Gly Ala Ile Phe Ser Trp
            435                 440                 445

Thr His Arg Ser Ala Glu Glu Thr Asn Thr Ile Glu Ser Asn Ile Ile
            450                 455                 460

Thr Gln Ile Pro Leu Val Lys Ala Tyr Gln Ile Gly Ser Gly Thr Thr
465                 470                 475                 480

Val Arg Lys Gly Pro Gly Phe Thr Gly Gly Asp Ile Leu Arg Arg Thr
                485                 490                 495

Gly Pro Gly Thr Phe Gly Asp Met Arg Ile Asn Ile Asn Ala Pro Leu
                500                 505                 510

Ser Gln Arg Tyr Arg Val Arg Ile Arg Tyr Ala Ser Thr Thr Asp Leu
```

```
                    515                 520                 525
Gln Phe Val Thr Ser Ile Asn Gly Thr Thr Ile Asn Ile Gly Asn Phe
    530                 535                 540

Pro Lys Thr Ile Asn Asn Leu Asn Thr Leu Gly Ser Glu Gly Tyr Arg
545                 550                 555                 560

Thr Val Ser Phe Ser Thr Pro Phe Ser Phe Ser Asn Ala Gln Ser Ile
                565                 570                 575

Phe Arg Leu Gly Ile Gln Ala Phe Ser Gly Val Gln Glu Val Tyr Val
                580                 585                 590

Asp Lys Ile Glu Phe Ile Pro Val Glu
            595                 600

<210> SEQ ID NO 7
<211> LENGTH: 1803
<212> TYPE: DNA
<213> ORGANISM: Bacillus thuringiensis
<220> FEATURE:
<221> NAME/KEY: CDS
<222> LOCATION: (1)..(1803)
<223> OTHER INFORMATION: TIC403

<400> SEQUENCE: 7
```

| | | | | | | | | | | | | | | | | |
|---|---|---|---|---|---|---|---|---|---|---|---|---|---|---|---|---|
| atg | aat | tca | aag | gaa | cat | gat | tat | cta | aaa | gtt | tgt | aat | gat | tta | agt | 48 |
| Met | Asn | Ser | Lys | Glu | His | Asp | Tyr | Leu | Lys | Val | Cys | Asn | Asp | Leu | Ser | |
| 1 | | | | 5 | | | | | 10 | | | | | 15 | | |
| gac | gcc | aat | att | aat | atg | gag | cgg | ttt | gat | aag | aat | gat | gca | ctg | gaa | 96 |
| Asp | Ala | Asn | Ile | Asn | Met | Glu | Arg | Phe | Asp | Lys | Asn | Asp | Ala | Leu | Glu | |
| | | 20 | | | | | 25 | | | | | 30 | | | | |
| att | ggt | atg | tcc | att | gta | tct | gaa | ctt | att | ggt | atg | att | cca | ggc | gga | 144 |
| Ile | Gly | Met | Ser | Ile | Val | Ser | Glu | Leu | Ile | Gly | Met | Ile | Pro | Gly | Gly | |
| | | | 35 | | | | | 40 | | | | | 45 | | | |
| aca | gct | ttg | caa | ttt | gtg | ttt | aat | caa | ttg | tgg | tct | cgt | tta | ggt | gat | 192 |
| Thr | Ala | Leu | Gln | Phe | Val | Phe | Asn | Gln | Leu | Trp | Ser | Arg | Leu | Gly | Asp | |
| | 50 | | | | | 55 | | | | | 60 | | | | | |
| tct | gga | tgg | aat | gcg | ttc | atg | gaa | cat | gtg | gag | gaa | tta | att | gat | act | 240 |
| Ser | Gly | Trp | Asn | Ala | Phe | Met | Glu | His | Val | Glu | Glu | Leu | Ile | Asp | Thr | |
| 65 | | | | | 70 | | | | | 75 | | | | | 80 | |
| aaa | ata | gaa | ggg | tat | gca | aaa | aat | aaa | gcc | tta | tct | gaa | tta | gca | ggt | 288 |
| Lys | Ile | Glu | Gly | Tyr | Ala | Lys | Asn | Lys | Ala | Leu | Ser | Glu | Leu | Ala | Gly | |
| | | | | 85 | | | | | 90 | | | | | 95 | | |
| ata | caa | aga | aac | ctt | gaa | aca | tat | ata | caa | tta | cgt | aat | gaa | tgg | gaa | 336 |
| Ile | Gln | Arg | Asn | Leu | Glu | Thr | Tyr | Ile | Gln | Leu | Arg | Asn | Glu | Trp | Glu | |
| | | | 100 | | | | | 105 | | | | | 110 | | | |
| aat | gat | att | gaa | aac | tca | aag | gct | caa | ggt | aag | gta | gct | aat | tac | tat | 384 |
| Asn | Asp | Ile | Glu | Asn | Ser | Lys | Ala | Gln | Gly | Lys | Val | Ala | Asn | Tyr | Tyr | |
| | | 115 | | | | | 120 | | | | | 125 | | | | |
| gaa | agt | ctt | gag | cag | gcg | gtt | gaa | agg | agt | atg | cct | caa | ttt | gca | gtg | 432 |
| Glu | Ser | Leu | Glu | Gln | Ala | Val | Glu | Arg | Ser | Met | Pro | Gln | Phe | Ala | Val | |
| | 130 | | | | | 135 | | | | | 140 | | | | | |
| ggg | aat | ttt | gaa | gta | cca | ctt | tta | act | gtc | tat | gtg | caa | gct | gct | aat | 480 |
| Gly | Asn | Phe | Glu | Val | Pro | Leu | Leu | Thr | Val | Tyr | Val | Gln | Ala | Ala | Asn | |
| 145 | | | | | 150 | | | | | 155 | | | | | 160 | |
| ctt | cat | tta | tta | tta | tta | aga | gat | gtt | tca | gtt | tat | gga | aag | cgt | tgg | 528 |
| Leu | His | Leu | Leu | Leu | Leu | Arg | Asp | Val | Ser | Val | Tyr | Gly | Lys | Arg | Trp | |
| | | | | 165 | | | | | 170 | | | | | 175 | | |
| gga | tgg | tcg | gag | cag | aaa | att | aaa | att | tat | tat | gat | aaa | cag | att | aag | 576 |
| Gly | Trp | Ser | Glu | Gln | Lys | Ile | Lys | Ile | Tyr | Tyr | Asp | Lys | Gln | Ile | Lys | |
| | | | 180 | | | | | 185 | | | | | 190 | | | |
| tat | acc | cat | gaa | tac | aca | aat | cat | tgt | gta | aat | tgg | tat | aat | aaa | gga | 624 |
| Tyr | Thr | His | Glu | Tyr | Thr | Asn | His | Cys | Val | Asn | Trp | Tyr | Asn | Lys | Gly | |
| | | 195 | | | | | 200 | | | | | 205 | | | | |

```
ctt gag aga tta aaa aat aaa ggt tct tct tat caa gat tgg tac aat      672
Leu Glu Arg Leu Lys Asn Lys Gly Ser Ser Tyr Gln Asp Trp Tyr Asn
    210                 215                 220 tat aat cgt ttc cgt aga gaa atg act ctt act gtt tta gat atc gtt      720
Tyr Asn Arg Phe Arg Arg Glu Met Thr Leu Thr Val Leu Asp Ile Val
225                 230                 235                 240 gct tta ttc ccg cac tat gat gta caa act tat cca ata aca acc gtt      768
Ala Leu Phe Pro His Tyr Asp Val Gln Thr Tyr Pro Ile Thr Thr Val
                245                 250                 255 gct cag cta aca agg gaa gtt tat acg gat cct tta ctt aat ttt aat      816
Ala Gln Leu Thr Arg Glu Val Tyr Thr Asp Pro Leu Leu Asn Phe Asn
        260                 265                 270 cct aaa tta cat cct gtg tct caa tta cct agt ttt agt gac atg gaa      864
Pro Lys Leu His Pro Val Ser Gln Leu Pro Ser Phe Ser Asp Met Glu
    275                 280                 285 aat gca aca att aga act cca cat ctg atg gaa ttt tta aga atg cta      912
Asn Ala Thr Ile Arg Thr Pro His Leu Met Glu Phe Leu Arg Met Leu
290                 295                 300 aca att tat aca gat tgg tat agt gtg gga aga aac tat tat tgg gga      960
Thr Ile Tyr Thr Asp Trp Tyr Ser Val Gly Arg Asn Tyr Tyr Trp Gly
305                 310                 315                 320 gga cat cgc gtg acg tct tac cat gta gga gga gag aat ata aga tca     1008
Gly His Arg Val Thr Ser Tyr His Val Gly Gly Glu Asn Ile Arg Ser
                325                 330                 335 cct cta tat ggt aga gag gca aat caa gag gtt cct aga gat ttt tat     1056
Pro Leu Tyr Gly Arg Glu Ala Asn Gln Glu Val Pro Arg Asp Phe Tyr
        340                 345                 350 ttt tat gga ccc gtt ttt aag acg tta tca aag ccg act cta aga cca     1104
Phe Tyr Gly Pro Val Phe Lys Thr Leu Ser Lys Pro Thr Leu Arg Pro
    355                 360                 365 tta cag cag cct gca cca gct cct cct ttt aat tta cgt agc tta gag     1152
Leu Gln Gln Pro Ala Pro Ala Pro Pro Phe Asn Leu Arg Ser Leu Glu
370                 375                 380 gga gta gaa ttc cac act cct aca ggt agt ttt atg tat cgt gaa aga     1200
Gly Val Glu Phe His Thr Pro Thr Gly Ser Phe Met Tyr Arg Glu Arg
385                 390                 395                 400 gga tcg gta gat tct ttt aat gag tta ccg cct ttt aat cca gtt ggg     1248
Gly Ser Val Asp Ser Phe Asn Glu Leu Pro Pro Phe Asn Pro Val Gly
                405                 410                 415 tta cct cat aag gta tac agt cac cgt tta tgt cat gca acg ttt gtt     1296
Leu Pro His Lys Val Tyr Ser His Arg Leu Cys His Ala Thr Phe Val
        420                 425                 430 cgt aaa tct ggg acc cct tat tta aca aca ggt gcc atc ttt tct tgg     1344
Arg Lys Ser Gly Thr Pro Tyr Leu Thr Thr Gly Ala Ile Phe Ser Trp
    435                 440                 445 aca cat cgt agt gct gaa gaa acc aat aca att gaa tca aat att att     1392
Thr His Arg Ser Ala Glu Glu Thr Asn Thr Ile Glu Ser Asn Ile Ile
450                 455                 460 acg caa atc ccg tta gta aaa gca tat caa att ggg tca ggc act act     1440
Thr Gln Ile Pro Leu Val Lys Ala Tyr Gln Ile Gly Ser Gly Thr Thr
465                 470                 475                 480 gta agg aaa gga cca gga ttc aca gga ggg gat ata ctt cga aga aca     1488
Val Arg Lys Gly Pro Gly Phe Thr Gly Gly Asp Ile Leu Arg Arg Thr
                485                 490                 495 ggt cct gga aca ttt gga gat atg aga ata aat att aat gca cca tta     1536
Gly Pro Gly Thr Phe Gly Asp Met Arg Ile Asn Ile Asn Ala Pro Leu
        500                 505                 510 tct caa aga tat cgt gta agg att cgt tat gct tct acg aca gat tta     1584
Ser Gln Arg Tyr Arg Val Arg Ile Arg Tyr Ala Ser Thr Thr Asp Leu
    515                 520                 525
```

```
caa ttt gtc acg agt att aat ggg acc acc att aat att ggt aac ttc    1632
Gln Phe Val Thr Ser Ile Asn Gly Thr Thr Ile Asn Ile Gly Asn Phe
    530                 535                 540 cca aaa act att aat aat cta aat act tta ggt tct gag ggc tat aga    1680
Pro Lys Thr Ile Asn Asn Leu Asn Thr Leu Gly Ser Glu Gly Tyr Arg
545                 550                 555                 560 aca gta tcg ttt agt acc cca ttt agt ttc tca aat gca caa agc ata    1728
Thr Val Ser Phe Ser Thr Pro Phe Ser Phe Ser Asn Ala Gln Ser Ile
                565                 570                 575 ttt aga tta ggt ata caa gca ttt tct gga gtt caa gaa gtt tat gtg    1776
Phe Arg Leu Gly Ile Gln Ala Phe Ser Gly Val Gln Glu Val Tyr Val
            580                 585                 590 gat aaa att gaa ttt att cct gtt gaa                                1803
Asp Lys Ile Glu Phe Ile Pro Val Glu
        595                 600

<210> SEQ ID NO 8
<211> LENGTH: 601
<212> TYPE: PRT
<213> ORGANISM: Bacillus thuringiensis

<400> SEQUENCE: 8

Met Asn Ser Lys Glu His Asp Tyr Leu Lys Val Cys Asn Asp Leu Ser
1               5                   10                  15

Asp Ala Asn Ile Asn Met Glu Arg Phe Asp Lys Asn Asp Ala Leu Glu
            20                  25                  30

Ile Gly Met Ser Ile Val Ser Glu Leu Ile Gly Met Ile Pro Gly Gly
        35                  40                  45

Thr Ala Leu Gln Phe Val Phe Asn Gln Leu Trp Ser Arg Leu Gly Asp
    50                  55                  60

Ser Gly Trp Asn Ala Phe Met Glu His Val Glu Glu Leu Ile Asp Thr
65                  70                  75                  80

Lys Ile Glu Gly Tyr Ala Lys Asn Lys Ala Leu Ser Glu Leu Ala Gly
                85                  90                  95

Ile Gln Arg Asn Leu Glu Thr Tyr Ile Gln Leu Arg Asn Glu Trp Glu
            100                 105                 110

Asn Asp Ile Glu Asn Ser Lys Ala Gln Gly Lys Val Ala Asn Tyr Tyr
        115                 120                 125

Glu Ser Leu Glu Gln Ala Val Glu Arg Ser Met Pro Gln Phe Ala Val
    130                 135                 140

Gly Asn Phe Glu Val Pro Leu Leu Thr Val Tyr Val Gln Ala Ala Asn
145                 150                 155                 160

Leu His Leu Leu Leu Leu Arg Asp Val Ser Val Tyr Gly Lys Arg Trp
                165                 170                 175

Gly Trp Ser Glu Gln Lys Ile Lys Ile Tyr Tyr Asp Lys Gln Ile Lys
            180                 185                 190

Tyr Thr His Glu Tyr Thr Asn His Cys Val Asn Trp Tyr Asn Lys Gly
        195                 200                 205

Leu Glu Arg Leu Lys Asn Lys Gly Ser Ser Tyr Gln Asp Trp Tyr Asn
    210                 215                 220

Tyr Asn Arg Phe Arg Arg Glu Met Thr Leu Thr Val Leu Asp Ile Val
225                 230                 235                 240

Ala Leu Phe Pro His Tyr Asp Val Gln Thr Tyr Pro Ile Thr Thr Val
                245                 250                 255

Ala Gln Leu Thr Arg Glu Val Tyr Thr Asp Pro Leu Leu Asn Phe Asn
            260                 265                 270
```

```
Pro Lys Leu His Pro Val Ser Gln Leu Pro Ser Phe Ser Asp Met Glu
    275                 280                 285
Asn Ala Thr Ile Arg Thr Pro His Leu Met Glu Phe Leu Arg Met Leu
290                 295                 300
Thr Ile Tyr Thr Asp Trp Tyr Ser Val Gly Arg Asn Tyr Tyr Trp Gly
305                 310                 315                 320
Gly His Arg Val Thr Ser Tyr His Val Gly Gly Glu Asn Ile Arg Ser
                325                 330                 335
Pro Leu Tyr Gly Arg Glu Ala Asn Gln Glu Val Pro Arg Asp Phe Tyr
            340                 345                 350
Phe Tyr Gly Pro Val Phe Lys Thr Leu Ser Lys Pro Thr Leu Arg Pro
        355                 360                 365
Leu Gln Gln Pro Ala Pro Ala Pro Pro Phe Asn Leu Arg Ser Leu Glu
    370                 375                 380
Gly Val Glu Phe His Thr Pro Thr Gly Ser Phe Met Tyr Arg Glu Arg
385                 390                 395                 400
Gly Ser Val Asp Ser Phe Asn Glu Leu Pro Pro Phe Asn Pro Val Gly
                405                 410                 415
Leu Pro His Lys Val Tyr Ser Arg Leu Cys His Ala Thr Phe Val
            420                 425                 430
Arg Lys Ser Gly Thr Pro Tyr Leu Thr Thr Gly Ala Ile Phe Ser Trp
        435                 440                 445
Thr His Arg Ser Ala Glu Glu Thr Asn Thr Ile Glu Ser Asn Ile Ile
    450                 455                 460
Thr Gln Ile Pro Leu Val Lys Ala Tyr Gln Ile Gly Ser Gly Thr Thr
465                 470                 475                 480
Val Arg Lys Gly Pro Gly Phe Thr Gly Gly Asp Ile Leu Arg Arg Thr
                485                 490                 495
Gly Pro Gly Thr Phe Gly Asp Met Arg Ile Asn Ile Asn Ala Pro Leu
            500                 505                 510
Ser Gln Arg Tyr Arg Val Arg Ile Arg Tyr Ala Ser Thr Thr Asp Leu
        515                 520                 525
Gln Phe Val Thr Ser Ile Asn Gly Thr Thr Ile Asn Ile Gly Asn Phe
    530                 535                 540
Pro Lys Thr Ile Asn Asn Leu Asn Thr Leu Gly Ser Glu Gly Tyr Arg
545                 550                 555                 560
Thr Val Ser Phe Ser Thr Pro Phe Ser Phe Ser Asn Ala Gln Ser Ile
                565                 570                 575
Phe Arg Leu Gly Ile Gln Ala Phe Ser Gly Val Gln Glu Val Tyr Val
            580                 585                 590
Asp Lys Ile Glu Phe Ile Pro Val Glu
        595                 600

<210> SEQ ID NO 9
<211> LENGTH: 1803
<212> TYPE: DNA
<213> ORGANISM: Bacillus thuringiensis
<220> FEATURE:
<221> NAME/KEY: CDS
<222> LOCATION: (1)..(1803)
<223> OTHER INFORMATION: TIC404

<400> SEQUENCE: 9 atg aat tca aag gaa cat gat tat cta aaa gtt tgt aat gat tta agt      48
Met Asn Ser Lys Glu His Asp Tyr Leu Lys Val Cys Asn Asp Leu Ser
1               5                   10                  15 gac gcc aat att aat atg gag cgg ttt gat aag aat gat gca cta gaa      96
```

-continued

```
                Asp Ala Asn Ile Asn Met Glu Arg Phe Asp Lys Asn Asp Ala Leu Glu
                         20                  25                  30 att ggc atg tcc att gta tct gaa ctt att ggt atg att cca ggc gga       144
Ile Gly Met Ser Ile Val Ser Glu Leu Ile Gly Met Ile Pro Gly Gly
             35                  40                  45 aca gct tta caa ttt gtg ttt aat caa ttg tgg tct cgt tta ggt gat       192
Thr Ala Leu Gln Phe Val Phe Asn Gln Leu Trp Ser Arg Leu Gly Asp
     50                  55                  60 tct gga tgg agt gca ttc atg gaa cat gtg gag gaa tta att gat act       240
Ser Gly Trp Ser Ala Phe Met Glu His Val Glu Glu Leu Ile Asp Thr
65                  70                  75                  80 aaa ata gaa ggg tat gca aaa aat aaa gcc tca tct gaa tta gca ggt       288
Lys Ile Glu Gly Tyr Ala Lys Asn Lys Ala Ser Ser Glu Leu Ala Gly
                 85                  90                  95 ata caa aga aac ctt gaa aca tat ata caa tta cgt aat gca tgg gaa       336
Ile Gln Arg Asn Leu Glu Thr Tyr Ile Gln Leu Arg Asn Ala Trp Glu
             100                 105                 110 aat gat atc gaa aac tca aag gct caa ggt aag gta gct aat tac tat       384
Asn Asp Ile Glu Asn Ser Lys Ala Gln Gly Lys Val Ala Asn Tyr Tyr
         115                 120                 125 gaa agt ctt gag cag gcg gtt gaa agg agt atg cct caa ttt gca gtg       432
Glu Ser Leu Glu Gln Ala Val Glu Arg Ser Met Pro Gln Phe Ala Val
     130                 135                 140 ggg aat ttt gaa gta cca ctt tta act gtt tat gtg caa gct gct aat       480
Gly Asn Phe Glu Val Pro Leu Leu Thr Val Tyr Val Gln Ala Ala Asn
145                 150                 155                 160 ctt cat ata tta tta tta aga gat gtt cta att tac gga aag cgt tgg       528
Leu His Ile Leu Leu Leu Arg Asp Val Leu Ile Tyr Gly Lys Arg Trp
                 165                 170                 175 gga tgg tcg gag cag aaa att aaa att tat tat gat aga cag att aag       576
Gly Trp Ser Glu Gln Lys Ile Lys Ile Tyr Tyr Asp Arg Gln Ile Lys
             180                 185                 190 tat act cat gaa tac aca aat cat tgt gta aat tgg tat aat aaa ggg       624
Tyr Thr His Glu Tyr Thr Asn His Cys Val Asn Trp Tyr Asn Lys Gly
         195                 200                 205 ctt gag aga tta aaa aat aaa ggt tct tct tat caa gat tgg tac aat       672
Leu Glu Arg Leu Lys Asn Lys Gly Ser Ser Tyr Gln Asp Trp Tyr Asn
     210                 215                 220 tat aat cgt ttc cgt aga gaa atg act ctt act gtt tta gat atc gtt       720
Tyr Asn Arg Phe Arg Arg Glu Met Thr Leu Thr Val Leu Asp Ile Val
225                 230                 235                 240 gct tta ttc ccg cac tat gat gta caa act tat cca ata aca acc gtt       768
Ala Leu Phe Pro His Tyr Asp Val Gln Thr Tyr Pro Ile Thr Thr Val
                 245                 250                 255 gct cag cta aca agg gaa gtt tat acg gat cct tta ctt aat ttt aat       816
Ala Gln Leu Thr Arg Glu Val Tyr Thr Asp Pro Leu Leu Asn Phe Asn
             260                 265                 270 cct aaa tta cat tct gtg tct caa tta cct agt ttt agt gac atg gaa       864
Pro Lys Leu His Ser Val Ser Gln Leu Pro Ser Phe Ser Asp Met Glu
         275                 280                 285 aat gca aca att aga act cca cat ttg atg gaa ttt tta aga atg tta       912
Asn Ala Thr Ile Arg Thr Pro His Leu Met Glu Phe Leu Arg Met Leu
     290                 295                 300 aca att tat aca gat tgg tat agt gtg gga aga aac tat tat tgg gga       960
Thr Ile Tyr Thr Asp Trp Tyr Ser Val Gly Arg Asn Tyr Tyr Trp Gly
305                 310                 315                 320 gga cat cgc gtg acg tct tac cat gta gga gga gag aat ata aga tcc      1008
Gly His Arg Val Thr Ser Tyr His Val Gly Gly Glu Asn Ile Arg Ser
                 325                 330                 335 cct cta tat ggt aga gag gca aat caa gag gtt cct aga gat ttt tat      1056
Pro Leu Tyr Gly Arg Glu Ala Asn Gln Glu Val Pro Arg Asp Phe Tyr
```

-continued

| | | | | | | | | | | | | | | |
|---|---|---|---|---|---|---|---|---|---|---|---|---|---|---|
| Pro | Leu | Tyr | Gly | Arg | Glu | Ala | Asn | Gln | Glu | Val | Pro | Arg | Asp | Phe | Tyr |
| | | | 340 | | | | | 345 | | | | 350 | | | |

```
ttt tat gga ccc gtt ttt aag acg tta tca aaa ccg act cta aga cca    1104
Phe Tyr Gly Pro Val Phe Lys Thr Leu Ser Lys Pro Thr Leu Arg Pro
        355                 360                 365 tta cag cag cct gca cca gct cct cct ttt aat tta cgt agc tta gag    1152
Leu Gln Gln Pro Ala Pro Ala Pro Pro Phe Asn Leu Arg Ser Leu Glu
370                 375                 380 gga gta gaa ttc cac act cct aca ggt agt ttt atg tat cgt gaa aga    1200
Gly Val Glu Phe His Thr Pro Thr Gly Ser Phe Met Tyr Arg Glu Arg
385                 390                 395                 400 gga tca gta gat tct ttt aat gag tta ccg cct ttt aat cca gtt ggg    1248
Gly Ser Val Asp Ser Phe Asn Glu Leu Pro Pro Phe Asn Pro Val Gly
                405                 410                 415 tta cct cat aag gta tat agt cac cgt tta tgt cat gca acg ttt gtt    1296
Leu Pro His Lys Val Tyr Ser His Arg Leu Cys His Ala Thr Phe Val
                420                 425                 430 cgt aaa tcg ggg acc cct tat tta aca aca ggt gcc atc ttt act tgg    1344
Arg Lys Ser Gly Thr Pro Tyr Leu Thr Thr Gly Ala Ile Phe Thr Trp
            435                 440                 445 aca cat cgt agt gct gaa gaa acc aat aca att gaa tca aat att att    1392
Thr His Arg Ser Ala Glu Glu Thr Asn Thr Ile Glu Ser Asn Ile Ile
450                 455                 460 acg caa atc ccg tta gta aaa gca tat caa att gga tcg ggc act act    1440
Thr Gln Ile Pro Leu Val Lys Ala Tyr Gln Ile Gly Ser Gly Thr Thr
465                 470                 475                 480 gta agg aaa gga cca gga ttc acg gga ggg gat ata ctt cgg aga aca    1488
Val Arg Lys Gly Pro Gly Phe Thr Gly Gly Asp Ile Leu Arg Arg Thr
                485                 490                 495 ggt cct gga aca ttt gga gat atg aaa gta aat att cat gca cca tta    1536
Gly Pro Gly Thr Phe Gly Asp Met Lys Val Asn Ile His Ala Pro Leu
            500                 505                 510 tcc caa aaa tat cgt gta agg att cgt tat gct tct acg aca gat tta    1584
Ser Gln Lys Tyr Arg Val Arg Ile Arg Tyr Ala Ser Thr Thr Asp Leu
            515                 520                 525 caa ttt gtc acg agt att aat gga acc acc att aat att ggt aac ttc    1632
Gln Phe Val Thr Ser Ile Asn Gly Thr Thr Ile Asn Ile Gly Asn Phe
530                 535                 540 cca aaa act act aat aat cta aat act tta ggt tct gag agc tat aga    1680
Pro Lys Thr Thr Asn Asn Leu Asn Thr Leu Gly Ser Glu Ser Tyr Arg
545                 550                 555                 560 aca gta tcg ttt agt acg cca ttt agt ttc tca aat gca caa agc ata    1728
Thr Val Ser Phe Ser Thr Pro Phe Ser Phe Ser Asn Ala Gln Ser Ile
                565                 570                 575 ttt aga tta ggt ata caa gca ttt tct gga gtt caa gaa gtt tat gtg    1776
Phe Arg Leu Gly Ile Gln Ala Phe Ser Gly Val Gln Glu Val Tyr Val
            580                 585                 590 gat aaa att gaa ttt att cct gtt gaa                                1803
Asp Lys Ile Glu Phe Ile Pro Val Glu
        595                 600
```

<210> SEQ ID NO 10
<211> LENGTH: 601
<212> TYPE: PRT
<213> ORGANISM: Bacillus thuringiensis

<400> SEQUENCE: 10

| | | | | | | | | | | | | | | |
|---|---|---|---|---|---|---|---|---|---|---|---|---|---|---|---|
| Met | Asn | Ser | Lys | Glu | His | Asp | Tyr | Leu | Lys | Val | Cys | Asn | Asp | Leu | Ser |
| 1 | | | | 5 | | | | | 10 | | | | | 15 | |
| Asp | Ala | Asn | Ile | Asn | Met | Glu | Arg | Phe | Asp | Lys | Asn | Asp | Ala | Leu | Glu |
| | | | 20 | | | | | 25 | | | | | 30 | | |

```
Ile Gly Met Ser Ile Val Ser Glu Leu Ile Gly Met Ile Pro Gly Gly
             35                  40                  45

Thr Ala Leu Gln Phe Val Phe Asn Gln Leu Trp Ser Arg Leu Gly Asp
         50                  55                  60

Ser Gly Trp Ser Ala Phe Met Glu His Val Glu Leu Ile Asp Thr
 65                  70                  75                  80

Lys Ile Glu Gly Tyr Ala Lys Asn Lys Ala Ser Ser Glu Leu Ala Gly
                 85                  90                  95

Ile Gln Arg Asn Leu Glu Thr Tyr Ile Gln Leu Arg Asn Ala Trp Glu
             100                 105                 110

Asn Asp Ile Glu Asn Ser Lys Ala Gln Gly Lys Val Ala Asn Tyr Tyr
             115                 120                 125

Glu Ser Leu Glu Gln Ala Val Glu Arg Ser Met Pro Gln Phe Ala Val
             130                 135                 140

Gly Asn Phe Glu Val Pro Leu Leu Thr Val Tyr Val Gln Ala Ala Asn
145                 150                 155                 160

Leu His Ile Leu Leu Leu Arg Asp Val Leu Ile Tyr Gly Lys Arg Trp
                 165                 170                 175

Gly Trp Ser Glu Gln Lys Ile Lys Ile Tyr Tyr Asp Arg Gln Ile Lys
             180                 185                 190

Tyr Thr His Glu Tyr Thr Asn His Cys Val Asn Trp Tyr Asn Lys Gly
             195                 200                 205

Leu Glu Arg Leu Lys Asn Lys Gly Ser Ser Tyr Gln Asp Trp Tyr Asn
             210                 215                 220

Tyr Asn Arg Phe Arg Arg Glu Met Thr Leu Thr Val Leu Asp Ile Val
225                 230                 235                 240

Ala Leu Phe Pro His Tyr Asp Val Gln Thr Tyr Pro Ile Thr Thr Val
                 245                 250                 255

Ala Gln Leu Thr Arg Glu Val Tyr Thr Asp Pro Leu Leu Asn Phe Asn
             260                 265                 270

Pro Lys Leu His Ser Val Ser Gln Leu Pro Ser Phe Ser Asp Met Glu
             275                 280                 285

Asn Ala Thr Ile Arg Thr Pro His Leu Met Glu Phe Leu Arg Met Leu
             290                 295                 300

Thr Ile Tyr Thr Asp Trp Tyr Ser Val Gly Arg Asn Tyr Tyr Trp Gly
305                 310                 315                 320

Gly His Arg Val Thr Ser Tyr His Val Gly Gly Glu Asn Ile Arg Ser
                 325                 330                 335

Pro Leu Tyr Gly Arg Glu Ala Asn Gln Glu Val Pro Arg Asp Phe Tyr
             340                 345                 350

Phe Tyr Gly Pro Val Phe Lys Thr Leu Ser Lys Pro Thr Leu Arg Pro
             355                 360                 365

Leu Gln Gln Pro Ala Pro Ala Pro Pro Phe Asn Leu Arg Ser Leu Glu
             370                 375                 380

Gly Val Glu Phe His Thr Pro Thr Gly Ser Phe Met Tyr Arg Glu Arg
385                 390                 395                 400

Gly Ser Val Asp Ser Phe Asn Glu Leu Pro Pro Phe Asn Pro Val Gly
                 405                 410                 415

Leu Pro His Lys Val Tyr Ser His Arg Leu Cys His Ala Thr Phe Val
             420                 425                 430

Arg Lys Ser Gly Thr Pro Tyr Leu Thr Thr Gly Ala Ile Phe Thr Trp
             435                 440                 445

Thr His Arg Ser Ala Glu Glu Thr Asn Thr Ile Glu Ser Asn Ile Ile
```

```
                450                 455                 460
Thr Gln Ile Pro Leu Val Lys Ala Tyr Gln Ile Gly Ser Gly Thr Thr
465                 470                 475                 480

Val Arg Lys Gly Pro Gly Phe Thr Gly Gly Asp Ile Leu Arg Arg Thr
                485                 490                 495

Gly Pro Gly Thr Phe Gly Asp Met Lys Val Asn Ile His Ala Pro Leu
                500                 505                 510

Ser Gln Lys Tyr Arg Val Arg Ile Arg Tyr Ala Ser Thr Thr Asp Leu
                515                 520                 525

Gln Phe Val Thr Ser Ile Asn Gly Thr Thr Ile Asn Ile Gly Asn Phe
                530                 535                 540

Pro Lys Thr Thr Asn Asn Leu Asn Thr Leu Gly Ser Glu Ser Tyr Arg
545                 550                 555                 560

Thr Val Ser Phe Ser Thr Pro Phe Ser Phe Ser Asn Ala Gln Ser Ile
                565                 570                 575

Phe Arg Leu Gly Ile Gln Ala Phe Ser Gly Val Gln Glu Val Tyr Val
                580                 585                 590

Asp Lys Ile Glu Phe Ile Pro Val Glu
                595                 600

<210> SEQ ID NO 11
<211> LENGTH: 1803
<212> TYPE: DNA
<213> ORGANISM: Bacillus thuringiensis
<220> FEATURE:
<221> NAME/KEY: CDS
<222> LOCATION: (1)..(1803)
<223> OTHER INFORMATION: TIC961

<400> SEQUENCE: 11 atg aat tca acg gaa cat gat tat cta aaa gtt tgt aat gat tta agt        48
Met Asn Ser Thr Glu His Asp Tyr Leu Lys Val Cys Asn Asp Leu Ser
1               5                   10                  15 gac gcc aat att aat atg gag cgg ttt gat aag aat gat gca ctg gaa        96
Asp Ala Asn Ile Asn Met Glu Arg Phe Asp Lys Asn Asp Ala Leu Glu
                20                  25                  30 att ggt atg tcc att gta tct gaa ctt att ggt atg att cca ggc gga       144
Ile Gly Met Ser Ile Val Ser Glu Leu Ile Gly Met Ile Pro Gly Gly
            35                  40                  45 aca gct ttg caa ttt gtg ttt aat caa ttg tgg tct cgt tta ggt gat       192
Thr Ala Leu Gln Phe Val Phe Asn Gln Leu Trp Ser Arg Leu Gly Asp
        50                  55                  60 tct gga tgg aat gcg ttc atg gaa cat gtg gag gaa tta att gat act       240
Ser Gly Trp Asn Ala Phe Met Glu His Val Glu Glu Leu Ile Asp Thr
65                  70                  75                  80 aaa ata gaa ggg tat gca aaa aat aaa gcc tta tct gaa tta gca ggt       288
Lys Ile Glu Gly Tyr Ala Lys Asn Lys Ala Leu Ser Glu Leu Ala Gly
                85                  90                  95 ata caa aga aac ctt gaa aca tat ata caa tta cgt aat gaa tgg gaa       336
Ile Gln Arg Asn Leu Glu Thr Tyr Ile Gln Leu Arg Asn Glu Trp Glu
            100                 105                 110 aat gat att gaa aac tca aag gct caa ggt aag gta gct aat tac tat       384
Asn Asp Ile Glu Asn Ser Lys Ala Gln Gly Lys Val Ala Asn Tyr Tyr
        115                 120                 125 gaa agt ctt gag cag gcg gtt gaa agg agt atg cct caa ttt gca gtg       432
Glu Ser Leu Glu Gln Ala Val Glu Arg Ser Met Pro Gln Phe Ala Val
    130                 135                 140 ggg aat ttt gaa gta cca ctt tta act gtc tat gtg caa gct gct aat       480
Gly Asn Phe Glu Val Pro Leu Leu Thr Val Tyr Val Gln Ala Ala Asn
145                 150                 155                 160
```

```
ctt cat tta tta tta tta aga gat gtt tca gtt tat gga aag cgt tgg       528
Leu His Leu Leu Leu Leu Arg Asp Val Ser Val Tyr Gly Lys Arg Trp
            165                 170                 175 gga tgg tcg gag cag aaa att aaa att tat tat gat aaa cag att aag       576
Gly Trp Ser Glu Gln Lys Ile Lys Ile Tyr Tyr Asp Lys Gln Ile Lys
        180                 185                 190 tat acc cat gaa tac aca aat cat tgt gta aat tgg tat aat aaa gga       624
Tyr Thr His Glu Tyr Thr Asn His Cys Val Asn Trp Tyr Asn Lys Gly
    195                 200                 205 ctt gag aga tta aaa aat aaa ggt tct tct tat caa gat tgg tac aat       672
Leu Glu Arg Leu Lys Asn Lys Gly Ser Ser Tyr Gln Asp Trp Tyr Asn
210                 215                 220 tat aat cgt ttc cgt aga gaa atg act ctt act gtt tta gat atc gtt       720
Tyr Asn Arg Phe Arg Arg Glu Met Thr Leu Thr Val Leu Asp Ile Val
225                 230                 235                 240 gct tta ttc ccg cac tat gat gta caa act tat cca ata aca acc gtt       768
Ala Leu Phe Pro His Tyr Asp Val Gln Thr Tyr Pro Ile Thr Thr Val
            245                 250                 255 gct cag cta aca agg gaa gtt tat acg gat cct tta ctt aat ttt aat       816
Ala Gln Leu Thr Arg Glu Val Tyr Thr Asp Pro Leu Leu Asn Phe Asn
        260                 265                 270 cct aaa tta cat tct gtg tct caa tta cct agt ttt agt gac atg gaa       864
Pro Lys Leu His Ser Val Ser Gln Leu Pro Ser Phe Ser Asp Met Glu
    275                 280                 285 aat gca aca att aga act cca cat ctg atg gaa ttt tta aga atg cta       912
Asn Ala Thr Ile Arg Thr Pro His Leu Met Glu Phe Leu Arg Met Leu
290                 295                 300 aca att tat aca gat tgg tat agt gtg gga aga aac tat tat tgg gga       960
Thr Ile Tyr Thr Asp Trp Tyr Ser Val Gly Arg Asn Tyr Tyr Trp Gly
305                 310                 315                 320 gga cat cgc gtg acg tct tac cat gta gga gga gag aat ata aga tca      1008
Gly His Arg Val Thr Ser Tyr His Val Gly Gly Glu Asn Ile Arg Ser
            325                 330                 335 cct cta tat ggt aga gag gca aat caa gag gtt cct aga gat ttt tat      1056
Pro Leu Tyr Gly Arg Glu Ala Asn Gln Glu Val Pro Arg Asp Phe Tyr
        340                 345                 350 ttt tat gga ccc gtt ttt aag acg tta tca aag ccg act cta aga cca      1104
Phe Tyr Gly Pro Val Phe Lys Thr Leu Ser Lys Pro Thr Leu Arg Pro
    355                 360                 365 tta cag cag cct gca cca gct cct cct ttt aat tta cgt agc tta gag      1152
Leu Gln Gln Pro Ala Pro Ala Pro Pro Phe Asn Leu Arg Ser Leu Glu
370                 375                 380 gga gta gaa ttc cac act cct aca ggt agt ttt atg tat cgt gaa aga      1200
Gly Val Glu Phe His Thr Pro Thr Gly Ser Phe Met Tyr Arg Glu Arg
385                 390                 395                 400 gga tcg gta gat cct ttt aat gag tta ccg cct ttt aat cca gtt ggg      1248
Gly Ser Val Asp Pro Phe Asn Glu Leu Pro Pro Phe Asn Pro Val Gly
            405                 410                 415 tta cct cat aag gta tac agt cac cgt tta tgt cat gca acg ttt gtt      1296
Leu Pro His Lys Val Tyr Ser His Arg Leu Cys His Ala Thr Phe Val
        420                 425                 430 cgt aaa tct ggg acc cct tat tta aca aca ggt gcc atc ttt tct tgg      1344
Arg Lys Ser Gly Thr Pro Tyr Leu Thr Thr Gly Ala Ile Phe Ser Trp
    435                 440                 445 aca cat cgt agt gct gaa gaa acc aat aca att gaa tca aat att att      1392
Thr His Arg Ser Ala Glu Glu Thr Asn Thr Ile Glu Ser Asn Ile Ile
450                 455                 460 acg caa atc ccg tta gta aaa gca tat caa att ggg tca ggc act act      1440
Thr Gln Ile Pro Leu Val Lys Ala Tyr Gln Ile Gly Ser Gly Thr Thr
465                 470                 475                 480
```

-continued

| | | |
|---|---|---|
| gta agg aaa gga cca gga ttc aca ggg gat ata ctt cga aga aca<br>Val Arg Lys Gly Pro Gly Phe Thr Gly Gly Asp Ile Leu Arg Arg Thr<br>                485                      490                    495 | 1488 |
| ggt cct gga aca ttt gga gat atg aga ata aat att aat gca cca tta<br>Gly Pro Gly Thr Phe Gly Asp Met Arg Ile Asn Ile Asn Ala Pro Leu<br>500                      505                    510 | 1536 |
| tct caa aga tat cgt gta agg att cgt tat gct tct acg aca gat tta<br>Ser Gln Arg Tyr Arg Val Arg Ile Arg Tyr Ala Ser Thr Thr Asp Leu<br>            515                    520                  525 | 1584 |
| caa ttt gtc acg agt att aat ggg acc acc att aat att ggt aac ttc<br>Gln Phe Val Thr Ser Ile Asn Gly Thr Thr Ile Asn Ile Gly Asn Phe<br>530                      535                    540 | 1632 |
| cca aaa act att aat aat cta aat act tta ggt tct gag ggc tat aga<br>Pro Lys Thr Ile Asn Asn Leu Asn Thr Leu Gly Ser Glu Gly Tyr Arg<br>545                      550                    555                    560 | 1680 |
| aca gta tcg ttt agt act cca ttt agt ttc tca aat gca caa agc ata<br>Thr Val Ser Phe Ser Thr Pro Phe Ser Phe Ser Asn Ala Gln Ser Ile<br>                565                    570                    575 | 1728 |
| ttt aga tta ggt ata caa gca ttt tct gga gtt caa gaa gtt tat gtg<br>Phe Arg Leu Gly Ile Gln Ala Phe Ser Gly Val Gln Glu Val Tyr Val<br>580                      585                    590 | 1776 |
| gat aaa att gaa ttt att cct gtt gaa<br>Asp Lys Ile Glu Phe Ile Pro Val Glu<br>            595                    600 | 1803 |

<210> SEQ ID NO 12
<211> LENGTH: 601
<212> TYPE: PRT
<213> ORGANISM: Bacillus thuringiensis

<400> SEQUENCE: 12

Met Asn Ser Thr Glu His Asp Tyr Leu Lys Val Cys Asn Asp Leu Ser
1               5                   10                  15

Asp Ala Asn Ile Asn Met Glu Arg Phe Asp Lys Asn Asp Ala Leu Glu
            20                  25                  30

Ile Gly Met Ser Ile Val Ser Glu Leu Ile Gly Met Ile Pro Gly Gly
        35                  40                  45

Thr Ala Leu Gln Phe Val Phe Asn Gln Leu Trp Ser Arg Leu Gly Asp
    50                  55                  60

Ser Gly Trp Asn Ala Phe Met Glu His Val Glu Glu Leu Ile Asp Thr
65                  70                  75                  80

Lys Ile Glu Gly Tyr Ala Lys Asn Lys Ala Leu Ser Glu Leu Ala Gly
                85                  90                  95

Ile Gln Arg Asn Leu Glu Thr Tyr Ile Gln Leu Arg Asn Glu Trp Glu
            100                 105                 110

Asn Asp Ile Glu Asn Ser Lys Ala Gln Gly Lys Val Ala Asn Tyr Tyr
        115                 120                 125

Glu Ser Leu Glu Gln Ala Val Glu Arg Ser Met Pro Gln Phe Ala Val
    130                 135                 140

Gly Asn Phe Glu Val Pro Leu Leu Thr Val Tyr Val Gln Ala Ala Asn
145                 150                 155                 160

Leu His Leu Leu Leu Leu Arg Asp Val Ser Val Tyr Gly Lys Arg Trp
                165                 170                 175

Gly Trp Ser Glu Gln Lys Ile Lys Ile Tyr Tyr Asp Lys Gln Ile Lys
            180                 185                 190

Tyr Thr His Glu Tyr Thr Asn His Cys Val Asn Trp Tyr Asn Lys Gly
        195                 200                 205

-continued

Leu Glu Arg Leu Lys Asn Lys Gly Ser Ser Tyr Gln Asp Trp Tyr Asn
    210                 215                 220

Tyr Asn Arg Phe Arg Arg Glu Met Thr Leu Thr Val Leu Asp Ile Val
225                 230                 235                 240

Ala Leu Phe Pro His Tyr Asp Val Gln Thr Tyr Pro Ile Thr Thr Val
                245                 250                 255

Ala Gln Leu Thr Arg Glu Val Tyr Thr Asp Pro Leu Leu Asn Phe Asn
            260                 265                 270

Pro Lys Leu His Ser Val Ser Gln Leu Pro Ser Phe Ser Asp Met Glu
        275                 280                 285

Asn Ala Thr Ile Arg Thr Pro His Leu Met Glu Phe Leu Arg Met Leu
    290                 295                 300

Thr Ile Tyr Thr Asp Trp Tyr Ser Val Gly Arg Asn Tyr Tyr Trp Gly
305                 310                 315                 320

Gly His Arg Val Thr Ser Tyr His Val Gly Gly Asn Ile Arg Ser
                325                 330                 335

Pro Leu Tyr Gly Arg Glu Ala Asn Gln Glu Val Pro Arg Asp Phe Tyr
            340                 345                 350

Phe Tyr Gly Pro Val Phe Lys Thr Leu Ser Lys Pro Thr Leu Arg Pro
        355                 360                 365

Leu Gln Gln Pro Ala Pro Ala Pro Pro Phe Asn Leu Arg Ser Leu Glu
    370                 375                 380

Gly Val Glu Phe His Thr Pro Thr Gly Ser Phe Met Tyr Arg Glu Arg
385                 390                 395                 400

Gly Ser Val Asp Pro Phe Asn Glu Leu Pro Phe Asn Pro Val Gly
                405                 410                 415

Leu Pro His Lys Val Tyr Ser His Arg Leu Cys His Ala Thr Phe Val
            420                 425                 430

Arg Lys Ser Gly Thr Pro Tyr Leu Thr Thr Gly Ala Ile Phe Ser Trp
        435                 440                 445

Thr His Arg Ser Ala Glu Glu Thr Asn Thr Ile Glu Ser Asn Ile Ile
    450                 455                 460

Thr Gln Ile Pro Leu Val Lys Ala Tyr Gln Ile Gly Ser Gly Thr Thr
465                 470                 475                 480

Val Arg Lys Gly Pro Gly Phe Thr Gly Gly Asp Ile Leu Arg Arg Thr
                485                 490                 495

Gly Pro Gly Thr Phe Gly Asp Met Arg Ile Asn Ile Asn Ala Pro Leu
            500                 505                 510

Ser Gln Arg Tyr Arg Val Arg Ile Arg Tyr Ala Ser Thr Thr Asp Leu
        515                 520                 525

Gln Phe Val Thr Ser Ile Asn Gly Thr Thr Ile Asn Ile Gly Asn Phe
    530                 535                 540

Pro Lys Thr Ile Asn Asn Leu Asn Thr Leu Gly Ser Glu Gly Tyr Arg
545                 550                 555                 560

Thr Val Ser Phe Ser Thr Pro Phe Ser Phe Ser Asn Ala Gln Ser Ile
                565                 570                 575

Phe Arg Leu Gly Ile Gln Ala Phe Ser Gly Val Gln Glu Val Tyr Val
            580                 585                 590

Asp Lys Ile Glu Phe Ile Pro Val Glu
        595                 600

<210> SEQ ID NO 13
<211> LENGTH: 1803
<212> TYPE: DNA
<213> ORGANISM: Bacillus thuringiensis -continued

```
<220> FEATURE:
<221> NAME/KEY: CDS
<222> LOCATION: (1)..(1803)
<223> OTHER INFORMATION: TIC962

<400> SEQUENCE: 13 atg aat tca aag gaa cat gat tat cta aaa gtt tgt aat gat tta agt        48
Met Asn Ser Lys Glu His Asp Tyr Leu Lys Val Cys Asn Asp Leu Ser
1               5                   10                  15 gac gcc aat att aat atg gaa cgg ttt gat aag aat gat gca ctg gaa        96
Asp Ala Asn Ile Asn Met Glu Arg Phe Asp Lys Asn Asp Ala Leu Glu
            20                  25                  30 att ggt atg tcc att gta tct gaa ctt att ggt atg att cca ggc ggg       144
Ile Gly Met Ser Ile Val Ser Glu Leu Ile Gly Met Ile Pro Gly Gly
        35                  40                  45 aca gct ttg caa ttt gtg ttt aat caa ttg tgg tct cgt tta ggt gat       192
Thr Ala Leu Gln Phe Val Phe Asn Gln Leu Trp Ser Arg Leu Gly Asp
    50                  55                  60 tct gga tgg aat gcg ttc atg gaa cat gtg gag gaa tta att gat gct       240
Ser Gly Trp Asn Ala Phe Met Glu His Val Glu Glu Leu Ile Asp Ala
65                  70                  75                  80 aaa ata gaa ggg tat gca aaa aat aaa gcc tta tct gaa tta gca ggt       288
Lys Ile Glu Gly Tyr Ala Lys Asn Lys Ala Leu Ser Glu Leu Ala Gly
                85                  90                  95 ata caa aga aac ctt gaa aca tat ata caa tta cgt aat gaa tgg gaa       336
Ile Gln Arg Asn Leu Glu Thr Tyr Ile Gln Leu Arg Asn Glu Trp Glu
            100                 105                 110 aat gat att gaa aac tca aag gct caa ggt aag gta gct aat tac tat       384
Asn Asp Ile Glu Asn Ser Lys Ala Gln Gly Lys Val Ala Asn Tyr Tyr
        115                 120                 125 gaa agt ctt gag cag gcg gtt gaa agg agt atg cct caa ttt gca gtg       432
Glu Ser Leu Glu Gln Ala Val Glu Arg Ser Met Pro Gln Phe Ala Val
    130                 135                 140 gag aat ttt gaa gta cca ctt tta act gtc tat gtg caa gct gct aat       480
Glu Asn Phe Glu Val Pro Leu Leu Thr Val Tyr Val Gln Ala Ala Asn
145                 150                 155                 160 ctt cat tta tta tta tta aga gat gtt tca gtt tat gga aag tgt tgg       528
Leu His Leu Leu Leu Leu Arg Asp Val Ser Val Tyr Gly Lys Cys Trp
                165                 170                 175 gga tgg tcg gag cag aaa att aaa att tat tat gat aaa cag att aag       576
Gly Trp Ser Glu Gln Lys Ile Lys Ile Tyr Tyr Asp Lys Gln Ile Lys
            180                 185                 190 tat acc cat gaa tac aca aat cat tgt gta aat tgg tat aat aaa gga       624
Tyr Thr His Glu Tyr Thr Asn His Cys Val Asn Trp Tyr Asn Lys Gly
        195                 200                 205 ctt gag aga tta aaa aat aaa ggt tct tct tat caa gat tgg tac aat       672
Leu Glu Arg Leu Lys Asn Lys Gly Ser Ser Tyr Gln Asp Trp Tyr Asn
    210                 215                 220 tat aat cgt ttc cgt aga gaa atg act ctt act gtt tta gat atc gtt       720
Tyr Asn Arg Phe Arg Arg Glu Met Thr Leu Thr Val Leu Asp Ile Val
225                 230                 235                 240 gct tta ttc ccg cac tat gat gta caa act tat cca ata aca acc gtt       768
Ala Leu Phe Pro His Tyr Asp Val Gln Thr Tyr Pro Ile Thr Thr Val
                245                 250                 255 gct cag cta aca agg gaa gtt tat acg gat cct tta ctt aat ttt aat       816
Ala Gln Leu Thr Arg Glu Val Tyr Thr Asp Pro Leu Leu Asn Phe Asn
            260                 265                 270 cct aaa tta cat tct gtg tct caa tta cct agt ttt agt gac atg gaa       864
Pro Lys Leu His Ser Val Ser Gln Leu Pro Ser Phe Ser Asp Met Glu
        275                 280                 285 aat gca aca att aga act cca cat ctg atg gaa ttt tta aga atg cta       912
Asn Ala Thr Ile Arg Thr Pro His Leu Met Glu Phe Leu Arg Met Leu
```

```
Asn Ala Thr Ile Arg Thr Pro His Leu Met Glu Phe Leu Arg Met Leu
        290                 295                 300 aca att tat aca gat tgg tat agt gtg gga aga aac tat tat tgg gga      960
Thr Ile Tyr Thr Asp Trp Tyr Ser Val Gly Arg Asn Tyr Tyr Trp Gly
305                 310                 315                 320 gga cat cgc gtg acg tct tac cat gta gga gga gag aat ata aga tca     1008
Gly His Arg Val Thr Ser Tyr His Val Gly Gly Glu Asn Ile Arg Ser
                325                 330                 335 cct cta tat ggt aga gag gca aat caa gag gtt cct aga gat ttt tat     1056
Pro Leu Tyr Gly Arg Glu Ala Asn Gln Glu Val Pro Arg Asp Phe Tyr
            340                 345                 350 ttt tat gga ccc gtt ttt aag acg tta tca aag ccg act cta aga cca     1104
Phe Tyr Gly Pro Val Phe Lys Thr Leu Ser Lys Pro Thr Leu Arg Pro
        355                 360                 365 tta cag cag cct gca cca gct cct cct ttt aat tta cgt agc tta gag     1152
Leu Gln Gln Pro Ala Pro Ala Pro Pro Phe Asn Leu Arg Ser Leu Glu
    370                 375                 380 gga gta gaa ttc cac act cct aca ggt agt ttt atg tat cgt gaa aga     1200
Gly Val Glu Phe His Thr Pro Thr Gly Ser Phe Met Tyr Arg Glu Arg
385                 390                 395                 400 gga tcg gta gat tct ttt aat gag ttg ccg cct ttt aat cca gtt ggg     1248
Gly Ser Val Asp Ser Phe Asn Glu Leu Pro Pro Phe Asn Pro Val Gly
                405                 410                 415 tta cct cat aag gta tac agt cac cgt tta tgt cat gca acg ttt gtt     1296
Leu Pro His Lys Val Tyr Ser His Arg Leu Cys His Ala Thr Phe Val
            420                 425                 430 cgt aaa tct ggg acc cct tat tta aca aca ggt gcc atc ttt tct tgg     1344
Arg Lys Ser Gly Thr Pro Tyr Leu Thr Thr Gly Ala Ile Phe Ser Trp
        435                 440                 445 aca cat cgt agt gct gaa gaa acc aat aca att gaa tca aat att att     1392
Thr His Arg Ser Ala Glu Glu Thr Asn Thr Ile Glu Ser Asn Ile Ile
    450                 455                 460 acg caa atc ccg tta gta aaa gca tat caa att ggg tca ggc act act     1440
Thr Gln Ile Pro Leu Val Lys Ala Tyr Gln Ile Gly Ser Gly Thr Thr
465                 470                 475                 480 gta agg aaa gga cca gga ttc aca gga ggg gat ata ctt cga aga aca     1488
Val Arg Lys Gly Pro Gly Phe Thr Gly Gly Asp Ile Leu Arg Arg Thr
                485                 490                 495 ggt cct gga aca ttt gga gat atg aga ata aat att aat gca cca tta     1536
Gly Pro Gly Thr Phe Gly Asp Met Arg Ile Asn Ile Asn Ala Pro Leu
            500                 505                 510 tct caa aga tat cgt gta agg att cgt tat gct tct acg aca gat tta     1584
Ser Gln Arg Tyr Arg Val Arg Ile Arg Tyr Ala Ser Thr Thr Asp Leu
        515                 520                 525 caa ttt gtc acg agt att aat ggg acc acc att aat att ggt aac ttc     1632
Gln Phe Val Thr Ser Ile Asn Gly Thr Thr Ile Asn Ile Gly Asn Phe
    530                 535                 540 ccg aaa act att aat aat cta aat act tta ggt tct gag ggc tat aga     1680
Pro Lys Thr Ile Asn Asn Leu Asn Thr Leu Gly Ser Glu Gly Tyr Arg
545                 550                 555                 560 aca gta tcg ttt agt act cca ttt agt ttc tca aat gca caa agc ata     1728
Thr Val Ser Phe Ser Thr Pro Phe Ser Phe Ser Asn Ala Gln Ser Ile
                565                 570                 575 ttt aga tta ggt ata caa gca ttt tct gga gtt caa gaa gtt tat gtg     1776
Phe Arg Leu Gly Ile Gln Ala Phe Ser Gly Val Gln Glu Val Tyr Val
            580                 585                 590 gat aaa att gaa ttt att cct gtt gaa                                  1803
Asp Lys Ile Glu Phe Ile Pro Val Glu
        595                 600
```

<210> SEQ ID NO 14
<211> LENGTH: 601
<212> TYPE: PRT
<213> ORGANISM: Bacillus thuringiensis

<400> SEQUENCE: 14

```
Met Asn Ser Lys Glu His Asp Tyr Leu Lys Val Cys Asn Asp Leu Ser
1               5                   10                  15

Asp Ala Asn Ile Asn Met Glu Arg Phe Asp Lys Asn Asp Ala Leu Glu
            20                  25                  30

Ile Gly Met Ser Ile Val Ser Glu Leu Ile Gly Met Ile Pro Gly Gly
        35                  40                  45

Thr Ala Leu Gln Phe Val Phe Asn Gln Leu Trp Ser Arg Leu Gly Asp
    50                  55                  60

Ser Gly Trp Asn Ala Phe Met Glu His Val Glu Glu Leu Ile Asp Ala
65                  70                  75                  80

Lys Ile Glu Gly Tyr Ala Lys Asn Lys Ala Leu Ser Glu Leu Ala Gly
                85                  90                  95

Ile Gln Arg Asn Leu Glu Thr Tyr Ile Gln Leu Arg Asn Glu Trp Glu
            100                 105                 110

Asn Asp Ile Glu Asn Ser Lys Ala Gln Gly Lys Val Ala Asn Tyr Tyr
        115                 120                 125

Glu Ser Leu Glu Gln Ala Val Glu Arg Ser Met Pro Gln Phe Ala Val
    130                 135                 140

Glu Asn Phe Glu Val Pro Leu Leu Thr Val Tyr Val Gln Ala Ala Asn
145                 150                 155                 160

Leu His Leu Leu Leu Leu Arg Asp Val Ser Val Tyr Gly Lys Cys Trp
                165                 170                 175

Gly Trp Ser Glu Gln Lys Ile Lys Ile Tyr Tyr Asp Lys Gln Ile Lys
            180                 185                 190

Tyr Thr His Glu Tyr Thr Asn His Cys Val Asn Trp Tyr Asn Lys Gly
        195                 200                 205

Leu Glu Arg Leu Lys Asn Lys Gly Ser Ser Tyr Gln Asp Trp Tyr Asn
    210                 215                 220

Tyr Asn Arg Phe Arg Arg Glu Met Thr Leu Thr Val Leu Asp Ile Val
225                 230                 235                 240

Ala Leu Phe Pro His Tyr Asp Val Gln Thr Tyr Pro Ile Thr Thr Val
                245                 250                 255

Ala Gln Leu Thr Arg Glu Val Tyr Thr Asp Pro Leu Leu Asn Phe Asn
            260                 265                 270

Pro Lys Leu His Ser Val Ser Gln Leu Pro Ser Phe Ser Asp Met Glu
        275                 280                 285

Asn Ala Thr Ile Arg Thr Pro His Leu Met Glu Phe Leu Arg Met Leu
    290                 295                 300

Thr Ile Tyr Thr Asp Trp Tyr Ser Val Gly Arg Asn Tyr Tyr Trp Gly
305                 310                 315                 320

Gly His Arg Val Thr Ser Tyr His Val Gly Gly Glu Asn Ile Arg Ser
                325                 330                 335

Pro Leu Tyr Gly Arg Glu Ala Asn Gln Glu Val Pro Arg Asp Phe Tyr
            340                 345                 350

Phe Tyr Gly Pro Val Phe Lys Thr Leu Ser Lys Pro Thr Leu Arg Pro
        355                 360                 365

Leu Gln Gln Pro Ala Pro Ala Pro Pro Phe Asn Leu Arg Ser Leu Glu
    370                 375                 380

Gly Val Glu Phe His Thr Pro Thr Gly Ser Phe Met Tyr Arg Glu Arg
```

```
                385                 390                 395                 400
Gly Ser Val Asp Ser Phe Asn Glu Leu Pro Pro Phe Asn Pro Val Gly
                    405                 410                 415
Leu Pro His Lys Val Tyr Ser His Arg Leu Cys His Ala Thr Phe Val
        420                 425                 430
Arg Lys Ser Gly Thr Pro Tyr Leu Thr Thr Gly Ala Ile Phe Ser Trp
    435                 440                 445
Thr His Arg Ser Ala Glu Glu Thr Asn Thr Ile Glu Ser Asn Ile Ile
    450                 455                 460
Thr Gln Ile Pro Leu Val Lys Ala Tyr Gln Ile Gly Ser Gly Thr Thr
465                 470                 475                 480
Val Arg Lys Gly Pro Gly Phe Thr Gly Gly Asp Ile Leu Arg Arg Thr
                485                 490                 495
Gly Pro Gly Thr Phe Gly Asp Met Arg Ile Asn Ile Asn Ala Pro Leu
            500                 505                 510
Ser Gln Arg Tyr Arg Val Arg Ile Arg Tyr Ala Ser Thr Thr Asp Leu
        515                 520                 525
Gln Phe Val Thr Ser Ile Asn Gly Thr Thr Ile Asn Ile Gly Asn Phe
    530                 535                 540
Pro Lys Thr Ile Asn Asn Leu Asn Thr Leu Gly Ser Glu Gly Tyr Arg
545                 550                 555                 560
Thr Val Ser Phe Ser Thr Pro Phe Ser Phe Ser Asn Ala Gln Ser Ile
                565                 570                 575
Phe Arg Leu Gly Ile Gln Ala Phe Ser Gly Val Gln Glu Val Tyr Val
            580                 585                 590
Asp Lys Ile Glu Phe Ile Pro Val Glu
        595                 600

<210> SEQ ID NO 15
<211> LENGTH: 1803
<212> TYPE: DNA
<213> ORGANISM: Bacillus thuringiensis
<220> FEATURE:
<221> NAME/KEY: CDS
<222> LOCATION: (1)..(1803)
<223> OTHER INFORMATION: TIC963

<400> SEQUENCE: 15 atg aat tca aag gaa cat gat tat ata aaa gtt tgt aat gat tta agt      48
Met Asn Ser Lys Glu His Asp Tyr Ile Lys Val Cys Asn Asp Leu Ser
1               5                  10                  15 gac gcc aat att aat atg gag cgg ttt gat aag aat gat gca cta gaa      96
Asp Ala Asn Ile Asn Met Glu Arg Phe Asp Lys Asn Asp Ala Leu Glu
            20                  25                  30 att ggc atg tcc att gta tct gaa ctt att ggt atg att cca ggc gga     144
Ile Gly Met Ser Ile Val Ser Glu Leu Ile Gly Met Ile Pro Gly Gly
        35                  40                  45 aca gct tta caa ttt gtg ttt aat caa ttg tgg tct cgt tta ggt gat     192
Thr Ala Leu Gln Phe Val Phe Asn Gln Leu Trp Ser Arg Leu Gly Asp
    50                  55                  60 tct gga tgg agt gca ttc atg gaa cat gtg gag gaa tta att gat act     240
Ser Gly Trp Ser Ala Phe Met Glu His Val Glu Glu Leu Ile Asp Thr
65                  70                  75                  80 aaa ata gaa ggg tat gca aaa aat aaa gcc tta tct gaa tta gca ggt     288
Lys Ile Glu Gly Tyr Ala Lys Asn Lys Ala Leu Ser Glu Leu Ala Gly
                85                  90                  95 ata caa aga aac ctt gaa aca tat ata caa tta cgt aat gca tgg gaa     336
Ile Gln Arg Asn Leu Glu Thr Tyr Ile Gln Leu Arg Asn Ala Trp Glu
            100                 105                 110
```

```
aat gat atc gaa aac tca aag gct caa ggt aag gta gct aat tac tat      384
Asn Asp Ile Glu Asn Ser Lys Ala Gln Gly Lys Val Ala Asn Tyr Tyr
            115                 120                 125 gaa agt ctt gag cag gcg gtt gaa agg agt atg cct caa tct gca gtg      432
Glu Ser Leu Glu Gln Ala Val Glu Arg Ser Met Pro Gln Ser Ala Val
130                 135                 140 ggg aat ttt gaa gta cca ctt tta act gtt tat gtg caa gct gct aat      480
Gly Asn Phe Glu Val Pro Leu Leu Thr Val Tyr Val Gln Ala Ala Asn
145                 150                 155                 160 ctt cat ata tta tta tta aga gat gtt cta att tac gga aag cgt tgg      528
Leu His Ile Leu Leu Leu Arg Asp Val Leu Ile Tyr Gly Lys Arg Trp
                165                 170                 175 gga tgg tcg gag cag aaa att aaa att tat tat gat aga cag att aag      576
Gly Trp Ser Glu Gln Lys Ile Lys Ile Tyr Tyr Asp Arg Gln Ile Lys
            180                 185                 190 tat act cat gaa tac aca aat cat tgt gta aat tgg tat aat aaa ggg      624
Tyr Thr His Glu Tyr Thr Asn His Cys Val Asn Trp Tyr Asn Lys Gly
            195                 200                 205 ctt gag aga tta aaa aat aaa ggt tct tct tat caa gat tgg tac aat      672
Leu Glu Arg Leu Lys Asn Lys Gly Ser Ser Tyr Gln Asp Trp Tyr Asn
210                 215                 220 tat aat cgt ttc cgt aga gaa atg act ctt act gtt tta gat atc gtt      720
Tyr Asn Arg Phe Arg Arg Glu Met Thr Leu Thr Val Leu Asp Ile Val
225                 230                 235                 240 gct tta ttc ccg cac tat gat gta caa act tat cca ata aca acc gtt      768
Ala Leu Phe Pro His Tyr Asp Val Gln Thr Tyr Pro Ile Thr Thr Val
                245                 250                 255 gct cag cta aca agg gaa gtt tat acg gat cct tta ctt aat ttt aat      816
Ala Gln Leu Thr Arg Glu Val Tyr Thr Asp Pro Leu Leu Asn Phe Asn
            260                 265                 270 cct aaa tta cat tct gtg tct caa tta cct agt ttt agt gac atg gaa      864
Pro Lys Leu His Ser Val Ser Gln Leu Pro Ser Phe Ser Asp Met Glu
            275                 280                 285 aat gca aca att aga act cca cat ttg atg gaa ttt tta aga atg tta      912
Asn Ala Thr Ile Arg Thr Pro His Leu Met Glu Phe Leu Arg Met Leu
290                 295                 300 aca att tat aca gat tgg tat agt gtg gga aga aac tat tat tgg gga      960
Thr Ile Tyr Thr Asp Trp Tyr Ser Val Gly Arg Asn Tyr Tyr Trp Gly
305                 310                 315                 320 gga cat cgc gtg acg tct tac cat gta gga gga gag aat ata aga tcc     1008
Gly His Arg Val Thr Ser Tyr His Val Gly Gly Glu Asn Ile Arg Ser
                325                 330                 335 cct cta tat ggt aga gag gca aat caa gag gtt cct aga gat ttt tat     1056
Pro Leu Tyr Gly Arg Glu Ala Asn Gln Glu Val Pro Arg Asp Phe Tyr
            340                 345                 350 ttt tat gga ccc gtt ttt aag acg tta tca aaa ccg act cta aga cca     1104
Phe Tyr Gly Pro Val Phe Lys Thr Leu Ser Lys Pro Thr Leu Arg Pro
            355                 360                 365 tta cag cag cct gca cca gct cct cct ttt aat tta cgt agc tta gag     1152
Leu Gln Gln Pro Ala Pro Ala Pro Pro Phe Asn Leu Arg Ser Leu Glu
370                 375                 380 gga gta gaa ttc cac act cct aca ggt agt ttt atg tat cgt gaa aga     1200
Gly Val Glu Phe His Thr Pro Thr Gly Ser Phe Met Tyr Arg Glu Arg
385                 390                 395                 400 gga tca gta gat tct ttt aat gag tta ccg cct ttt aat cca gtt ggg     1248
Gly Ser Val Asp Ser Phe Asn Glu Leu Pro Pro Phe Asn Pro Val Gly
                405                 410                 415 tta cct cat aag gta tat agt cac cgt tta tgt cat gca acg ttt gtt     1296
Leu Pro His Lys Val Tyr Ser His Arg Leu Cys His Ala Thr Phe Val
            420                 425                 430
```

```
cgt aaa tcg ggg acc cct tat tta aca aca ggt gcc atc ttt act tgg      1344
Arg Lys Ser Gly Thr Pro Tyr Leu Thr Thr Gly Ala Ile Phe Thr Trp
        435                 440                 445 aca cat cgt agt gct gaa gaa acc aat aca att gaa tca aat att att      1392
Thr His Arg Ser Ala Glu Glu Thr Asn Thr Ile Glu Ser Asn Ile Ile
450                 455                 460 acg caa atc ccg tta gta aaa gca tat caa att gga tcg ggc act act      1440
Thr Gln Ile Pro Leu Val Lys Ala Tyr Gln Ile Gly Ser Gly Thr Thr
465                 470                 475                 480 gta agg aaa gga cca gga ttc acg gga ggg gat ata ctt cgg aga aca      1488
Val Arg Lys Gly Pro Gly Phe Thr Gly Gly Asp Ile Leu Arg Arg Thr
        485                 490                 495 ggt cct gga aca ttt gga gat atg aaa gta aat att cat gca cca tta      1536
Gly Pro Gly Thr Phe Gly Asp Met Lys Val Asn Ile His Ala Pro Leu
500                 505                 510 tcc caa aaa tat cgt gta agg att cgt tat gct tct acg aca gat tta      1584
Ser Gln Lys Tyr Arg Val Arg Ile Arg Tyr Ala Ser Thr Thr Asp Leu
        515                 520                 525 caa ttt gtc acg agt att aat gga acc acc att aat att ggt aac ttc      1632
Gln Phe Val Thr Ser Ile Asn Gly Thr Thr Ile Asn Ile Gly Asn Phe
530                 535                 540 cca aaa act act aat aat cta aat act tta ggt tct gag agc tat aga      1680
Pro Lys Thr Thr Asn Asn Leu Asn Thr Leu Gly Ser Glu Ser Tyr Arg
545                 550                 555                 560 aca gta tcg ttt agt acg cca ttt agt ttc tca aat gca caa agc ata      1728
Thr Val Ser Phe Ser Thr Pro Phe Ser Phe Ser Asn Ala Gln Ser Ile
        565                 570                 575 ttt aga tta ggt ata caa gca ttt tct gga gtt caa gaa gtt tgt gtg      1776
Phe Arg Leu Gly Ile Gln Ala Phe Ser Gly Val Gln Glu Val Cys Val
580                 585                 590 gat aaa att gaa ttt att cct gtt gaa                                   1803
Asp Lys Ile Glu Phe Ile Pro Val Glu
        595                 600

<210> SEQ ID NO 16
<211> LENGTH: 601
<212> TYPE: PRT
<213> ORGANISM: Bacillus thuringiensis

<400> SEQUENCE: 16

Met Asn Ser Lys Glu His Asp Tyr Ile Lys Val Cys Asn Asp Leu Ser
1               5                   10                  15

Asp Ala Asn Ile Asn Met Glu Arg Phe Asp Lys Asn Asp Ala Leu Glu
            20                  25                  30

Ile Gly Met Ser Ile Val Ser Glu Leu Ile Gly Met Ile Pro Gly Gly
        35                  40                  45

Thr Ala Leu Gln Phe Val Phe Asn Gln Leu Trp Ser Arg Leu Gly Asp
    50                  55                  60

Ser Gly Trp Ser Ala Phe Met Glu His Val Glu Glu Leu Ile Asp Thr
65                  70                  75                  80

Lys Ile Glu Gly Tyr Ala Lys Asn Lys Ala Leu Ser Glu Leu Ala Gly
                85                  90                  95

Ile Gln Arg Asn Leu Glu Thr Tyr Ile Gln Leu Arg Asn Ala Trp Glu
            100                 105                 110

Asn Asp Ile Glu Asn Ser Lys Ala Gln Gly Lys Val Ala Asn Tyr Tyr
        115                 120                 125

Glu Ser Leu Glu Gln Ala Val Glu Arg Ser Met Pro Gln Ser Ala Val
    130                 135                 140
```

```
Gly Asn Phe Glu Val Pro Leu Leu Thr Val Tyr Val Gln Ala Ala Asn
145                 150                 155                 160

Leu His Ile Leu Leu Leu Arg Asp Val Leu Ile Tyr Gly Lys Arg Trp
            165                 170                 175

Gly Trp Ser Glu Gln Lys Ile Lys Ile Tyr Tyr Asp Arg Gln Ile Lys
            180                 185                 190

Tyr Thr His Glu Tyr Thr Asn His Cys Val Asn Trp Tyr Asn Lys Gly
            195                 200                 205

Leu Glu Arg Leu Lys Asn Lys Gly Ser Ser Tyr Gln Asp Trp Tyr Asn
            210                 215                 220

Tyr Asn Arg Phe Arg Arg Glu Met Thr Leu Thr Val Leu Asp Ile Val
225                 230                 235                 240

Ala Leu Phe Pro His Tyr Asp Val Gln Thr Tyr Pro Ile Thr Thr Val
                245                 250                 255

Ala Gln Leu Thr Arg Glu Val Tyr Thr Asp Pro Leu Leu Asn Phe Asn
            260                 265                 270

Pro Lys Leu His Ser Val Ser Gln Leu Pro Ser Phe Ser Asp Met Glu
            275                 280                 285

Asn Ala Thr Ile Arg Thr Pro His Leu Met Glu Phe Leu Arg Met Leu
290                 295                 300

Thr Ile Tyr Thr Asp Trp Tyr Ser Val Gly Arg Asn Tyr Tyr Trp Gly
305                 310                 315                 320

Gly His Arg Val Thr Ser Tyr His Val Gly Gly Glu Asn Ile Arg Ser
                325                 330                 335

Pro Leu Tyr Gly Arg Glu Ala Asn Gln Glu Val Pro Arg Asp Phe Tyr
            340                 345                 350

Phe Tyr Gly Pro Val Phe Lys Thr Leu Ser Lys Pro Thr Leu Arg Pro
            355                 360                 365

Leu Gln Gln Pro Ala Pro Ala Pro Pro Phe Asn Leu Arg Ser Leu Glu
            370                 375                 380

Gly Val Glu Phe His Thr Pro Thr Gly Ser Phe Met Tyr Arg Glu Arg
385                 390                 395                 400

Gly Ser Val Asp Ser Phe Asn Glu Leu Pro Pro Phe Asn Pro Val Gly
                405                 410                 415

Leu Pro His Lys Val Tyr Ser His Arg Leu Cys His Ala Thr Phe Val
            420                 425                 430

Arg Lys Ser Gly Thr Pro Tyr Leu Thr Thr Gly Ala Ile Phe Thr Trp
            435                 440                 445

Thr His Arg Ser Ala Glu Glu Thr Asn Thr Ile Glu Ser Asn Ile Ile
450                 455                 460

Thr Gln Ile Pro Leu Val Lys Ala Tyr Gln Ile Gly Ser Gly Thr Thr
465                 470                 475                 480

Val Arg Lys Gly Pro Gly Phe Thr Gly Gly Asp Ile Leu Arg Arg Thr
                485                 490                 495

Gly Pro Gly Thr Phe Gly Asp Met Lys Val Asn Ile His Ala Pro Leu
            500                 505                 510

Ser Gln Lys Tyr Arg Val Arg Ile Arg Tyr Ala Ser Thr Thr Asp Leu
            515                 520                 525

Gln Phe Val Thr Ser Ile Asn Gly Thr Thr Ile Asn Ile Gly Asn Phe
            530                 535                 540

Pro Lys Thr Thr Asn Asn Leu Asn Thr Leu Gly Ser Glu Ser Tyr Arg
545                 550                 555                 560

Thr Val Ser Phe Ser Thr Pro Phe Ser Phe Ser Asn Ala Gln Ser Ile
                565                 570                 575
```

```
Phe Arg Leu Gly Ile Gln Ala Phe Ser Gly Val Gln Glu Val Cys Val
                580                 585                 590

Asp Lys Ile Glu Phe Ile Pro Val Glu
                595                 600

<210> SEQ ID NO 17
<211> LENGTH: 1803
<212> TYPE: DNA
<213> ORGANISM: Bacillus thuringiensis
<220> FEATURE:
<221> NAME/KEY: CDS
<222> LOCATION: (1)..(1803)
<223> OTHER INFORMATION: TIC965

<400> SEQUENCE: 17 atg aat tca acg gaa cat gat tat cta aaa gtt tgt aat gat tta agt        48
Met Asn Ser Thr Glu His Asp Tyr Leu Lys Val Cys Asn Asp Leu Ser
1               5                   10                  15 gac gcc aat att aat atg gaa cgg ttt gat aag aat gat gca ctg gaa        96
Asp Ala Asn Ile Asn Met Glu Arg Phe Asp Lys Asn Asp Ala Leu Glu
            20                  25                  30 att ggt atg tcc att gta tct gaa ctt att ggt atg att cca ggc gga       144
Ile Gly Met Ser Ile Val Ser Glu Leu Ile Gly Met Ile Pro Gly Gly
        35                  40                  45 aca gct ttg caa ttt gtg ttt aat caa ttg tgg tct cgt tta ggt gat       192
Thr Ala Leu Gln Phe Val Phe Asn Gln Leu Trp Ser Arg Leu Gly Asp
    50                  55                  60 tct gga tgg aat gcg ttc atg gaa cat gtg gag gaa tta att gat act       240
Ser Gly Trp Asn Ala Phe Met Glu His Val Glu Glu Leu Ile Asp Thr
65                  70                  75                  80 aaa ata gaa ggg tat gca aaa aat aaa gcc tta tct gaa tta gca ggt       288
Lys Ile Glu Gly Tyr Ala Lys Asn Lys Ala Leu Ser Glu Leu Ala Gly
                85                  90                  95 ata caa agg aac ctt gaa aca tat ata caa tta cgt aat gaa tgg gaa       336
Ile Gln Arg Asn Leu Glu Thr Tyr Ile Gln Leu Arg Asn Glu Trp Glu
            100                 105                 110 aat gat att gaa aac tca aag gct caa ggt aag gta gct aat tac tat       384
Asn Asp Ile Glu Asn Ser Lys Ala Gln Gly Lys Val Ala Asn Tyr Tyr
        115                 120                 125 gaa agt ctt gag cag gcg gtt gaa agg agt atg cct caa ttt gca gtg       432
Glu Ser Leu Glu Gln Ala Val Glu Arg Ser Met Pro Gln Phe Ala Val
    130                 135                 140 gag aat ttt gaa gta cca ctt tta act gtc tat gtg caa gct gct aat       480
Glu Asn Phe Glu Val Pro Leu Leu Thr Val Tyr Val Gln Ala Ala Asn
145                 150                 155                 160 ctt cat tta tta tta tta aga gat gtt tca gtt tat gga aag tgt tgg       528
Leu His Leu Leu Leu Leu Arg Asp Val Ser Val Tyr Gly Lys Cys Trp
                165                 170                 175 gga tgg tcg gag cag aaa att aaa att tat tat gat aaa cag att aag       576
Gly Trp Ser Glu Gln Lys Ile Lys Ile Tyr Tyr Asp Lys Gln Ile Lys
            180                 185                 190 tat acc cat gaa tac aca aat cat tgt gta aat tgg tat aat aaa gga       624
Tyr Thr His Glu Tyr Thr Asn His Cys Val Asn Trp Tyr Asn Lys Gly
        195                 200                 205 ctt gag aga tta aaa aat aaa ggt tct tct tat caa gat tgg tac aat       672
Leu Glu Arg Leu Lys Asn Lys Gly Ser Ser Tyr Gln Asp Trp Tyr Asn
    210                 215                 220 tat aat cgt ttc cgt aga gaa atg act ctt act gtt tta gat atc gtt       720
Tyr Asn Arg Phe Arg Arg Glu Met Thr Leu Thr Val Leu Asp Ile Val
225                 230                 235                 240 gct tta ttc ccg cac tat gat gta caa act tat cca ata aca acc gtt       768
```

```
                Ala Leu Phe Pro His Tyr Asp Val Gln Thr Tyr Pro Ile Thr Thr Val
                                245                 250                 255 gct cag cta aca agg gaa gtt tat acg gat cct tta ctt aat ttt aat          816
Ala Gln Leu Thr Arg Glu Val Tyr Thr Asp Pro Leu Leu Asn Phe Asn
                260                 265                 270 cct aaa tta cat tct gtg tct caa tta cct agt ttt agt gac atg gaa          864
Pro Lys Leu His Ser Val Ser Gln Leu Pro Ser Phe Ser Asp Met Glu
                275                 280                 285 aat gca aca att aga act cca cat ctg atg gaa ttt tta aga atg cta          912
Asn Ala Thr Ile Arg Thr Pro His Leu Met Glu Phe Leu Arg Met Leu
            290                 295                 300 aca att tat aca gat tgg tat agt gtg gga aga aac tat tat tgg gga          960
Thr Ile Tyr Thr Asp Trp Tyr Ser Val Gly Arg Asn Tyr Tyr Trp Gly
305                 310                 315                 320 gga cat cgc gtg acg tct tac cat gta gga gga gag aat ata aga tca         1008
Gly His Arg Val Thr Ser Tyr His Val Gly Gly Glu Asn Ile Arg Ser
                325                 330                 335 cct cta tat ggt aga gag gca aat caa gag gtt cct aga gat ttt tat         1056
Pro Leu Tyr Gly Arg Glu Ala Asn Gln Glu Val Pro Arg Asp Phe Tyr
            340                 345                 350 ttt tat gga ccc gtt ttt aag acg tta tca aag ccg act cta aga cca         1104
Phe Tyr Gly Pro Val Phe Lys Thr Leu Ser Lys Pro Thr Leu Arg Pro
        355                 360                 365 tta cag cag cct gca cca gct cct cct ttt aat tta cgt agc tta gag         1152
Leu Gln Gln Pro Ala Pro Ala Pro Pro Phe Asn Leu Arg Ser Leu Glu
    370                 375                 380 gga gta gaa ttc cac act cct aca ggt agt ttt atg tat cgt gaa aga         1200
Gly Val Glu Phe His Thr Pro Thr Gly Ser Phe Met Tyr Arg Glu Arg
385                 390                 395                 400 gga tcg gta gat tct ttt aat gag ttg ccg cct ttt aat cca gtt ggg         1248
Gly Ser Val Asp Ser Phe Asn Glu Leu Pro Pro Phe Asn Pro Val Gly
                405                 410                 415 tta cct cat aag gta tac agt cac cgt tta tgt cat gca acg ttt gtt         1296
Leu Pro His Lys Val Tyr Ser His Arg Leu Cys His Ala Thr Phe Val
                420                 425                 430 cgt aaa tct ggg acc cct tat tta aca aca ggt gcc atc ttt tct tgg         1344
Arg Lys Ser Gly Thr Pro Tyr Leu Thr Thr Gly Ala Ile Phe Ser Trp
            435                 440                 445 aca cat cgt agt gct gaa gaa acc aat aca att gaa tca aat att att         1392
Thr His Arg Ser Ala Glu Glu Thr Asn Thr Ile Glu Ser Asn Ile Ile
450                 455                 460 acg caa atc ccg tta gta aaa gca tat caa att ggg tca ggc act act         1440
Thr Gln Ile Pro Leu Val Lys Ala Tyr Gln Ile Gly Ser Gly Thr Thr
465                 470                 475                 480 gta agg aaa gga cca gga ttc aca gga ggg gat ata ctt cga aga aca         1488
Val Arg Lys Gly Pro Gly Phe Thr Gly Gly Asp Ile Leu Arg Arg Thr
                485                 490                 495 ggt cct gga aca ttt gga gat atg aga ata aat att aat gca cca tta         1536
Gly Pro Gly Thr Phe Gly Asp Met Arg Ile Asn Ile Asn Ala Pro Leu
            500                 505                 510 tct caa aga tat cgt gta agg att cgt tat gct tct acg aca gat tta         1584
Ser Gln Arg Tyr Arg Val Arg Ile Arg Tyr Ala Ser Thr Thr Asp Leu
        515                 520                 525 caa ttt gtc acg agt att aat ggg acc acc att aat att ggt aac ttc         1632
Gln Phe Val Thr Ser Ile Asn Gly Thr Thr Ile Asn Ile Gly Asn Phe
    530                 535                 540 ccg aaa act att aat aat cta aat act tta ggt tct gag ggc tat aga         1680
Pro Lys Thr Ile Asn Asn Leu Asn Thr Leu Gly Ser Glu Gly Tyr Arg
545                 550                 555                 560 aca gta tcg ttt agt act cca ttt agt ttc tca aat gca caa agc ata         1728
```

```
Thr Val Ser Phe Ser Thr Pro Phe Ser Phe Ser Asn Ala Gln Ser Ile
            565                 570                 575 ttt aga tta ggt ata caa gca ttt tct gga gtt caa gaa gtt tat gtg      1776
Phe Arg Leu Gly Ile Gln Ala Phe Ser Gly Val Gln Glu Val Tyr Val
            580                 585                 590 gat aaa att gaa ttt att cct gtt gaa                                  1803
Asp Lys Ile Glu Phe Ile Pro Val Glu
            595                 600

<210> SEQ ID NO 18
<211> LENGTH: 601
<212> TYPE: PRT
<213> ORGANISM: Bacillus thuringiensis

<400> SEQUENCE: 18

Met Asn Ser Thr Glu His Asp Tyr Leu Lys Val Cys Asn Asp Leu Ser
1               5                   10                  15

Asp Ala Asn Ile Asn Met Glu Arg Phe Asp Lys Asn Asp Ala Leu Glu
            20                  25                  30

Ile Gly Met Ser Ile Val Ser Glu Leu Ile Gly Met Ile Pro Gly Gly
        35                  40                  45

Thr Ala Leu Gln Phe Val Phe Asn Gln Leu Trp Ser Arg Leu Gly Asp
    50                  55                  60

Ser Gly Trp Asn Ala Phe Met Glu His Val Glu Glu Leu Ile Asp Thr
65                  70                  75                  80

Lys Ile Glu Gly Tyr Ala Lys Asn Lys Ala Leu Ser Glu Leu Ala Gly
                85                  90                  95

Ile Gln Arg Asn Leu Glu Thr Tyr Ile Gln Leu Arg Asn Glu Trp Glu
            100                 105                 110

Asn Asp Ile Glu Asn Ser Lys Ala Gln Gly Lys Val Ala Asn Tyr Tyr
        115                 120                 125

Glu Ser Leu Glu Gln Ala Val Glu Arg Ser Met Pro Gln Phe Ala Val
    130                 135                 140

Glu Asn Phe Glu Val Pro Leu Leu Thr Val Tyr Val Gln Ala Ala Asn
145                 150                 155                 160

Leu His Leu Leu Leu Leu Arg Asp Val Ser Val Tyr Gly Lys Cys Trp
                165                 170                 175

Gly Trp Ser Glu Gln Lys Ile Lys Ile Tyr Tyr Asp Lys Gln Ile Lys
            180                 185                 190

Tyr Thr His Glu Tyr Thr Asn His Cys Val Asn Trp Tyr Asn Lys Gly
        195                 200                 205

Leu Glu Arg Leu Lys Asn Lys Gly Ser Ser Tyr Gln Asp Trp Tyr Asn
    210                 215                 220

Tyr Asn Arg Phe Arg Arg Glu Met Thr Leu Thr Val Leu Asp Ile Val
225                 230                 235                 240

Ala Leu Phe Pro His Tyr Asp Val Gln Thr Tyr Pro Ile Thr Thr Val
                245                 250                 255

Ala Gln Leu Thr Arg Glu Val Tyr Thr Asp Pro Leu Leu Asn Phe Asn
            260                 265                 270

Pro Lys Leu His Ser Val Ser Gln Leu Pro Ser Phe Ser Asp Met Glu
        275                 280                 285

Asn Ala Thr Ile Arg Thr Pro His Leu Met Glu Phe Leu Arg Met Leu
    290                 295                 300

Thr Ile Tyr Thr Asp Trp Tyr Ser Val Gly Arg Asn Tyr Tyr Trp Gly
305                 310                 315                 320

Gly His Arg Val Thr Ser Tyr His Val Gly Gly Glu Asn Ile Arg Ser
```

```
                 325                 330                 335
Pro Leu Tyr Gly Arg Glu Ala Asn Gln Glu Val Pro Arg Asp Phe Tyr
            340                 345                 350

Phe Tyr Gly Pro Val Phe Lys Thr Leu Ser Lys Pro Thr Leu Arg Pro
            355                 360                 365

Leu Gln Gln Pro Ala Pro Ala Pro Pro Phe Asn Leu Arg Ser Leu Glu
            370                 375                 380

Gly Val Glu Phe His Thr Pro Thr Gly Ser Phe Met Tyr Arg Glu Arg
385                 390                 395                 400

Gly Ser Val Asp Ser Phe Asn Glu Leu Pro Pro Phe Asn Pro Val Gly
                405                 410                 415

Leu Pro His Lys Val Tyr Ser His Arg Leu Cys His Ala Thr Phe Val
            420                 425                 430

Arg Lys Ser Gly Thr Pro Tyr Leu Thr Thr Gly Ala Ile Phe Ser Trp
            435                 440                 445

Thr His Arg Ser Ala Glu Glu Thr Asn Thr Ile Glu Ser Asn Ile Ile
            450                 455                 460

Thr Gln Ile Pro Leu Val Lys Ala Tyr Gln Ile Gly Ser Gly Thr Thr
465                 470                 475                 480

Val Arg Lys Gly Pro Gly Phe Thr Gly Gly Asp Ile Leu Arg Thr
                485                 490                 495

Gly Pro Gly Thr Phe Gly Asp Met Arg Ile Asn Ile Asn Ala Pro Leu
            500                 505                 510

Ser Gln Arg Tyr Arg Val Arg Ile Arg Tyr Ala Ser Thr Thr Asp Leu
            515                 520                 525

Gln Phe Val Thr Ser Ile Asn Gly Thr Thr Ile Asn Ile Gly Asn Phe
            530                 535                 540

Pro Lys Thr Ile Asn Asn Leu Asn Thr Leu Gly Ser Glu Gly Tyr Arg
545                 550                 555                 560

Thr Val Ser Phe Ser Thr Pro Phe Ser Phe Ser Asn Ala Gln Ser Ile
                565                 570                 575

Phe Arg Leu Gly Ile Gln Ala Phe Ser Gly Val Gln Glu Val Tyr Val
            580                 585                 590

Asp Lys Ile Glu Phe Ile Pro Val Glu
            595                 600

<210> SEQ ID NO 19
<211> LENGTH: 1803
<212> TYPE: DNA
<213> ORGANISM: Bacillus thuringiensis
<220> FEATURE:
<221> NAME/

| | | |
|---|---|---|
| tct gga tgg aat gcg ttc atg gaa cat gtg gag gaa tta att gat act<br>Ser Gly Trp Asn Ala Phe Met Glu His Val Glu Glu Leu Ile Asp Thr<br>65                     70                         75                   80 | 240 |
| aaa ata gaa ggg tat gca aaa aat aaa gcc tta tct gaa tta gca ggt<br>Lys Ile Glu Gly Tyr Ala Lys Asn Lys Ala Leu Ser Glu Leu Ala Gly<br>                    85                   90                   95 | 288 |
| ata caa aga aac ctt gaa aca tat ata caa tta cgt aat gaa tgg gaa<br>Ile Gln Arg Asn Leu Glu Thr Tyr Ile Gln Leu Arg Asn Glu Trp Glu<br>100                   105                  110 | 336 |
| aat gat att gaa aac tca aag gct caa ggt aag gta gct aat tac tat<br>Asn Asp Ile Glu Asn Ser Lys Ala Gln Gly Lys Val Ala Asn Tyr Tyr<br>     115                 120                  125 | 384 |
| gaa agt ctt gag cag gcg gtt gaa agg agt atg cct caa ttt gca gtg<br>Glu Ser Leu Glu Gln Ala Val Glu Arg Ser Met Pro Gln Phe Ala Val<br>130                     135                  140 | 432 |
| ggg aat ttt gaa gta cca ctt tta act gtc tat gtg caa gct gct aat<br>Gly Asn Phe Glu Val Pro Leu Leu Thr Val Tyr Val Gln Ala Ala Asn<br>145                   150                 155                 160 | 480 |
| ctt cat tta tta tta tta aga gat gtt tca gtt tat gga aag cgt tgg<br>Leu His Leu Leu Leu Leu Arg Asp Val Ser Val Tyr Gly Lys Arg Trp<br>             165                  170                  175 | 528 |
| gga tgg tcg gag cag aaa att aaa att tat tat gat aaa cag att aag<br>Gly Trp Ser Glu Gln Lys Ile Lys Ile Tyr Tyr Asp Lys Gln Ile Lys<br>                180                  185                  190 | 576 |
| tat acc cat gaa tac aca aat cat tgt gta aat tgg tat aat aaa gga<br>Tyr Thr His Glu Tyr Thr Asn His Cys Val Asn Trp Tyr Asn Lys Gly<br>     195                 200                  205 | 624 |
| ctt gag aga tta aaa aat aaa ggt tct tct tat caa gat tgg tac aat<br>Leu Glu Arg Leu Lys Asn Lys Gly Ser Ser Tyr Gln Asp Trp Tyr Asn<br>210                   215                  220 | 672 |
| tat aat cgt ttc cgt aga gaa atg act ctt act gtt tta gat atc gtt<br>Tyr Asn Arg Phe Arg Arg Glu Met Thr Leu Thr Val Leu Asp Ile Val<br>225                   230                  235                 240 | 720 |
| gct tta ttc ccg cac tat gat gta caa act tat cca ata aca acc gtt<br>Ala Leu Phe Pro His Tyr Asp Val Gln Thr Tyr Pro Ile Thr Thr Val<br>                245                  250                  255 | 768 |
| gct cag cta aca agg gaa gtt tat acg gat cct tta ctt aat ttt aat<br>Ala Gln Leu Thr Arg Glu Val Tyr Thr Asp Pro Leu Leu Asn Phe Asn<br>          260                  265                  270 | 816 |
| cct aaa tta cat tct gtg tct caa tta cct agt ttt agt gac atg gaa<br>Pro Lys Leu His Ser Val Ser Gln Leu Pro Ser Phe Ser Asp Met Glu<br>275                   280                 285 | 864 |
| aat gca aca att aga act cca cat ctg atg gaa ttt tta aga atg cta<br>Asn Ala Thr Ile Arg Thr Pro His Leu Met Glu Phe Leu Arg Met Leu<br>     290                 295                  300 | 912 |
| aca att tat aca gat tgg tat agt gtg gga aga aac tat tat tgg gga<br>Thr Ile Tyr Thr Asp Trp Tyr Ser Val Gly Arg Asn Tyr Tyr Trp Gly<br>305                   310                 315                 320 | 960 |
| gga cat cgc gtg acg tct tac cat gta gga gga gag aat ata aga tca<br>Gly His Arg Val Thr Ser Tyr His Val Gly Gly Glu Asn Ile Arg Ser<br>                325                  330                 335 | 1008 |
| cct cta tat ggt aga gag gca aat caa gag gtt cct aga gat ttt tat<br>Pro Leu Tyr Gly Arg Glu Ala Asn Gln Glu Val Pro Arg Asp Phe Tyr<br>340                   345                  350 | 1056 |
| ttt tat gga ccc gtt ttt aag acg tta tca aag ccg act cta aga cca<br>Phe Tyr Gly Pro Val Phe Lys Thr Leu Ser Lys Pro Thr Leu Arg Pro<br>     355                 360                  365 | 1104 |
| tta cag cag cct gca cca gct cct cct ttt aat tta cgt agc tta gag<br>Leu Gln Gln Pro Ala Pro Ala Pro Pro Phe Asn Leu Arg Ser Leu Glu<br>370                   375                  380 | 1152 |

| | | |
|---|---|---|
| gga gta gaa ttc cac act cct aca ggt agt ttt atg tat cgt gaa aga<br>Gly Val Glu Phe His Thr Pro Thr Gly Ser Phe Met Tyr Arg Glu Arg<br>385                390               395              400 | | 1200 |
| gga tcg gta gat tct ttt aat gag tta ccg cct ttt aat cca gtt ggg<br>Gly Ser Val Asp Ser Phe Asn Glu Leu Pro Pro Phe Asn Pro Val Gly<br>              405               410              415 | | 1248 |
| tta cct cat aag gta tac agt cac cgt tta tgt cat gca acg ttt gtt<br>Leu Pro His Lys Val Tyr Ser His Arg Leu Cys His Ala Thr Phe Val<br>        420               425               430 | | 1296 |
| cgt aaa tct ggg acc cct tat tta aca aca ggt gcc atc ttt tct tgg<br>Arg Lys Ser Gly Thr Pro Tyr Leu Thr Thr Gly Ala Ile Phe Ser Trp<br>435                440               445 | | 1344 |
| aca cat cgt agt gct gaa gaa acc aat aca att gaa tca aat att att<br>Thr His Arg Ser Ala Glu Glu Thr Asn Thr Ile Glu Ser Asn Ile Ile<br>        450               455              460 | | 1392 |
| acg caa atc ccg tta gta aaa gca tat caa att ggg tca ggc act act<br>Thr Gln Ile Pro Leu Val Lys Ala Tyr Gln Ile Gly Ser Gly Thr Thr<br>465                470               475              480 | | 1440 |
| gta agg aaa gga cca gga ctc aca gga ggg gat ata ctt cga aga aca<br>Val Arg Lys Gly Pro Gly Leu Thr Gly Gly Asp Ile Leu Arg Arg Thr<br>              485               490              495 | | 1488 |
| ggt cct gga aca ttt gga gat atg aga ata aat att aat gca cca tta<br>Gly Pro Gly Thr Phe Gly Asp Met Arg Ile Asn Ile Asn Ala Pro Leu<br>500                505               510 | | 1536 |
| tct caa aga tat cgt gta agg att cgt tat gct tct acg aca gat tta<br>Ser Gln Arg Tyr Arg Val Arg Ile Arg Tyr Ala Ser Thr Thr Asp Leu<br>              515               520              525 | | 1584 |
| caa ttt gtc acg agt att aat ggg acc acc att aat att ggt aac ttc<br>Gln Phe Val Thr Ser Ile Asn Gly Thr Thr Ile Asn Ile Gly Asn Phe<br>530                535               540 | | 1632 |
| cca aaa act att aat aat cta aat act tta ggt tct gag ggc tat aga<br>Pro Lys Thr Ile Asn Asn Leu Asn Thr Leu Gly Ser Glu Gly Tyr Arg<br>545                550               555              560 | | 1680 |
| aca gta tcg ttt agt act cca ttt agt ttc tca aat gca caa agc ata<br>Thr Val Ser Phe Ser Thr Pro Phe Ser Phe Ser Asn Ala Gln Ser Ile<br>              565               570              575 | | 1728 |
| ttt aga tta ggt ata caa gca ttt tct gga gtt caa gaa gtt tat gtg<br>Phe Arg Leu Gly Ile Gln Ala Phe Ser Gly Val Gln Glu Val Tyr Val<br>580                585               590 | | 1776 |
| gat aaa att gaa ttt att cct gtt gaa<br>Asp Lys Ile Glu Phe Ile Pro Val Glu<br>              595               600 | | 1803 |

<210> SEQ ID NO 20
<211> LENGTH: 601
<212> TYPE: PRT
<213> ORGANISM: Bacillus thuringiensis

<400> SEQUENCE: 20

Met Asn Ser Lys Glu His Asp Tyr Leu Lys Val Cys Asn Asp Leu Ser
1               5                  10               15

Asp Ala Asn Ile Asn Met Glu Arg Phe Asp Lys Asn Asp Ala Leu Glu
              20                 25               30

Ile Gly Met Ser Ile Val Ser Glu Leu Ile Gly Met Ile Pro Gly Gly
        35               40               45

Thr Ala Leu Gln Phe Val Phe Asn Gln Leu Trp Ser Arg Leu Gly Asp
50                55               60

Ser Gly Trp Asn Ala Phe Met Glu His Val Glu Glu Leu Ile Asp Thr
65               70               75              80

-continued

```
Lys Ile Glu Gly Tyr Ala Lys Asn Lys Ala Leu Ser Glu Leu Ala Gly
             85                  90                  95
Ile Gln Arg Asn Leu Glu Thr Tyr Ile Gln Leu Arg Asn Glu Trp Glu
            100                 105                 110
Asn Asp Ile Glu Asn Ser Lys Ala Gln Gly Lys Val Ala Asn Tyr Tyr
            115                 120                 125
Glu Ser Leu Glu Gln Ala Val Glu Arg Ser Met Pro Gln Phe Ala Val
            130                 135                 140
Gly Asn Phe Glu Val Pro Leu Leu Thr Val Tyr Val Gln Ala Ala Asn
145                 150                 155                 160
Leu His Leu Leu Leu Arg Asp Val Ser Val Tyr Gly Lys Arg Trp
            165                 170                 175
Gly Trp Ser Glu Gln Lys Ile Lys Ile Tyr Tyr Asp Lys Gln Ile Lys
            180                 185                 190
Tyr Thr His Glu Tyr Thr Asn His Cys Val Asn Trp Tyr Asn Lys Gly
            195                 200                 205
Leu Glu Arg Leu Lys Asn Lys Gly Ser Ser Tyr Gln Asp Trp Tyr Asn
            210                 215                 220
Tyr Asn Arg Phe Arg Arg Glu Met Thr Leu Thr Val Leu Asp Ile Val
225                 230                 235                 240
Ala Leu Phe Pro His Tyr Asp Val Gln Thr Tyr Pro Ile Thr Thr Val
            245                 250                 255
Ala Gln Leu Thr Arg Glu Val Tyr Thr Asp Pro Leu Leu Asn Phe Asn
            260                 265                 270
Pro Lys Leu His Ser Val Ser Gln Leu Pro Ser Phe Ser Asp Met Glu
            275                 280                 285
Asn Ala Thr Ile Arg Thr Pro His Leu Met Glu Phe Leu Arg Met Leu
            290                 295                 300
Thr Ile Tyr Thr Asp Trp Tyr Ser Val Gly Arg Asn Tyr Tyr Trp Gly
305                 310                 315                 320
Gly His Arg Val Thr Ser Tyr His Val Gly Gly Glu Asn Ile Arg Ser
            325                 330                 335
Pro Leu Tyr Gly Arg Glu Ala Asn Gln Glu Val Pro Arg Asp Phe Tyr
            340                 345                 350
Phe Tyr Gly Pro Val Phe Lys Thr Leu Ser Lys Pro Thr Leu Arg Pro
            355                 360                 365
Leu Gln Gln Pro Ala Pro Ala Pro Pro Phe Asn Leu Arg Ser Leu Glu
            370                 375                 380
Gly Val Glu Phe His Thr Pro Thr Gly Ser Phe Met Tyr Arg Glu Arg
385                 390                 395                 400
Gly Ser Val Asp Ser Phe Asn Glu Leu Pro Pro Phe Asn Pro Val Gly
            405                 410                 415
Leu Pro His Lys Val Tyr Ser His Arg Leu Cys His Ala Thr Phe Val
            420                 425                 430
Arg Lys Ser Gly Thr Pro Tyr Leu Thr Thr Gly Ala Ile Phe Ser Trp
            435                 440                 445
Thr His Arg Ser Ala Glu Glu Thr Asn Thr Ile Glu Ser Asn Ile Ile
            450                 455                 460
Thr Gln Ile Pro Leu Val Lys Ala Tyr Gln Ile Gly Ser Gly Thr Thr
465                 470                 475                 480
Val Arg Lys Gly Pro Gly Leu Thr Gly Gly Asp Ile Leu Arg Arg Thr
            485                 490                 495
Gly Pro Gly Thr Phe Gly Asp Met Arg Ile Asn Ile Asn Ala Pro Leu
            500                 505                 510
```

-continued

```
Ser Gln Arg Tyr Arg Val Arg Ile Arg Tyr Ala Ser Thr Thr Asp Leu
        515                 520                 525

Gln Phe Val Thr Ser Ile Asn Gly Thr Thr Ile Asn Ile Gly Asn Phe
    530                 535                 540

Pro Lys Thr Ile Asn Asn Leu Asn Thr Leu Gly Ser Glu Gly Tyr Arg
545                 550                 555                 560

Thr Val Ser Phe Ser Thr Pro Phe Ser Phe Ser Asn Ala Gln Ser Ile
                565                 570                 575

Phe Arg Leu Gly Ile Gln Ala Phe Ser Gly Val Gln Glu Val Tyr Val
            580                 585                 590

Asp Lys Ile Glu Phe Ile Pro Val Glu
        595                 600
```

```
<210> SEQ ID NO 21
<211> LENGTH: 39
<212> TYPE: DNA
<213> ORGANISM: Artificial Sequence
<220> FEATURE:
<223> OTHER INFORMATION: tic900 5' thermal amplification primer
<220> FEATURE:
<221> NAME/KEY: misc_feature
<222> LOCATION: (1)..(39)
<223> OTHER INFORMATION: tic900 5' thermal amplification primer

<400> SEQUENCE: 21
gcgctagcat gaattcaaag gaacatgatt atctaaaag                          39

<210> SEQ ID NO 22
<211> LENGTH: 41
<212> TYPE: DNA
<213> ORGANISM: Artificial Sequence
<220> FEATURE:
<223> OTHER INFORMATION: tic900 3' thermal amplification primer
<220> FEATURE:
<221> NAME/KEY: misc_feature
<222> LOCATION: (1)..(41)
<223> OTHER INFORMATION: tic900 3' thermal amplification primer

<400> SEQUENCE: 22
cgggctcgag ctattcaaca ggaataaatt caattttatc c                       41

<210> SEQ ID NO 23
<211> LENGTH: 3504
<212> TYPE: DNA
<213> ORGANISM: Artificial Sequence
<220> FEATURE:
<223> OTHER INFORMATION: tic109 CDS consisting of CDS for TIC900 linked
      in frame to CDS for Cry1Ac protoxin
<220> FEATURE:
<221> NAME/KEY: CDS
<222> LOCATION: (1)..(3504)
<223> OTHER INFORMATION: 1-1803 TIC900 toxin domains I-III; 1804-1809
      XhoI linker; 1810-3

-continued

| | | | | | | | | | | | | | | |
|---|---|---|---|---|---|---|---|---|---|---|---|---|---|---|
| Thr | Ala | Leu | Gln | Phe | Val | Phe | Asn | Gln | Leu | Trp | Ser | Arg | Leu | Gly | Asp |
| | 50 | | | | 55 | | | | 60 | | | | | | |

| tct | gga | tgg | aat | gcg | ttc | atg | gaa | cat | gtg | gag | gaa | tta | att | gat | act | 240 |
|---|---|---|---|---|---|---|---|---|---|---|---|---|---|---|---|---|
| Ser | Gly | Trp | Asn | Ala | Phe | Met | Glu | His | Val | Glu | Glu | Leu | Ile | Asp | Thr | |
| 65 | | | | 70 | | | | 75 | | | | | 80 | | | |

| aaa | ata | gaa | ggg | tat | gca | aaa | aat | aaa | gcc | tta | tct | gaa | tta | gca | ggt | 288 |
|---|---|---|---|---|---|---|---|---|---|---|---|---|---|---|---|---|
| Lys | Ile | Glu | Gly | Tyr | Ala | Lys | Asn | Lys | Ala | Leu | Ser | Glu | Leu | Ala | Gly | |
| | | | | 85 | | | | 90 | | | | | 95 | | | |

| ata | caa | aga | aac | ctt | gaa | aca | tat | ata | caa | tta | cgt | aat | gaa | tgg | gaa | 336 |
|---|---|---|---|---|---|---|---|---|---|---|---|---|---|---|---|---|
| Ile | Gln | Arg | Asn | Leu | Glu | Thr | Tyr | Ile | Gln | Leu | Arg | Asn | Glu | Trp | Glu | |
| | | 100 | | | | | 105 | | | | 110 | | | | | |

| aat | gat | att | gaa | aac | tca | aag | gct | caa | ggt | aag | gta | gct | aat | tac | tat | 384 |
|---|---|---|---|---|---|---|---|---|---|---|---|---|---|---|---|---|
| Asn | Asp | Ile | Glu | Asn | Ser | Lys | Ala | Gln | Gly | Lys | Val | Ala | Asn | Tyr | Tyr | |
| | | | 115 | | | | 120 | | | | | 125 | | | | |

| gaa | agt | ctt | gag | cag | gcg | gtt | gaa | agg | agt | atg | cct | caa | ttt | gca | gtg | 432 |
|---|---|---|---|---|---|---|---|---|---|---|---|---|---|---|---|---|
| Glu | Ser | Leu | Glu | Gln | Ala | Val | Glu | Arg | Ser | Met | Pro | Gln | Phe | Ala | Val | |
| | 130 | | | | | 135 | | | | | 140 | | | | | |

| ggg | aat | ttt | gaa | gta | cca | ctt | tta | act | gtt | tat | gtg | caa | gct | gct | aat | 480 |
|---|---|---|---|---|---|---|---|---|---|---|---|---|---|---|---|---|
| Gly | Asn | Phe | Glu | Val | Pro | Leu | Leu | Thr | Val | Tyr | Val | Gln | Ala | Ala | Asn | |
| 145 | | | | | 150 | | | | | 155 | | | | | 160 | |

| ctt | cat | tta | tta | tta | tta | aga | gat | gtt | tca | gtt | tat | gga | aag | cgt | tgg | 528 |
|---|---|---|---|---|---|---|---|---|---|---|---|---|---|---|---|---|
| Leu | His | Leu | Leu | Leu | Leu | Arg | Asp | Val | Ser | Val | Tyr | Gly | Lys | Arg | Trp | |
| | | | | | 165 | | | | | 170 | | | | | 175 | |

| gga | tgg | tcg | gag | cag | aaa | att | aaa | att | tat | tat | gat | aga | cag | att | aag | 576 |
|---|---|---|---|---|---|---|---|---|---|---|---|---|---|---|---|---|
| Gly | Trp | Ser | Glu | Gln | Lys | Ile | Lys | Ile | Tyr | Tyr | Asp | Arg | Gln | Ile | Lys | |
| | | | 180 | | | | | 185 | | | | | 190 | | | |

| tat | acc | cat | gaa | tac | aca | aat | cat | tgt | gta | aat | tgg | tat | aat | aaa | gga | 624 |
|---|---|---|---|---|---|---|---|---|---|---|---|---|---|---|---|---|
| Tyr | Thr | His | Glu | Tyr | Thr | Asn | His | Cys | Val | Asn | Trp | Tyr | Asn | Lys | Gly | |
| | | | 195 | | | | | 200 | | | | | 205 | | | |

| ctt | gag | aga | tta | aaa | aat | aaa | ggt | tct | tct | tat | caa | gat | tgg | tac | aat | 672 |
|---|---|---|---|---|---|---|---|---|---|---|---|---|---|---|---|---|
| Leu | Glu | Arg | Leu | Lys | Asn | Lys | Gly | Ser | Ser | Tyr | Gln | Asp | Trp | Tyr | Asn | |
| | 210 | | | | | 215 | | | | | 220 | | | | | |

| tat | aat | cgt | ttc | cgt | aga | gaa | atg | act | ctt | act | gtt | tta | gat | atc | gtt | 720 |
|---|---|---|---|---|---|---|---|---|---|---|---|---|---|---|---|---|
| Tyr | Asn | Arg | Phe | Arg | Arg | Glu | Met | Thr | Leu | Thr | Val | Leu | Asp | Ile | Val | |
| 225 | | | | 230 | | | | | 235 | | | | | 240 | | |

| gct | tta | ttc | ccg | cac | tat | gat | gta | caa | act | tat | cca | ata | aca | acc | gtt | 768 |
|---|---|---|---|---|---|---|---|---|---|---|---|---|---|---|---|---|
| Ala | Leu | Phe | Pro | His | Tyr | Asp | Val | Gln | Thr | Tyr | Pro | Ile | Thr | Thr | Val | |
| | | | | 245 | | | | | 250 | | | | | 255 | | |

| gct | cag | tta | aca | agg | gaa | gtt | tat | acg | gat | cct | tta | ctt | aat | ttt | aat | 816 |
|---|---|---|---|---|---|---|---|---|---|---|---|---|---|---|---|---|
| Ala | Gln | Leu | Thr | Arg | Glu | Val | Tyr | Thr | Asp | Pro | Leu | Leu | Asn | Phe | Asn | |
| | | | 260 | | | | | 265 | | | | | 270 | | | |

| cct | aaa | tta | cat | tct | gtg | tct | caa | tta | cct | agt | ttt | agt | gac | atg | gaa | 864 |
|---|---|---|---|---|---|---|---|---|---|---|---|---|---|---|---|---|
| Pro | Lys | Leu | His | Ser | Val | Ser | Gln | Leu | Pro | Ser | Phe | Ser | Asp | Met | Glu | |
| | | 275 | | | | | 280 | | | | | 285 | | | | |

| aat | gca | aca | att | aga | act | cca | cat | ctg | atg | gaa | ttt | tta | aga | atg | cta | 912 |
|---|---|---|---|---|---|---|---|---|---|---|---|---|---|---|---|---|
| Asn | Ala | Thr | Ile | Arg | Thr | Pro | His | Leu | Met | Glu | Phe | Leu | Arg | Met | Leu | |
| | | 290 | | | | | 295 | | | | | 300 | | | | |

| aca | att | tat | aca | gat | tgg | tat | agt | gtg | gga | aga | aac | tat | tat | tgg | gga | 960 |
|---|---|---|---|---|---|---|---|---|---|---|---|---|---|---|---|---|
| Thr | Ile | Tyr | Thr | Asp | Trp | Tyr | Ser | Val | Gly | Arg | Asn | Tyr | Tyr | Trp | Gly | |
| 305 | | | | 310 | | | | | 315 | | | | | 320 | | |

| gga | cat | cgc | gtg | acg | tct | tac | cat | gta | gga | gga | gag | aat | ata | aga | tca | 1008 |
|---|---|---|---|---|---|---|---|---|---|---|---|---|---|---|---|---|
| Gly | His | Arg | Val | Thr | Ser | Tyr | His | Val | Gly | Gly | Glu | Asn | Ile | Arg | Ser | |
| | | | | 325 | | | | | 330 | | | | | 335 | | |

| cct | cta | tat | ggt | aga | gag | gca | aat | caa | gag | gtt | cct | aga | gat | ttt | tat | 1056 |
|---|---|---|---|---|---|---|---|---|---|---|---|---|---|---|---|---|
| Pro | Leu | Tyr | Gly | Arg | Glu | Ala | Asn | Gln | Glu | Val | Pro | Arg | Asp | Phe | Tyr | |
| | | | 340 | | | | | 345 | | | | | 350 | | | |

| ttt | tat | gga | ccc | gtt | ttt | aag | acg | tta | tca | aag | ccg | act | cta | aga | cca | 1104 |
|---|---|---|---|---|---|---|---|---|---|---|---|---|---|---|---|---|
| Phe | Tyr | Gly | Pro | Val | Phe | Lys | Thr | Leu | Ser | Lys | Pro | Thr | Leu | Arg | Pro | |
| | | 355 | | | | | 360 | | | | | 365 | | | | |

| tta | cag | cag | cct | gca | cca | gct | cct | cct | ttt | aat | tta | cgt | agc | tta | gag | 1152 |
|---|---|---|---|---|---|---|---|---|---|---|---|---|---|---|---|---|

-continued

| | | |
|---|---|---|
| Leu Gln Gln Pro Ala Pro Ala Pro Pro Phe Asn Leu Arg Ser Leu Glu<br>370                 375                380 | | |
| gga gta gaa ttc cac act tct aca ggt agt ttt atg tat cgt gaa aga<br>Gly Val Glu Phe His Thr Ser Thr Gly Ser Phe Met Tyr Arg Glu Arg<br>385                 390                395                400 | 1200 |
| gga tcg gta gat tct ttt aat gag tta ccg cct ttt aat cca gtt ggg<br>Gly Ser Val Asp Ser Phe Asn Glu Leu Pro Pro Phe Asn Pro Val Gly<br>                 405                410                415 | 1248 |
| tta cct cat aag gta tac agt cac cgt tta tgt cat gca acg ttt gtt<br>Leu Pro His Lys Val Tyr Ser His Arg Leu Cys His Ala Thr Phe Val<br>             420                    425                430 | 1296 |
| cgt aaa tct ggg acc cct tat tta aca aca ggt gcc atc ttt tct tgg<br>Arg Lys Ser Gly Thr Pro Tyr Leu Thr Thr Gly Ala Ile Phe Ser Trp<br>           435                  440                445 | 1344 |
| aca cat cgt agt gct gaa gaa acc aat aca att gaa tca aat att att<br>Thr His Arg Ser Ala Glu Glu Thr Asn Thr Ile Glu Ser Asn Ile Ile<br>450                 455                460 | 1392 |
| acg caa atc ccg tta gta aaa gca tat caa att gga tca ggc act act<br>Thr Gln Ile Pro Leu Val Lys Ala Tyr Gln Ile Gly Ser Gly Thr Thr<br>465                 470                475                480 | 1440 |
| gta agg aaa gga cca gga ttc aca gga ggg gat ata ctt cga aga aca<br>Val Arg Lys Gly Pro Gly Phe Thr Gly Gly Asp Ile Leu Arg Arg Thr<br>             485                  490                495 | 1488 |
| ggt cct gga aca ttt gga gat atg aga ata aat att aat gca cca tta<br>Gly Pro Gly Thr Phe Gly Asp Met Arg Ile Asn Ile Asn Ala Pro Leu<br>                 500                505                510 | 1536 |
| tct gaa aga tat cgt gta agg att cgt tat gct tct acg aca gat tta<br>Ser Glu Arg Tyr Arg Val Arg Ile Arg Tyr Ala Ser Thr Thr Asp Leu<br>           515                  520                525 | 1584 |
| caa ttt gtc acg agt att aat ggg gcc acc att aat att ggt aac ttc<br>Gln Phe Val Thr Ser Ile Asn Gly Ala Thr Ile Asn Ile Gly Asn Phe<br>530                 535                540 | 1632 |
| cca aaa act att aat aat cta aat act tta ggt tct gag ggc tat aga<br>Pro Lys Thr Ile Asn Asn Leu Asn Thr Leu Gly Ser Glu Gly Tyr Arg<br>545                 550                555                560 | 1680 |
| aca gta tcg ttt agt act cca ttt agt ttc tca aat gca caa agc ata<br>Thr Val Ser Phe Ser Thr Pro Phe Ser Phe Ser Asn Ala Gln Ser Ile<br>             565                  570                575 | 1728 |
| ttt aga tta ggt ata caa gca ttt tct gga gtt caa gaa gtt tat gtg<br>Phe Arg Leu Gly Ile Gln Ala Phe Ser Gly Val Gln Glu Val Tyr Val<br>           580                  585                590 | 1776 |
| gat aaa att gaa ttt att cct gtt gaa ctc gag gct gaa tat aat ctg<br>Asp Lys Ile Glu Phe Ile Pro Val Glu Leu Glu Ala Glu Tyr Asn Leu<br>           595                  600                605 | 1824 |
| gaa aga gcg cag aag gcg gtg aat gcg ctg ttt acg tct aca aac caa<br>Glu Arg Ala Gln Lys Ala Val Asn Ala Leu Phe Thr Ser Thr Asn Gln<br>610                 615                620 | 1872 |
| cta ggg cta aaa aca aat gta acg gat tat cat att gat caa gtg tcc<br>Leu Gly Leu Lys Thr Asn Val Thr Asp Tyr His Ile Asp Gln Val Ser<br>625                 630                635                640 | 1920 |
| aat tta gtt acg tat tta tcg gat gaa ttt tgt ctg gat gaa aag cga<br>Asn Leu Val Thr Tyr Leu Ser Asp Glu Phe Cys Leu Asp Glu Lys Arg<br>             645                  650                655 | 1968 |
| gaa ttg tcc gag aaa gtc aaa cat gcg aag cga ctc agt gat gaa cgc<br>Glu Leu Ser Glu Lys Val Lys His Ala Lys Arg Leu Ser Asp Glu Arg<br>           660                  665                670 | 2016 |
| aat tta ctc caa gat tca aat ttc aaa gac att aat agg caa cca gaa<br>Asn Leu Leu Gln Asp Ser Asn Phe Lys Asp Ile Asn Arg Gln Pro Glu<br>675                 680                685 | 2064 |
| cgt ggg tgg ggc gga agt aca ggg att acc atc caa gga ggg gat gac | 2112 |

-continued

| | | |
|---|---|---|
| Arg Gly Trp Gly Gly Ser Thr Gly Ile Thr Ile Gln Gly Asp Asp<br>690                         695                      700 | | |
| gta ttt aaa gaa aat tac gtc aca cta tca ggt acc ttt gat gag tgc<br>Val Phe Lys Glu Asn Tyr Val Thr Leu Ser Gly Thr Phe Asp Glu Cys<br>705                      710                    715                  720 | 2160 | |
| tat cca aca tat ttg tat caa aaa atc gat gaa tca aaa tta aaa gcc<br>Tyr Pro Thr Tyr Leu Tyr Gln Lys Ile Asp Glu Ser Lys Leu Lys Ala<br>                725                    730                    735 | 2208 | |
| ttt acc cgt tat caa tta aga ggg tat atc gaa gat agt caa gac tta<br>Phe Thr Arg Tyr Gln Leu Arg Gly Tyr Ile Glu Asp Ser Gln Asp Leu<br>              740                    745                    750 | 2256 | |
| gaa atc tat tta att cgc tac aat gca aaa cat gaa aca gta aat gtg<br>Glu Ile Tyr Leu Ile Arg Tyr Asn Ala Lys His Glu Thr Val Asn Val<br>          755                    760                    765 | 2304 | |
| cca ggt acg ggt tcc tta tgg ccg ctt tca gcc caa agt cca atc gga<br>Pro Gly Thr Gly Ser Leu Trp Pro Leu Ser Ala Gln Ser Pro Ile Gly<br>770                        775                    780 | 2352 | |
| aag tgt gga gag ccg aat cga tgc gcg cca cac ctt gaa tgg aat cct<br>Lys Cys Gly Glu Pro Asn Arg Cys Ala Pro His Leu Glu Trp Asn Pro<br>785                        790                  795                  800 | 2400 | |
| gac tta gat tgt tcg tgt agg gat gga gaa aag tgt gcc cat cat tcg<br>Asp Leu Asp Cys Ser Cys Arg Asp Gly Glu Lys Cys Ala His His Ser<br>                        805                    810                    815 | 2448 | |
| cat cat ttc tcc tta gac att gat gta gga tgt aca gac tta aat gag<br>His His Phe Ser Leu Asp Ile Asp Val Gly Cys Thr Asp Leu Asn Glu<br>            820                    825                    830 | 2496 | |
| gac cta ggt gta tgg gtg atc ttt aag att aag acg caa gat ggg cac<br>Asp Leu Gly Val Trp Val Ile Phe Lys Ile Lys Thr Gln Asp Gly His<br>                835                    840                    845 | 2544 | |
| gca aga cta ggg aat cta gag ttt ctc gaa gag aaa cca tta gta gga<br>Ala Arg Leu Gly Asn Leu Glu Phe Leu Glu Glu Lys Pro Leu Val Gly<br>850                        855                    860 | 2592 | |
| gaa gcg cta gct cgt gtg aaa aga gcg gag aaa aaa tgg aga gac aaa<br>Glu Ala Leu Ala Arg Val Lys Arg Ala Glu Lys Lys Trp Arg Asp Lys<br>865                        870                  875                  880 | 2640 | |
| cgt gaa aaa ttg gaa tgg gaa aca aat atc gtt tat aaa gag gca aaa<br>Arg Glu Lys Leu Glu Trp Glu Thr Asn Ile Val Tyr Lys Glu Ala Lys<br>                885                    890                    895 | 2688 | |
| gaa tct gta gat gct tta ttt gta aac tct caa tat gat caa tta caa<br>Glu Ser Val Asp Ala Leu Phe Val Asn Ser Gln Tyr Asp Gln Leu Gln<br>            900                    905                    910 | 2736 | |
| gcg gat acg aat att gcc atg att cat gcg gca gat aaa cgt gtt cat<br>Ala Asp Thr Asn Ile Ala Met Ile His Ala Ala Asp Lys Arg Val His<br>              915                    920                    925 | 2784 | |
| agc att cga gaa gct tat ctg cct gag ctg tct gtg att ccg ggt gtc<br>Ser Ile Arg Glu Ala Tyr Leu Pro Glu Leu Ser Val Ile Pro Gly Val<br>930                        935                    940 | 2832 | |
| aat gcg gct att ttt gaa gaa tta gaa ggg cgt att ttc act gca ttc<br>Asn Ala Ala Ile Phe Glu Glu Leu Glu Gly Arg Ile Phe Thr Ala Phe<br>945                        950                  955                  960 | 2880 | |
| tcc cta tat gat gcg aga aat gtc att aaa aat ggt gat ttt aat aat<br>Ser Leu Tyr Asp Ala Arg Asn Val Ile Lys Asn Gly Asp Phe Asn Asn<br>                965                    970                    975 | 2928 | |
| ggc tta tcc tgc tgg aac gtg aaa ggg cat gta gat gta gaa gaa caa<br>Gly Leu Ser Cys Trp Asn Val Lys Gly His Val Asp Val Glu Glu Gln<br>            980                    985                    990 | 2976 | |
| aac aac caa cgt tcg gtc ctt gtt  gtt ccg gaa tgg gaa  gca gaa gtg<br>Asn Asn Gln Arg Ser Val Leu Val  Val Pro Glu Trp Glu  Ala Glu Val<br>          995                    1000                  1005 | 3024 | |
| tca caa  gaa gtt cgt gtc tgt  ccg ggt cgt ggc tat  atc ctt cgt | 3069 | |

```
Ser Gln Glu Val Arg Val Cys Pro Gly Arg Gly Tyr Ile Leu Arg
    1010                1015                1020 gtc aca gcg tac aag gag gga tat gga gaa ggt tgc gta acc att    3114
Val Thr Ala Tyr Lys Glu Gly Tyr Gly Glu Gly Cys Val Thr Ile
    1025                1030                1035 cat gag atc gag aac aat aca gac gaa ctg aag ttt agc aac tgc    3159
His Glu Ile Glu Asn Asn Thr Asp Glu Leu Lys Phe Ser Asn Cys
    1040                1045                1050 gta gaa gag gaa atc tat cca aat aac acg gta acg tgt aat gat    3204
Val Glu Glu Glu Ile Tyr Pro Asn Asn Thr Val Thr Cys Asn Asp
    1055                1060                1065 tat act gta aat caa gaa gaa tac gga ggt gcg tac act tct cgt    3249
Tyr Thr Val Asn Gln Glu Glu Tyr Gly Gly Ala Tyr Thr Ser Arg
    1070                1075                1080 aat cga gga tat aac gaa gct cct tcc gta cca gct gat tat gcg    3294
Asn Arg Gly Tyr Asn Glu Ala Pro Ser Val Pro Ala Asp Tyr Ala
    1085                1090                1095 tca gtc tat gaa gaa aaa tcg tat aca gat gga cga aga gag aat    3339
Ser Val Tyr Glu Glu Lys Ser Tyr Thr Asp Gly Arg Arg Glu Asn
    1100                1105                1110 cct tgt gaa ttt aac aga ggg tat agg gat tac acg cca cta cca    3384
Pro Cys Glu Phe Asn Arg Gly Tyr Arg Asp Tyr Thr Pro Leu Pro
    1115                1120                1125 gtt ggt tat gtg aca aaa gaa tta gaa tac ttc cca gaa acc gat    3429
Val Gly Tyr Val Thr Lys Glu Leu Glu Tyr Phe Pro Glu Thr Asp
    1130                1135                1140 aag gta tgg att gag att gga gaa acg gaa gga aca ttt atc gtg    3474
Lys Val Trp Ile Glu Ile Gly Glu Thr Glu Gly Thr Phe Ile Val
    1145                1150                1155 gac agc gtg gaa tta ctc ctt atg gag gaa                        3504
Asp Ser Val Glu Leu Leu Leu Met Glu Glu
    1160                1165

<210> SEQ ID NO 24
<211> LENGTH: 1168
<212> TYPE: PRT
<213> ORGANISM: Artificial Sequence
<220> FEATURE:
<223> OTHER INFORMATION: Synthetic Construct

<400> SEQUENCE: 24

Met Asn Ser Lys Glu His Asp Tyr Leu Lys Val Cys Asn Asp Leu Ser
1               5                   10                  15

Asp Ala Asn Ile Asn Met Glu Arg Phe Asp Lys Asn Asp Ala Leu Glu
            20                  25                  30

Ile Gly Met Ser Ile Val Ser Glu Leu Ile Gly Met Ile Pro Gly Gly
        35                  40                  45

Thr Ala Leu Gln Phe Val Phe Asn Gln Leu Trp Ser Arg Leu Gly Asp
    50                  55                  60

Ser Gly Trp Asn Ala Phe Met Glu His Val Glu Glu Leu Ile Asp Thr
65                  70                  75                  80

Lys Ile Glu Gly Tyr Ala Lys Asn Lys Ala Leu Ser Glu Leu Ala Gly
                85                  90                  95

Ile Gln Arg Asn Leu Glu Thr Tyr Ile Gln Leu Arg Asn Glu Trp Glu
            100                 105                 110

Asn Asp Ile Glu Asn Ser Lys Ala Gln Gly Lys Val Ala Asn Tyr Tyr
        115                 120                 125

Glu Ser Leu Glu Gln Ala Val Glu Arg Ser Met Pro Gln Phe Ala Val
    130                 135                 140
```

-continued

```
Gly Asn Phe Glu Val Pro Leu Leu Thr Val Tyr Val Gln Ala Ala Asn
145                 150                 155                 160

Leu His Leu Leu Leu Leu Arg Asp Val Ser Val Tyr Gly Lys Arg Trp
                165                 170                 175

Gly Trp Ser Glu Gln Lys Ile Lys Ile Tyr Tyr Asp Arg Gln Ile Lys
            180                 185                 190

Tyr Thr His Glu Tyr Thr Asn His Cys Val Asn Trp Tyr Asn Lys Gly
        195                 200                 205

Leu Glu Arg Leu Lys Asn Lys Gly Ser Ser Tyr Gln Asp Trp Tyr Asn
    210                 215                 220

Tyr Asn Arg Phe Arg Arg Glu Met Thr Leu Thr Val Leu Asp Ile Val
225                 230                 235                 240

Ala Leu Phe Pro His Tyr Asp Val Gln Thr Tyr Pro Ile Thr Thr Val
                245                 250                 255

Ala Gln Leu Thr Arg Glu Val Tyr Thr Asp Pro Leu Leu Asn Phe Asn
                260                 265                 270

Pro Lys Leu His Ser Val Ser Gln Leu Pro Ser Phe Ser Asp Met Glu
            275                 280                 285

Asn Ala Thr Ile Arg Thr Pro His Leu Met Glu Phe Leu Arg Met Leu
        290                 295                 300

Thr Ile Tyr Thr Asp Trp Tyr Ser Val Gly Arg Asn Tyr Tyr Trp Gly
305                 310                 315                 320

Gly His Arg Val Thr Ser Tyr His Val Gly Gly Glu Asn Ile Arg Ser
                325                 330                 335

Pro Leu Tyr Gly Arg Glu Ala Asn Gln Glu Val Pro Arg Asp Phe Tyr
            340                 345                 350

Phe Tyr Gly Pro Val Phe Lys Thr Leu Ser Lys Pro Thr Leu Arg Pro
        355                 360                 365

Leu Gln Gln Pro Ala Pro Ala Pro Phe Asn Leu Arg Ser Leu Glu
    370                 375                 380

Gly Val Glu Phe His Thr Ser Thr Gly Ser Phe Met Tyr Arg Glu Arg
385                 390                 395                 400

Gly Ser Val Asp Ser Phe Asn Glu Leu Pro Pro Phe Asn Pro Val Gly
                405                 410                 415

Leu Pro His Lys Val Tyr Ser His Arg Leu Cys His Ala Thr Phe Val
            420                 425                 430

Arg Lys Ser Gly Thr Pro Tyr Leu Thr Thr Gly Ala Ile Phe Ser Trp
        435                 440                 445

Thr His Arg Ser Ala Glu Glu Thr Asn Thr Ile Glu Ser Asn Ile Ile
450                 455                 460

Thr Gln Ile Pro Leu Val Lys Ala Tyr Gln Ile Gly Ser Gly Thr Thr
465                 470                 475                 480

Val Arg Lys Gly Pro Gly Phe Thr Gly Gly Asp Ile Leu Arg Arg Thr
                485                 490                 495

Gly Pro Gly Thr Phe Gly Asp Met Arg Ile Asn Ile Asn Ala Pro Leu
            500                 505                 510

Ser Glu Arg Tyr Arg Val Arg Ile Arg Tyr Ala Ser Thr Thr Asp Leu
        515                 520                 525

Gln Phe Val Thr Ser Ile Asn Gly Ala Thr Ile Asn Ile Gly Asn Phe
    530                 535                 540

Pro Lys Thr Ile Asn Asn Leu Asn Thr Leu Gly Ser Glu Gly Tyr Arg
545                 550                 555                 560

Thr Val Ser Phe Ser Thr Pro Phe Ser Phe Ser Asn Ala Gln Ser Ile
                565                 570                 575
```

```
Phe Arg Leu Gly Ile Gln Ala Phe Ser Gly Val Gln Glu Val Tyr Val
            580                 585                 590

Asp Lys Ile Glu Phe Ile Pro Val Glu Leu Glu Ala Glu Tyr Asn Leu
            595                 600                 605

Glu Arg Ala Gln Lys Ala Val Asn Ala Leu Phe Thr Ser Thr Asn Gln
        610                 615                 620

Leu Gly Leu Lys Thr Asn Val Thr Asp Tyr His Ile Asp Gln Val Ser
625                 630                 635                 640

Asn Leu Val Thr Tyr Leu Ser Asp Glu Phe Cys Leu Asp Glu Lys Arg
                645                 650                 655

Glu Leu Ser Glu Lys Val Lys His Ala Lys Arg Leu Ser Asp Glu Arg
            660                 665                 670

Asn Leu Leu Gln Asp Ser Asn Phe Lys Asp Ile Asn Arg Gln Pro Glu
        675                 680                 685

Arg Gly Trp Gly Gly Ser Thr Gly Ile Thr Ile Gln Gly Gly Asp Asp
    690                 695                 700

Val Phe Lys Glu Asn Tyr Val Thr Leu Ser Gly Thr Phe Asp Glu Cys
705                 710                 715                 720

Tyr Pro Thr Tyr Leu Tyr Gln Lys Ile Asp Glu Ser Lys Leu Lys Ala
                725                 730                 735

Phe Thr Arg Tyr Gln Leu Arg Gly Tyr Ile Glu Asp Ser Gln Asp Leu
            740                 745                 750

Glu Ile Tyr Leu Ile Arg Tyr Asn Ala Lys His Glu Thr Val Asn Val
        755                 760                 765

Pro Gly Thr Gly Ser Leu Trp Pro Leu Ser Ala Gln Ser Pro Ile Gly
    770                 775                 780

Lys Cys Gly Glu Pro Asn Arg Cys Ala Pro His Leu Glu Trp Asn Pro
785                 790                 795                 800

Asp Leu Asp Cys Ser Cys Arg Asp Gly Glu Lys Cys Ala His His Ser
                805                 810                 815

His His Phe Ser Leu Asp Ile Asp Val Gly Cys Thr Asp Leu Asn Glu
            820                 825                 830

Asp Leu Gly Val Trp Val Ile Phe Lys Ile Lys Thr Gln Asp Gly His
        835                 840                 845

Ala Arg Leu Gly Asn Leu Glu Phe Leu Glu Glu Lys Pro Leu Val Gly
    850                 855                 860

Glu Ala Leu Ala Arg Val Lys Arg Ala Glu Lys Lys Trp Arg Asp Lys
865                 870                 875                 880

Arg Glu Lys Leu Glu Trp Glu Thr Asn Ile Val Tyr Lys Glu Ala Lys
                885                 890                 895

Glu Ser Val Asp Ala Leu Phe Val Asn Ser Gln Tyr Asp Gln Leu Gln
            900                 905                 910

Ala Asp Thr Asn Ile Ala Met Ile His Ala Ala Asp Lys Arg Val His
        915                 920                 925

Ser Ile Arg Glu Ala Tyr Leu Pro Glu Leu Ser Val Ile Pro Gly Val
    930                 935                 940

Asn Ala Ala Ile Phe Glu Glu Leu Glu Gly Arg Ile Phe Thr Ala Phe
945                 950                 955                 960

Ser Leu Tyr Asp Ala Arg Asn Val Ile Lys Asn Gly Asp Phe Asn Asn
                965                 970                 975

Gly Leu Ser Cys Trp Asn Val Lys Gly His Val Asp Val Glu Glu Gln
            980                 985                 990

Asn Asn Gln Arg Ser Val Leu Val  Val Pro Glu Trp Glu  Ala Glu Val
```

-continued

```
        995                 1000                1005

Ser Gln  Glu Val Arg Val Cys  Pro Gly Arg Gly Tyr  Ile Leu Arg
    1010                 1015                 1020

Val Thr  Ala Tyr Lys Glu Gly  Tyr Gly Glu Gly Cys  Val Thr Ile
    1025                 1030                 1035

His Glu  Ile Glu Asn Asn Thr  Asp Glu Leu Lys Phe  Ser Asn Cys
    1040                 1045                 1050

Val Glu  Glu Glu Ile Tyr Pro  Asn Asn Thr Val Thr  Cys Asn Asp
    1055                 1060                 1065

Tyr Thr  Val Asn Gln Glu Glu  Tyr Gly Gly Ala Tyr  Thr Ser Arg
    1070                 1075                 1080

Asn Arg  Gly Tyr Asn Glu Ala  Pro Ser Val Pro Ala  Asp Tyr Ala
    1085                 1090                 1095

Ser Val  Tyr Glu Glu Lys Ser  Tyr Thr Asp Gly Arg  Arg Glu Asn
    1100                 1105                 1110

Pro Cys  Glu Phe Asn Arg Gly  Tyr Arg Asp Tyr Thr  Pro Leu Pro
    1115                 1120                 1125

Val Gly  Tyr Val Thr Lys Glu  Leu Glu Tyr Phe Pro  Glu Thr Asp
    1130                 1135                 1140

Lys Val  Trp Ile Glu Ile Gly  Glu Thr Glu Gly Thr  Phe Ile Val
    1145                 1150                 1155

Asp Ser  Val Glu Leu Leu Leu  Met Glu Glu
    1160                 1165

<210> SEQ ID NO 25
<211> LENGTH: 3510
<212> TYPE: DNA
<213> ORGANISM: Artificial Sequence
<220> FEATURE:
<223> OTHER INFORMATION: tic110 CDS consisting of CDS for Domain I of
      Cry1F linked in frame to CDS for Domain II-III of TIC900 linked
      in frame to CDS for Cry1Ac protoxin
<220> FEATURE:
<221> NAME/KEY: CDS
<222> LOCATION: (1)..(3510)
<223> OTHER INFORMATION: Cry1F Domain I nt 1-723 (amino acid 1-233);
      TIC900 Domain II-III nt 724-1809 (amino acid 234-603); Cry1Ac
      protoxin domain nt 1810-3510 (amino acid 604-1170)

<400> SEQUENCE: 25 atg gag aat aat att caa aat caa tgc gta cct tac aat tgt tta aat       48
Met Glu Asn Asn Ile Gln Asn Gln Cys Val Pro Tyr Asn Cys Leu Asn
1               5                   10                  15 aat cct gaa gta gaa ata tta aat gaa gaa aga agt act ggc aga tta       96
Asn Pro Glu Val Glu Ile Leu Asn Glu Glu Arg Ser Thr Gly Arg Leu
            20                  25                  30 ccg tta gat ata tcc tta tcg ctt aca cgt ttc ctt ttg agt gaa ttt      144
Pro Leu Asp Ile Ser Leu Ser Leu Thr Arg Phe Leu Leu Ser Glu Phe
        35                  40                  45 gtt cca ggt gtg gga gtt gcg ttt gga tta ttt gat tta ata tgg ggt      192
Val Pro Gly Val Gly Val Ala Phe Gly Leu Phe Asp Leu Ile Trp Gly
    50                  55                  60 ttt ata act cct tct gat tgg agc tta ttt ctt tta cag att gaa caa      240
Phe Ile Thr Pro Ser Asp Trp Ser Leu Phe Leu Leu Gln Ile Glu Gln
65                  70                  75                  80 ttg att gag caa aga ata gaa aca ttg gaa agg aac cgg gca att act      288
Leu Ile Glu Gln Arg Ile Glu Thr Leu Glu Arg Asn Arg Ala Ile Thr
                85                  90                  95 aca tta cga ggg tta gca gat agc tat gaa att tat att gaa gca cta      336
Thr Leu Arg Gly Leu Ala Asp Ser Tyr Glu Ile Tyr Ile Glu Ala Leu
            100                 105                 110

| | | |
|---|---|---|
| aga gag tgg gaa gca aat cct aat aat gca caa tta agg gaa gat gtg<br>Arg Glu Trp Glu Ala Asn Pro Asn Asn Ala Gln Leu Arg Glu Asp Val<br>                115                      120                  125 | | 384 |
| cgt att cga ttt gct aat aca gac gac gct tta ata aca gca ata aat<br>Arg Ile Arg Phe Ala Asn Thr Asp Asp Ala Leu Ile Thr Ala Ile Asn<br>130                      135                      140 | | 432 |
| aat ttt aca ctt aca agt ttt gaa atc cct ctt tta tcg gtc tat gtt<br>Asn Phe Thr Leu Thr Ser Phe Glu Ile Pro Leu Leu Ser Val Tyr Val<br>145                      150                      155                      160 | | 480 |
| caa gcg gcg aat tta cat tta tca cta tta aga gac gct gta tcg ttt<br>Gln Ala Ala Asn Leu His Leu Ser Leu Leu Arg Asp Ala Val Ser Phe<br>                165                      170                      175 | | 528 |
| ggg cag ggt tgg gga ctg gat ata gct act gtt aat aat cat tat aat<br>Gly Gln Gly Trp Gly Leu Asp Ile Ala Thr Val Asn Asn His Tyr Asn<br>                180                      185                      190 | | 576 |
| aga tta ata aat ctt att cat aga tat acg aaa cat tgt ttg gac aca<br>Arg Leu Ile Asn Leu Ile His Arg Tyr Thr Lys His Cys Leu Asp Thr<br>                195                      200                      205 | | 624 |
| tac aat caa gga tta gaa aac tta aga ggt act aat act cga caa tgg<br>Tyr Asn Gln Gly Leu Glu Asn Leu Arg Gly Thr Asn Thr Arg Gln Trp<br>        210                      215                      220 | | 672 |
| gca aga ttc aat cag ttt agg aga gat tta aca ctt act gta tta gat<br>Ala Arg Phe Asn Gln Phe Arg Arg Asp Leu Thr Leu Thr Val Leu Asp<br>225                      230                      235                      240 | | 720 |
| atc gtt gct tta ttc ccg cac tat gat gta caa act tat cca ata aca<br>Ile Val Ala Leu Phe Pro His Tyr Asp Val Gln Thr Tyr Pro Ile Thr<br>                245                      250                      255 | | 768 |
| acc gtt gct cag tta aca agg gaa gtt tat acg gat cct tta ctt aat<br>Thr Val Ala Gln Leu Thr Arg Glu Val Tyr Thr Asp Pro Leu Leu Asn<br>                260                      265                      270 | | 816 |
| ttt aat cct aaa tta cat tct gtg tct caa tta cct agt ttt agt gac<br>Phe Asn Pro Lys Leu His Ser Val Ser Gln Leu Pro Ser Phe Ser Asp<br>                275                      280                      285 | | 864 |
| atg gaa aat gca aca att aga act cca cat ctg atg gaa ttt tta aga<br>Met Glu Asn Ala Thr Ile Arg Thr Pro His Leu Met Glu Phe Leu Arg<br>        290                      295                      300 | | 912 |
| atg cta aca att tat aca gat tgg tat agt gtg gga aga aac tat tat<br>Met Leu Thr Ile Tyr Thr Asp Trp Tyr Ser Val Gly Arg Asn Tyr Tyr<br>305                      310                      315                      320 | | 960 |
| tgg gga gga cat cgc gtg acg tct tac cat gta gga gga gag aat ata<br>Trp Gly Gly His Arg Val Thr Ser Tyr His Val Gly Gly Glu Asn Ile<br>                325                      330                      335 | | 1008 |
| aga tca cct cta tat ggt aga gag gca aat caa gag gtt cct aga gat<br>Arg Ser Pro Leu Tyr Gly Arg Glu Ala Asn Gln Glu Val Pro Arg Asp<br>                340                      345                      350 | | 1056 |
| ttt tat ttt tat gga ccc gtt ttt aag acg tta tca aag ccg act cta<br>Phe Tyr Phe Tyr Gly Pro Val Phe Lys Thr Leu Ser Lys Pro Thr Leu<br>                355                      360                      365 | | 1104 |
| aga cca tta cag cag cct gca cca gct cct cct ttt aat tta cgt agc<br>Arg Pro Leu Gln Gln Pro Ala Pro Ala Pro Pro Phe Asn Leu Arg Ser<br>        370                      375                      380 | | 1152 |
| tta gag gga gta gaa ttc cac act tct aca ggt agt ttt atg tat cgt<br>Leu Glu Gly Val Glu Phe His Thr Ser Thr Gly Ser Phe Met Tyr Arg<br>385                      390                      395                      400 | | 1200 |
| gaa aga gga tcg gta gat tct ttt aat gag tta ccg cct ttt aat cca<br>Glu Arg Gly Ser Val Asp Ser Phe Asn Glu Leu Pro Pro Phe Asn Pro<br>                      405                      410                      415 | | 1248 |
| gtt ggg tta cct cat aag gta tac agt cac cgt tta tgt cat gca acg<br>Val Gly Leu Pro His Lys Val Tyr Ser His Arg Leu Cys His Ala Thr<br>                420                      425                      430 | | 1296 |

| | | | | | | | | | | | | | | | |
|---|---|---|---|---|---|---|---|---|---|---|---|---|---|---|---|
| ttt | gtt | cgt | aaa | tct | ggg | acc | cct | tat | tta | aca | aca | ggt | gcc | atc | ttt | 1344 |
| Phe | Val | Arg | Lys | Ser | Gly | Thr | Pro | Tyr | Leu | Thr | Thr | Gly | Ala | Ile | Phe |
| | | 435 | | | | 440 | | | | | 445 | | | | |
| tct | tgg | aca | cat | cgt | agt | gct | gaa | gaa | acc | aat | aca | att | gaa | tca | aat | 1392 |
| Ser | Trp | Thr | His | Arg | Ser | Ala | Glu | Glu | Thr | Asn | Thr | Ile | Glu | Ser | Asn |
| | 450 | | | | | 455 | | | | | 460 | | | | |
| att | att | acg | caa | atc | ccg | tta | gta | aaa | gca | tat | caa | att | gga | tca | ggc | 1440 |
| Ile | Ile | Thr | Gln | Ile | Pro | Leu | Val | Lys | Ala | Tyr | Gln | Ile | Gly | Ser | Gly |
| 465 | | | | | 470 | | | | | 475 | | | | | 480 |
| act | act | gta | agg | aaa | gga | cca | gga | ttc | aca | gga | ggg | gat | ata | ctt | cga | 1488 |
| Thr | Thr | Val | Arg | Lys | Gly | Pro | Gly | Phe | Thr | Gly | Gly | Asp | Ile | Leu | Arg |
| | | | | 485 | | | | | 490 | | | | | 495 | |
| aga | aca | ggt | cct | gga | aca | ttt | gga | gat | atg | aga | ata | aat | att | aat | gca | 1536 |
| Arg | Thr | Gly | Pro | Gly | Thr | Phe | Gly | Asp | Met | Arg | Ile | Asn | Ile | Asn | Ala |
| | | | 500 | | | | | 505 | | | | | 510 | | |
| cca | tta | tct | gaa | aga | tat | cgt | gta | agg | att | cgt | tat | gct | tct | acg | aca | 1584 |
| Pro | Leu | Ser | Glu | Arg | Tyr | Arg | Val | Arg | Ile | Arg | Tyr | Ala | Ser | Thr | Thr |
| | | | | 515 | | | | | 520 | | | | | 525 | |
| gat | tta | caa | ttt | gtc | acg | agt | att | aat | ggg | gcc | acc | att | aat | att | ggt | 1632 |
| Asp | Leu | Gln | Phe | Val | Thr | Ser | Ile | Asn | Gly | Ala | Thr | Ile | Asn | Ile | Gly |
| | 530 | | | | | 535 | | | | | 540 | | | | |
| aac | ttc | cca | aaa | act | att | aat | aat | cta | aat | act | tta | ggt | tct | gag | ggc | 1680 |
| Asn | Phe | Pro | Lys | Thr | Ile | Asn | Asn | Leu | Asn | Thr | Leu | Gly | Ser | Glu | Gly |
| 545 | | | | | 550 | | | | | 555 | | | | | 560 |
| tat | aga | aca | gta | tcg | ttt | agt | act | cca | ttt | agt | ttc | tca | aat | gca | caa | 1728 |
| Tyr | Arg | Thr | Val | Ser | Phe | Ser | Thr | Pro | Phe | Ser | Phe | Ser | Asn | Ala | Gln |
| | | | | 565 | | | | | 570 | | | | | 575 | |
| agc | ata | ttt | aga | tta | ggt | ata | caa | gca | ttt | tct | gga | gtt | caa | gaa | gtt | 1776 |
| Ser | Ile | Phe | Arg | Leu | Gly | Ile | Gln | Ala | Phe | Ser | Gly | Val | Gln | Glu | Val |
| | | | 580 | | | | | 585 | | | | | 590 | | |
| tat | gtg | gat | aaa | att | gaa | ttt | att | cct | gtt | gaa | ctc | gag | gct | gaa | tat | 1824 |
| Tyr | Val | Asp | Lys | Ile | Glu | Phe | Ile | Pro | Val | Glu | Leu | Glu | Ala | Glu | Tyr |
| | | 595 | | | | | 600 | | | | | 605 | | | |
| aat | ctg | gaa | aga | gcg | cag | aag | gcg | gtg | aat | gcg | ctg | ttt | acg | tct | aca | 1872 |
| Asn | Leu | Glu | Arg | Ala | Gln | Lys | Ala | Val | Asn | Ala | Leu | Phe | Thr | Ser | Thr |
| | 610 | | | | | 615 | | | | | 620 | | | | |
| aac | caa | cta | ggg | cta | aaa | aca | aat | gta | acg | gat | tat | cat | att | gat | caa | 1920 |
| Asn | Gln | Leu | Gly | Leu | Lys | Thr | Asn | Val | Thr | Asp | Tyr | His | Ile | Asp | Gln |
| 625 | | | | | 630 | | | | | 635 | | | | | 640 |
| gtg | tcc | aat | tta | gtt | acg | tat | tta | tcg | gat | gaa | ttt | tgt | ctg | gat | gaa | 1968 |
| Val | Ser | Asn | Leu | Val | Thr | Tyr | Leu | Ser | Asp | Glu | Phe | Cys | Leu | Asp | Glu |
| | | | | 645 | | | | | 650 | | | | | 655 | |
| aag | cga | gaa | ttg | tcc | gag | aaa | gtc | aaa | cat | gcg | aag | cga | ctc | agt | gat | 2016 |
| Lys | Arg | Glu | Leu | Ser | Glu | Lys | Val | Lys | His | Ala | Lys | Arg | Leu | Ser | Asp |
| | | | 660 | | | | | 665 | | | | | 670 | | |
| gaa | cgc | aat | tta | ctc | caa | gat | tca | aat | ttc | aaa | gac | att | aat | agg | caa | 2064 |
| Glu | Arg | Asn | Leu | Leu | Gln | Asp | Ser | Asn | Phe | Lys | Asp | Ile | Asn | Arg | Gln |
| | | 675 | | | | | 680 | | | | | 685 | | | |
| cca | gaa | cgt | ggg | tgg | ggc | gga | agt | aca | ggg | att | acc | atc | caa | gga | ggg | 2112 |
| Pro | Glu | Arg | Gly | Trp | Gly | Gly | Ser | Thr | Gly | Ile | Thr | Ile | Gln | Gly | Gly |
| | 690 | | | | | 695 | | | | | 700 | | | | |
| gat | gac | gta | ttt | aaa | gaa | aat | tac | gtc | aca | cta | tca | ggt | acc | ttt | gat | 2160 |
| Asp | Asp | Val | Phe | Lys | Glu | Asn | Tyr | Val | Thr | Leu | Ser | Gly | Thr | Phe | Asp |
| 705 | | | | | 710 | | | | | 715 | | | | | 720 |
| gag | tgc | tat | cca | aca | tat | ttg | tat | caa | aaa | atc | gat | gaa | tca | aaa | tta | 2208 |
| Glu | Cys | Tyr | Pro | Thr | Tyr | Leu | Tyr | Gln | Lys | Ile | Asp | Glu | Ser | Lys | Leu |
| | | | | 725 | | | | | 730 | | | | | 735 | |
| aaa | gcc | ttt | acc | cgt | tat | caa | tta | aga | ggg | tat | atc | gaa | gat | agt | caa | 2256 |
| Lys | Ala | Phe | Thr | Arg | Tyr | Gln | Leu | Arg | Gly | Tyr | Ile | Glu | Asp | Ser | Gln |
| | | | 740 | | | | | 745 | | | | | 750 | | |

```
gac tta gaa atc tat tta att cgc tac aat gca aaa cat gaa aca gta    2304
Asp Leu Glu Ile Tyr Leu Ile Arg Tyr Asn Ala Lys His Glu Thr Val
        755                 760                 765 aat gtg cca ggt acg ggt tcc tta tgg ccg ctt tca gcc caa agt cca    2352
Asn Val Pro Gly Thr Gly Ser Leu Trp Pro Leu Ser Ala Gln Ser Pro
770                 775                 780 atc gga aag tgt gga gag ccg aat cga tgc gcg cca cac ctt gaa tgg    2400
Ile Gly Lys Cys Gly Glu Pro Asn Arg Cys Ala Pro His Leu Glu Trp
785                 790                 795                 800 aat cct gac tta gat tgt tcg tgt agg gat gga gaa aag tgt gcc cat    2448
Asn Pro Asp Leu Asp Cys Ser Cys Arg Asp Gly Glu Lys Cys Ala His
            805                 810                 815 cat tcg cat cat ttc tcc tta gac att gat gta gga tgt aca gac tta    2496
His Ser His His Phe Ser Leu Asp Ile Asp Val Gly Cys Thr Asp Leu
        820                 825                 830 aat gag gac cta ggt gta tgg gtg atc ttt aag att aag acg caa gat    2544
Asn Glu Asp Leu Gly Val Trp Val Ile Phe Lys Ile Lys Thr Gln Asp
    835                 840                 845 ggg cac gca aga cta ggg aat cta gag ttt ctc gaa gag aaa cca tta    2592
Gly His Ala Arg Leu Gly Asn Leu Glu Phe Leu Glu Glu Lys Pro Leu
850                 855                 860 gta gga gaa gcg cta gct cgt gtg aaa aga gcg gag aaa aaa tgg aga    2640
Val Gly Glu Ala Leu Ala Arg Val Lys Arg Ala Glu Lys Lys Trp Arg
865                 870                 875                 880 gac aaa cgt gaa aaa ttg gaa tgg gaa aca aat atc gtt tat aaa gag    2688
Asp Lys Arg Glu Lys Leu Glu Trp Glu Thr Asn Ile Val Tyr Lys Glu
            885                 890                 895 gca aaa gaa tct gta gat gct tta ttt gta aac tct caa tat gat caa    2736
Ala Lys Glu Ser Val Asp Ala Leu Phe Val Asn Ser Gln Tyr Asp Gln
        900                 905                 910 tta caa gcg gat acg aat att gcc atg att cat gcg gca gat aaa cgt    2784
Leu Gln Ala Asp Thr Asn Ile Ala Met Ile His Ala Ala Asp Lys Arg
    915                 920                 925 gtt cat agc att cga gaa gct tat ctg cct gag ctg tct gtg att ccg    2832
Val His Ser Ile Arg Glu Ala Tyr Leu Pro Glu Leu Ser Val Ile Pro
930                 935                 940 ggt gtc aat gcg gct att ttt gaa gaa tta gaa ggg cgt att ttc act    2880
Gly Val Asn Ala Ala Ile Phe Glu Glu Leu Glu Gly Arg Ile Phe Thr
945                 950                 955                 960 gca ttc tcc cta tat gat gcg aga aat gtc att aaa aat ggt gat ttt    2928
Ala Phe Ser Leu Tyr Asp Ala Arg Asn Val Ile Lys Asn Gly Asp Phe
            965                 970                 975 aat aat ggc tta tcc tgc tgg aac gtg aaa ggg cat gta gat gta gaa    2976
Asn Asn Gly Leu Ser Cys Trp Asn Val Lys Gly His Val Asp Val Glu
        980                 985                 990 gaa caa aac aac caa cgt tcg gtc ctt gtt gtt ccg gaa tgg gaa gca    3024
Glu Gln Asn Asn Gln Arg Ser Val Leu Val Val Pro Glu Trp Glu Ala
    995                 1000                1005 gaa gtg tca caa gaa gtt cgt gtc tgt ccg ggt cgt ggc tat atc       3069
Glu Val Ser Gln Glu Val Arg Val Cys Pro Gly Arg Gly Tyr Ile
1010                1015                1020 ctt cgt gtc aca gcg tac aag gag gga tat gga gaa ggt tgc gta       3114
Leu Arg Val Thr Ala Tyr Lys Glu Gly Tyr Gly Glu Gly Cys Val
1025                1030                1035 acc att cat gag atc gag aac aat aca gac gaa ctg aag ttt agc       3159
Thr Ile His Glu Ile Glu Asn Asn Thr Asp Glu Leu Lys Phe Ser
1040                1045                1050 aac tgc gta gaa gag gaa atc tat cca aat aac acg gta acg tgt       3204
Asn Cys Val Glu Glu Glu Ile Tyr Pro Asn Asn Thr Val Thr Cys
1055                1060                1065
```

```
aat gat tat act gta aat caa gaa gaa tac gga ggt gcg tac act       3249
Asn Asp Tyr Thr Val Asn Gln Glu Glu Tyr Gly Gly Ala Tyr Thr
        1070            1075                1080 tct cgt aat cga gga tat aac gaa gct cct tcc gta cca gct gat       3294
Ser Arg Asn Arg Gly Tyr Asn Glu Ala Pro Ser Val Pro Ala Asp
    1085            1090                1095 tat gcg tca gtc tat gaa gaa aaa tcg tat aca gat gga cga aga       3339
Tyr Ala Ser Val Tyr Glu Glu Lys Ser Tyr Thr Asp Gly Arg Arg
1100                1105                1110 gag aat cct tgt gaa ttt aac aga ggg tat agg gat tac acg cca       3384
Glu Asn Pro Cys Glu Phe Asn Arg Gly Tyr Arg Asp Tyr Thr Pro
        1115            1120                1125 cta cca gtt ggt tat gtg aca aaa gaa tta gaa tac ttc cca gaa       3429
Leu Pro Val Gly Tyr Val Thr Lys Glu Leu Glu Tyr Phe Pro Glu
    1130            1135                1140 acc gat aag gta tgg att gag att gga gaa acg gaa gga aca ttt       3474
Thr Asp Lys Val Trp Ile Glu Ile Gly Glu Thr Glu Gly Thr Phe
1145                1150                1155 atc gtg gac agc gtg gaa tta ctc ctt atg gag gaa                   3510
Ile Val Asp Ser Val Glu Leu Leu Leu Met Glu Glu
        1160            1165                1170

<210> SEQ ID NO 26
<211> LENGTH: 1170
<212> TYPE: PRT
<213> ORGANISM: Artificial Sequence
<220> FEATURE:
<223> OTHER INFORMATION: Synthetic Construct

<400> SEQUENCE: 26

Met Glu Asn Asn Ile Gln Asn Gln Cys Val Pro Tyr Asn Cys Leu Asn
1               5                   10                  15

Asn Pro Glu Val Glu Ile Leu Asn Glu Glu Arg Ser Thr Gly Arg Leu
            20                  25                  30

Pro Leu Asp Ile Ser Leu Ser Leu Thr Arg Phe Leu Leu Ser Glu Phe
        35                  40                  45

Val Pro Gly Val Gly Val Ala Phe Gly Leu Phe Asp Leu Ile Trp Gly
    50                  55                  60

Phe Ile Thr Pro Ser Asp Trp Ser Leu Phe Leu Leu Gln Ile Glu Gln
65                  70                  75                  80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
                165                 170                 175

Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
        195                 200                 205

Tyr Asn Gln Gly Leu Glu Asn Leu Arg Gly Thr Asn Thr Arg Gln Trp
    210                 215                 220
```

```
Ala Arg Phe Asn Gln Phe Arg Arg Asp Leu Thr Leu Thr Val Leu Asp
225                 230                 235                 240

Ile Val Ala Leu Phe Pro His Tyr Asp Val Gln Thr Tyr Pro Ile Thr
            245                 250                 255

Thr Val Ala Gln Leu Thr Arg Glu Val Tyr Thr Asp Pro Leu Leu Asn
            260                 265                 270

Phe Asn Pro Lys Leu His Ser Val Ser Gln Leu Pro Ser Phe Ser Asp
        275                 280                 285

Met Glu Asn Ala Thr Ile Arg Thr Pro His Leu Met Glu Phe Leu Arg
    290                 295                 300

Met Leu Thr Ile Tyr Thr Asp Trp Tyr Ser Val Gly Arg Asn Tyr Tyr
305                 310                 315                 320

Trp Gly Gly His Arg Val Thr Ser Tyr His Val Gly Gly Glu Asn Ile
                325                 330                 335

Arg Ser Pro Leu Tyr Gly Arg Glu Ala Asn Gln Glu Val Pro Arg Asp
            340                 345                 350

Phe Tyr Phe Tyr Gly Pro Val Phe Lys Thr Leu Ser Lys Pro Thr Leu
        355                 360                 365

Arg Pro Leu Gln Gln Pro Ala Pro Pro Phe Asn Leu Arg Ser
    370                 375                 380

Leu Glu Gly Val Glu Phe His Thr Ser Thr Gly Ser Phe Met Tyr Arg
385                 390                 395                 400

Glu Arg Gly Ser Val Asp Ser Phe Asn Glu Leu Pro Pro Phe Asn Pro
                405                 410                 415

Val Gly Leu Pro His Lys Val Tyr Ser His Arg Leu Cys His Ala Thr
            420                 425                 430

Phe Val Arg Lys Ser Gly Thr Pro Tyr Leu Thr Thr Gly Ala Ile Phe
        435                 440                 445

Ser Trp Thr His Arg Ser Ala Glu Gly Thr Asn Thr Ile Glu Ser Asn
450                 455                 460

Ile Ile Thr Gln Ile Pro Leu Val Lys Ala Tyr Gln Ile Gly Ser Gly
465                 470                 475                 480

Thr Thr Val Arg Lys Gly Pro Gly Phe Thr Gly Gly Asp Ile Leu Arg
                485                 490                 495

Arg Thr Gly Pro Gly Thr Phe Gly Asp Met Arg Ile Asn Ile Asn Ala
            500                 505                 510

Pro Leu Ser Glu Arg Tyr Arg Val Arg Ile Arg Tyr Ala Ser Thr Thr
        515                 520                 525

Asp Leu Gln Phe Val Thr Ser Ile Asn Gly Ala Thr Ile Asn Ile Gly
    530                 535                 540

Asn Phe Pro Lys Thr Ile Asn Asn Leu Asn Thr Leu Gly Ser Glu Gly
545                 550                 555                 560

Tyr Arg Thr Val Ser Phe Ser Thr Pro Phe Ser Phe Ser Asn Ala Gln
                565                 570                 575

Ser Ile Phe Arg Leu Gly Ile Gln Ala Phe Ser Gly Val Gln Glu Val
            580                 585                 590

Tyr Val Asp Lys Ile Glu Phe Ile Pro Val Glu Leu Glu Ala Glu Tyr
        595                 600                 605

Asn Leu Glu Arg Ala Gln Lys Ala Val Asn Ala Leu Phe Thr Ser Thr
    610                 615                 620

Asn Gln Leu Gly Leu Lys Thr Asn Val Thr Asp Tyr His Ile Asp Gln
625                 630                 635                 640

Val Ser Asn Leu Val Thr Tyr Leu Ser Asp Glu Phe Cys Leu Asp Glu
```

```
                645                 650                 655
Lys Arg Glu Leu Ser Glu Lys Val Lys His Ala Lys Arg Leu Ser Asp
            660                 665                 670

Glu Arg Asn Leu Leu Gln Asp Ser Asn Phe Lys Asp Ile Asn Arg Gln
        675                 680                 685

Pro Glu Arg Gly Trp Gly Gly Ser Thr Gly Ile Thr Ile Gln Gly Gly
        690                 695                 700

Asp Asp Val Phe Lys Glu Asn Tyr Val Thr Leu Ser Gly Thr Phe Asp
705                 710                 715                 720

Glu Cys Tyr Pro Thr Tyr Leu Tyr Gln Lys Ile Asp Glu Ser Lys Leu
            725                 730                 735

Lys Ala Phe Thr Arg Tyr Gln Leu Arg Gly Tyr Ile Glu Asp Ser Gln
            740                 745                 750

Asp Leu Glu Ile Tyr Leu Ile Arg Tyr Asn Ala Lys His Glu Thr Val
            755                 760                 765

Asn Val Pro Gly Thr Gly Ser Leu Trp Pro Leu Ser Ala Gln Ser Pro
770                 775                 780

Ile Gly Lys Cys Gly Glu Pro Asn Arg Cys Ala Pro His Leu Glu Trp
785                 790                 795                 800

Asn Pro Asp Leu Asp Cys Ser Cys Arg Asp Gly Glu Lys Cys Ala His
            805                 810                 815

His Ser His His Phe Ser Leu Asp Ile Asp Val Gly Cys Thr Asp Leu
            820                 825                 830

Asn Glu Asp Leu Gly Val Trp Val Ile Phe Lys Ile Lys Thr Gln Asp
            835                 840                 845

Gly His Ala Arg Leu Gly Asn Leu Glu Phe Leu Glu Glu Lys Pro Leu
850                 855                 860

Val Gly Glu Ala Leu Ala Arg Val Lys Arg Ala Glu Lys Lys Trp Arg
865                 870                 875                 880

Asp Lys Arg Glu Lys Leu Glu Trp Glu Thr Asn Ile Val Tyr Lys Glu
            885                 890                 895

Ala Lys Glu Ser Val Asp Ala Leu Phe Val Asn Ser Gln Tyr Asp Gln
            900                 905                 910

Leu Gln Ala Asp Thr Asn Ile Ala Met Ile His Ala Ala Asp Lys Arg
            915                 920                 925

Val His Ser Ile Arg Glu Ala Tyr Leu Pro Glu Leu Ser Val Ile Pro
930                 935                 940

Gly Val Asn Ala Ala Ile Phe Glu Glu Leu Glu Gly Arg Ile Phe Thr
945                 950                 955                 960

Ala Phe Ser Leu Tyr Asp Ala Arg Asn Val Ile Lys Asn Gly Asp Phe
            965                 970                 975

Asn Asn Gly Leu Ser Cys Trp Asn Val Lys Gly His Val Asp Val Glu
            980                 985                 990

Glu Gln Asn Asn Gln Arg Ser Val  Leu Val Val Pro Glu  Trp Glu Ala
            995                 1000                1005

Glu Val  Ser Gln Glu Val Arg  Val Cys Pro Gly Arg  Gly Tyr Ile
    1010                1015                1020

Leu Arg Val Thr Ala Tyr Lys  Glu Gly Tyr Gly Glu  Gly Cys Val
    1025                1030                1035

Thr Ile  His Glu Ile Glu Asn  Asn Thr Asp Glu Leu  Lys Phe Ser
    1040                1045                1050

Asn Cys  Val Glu Glu Glu Ile  Tyr Pro Asn Asn Thr  Val Thr Cys
    1055                1060                1065
```

```
Asn Asp Tyr Thr Val Asn Gln Glu Glu Tyr Gly Gly Ala Tyr Thr
    1070                1075                1080

Ser Arg Asn Arg Gly Tyr Asn Glu Ala Pro Ser Val Pro Ala Asp
    1085                1090                1095

Tyr Ala Ser Val Tyr Glu Glu Lys Ser Tyr Thr Asp Gly Arg Arg
    1100                1105                1110

Glu Asn Pro Cys Glu Phe Asn Arg Gly Tyr Arg Asp Tyr Thr Pro
    1115                1120                1125

Leu Pro Val Gly Tyr Val Thr Lys Glu Leu Glu Tyr Phe Pro Glu
    1130                1135                1140

Thr Asp Lys Val Trp Ile Glu Ile Gly Glu Thr Glu Gly Thr Phe
    1145                1150                1155

Ile Val Asp Ser Val Glu Leu Leu Leu Met Glu Glu
    1160                1165                1170

<210> SEQ ID NO 27
<211> LENGTH: 3516
<212> TYPE: DNA
<213> ORGANISM: Artificial Sequence
<220> FEATURE:
<223> OTHER INFORMATION: TIC111 CDS consisting of CDS for Cry1Ac domain
      I linked in frame to CDS for TIC900 domain II-III linked in frame
      to CDS for Cry1Ac prot

| | | |
|---|---|---|
| tat gtt caa gct gca aat tta cat tta tca gtt ttg aga gat gtt tca<br>Tyr Val Gln Ala Ala Asn Leu His Leu Ser Val Leu Arg Asp Val Ser<br>                165                      170                      175 | 528 |
| gtg ttt gga caa agg tgg gga ttt gat gcc gcg act atc aat agt cgt<br>Val Phe Gly Gln Arg Trp Gly Phe Asp Ala Ala Thr Ile Asn Ser Arg<br>           180                      185                    190 | 576 |
| tat aat gat tta act agg ctt att ggc aac tat aca gat cat gct gta<br>Tyr Asn Asp Leu Thr Arg Leu Ile Gly Asn Tyr Thr Asp His Ala Val<br>195                    200                      205 | 624 |
| cgc tgg tac aat acg gga tta gag cgt gta tgg gga ccg gat tct aga<br>Arg Trp Tyr Asn Thr Gly Leu Glu Arg Val Trp Gly Pro Asp Ser Arg<br>        210                      215                    220 | 672 |
| gat tgg ata aga tat aat caa ttt aga aga gat cta acg ctt act gtt<br>Asp Trp Ile Arg Tyr Asn Gln Phe Arg Arg Asp Leu Thr Leu Thr Val<br>225                    230                      235                    240 | 720 |
| tta gat atc gtt gct tta ttc ccg cac tat gat gta caa act tat cca<br>Leu Asp Ile Val Ala Leu Phe Pro His Tyr Asp Val Gln Thr Tyr Pro<br>                245                      250                    255 | 768 |
| ata aca acc gtt gct cag tta aca agg gaa gtt tat acg gat cct tta<br>Ile Thr Thr Val Ala Gln Leu Thr Arg Glu Val Tyr Thr Asp Pro Leu<br>           260                      265                    270 | 816 |
| ctt aat ttt aat cct aaa tta cat tct gtg tct caa tta cct agt ttt<br>Leu Asn Phe Asn Pro Lys Leu His Ser Val Ser Gln Leu Pro Ser Phe<br>        275                      280                    285 | 864 |
| agt gac atg gaa aat gca aca att aga act cca cat ctg atg gaa ttt<br>Ser Asp Met Glu Asn Ala Thr Ile Arg Thr Pro His Leu Met Glu Phe<br>           290                      295                    300 | 912 |
| tta aga atg cta aca att tat aca gat tgg tat agt gtg gga aga aac<br>Leu Arg Met Leu Thr Ile Tyr Thr Asp Trp Tyr Ser Val Gly Arg Asn<br>305                    310                      315                    320 | 960 |
| tat tat tgg gga gga cat cgc gtg acg tct tac cat gta gga gga gag<br>Tyr Tyr Trp Gly Gly His Arg Val Thr Ser Tyr His Val Gly Gly Glu<br>                325                      330                    335 | 1008 |
| aat ata aga tca cct cta tat ggt aga gag gca aat caa gag gtt cct<br>Asn Ile Arg Ser Pro Leu Tyr Gly Arg Glu Ala Asn Gln Glu Val Pro<br>           340                      345                    350 | 1056 |
| aga gat ttt tat ttt tat gga ccc gtt ttt aag acg tta tca aag ccg<br>Arg Asp Phe Tyr Phe Tyr Gly Pro Val Phe Lys Thr Leu Ser Lys Pro<br>        355                      360                    365 | 1104 |
| act cta aga cca tta cag cag cct gca cca gct cct cct ttt aat tta<br>Thr Leu Arg Pro Leu Gln Gln Pro Ala Pro Ala Pro Pro Phe Asn Leu<br>           370                      375                    380 | 1152 |
| cgt agc tta gag gga gta gaa ttc cac act tct aca ggt agt ttt atg<br>Arg Ser Leu Glu Gly Val Glu Phe His Thr Ser Thr Gly Ser Phe Met<br>385                    390                      395                    400 | 1200 |
| tat cgt gaa aga gga tcg gta gat tct ttt aat gag tta ccg cct ttt<br>Tyr Arg Glu Arg Gly Ser Val Asp Ser Phe Asn Glu Leu Pro Pro Phe<br>                405                      410                    415 | 1248 |
| aat cca gtt ggg tta cct cat aag gta tac agt cac cgt tta tgt cat<br>Asn Pro Val Gly Leu Pro His Lys Val Tyr Ser His Arg Leu Cys His<br>           420                      425                    430 | 1296 |
| gca acg ttt gtt cgt aaa tct ggg acc cct tat tta aca aca ggt gcc<br>Ala Thr Phe Val Arg Lys Ser Gly Thr Pro Tyr Leu Thr Thr Gly Ala<br>        435                      440                    445 | 1344 |
| atc ttt tct tgg aca cat cgt agt gct gaa gaa acc aat aca att gaa<br>Ile Phe Ser Trp Thr His Arg Ser Ala Glu Glu Thr Asn Thr Ile Glu<br>450                    455                      460 | 1392 |
| tca aat att att acg caa atc ccg tta gta aaa gca tat caa att gga<br>Ser Asn Ile Ile Thr Gln Ile Pro Leu Val Lys Ala Tyr Gln Ile Gly<br>465                    470                      475                    480 | 1440 |

```
tca ggc act act gta agg aaa gga cca gga ttc aca gga ggg gat ata   1488
Ser Gly Thr Thr Val Arg Lys Gly Pro Gly Phe Thr Gly Gly Asp Ile
                485                 490                 495 ctt cga aga aca ggt cct gga aca ttt gga gat atg aga ata aat att   1536
Leu Arg Arg Thr Gly Pro Gly Thr Phe Gly Asp Met Arg Ile Asn Ile
            500                 505                 510 aat gca cca tta tct gaa aga tat cgt gta agg att cgt tat gct tct   1584
Asn Ala Pro Leu Ser Glu Arg Tyr Arg Val Arg Ile Arg Tyr Ala Ser
        515                 520                 525 acg aca gat tta caa ttt gtc acg agt att aat ggg gcc acc att aat   1632
Thr Thr Asp Leu Gln Phe Val Thr Ser Ile Asn Gly Ala Thr Ile Asn
    530                 535                 540 att ggt aac ttc cca aaa act att aat aat cta aat act tta ggt tct   1680
Ile Gly Asn Phe Pro Lys Thr Ile Asn Asn Leu Asn Thr Leu Gly Ser
545                 550                 555                 560 gag ggc tat aga aca gta tcg ttt agt act cca ttt agt ttc tca aat   1728
Glu Gly Tyr Arg Thr Val Ser Phe Ser Thr Pro Phe Ser Phe Ser Asn
                565                 570                 575 gca caa agc ata ttt aga tta gga ata caa gca ttt tct gga gtt caa   1776
Ala Gln Ser Ile Phe Arg Leu Gly Ile Gln Ala Phe Ser Gly Val Gln
            580                 585                 590 gaa gtt tat gtg gat aaa att gaa ttt att cct gtt gaa ctc gag gct   1824
Glu Val Tyr Val Asp Lys Ile Glu Phe Ile Pro Val Glu Leu Glu Ala
        595                 600                 605 gaa tat aat ctg gaa aga gcg cag aag gcg gtg aat gcg ctg ttt acg   1872
Glu Tyr Asn Leu Glu Arg Ala Gln Lys Ala Val Asn Ala Leu Phe Thr
    610                 615                 620 tct aca aac caa cta ggg cta aaa aca aat gta acg gat tat cat att   1920
Ser Thr Asn Gln Leu Gly Leu Lys Thr Asn Val Thr Asp Tyr His Ile
625                 630                 635                 640 gat caa gtg tcc aat tta gtt acg tat tta tcg gat gaa ttt tgt ctg   1968
Asp Gln Val Ser Asn Leu Val Thr Tyr Leu Ser Asp Glu Phe Cys Leu
                645                 650                 655 gat gaa aag cga gaa ttg tcc gag aaa gtc aaa cat gcg aag cga ctc   2016
Asp Glu Lys Arg Glu Leu Ser Glu Lys Val Lys His Ala Lys Arg Leu
            660                 665                 670 agt gat gaa cgc aat tta ctc caa gat tca aat ttc aaa gac att aat   2064
Ser Asp Glu Arg Asn Leu Leu Gln Asp Ser Asn Phe Lys Asp Ile Asn
        675                 680                 685 agg caa cca gaa cgt ggg tgg ggc gga agt aca ggg att acc atc caa   2112
Arg Gln Pro Glu Arg Gly Trp Gly Gly Ser Thr Gly Ile Thr Ile Gln
    690                 695                 700 gga ggg gat gac gta ttt aaa gaa aat tac gtc aca cta tca ggt acc   2160
Gly Gly Asp Asp Val Phe Lys Glu Asn Tyr Val Thr Leu Ser Gly Thr
705                 710                 715                 720 ttt gat gag tgc tat cca aca tat ttg tat caa aaa atc gat gaa tca   2208
Phe Asp Glu Cys Tyr Pro Thr Tyr Leu Tyr Gln Lys Ile Asp Glu Ser
                725                 730                 735 aaa tta aaa gcc ttt acc cgt tat caa tta aga ggg tat atc gaa gat   2256
Lys Leu Lys Ala Phe Thr Arg Tyr Gln Leu Arg Gly Tyr Ile Glu Asp
            740                 745                 750 agt caa gac tta gaa atc tat tta att cgc tac aat gca aaa cat gaa   2304
Ser Gln Asp Leu Glu Ile Tyr Leu Ile Arg Tyr Asn Ala Lys His Glu
        755                 760                 765 aca gta aat gtg cca ggt acg ggt tcc tta tgg ccg ctt tca gcc caa   2352
Thr Val Asn Val Pro Gly Thr Gly Ser Leu Trp Pro Leu Ser Ala Gln
    770                 775                 780 agt cca atc gga aag tgt gga gag ccg aat cga tgc gcg cca cac ctt   2400
Ser Pro Ile Gly Lys Cys Gly Glu Pro Asn Arg Cys Ala Pro His Leu
785                 790                 795                 800
```

-continued

```
gaa tgg aat cct gac tta gat tgt tcg tgt agg gat gga gaa aag tgt      2448
Glu Trp Asn Pro Asp Leu Asp Cys Ser Cys Arg Asp Gly Glu Lys Cys
            805                 810                 815 gcc cat cat tcg cat cat ttc tcc tta gac att gat gta gga tgt aca      2496
Ala His His Ser His His Phe Ser Leu Asp Ile Asp Val Gly Cys Thr
        820                 825                 830 gac tta aat gag gac cta ggt gta tgg gtg atc ttt aag att aag acg      2544
Asp Leu Asn Glu Asp Leu Gly Val Trp Val Ile Phe Lys Ile Lys Thr
    835                 840                 845 caa gat ggg cac gca aga cta ggg aat cta gag ttt ctc gaa gag aaa      2592
Gln Asp Gly His Ala Arg Leu Gly Asn Leu Glu Phe Leu Glu Glu Lys
850                 855                 860 cca tta gta gga gaa gcg cta gct cgt gtg aaa aga gcg gag aaa aaa      2640
Pro Leu Val Gly Glu Ala Leu Ala Arg Val Lys Arg Ala Glu Lys Lys
865                 870                 875                 880 tgg aga gac aaa cgt gaa aaa ttg gaa tgg gaa aca aat atc gtt tat      2688
Trp Arg Asp Lys Arg Glu Lys Leu Glu Trp Glu Thr Asn Ile Val Tyr
                885                 890                 895 aaa gag gca aaa gaa tct gta gat gct tta ttt gta aac tct caa tat      2736
Lys Glu Ala Lys Glu Ser Val Asp Ala Leu Phe Val Asn Ser Gln Tyr
            900                 905                 910 gat caa tta caa gcg gat acg aat att gcc atg att cat gcg gca gat      2784
Asp Gln Leu Gln Ala Asp Thr Asn Ile Ala Met Ile His Ala Ala Asp
        915                 920                 925 aaa cgt gtt cat agc att cga gaa gct tat ctg cct gag ctg tct gtg      2832
Lys Arg Val His Ser Ile Arg Glu Ala Tyr Leu Pro Glu Leu Ser Val
    930                 935                 940 att ccg ggt gtc aat gcg gct att ttt gaa gaa tta gaa ggg cgt att      2880
Ile Pro Gly Val Asn Ala Ala Ile Phe Glu Glu Leu Glu Gly Arg Ile
945                 950                 955                 960 ttc act gca ttc tcc cta tat gat gcg aga aat gtc att aaa aat ggt      2928
Phe Thr Ala Phe Ser Leu Tyr Asp Ala Arg Asn Val Ile Lys Asn Gly
                965                 970                 975 gat ttt aat aat ggc tta tcc tgc tgg aac gtg aaa ggg cat gta gat      2976
Asp Phe Asn Asn Gly Leu Ser Cys Trp Asn Val Lys Gly His Val Asp
            980                 985                 990 gta gaa gaa caa aac aac caa cgt  tcg gtc ctt gtt gtt  ccg gaa tgg   3024
Val Glu Glu Gln Asn Asn Gln Arg  Ser Val Leu Val Val  Pro Glu Trp
        995                 1000                1005 gaa gca gaa gtg tca caa gaa gtt cgt gtc tgt ccg  ggt cgt ggc        3069
Glu Ala Glu Val Ser Gln Glu Val Arg Val Cys Pro  Gly Arg Gly
    1010                1015                1020 tat atc ctt cgt gtc aca gcg tac aag gag gga tat  gga gaa ggt        3114
Tyr Ile Leu Arg Val Thr Ala Tyr Lys Glu Gly Tyr  Gly Glu Gly
    1025                1030                1035 tgc gta acc att cat gag atc gag aac aat aca gac  gaa ctg aag        3159
Cys Val Thr Ile His Glu Ile Glu Asn Asn Thr Asp  Glu Leu Lys
    1040                1045                1050 ttt agc aac tgc gta gaa gag gaa atc tat cca aat  aac acg gta        3204
Phe Ser Asn Cys Val Glu Glu Glu Ile Tyr Pro Asn  Asn Thr Val
    1055                1060                1065 acg tgt aat gat tat act gta aat caa gaa gaa tac  gga ggt gcg        3249
Thr Cys Asn Asp Tyr Thr Val Asn Gln Glu Glu Tyr  Gly Gly Ala
    1070                1075                1080 tac act tct cgt aat cga gga tat aac gaa gct cct  tcc gta cca        3294
Tyr Thr Ser Arg Asn Arg Gly Tyr Asn Glu Ala Pro  Ser Val Pro
    1085                1090                1095 gct gat tat gcg tca gtc tat gaa gaa aaa tcg tat  aca gat gga        3339
Ala Asp Tyr Ala Ser Val Tyr Glu Glu Lys Ser Tyr  Thr Asp Gly
    1100                1105                1110
```

| | | | | | | | | | | | |
|---|---|---|---|---|---|---|---|---|---|---|---|
| cga | aga | gag | aat | cct | tgt | gaa | ttt | aac | aga | ggg | tat | agg | gat | tac | 3384 |
| Arg | Arg | Glu | Asn | Pro | Cys | Glu | Phe | Asn | Arg | Gly | Tyr | Arg | Asp | Tyr | |
| | 1115 | | | | 1120 | | | | | 1125 | | | | | | acg cca cta cca gtt ggt tat gtg aca aaa gaa tta gaa tac ttc 3429
Thr Pro Leu Pro Val Gly Tyr Val Thr Lys Glu Leu Glu Tyr Phe
    1130            1135                1140 cca gaa acc gat aag gta tgg att gag att gga gaa acg gaa gga 3474
Pro Glu Thr Asp Lys Val Trp Ile Glu Ile Gly Glu Thr Glu Gly
1145            1150                1155 aca ttt atc gtg gac agc gtg gaa tta ctc ctt atg gag gaa 3516
Thr Phe Ile Val Asp Ser Val Glu Leu Leu Leu Met Glu Glu
1160            1165                1170

<210> SEQ ID NO 28
<211> LENGTH: 1172
<212> TYPE: PRT
<213> ORGANISM: Artificial Sequence
<220> FEATURE:
<223> OTHER INFORMATION: Synthetic Construct

<400> SEQUENCE: 28

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Asp Leu Thr Leu Thr Val
225                 230                 235                 240

Leu Asp Ile Val Ala Leu Phe Pro His Tyr Asp Val Gln Thr Tyr Pro
                245                 250                 255

Ile Thr Thr Val Ala Gln Leu Thr Arg Glu Val Tyr Thr Asp Pro Leu
            260                 265                 270

Leu Asn Phe Asn Pro Lys Leu His Ser Val Ser Gln Leu Pro Ser Phe
        275                 280                 285

```
Ser Asp Met Glu Asn Ala Thr Ile Arg Thr Pro His Leu Met Glu Phe
    290                 295                 300

Leu Arg Met Leu Thr Ile Tyr Thr Asp Trp Tyr Ser Val Gly Arg Asn
305                 310                 315                 320

Tyr Tyr Trp Gly Gly His Arg Val Thr Ser Tyr His Val Gly Gly Glu
                325                 330                 335

Asn Ile Arg Ser Pro Leu Tyr Gly Arg Glu Ala Asn Gln Glu Val Pro
            340                 345                 350

Arg Asp Phe Tyr Phe Tyr Gly Pro Val Phe Lys Thr Leu Ser Lys Pro
        355                 360                 365

Thr Leu Arg Pro Leu Gln Gln Pro Ala Pro Ala Pro Pro Phe Asn Leu
370                 375                 380

Arg Ser Leu Glu Gly Val Glu Phe His Thr Ser Thr Gly Ser Phe Met
385                 390                 395                 400

Tyr Arg Glu Arg Gly Ser Val Asp Ser Phe Asn Glu Leu Pro Pro Phe
                405                 410                 415

Asn Pro Val Gly Leu Pro His Lys Val Tyr Ser His Arg Leu Cys His
            420                 425                 430

Ala Thr Phe Val Arg Lys Ser Gly Thr Pro Tyr Leu Thr Thr Gly Ala
        435                 440                 445

Ile Phe Ser Trp Thr His Arg Ser Ala Glu Glu Thr Asn Thr Ile Glu
450                 455                 460

Ser Asn Ile Ile Thr Gln Ile Pro Leu Val Lys Ala Tyr Gln Ile Gly
465                 470                 475                 480

Ser Gly Thr Thr Val Arg Lys Gly Pro Gly Phe Thr Gly Gly Asp Ile
                485                 490                 495

Leu Arg Arg Thr Gly Pro Gly Thr Phe Gly Asp Met Arg Ile Asn Ile
            500                 505                 510

Asn Ala Pro Leu Ser Glu Arg Tyr Arg Val Arg Ile Arg Tyr Ala Ser
        515                 520                 525

Thr Thr Asp Leu Gln Phe Val Thr Ser Ile Asn Gly Ala Thr Ile Asn
530                 535                 540

Ile Gly Asn Phe Pro Lys Thr Ile Asn Asn Leu Asn Thr Leu Gly Ser
545                 550                 555                 560

Glu Gly Tyr Arg Thr Val Ser Phe Ser Thr Pro Phe Ser Phe Ser Asn
                565                 570                 575

Ala Gln Ser Ile Phe Arg Leu Gly Ile Gln Ala Phe Ser Gly Val Gln
            580                 585                 590

Glu Val Tyr Val Asp Lys Ile Glu Phe Ile Pro Val Glu Leu Glu Ala
        595                 600                 605

Glu Tyr Asn Leu Glu Arg Ala Gln Lys Ala Val Asn Ala Leu Phe Thr
610                 615                 620

Ser Thr Asn Gln Leu Gly Leu Lys Thr Asn Val Thr Asp Tyr His Ile
625                 630                 635                 640

Asp Gln Val Ser Asn Leu Val Thr Tyr Leu Ser Asp Glu Phe Cys Leu
                645                 650                 655

Asp Glu Lys Arg Glu Leu Ser Glu Lys Val Lys His Ala Lys Arg Leu
            660                 665                 670

Ser Asp Glu Arg Asn Leu Leu Gln Asp Ser Asn Phe Lys Asp Ile Asn
        675                 680                 685

Arg Gln Pro Glu Arg Gly Trp Gly Gly Ser Thr Gly Ile Thr Ile Gln
690                 695                 700

Gly Gly Asp Asp Val Phe Lys Glu Asn Tyr Val Thr Leu Ser Gly Thr
705                 710                 715                 720
```

-continued

Phe Asp Glu Cys Tyr Pro Thr Tyr Leu Tyr Gln Lys Ile Asp Glu Ser
                725                 730                 735

Lys Leu Lys Ala Phe Thr Arg Tyr Gln Leu Arg Gly Tyr Ile Glu Asp
                740                 745                 750

Ser Gln Asp Leu Glu Ile Tyr Leu Ile Arg Tyr Asn Ala Lys His Glu
                755                 760                 765

Thr Val Asn Val Pro Gly Thr Gly Ser Leu Trp Pro Leu Ser Ala Gln
                770                 775                 780

Ser Pro Ile Gly Lys Cys Gly Glu Pro Asn Arg Cys Ala Pro His Leu
785                 790                 795                 800

Glu Trp Asn Pro Asp Leu Asp Cys Ser Cys Arg Asp Gly Glu Lys Cys
                805                 810                 815

Ala His His Ser His His Phe Ser Leu Asp Ile Asp Val Gly Cys Thr
                820                 825                 830

Asp Leu Asn Glu Asp Leu Gly Val Trp Val Ile Phe Lys Ile Lys Thr
                835                 840                 845

Gln Asp Gly His Ala Arg Leu Gly Asn Leu Glu Phe Leu Glu Glu Lys
                850                 855                 860

Pro Leu Val Gly Glu Ala Leu Ala Arg Val Lys Arg Ala Glu Lys Lys
865                 870                 875                 880

Trp Arg Asp Lys Arg Glu Lys Leu Glu Trp Glu Thr Asn Ile Val Tyr
                885                 890                 895

Lys Glu Ala Lys Glu Ser Val Asp Ala Leu Phe Val Asn Ser Gln Tyr
                900                 905                 910

Asp Gln Leu Gln Ala Asp Thr Asn Ile Ala Met Ile His Ala Ala Asp
                915                 920                 925

Lys Arg Val His Ser Ile Arg Glu Ala Tyr Leu Pro Glu Leu Ser Val
                930                 935                 940

Ile Pro Gly Val Asn Ala Ala Ile Phe Glu Glu Leu Glu Gly Arg Ile
945                 950                 955                 960

Phe Thr Ala Phe Ser Leu Tyr Asp Ala Arg Asn Val Ile Lys Asn Gly
                965                 970                 975

Asp Phe Asn Asn Gly Leu Ser Cys Trp Asn Val Lys Gly His Val Asp
                980                 985                 990

Val Glu Glu Gln Asn Asn Gln Arg Ser Val Leu Val Val Pro Glu Trp
                995                 1000                1005

Glu Ala Glu Val Ser Gln Glu Val Arg Val Cys Pro Gly Arg Gly
                1010                1015                1020

Tyr Ile Leu Arg Val Thr Ala Tyr Lys Glu Gly Tyr Gly Glu Gly
                1025                1030                1035

Cys Val Thr Ile His Glu Ile Glu Asn Asn Thr Asp Glu Leu Lys
                1040                1045                1050

Phe Ser Asn Cys Val Glu Glu Ile Tyr Pro Asn Asn Thr Val
                1055                1060                1065

Thr Cys Asn Asp Tyr Thr Val Asn Gln Glu Glu Tyr Gly Gly Ala
                1070                1075                1080

Tyr Thr Ser Arg Asn Arg Gly Tyr Asn Glu Ala Pro Ser Val Pro
                1085                1090                1095

Ala Asp Tyr Ala Ser Val Tyr Glu Glu Lys Ser Tyr Thr Asp Gly
                1100                1105                1110

Arg Arg Glu Asn Pro Cys Glu Phe Asn Arg Gly Tyr Arg Asp Tyr
                1115                1120                1125

Thr Pro Leu Pro Val Gly Tyr Val Thr Lys Glu Leu Glu Tyr Phe

```
                       1130                 1135                 1140
Pro Glu  Thr Asp Lys Val  Trp Ile Glu Ile Gly  Glu  Thr Glu Gly
    1145                 1150                 1155

Thr Phe  Ile Val Asp Ser  Val  Glu Leu Leu Leu Met  Glu Glu
    1160                 1165                 1170

<210> SEQ ID NO 29
<211> LENGTH: 7585
<212> TYPE: DNA
<213> ORGANISM: Bacillus thuringiensis
<220> FEATURE:
<221> NAME/KEY: CDS
<222> LOCATION: (415)..(2238)
<223> OTHER INFORMATION: TIC434 CDS

<400> SEQUENCE: 29
ttatatcaaa cgaacttaca tctaaaccaa caaataatct catgtaagag acctcccttc       60
tatttagaat cattgcttgg acgtctcgag atatctctag tgtgtacgcc gaccaacaac      120
ctcgtgtatg agagcttgtc ctgaatcgaa agccgcccta gagctactaa catctaggtt      180
cgaggatcag gctgctcagc ctgcgagtag ggagtcccgc acgttcactg agaaacactc      240
taagttatgt ggtaagtcca caggaggaat aagaattgtc ccaaatgatc ctaacatcat      300
tatctagaaa tatcttgaga cgtccaagta ttttatttat tacaggactc ttattaaaga      360
aaaaatctaa gtctgaaata ggacttaaat attaatatac gaggaggaag aggt atg       417
                                                            Met
                                                            1 aat tca aag gaa cat gat tat cta aaa gtt tgt aat gat tta agt gac       465
Asn Ser Lys Glu His Asp Tyr Leu Lys Val Cys Asn Asp Leu Ser Asp
        5                  10                  15 gcc aat att aat atg gag cgg ttt gat aag aat gat gca ctg gaa att       513
Ala Asn Ile Asn Met Glu Arg Phe Asp Lys Asn Asp Ala Leu Glu Ile
    20                  25                  30 ggt atg tct att gta tct gag ctc ctt ggt atg att cca ggt gga aaa       561
Gly Met Ser Ile Val Ser Glu Leu Leu Gly Met Ile Pro Gly Gly Lys
35                  40                  45 gcc ttg caa ttt gtg ttt gat caa ttg tgg tct cgt ttg ggt gat tct       609
Ala Leu Gln Phe Val Phe Asp Gln Leu Trp Ser Arg Leu Gly Asp Ser
50                  55                  60                  65 gga tgg agt gcg ttc atg gaa cat gtg gag gaa tta att gat act aaa       657
Gly Trp Ser Ala Phe Met Glu His Val Glu Glu Leu Ile Asp Thr Lys
                70                  75                  80 ata gaa ggg tat gca aaa aat aaa gcc tta tct gaa tta gca ggt ata       705
Ile Glu Gly Tyr Ala Lys Asn Lys Ala Leu Ser Glu Leu Ala Gly Ile
            85                  90                  95 caa aga aac ctt gaa aca tat ata caa tta cgt aat gaa tgg gaa aat       753
Gln Arg Asn Leu Glu Thr Tyr Ile Gln Leu Arg Asn Glu Trp Glu Asn
        100                 105                 110 gat atc gaa aac tca aag gct caa gtt aag gta gct aat tac tat gaa       801
Asp Ile Glu Asn Ser Lys Ala Gln Val Lys Val Ala Asn Tyr Tyr Glu
    115                 120                 125 agt ctt gag cag gcg gtt gaa agg agt atg cct caa ttt gca gtg ggg       849
Ser Leu Glu Gln Ala Val Glu Arg Ser Met Pro Gln Phe Ala Val Gly
130                 135                 140                 145 aat ttt gaa gta cca ctt tta act gtt tat gtg caa gct gct aat ctt       897
Asn Phe Glu Val Pro Leu Leu Thr Val Tyr Val Gln Ala Ala Asn Leu
                150                 155                 160 cat ata tta tta tta aga gat gtt cta att tat gga aag cgt tgg gga       945
His Ile Leu Leu Leu Arg Asp Val Leu Ile Tyr Gly Lys Arg Trp Gly
            165                 170                 175
```

```
tgg tcg gag cag aaa att aaa att tat tat gat aga cag att aag tat      993
Trp Ser Glu Gln Lys Ile Lys Ile Tyr Tyr Asp Arg Gln Ile Lys Tyr
        180                 185                 190 acc cat gaa tac aca aat cat tgt gta aat tgg tat aat aaa gga ctt     1041
Thr His Glu Tyr Thr Asn His Cys Val Asn Trp Tyr Asn Lys Gly Leu
195                 200                 205 gag aga tta aaa aat aaa ggt tct tct tat caa gat tgg tac aat tat     1089
Glu Arg Leu Lys Asn Lys Gly Ser Ser Tyr Gln Asp Trp Tyr Asn Tyr
210                 215                 220                 225 aat cgt ttc cgt aga gaa atg act ctt act gtt tta gat atc gtt gct     1137
Asn Arg Phe Arg Arg Glu Met Thr Leu Thr Val Leu Asp Ile Val Ala
            230                 235                 240 tta ttc ccg cac tat gat gta caa act tat cca ata aca acc gtt gct     1185
Leu Phe Pro His Tyr Asp Val Gln Thr Tyr Pro Ile Thr Thr Val Ala
        245                 250                 255 cag cta aca agg gaa gtt tat acg gat cct tta ctt aat ttt aat cct     1233
Gln Leu Thr Arg Glu Val Tyr Thr Asp Pro Leu Leu Asn Phe Asn Pro
    260                 265                 270 aaa tta cat tct gtg tct caa tta cct agt ttt agt gac atg gaa aat     1281
Lys Leu His Ser Val Ser Gln Leu Pro Ser Phe Ser Asp Met Glu Asn
275                 280                 285 gca aca att aga acc cca cat cta atg gaa ttt tta aga atg cta aca     1329
Ala Thr Ile Arg Thr Pro His Leu Met Glu Phe Leu Arg Met Leu Thr
290                 295                 300                 305 att tat aca gat tgg tat agt gtg gga aga aac tat tat tgg gga gga     1377
Ile Tyr Thr Asp Trp Tyr Ser Val Gly Arg Asn Tyr Tyr Trp Gly Gly
            310                 315                 320 cat cgc gtg acg tct tac cat gta gga gga gag aat ata aga tca cct     1425
His Arg Val Thr Ser Tyr His Val Gly Gly Glu Asn Ile Arg Ser Pro
        325                 330                 335 cta tat ggt aga gag gca aat caa gag gtt cct aga gat ttt tat ttt     1473
Leu Tyr Gly Arg Glu Ala Asn Gln Glu Val Pro Arg Asp Phe Tyr Phe
    340                 345                 350 tat gga ccc gtt ttt aag acg tta tca aag ccg act cta aga cca tta     1521
Tyr Gly Pro Val Phe Lys Thr Leu Ser Lys Pro Thr Leu Arg Pro Leu
355                 360                 365 cag cag cct gca cca gct cct ccc ttt aat tta cgt agc tta gag gga     1569
Gln Gln Pro Ala Pro Ala Pro Pro Phe Asn Leu Arg Ser Leu Glu Gly
370                 375                 380                 385 gta gaa ttc cac act cct aca ggt agt ttt ttg tat cgt gaa aga gga     1617
Val Glu Phe His Thr Pro Thr Gly Ser Phe Leu Tyr Arg Glu Arg Gly
            390                 395                 400 tcg gta gat tct ttt aat gag tta ccg cct ttt aat cta gtt ggg tta     1665
Ser Val Asp Ser Phe Asn Glu Leu Pro Pro Phe Asn Leu Val Gly Leu
        405                 410                 415 cct cat aag gta tac agt cac cgt tta tgt cat gca acg ttt gtt cgt     1713
Pro His Lys Val Tyr Ser His Arg Leu Cys His Ala Thr Phe Val Arg
    420                 425                 430 aaa tct ggg acc cct tat tta aca aca ggt gcc atc ttt tct tgg aca     1761
Lys Ser Gly Thr Pro Tyr Leu Thr Thr Gly Ala Ile Phe Ser Trp Thr
435                 440                 445 cat cgt agt gct gaa gaa acc aat aca att gaa tca aat atc att acg     1809
His Arg Ser Ala Glu Glu Thr Asn Thr Ile Glu Ser Asn Ile Ile Thr
450                 455                 460                 465 caa atc ccg tta gta aaa gca tat caa att gga tcg ggc act act gta     1857
Gln Ile Pro Leu Val Lys Ala Tyr Gln Ile Gly Ser Gly Thr Thr Val
            470                 475                 480 agg aaa gga cca gga ttc aca gga ggg gat ata ctt cga aga aca ggt     1905
Arg Lys Gly Pro Gly Phe Thr Gly Gly Asp Ile Leu Arg Arg Thr Gly
        485                 490                 495
```

```
cct gga aca ttt gga gat atg aga ata aat att aat gca cca tta tct    1953
Pro Gly Thr Phe Gly Asp Met Arg Ile Asn Ile Asn Ala Pro Leu Ser
        500                 505                 510 caa aga tat cgt gta agg att cgt tat gct tct acg aca gat tta caa    2001
Gln Arg Tyr Arg Val Arg Ile Arg Tyr Ala Ser Thr Thr Asp Leu Gln
        515                 520                 525 ttt ttc acg agc att aat gga acc act att aat atc ggc aat ttc ccc    2049
Phe Phe Thr Ser Ile Asn Gly Thr Thr Ile Asn Ile Gly Asn Phe Pro
530                 535                 540                 545 aaa act att aat aat gtg aat cct tta agt tct gag agc tat aga aca    2097
Lys Thr Ile Asn Asn Val Asn Pro Leu Ser Ser Glu Ser Tyr Arg Thr
                550                 555                 560 gta tct ttt agt acg cca ttt agt ttt tca gat gca caa agt ata ttt    2145
Val Ser Phe Ser Thr Pro Phe Ser Phe Ser Asp Ala Gln Ser Ile Phe
            565                 570                 575 aga tta ggt ata caa gct ttt tct gga gtt caa gaa gtt tat gtg gat    2193
Arg Leu Gly Ile Gln Ala Phe Ser Gly Val Gln Glu Val Tyr Val Asp
        580                 585                 590 aaa att gaa ttt atc cct ttt gaa gta gga ttc aat aat aca atc        2238
Lys Ile Glu Phe Ile Pro Phe Glu Val Gly Phe Asn Asn Thr Ile
        595                 600                 605 tagaaagagc acagaagatt taaaatcaga tagaatgtat taacatatta atcaagcatc   2298
taatttaata gaatgtttat cgaatgaatt ctgtttagat aaaaagatag gattgttcga   2358
gaaagtcaag tgtgagaaac atatcagtat taaacgtaat atgtagaatg aaacttatct   2418
aagaatatac tcatattagt attcatcctt actattagag ggaatccgca attcaatgag   2478
tggcccgctt atctttgtta aaaagcagat aaataaatca ttttaataaa agaaaagaa    2538
ggccattgct cttatacata agagtaatat tctcagtctg tggagaaaaa catcccatta   2598
aggggtgctt ttctttgaat tcattattta tttgaagacc gactgtttcc gcagtcccct   2658
ttaatggact aagattttat gattttttg gcagtagaat actttcacca tagttggaag    2718
tatgcttttt aggaccactc tttactaaag aatcgaaaaa aatatataaa tttttaaatg   2778
aaatatttaa gtgagataca aaatctcctt aaatttaggg caataaaatc tatttaatta   2838
cttgcattct agttataaaa actttgtatg tttgcatgaa ttgagagatt gaatttctca   2898
aactaattta catcattata tatggattaa aaacaaaaat aactaaaaga atctaatcta   2958
ctgttagatc cttttagtta ttttttaaga gtatcgccca aaaacaaaat catacattat   3018
aaaaatatac atactgaagc aacgattata gtgcttaaac ttgaaaatgt cacgagatat   3078
taattattca aacataaaga gattttttag agcagctcat caactttac aactttctag    3138
atattttgtg tggaaaagca tggctaacgt catccatagg tgaaaatatc tatgctttta   3198
tattttcaaa tagagatata ctgtactcgt aaacggagaa ataggtactt atagaaaaac   3258
aaaatcatct taaaaaaata tataggagat gcagttatat gacagtattc aattttaaac   3318
atattaataa agtaccttt gaaagtagta ttattccaaa aggaaatcgg aaccatcctg    3378
gatatggcat gcagggggcg ggaatggagc ggggaatcgt tcttctatcg gtattgaaat   3438
ttgcgaaaat aaggatggtg gctttgaaaa agcattagaa aatgccgcaa agctagtaaa   3498
gttcctcatg aatcatactg gaagtgcgct tagaaatgtc gtgccacacc aacattggaa   3558
cggtaaacat tgtccgcgtc caattctaaa ccgaacaggg ggatttgaag gattcaagaa   3618
gatggtcgaa ggtagtacga atgatatagg tgaggaaagt aatagtaagg atacgggtac   3678
taaaggatta ggaattgcgt acatggaggg cgtaaatatt aaccttcgta gaggccctag   3738
catgagtagc gaggtaattc gtaagttgaa caagcctgaa tcttatattg tttggaaaga   3798
```

```
acgtgatggg tggctgaacc taggtaactc atgggtgaaa tatgatcctt cttatatctt    3858
ttttgcctgt agacaaacga gtaatgtggg gcgattagtt gttgtagata cgaatgaatt    3918
atgggtctat ggttctgctg actggaacaa caaaattaaa acggtgaaaa agggagaagc    3978
ttttacaatt ttagaagagg tactggtgca gggttctaga atgtataaat gtaaatattt    4038
ctacattacc gcaaattcgc agttcgttca tgtgaaatga tgagaaaaaa aggttgctat    4098
cgttttctcg tatgaataat tgacatatca aaatctgacc cgagattata ccaatcattg    4158
cgtaacgacg tataatactg gtttaaatag attaataggc acaaatgctg ctagttggga    4218
aaattatcac cgattccgta gagagatgac gttgatggca ttagatttag tagcattatt    4278
cccatattat aacgtaagac aatatccaaa tggagtaaat cctcagaggt atatacagaa    4338
ccggtcctat ataatccacc aagtgggtcg ggactttgtc gcccttggct gatagccaat    4398
aataatatta cttttcctga acttgagaat gcatatattc gcccaccaca cttatttgat    4458
agaatgaata ccctaataat tagtaggacc cgagttagtg caccatctaa taacgcatat    4518
actggggctt ggtcagggca cgtaatccga agtcgttacg caaatgatac gaaattacat    4578
gagtatagat acgtaacat tacctctta actaaaacaa taaatacatc agccggtata    4638
attaatcgcg ttgaatcgag aataagtaat cttacgccta ccgacaagca tctcccacct    4698
aaaactggtg tttcacacct tcaaattttt gaagaaggag ttattctatc ggaaaatgat    4758
aaaatatcag caaagctttt caataaaata ctaacttggc ttaaaagttc gattattcat    4818
ttccttttag aatcaaccat ataattttag gttttactca aatattaatc gatggtgttt    4878
tctttagaat ctactgaacg atacaaatac ttacatagtt ctatgctcta atagattact    4938
atatgcatag tggttaataa gtaaacaatt cttaagggt ttgagtgtta tttgtatgga    4998
tctaccccta atttaatata taaataaaaa gattaatctt atttagctgg cctattttga    5058
gcataaatta aatttcacat atgtaatcat gagatttatg aaacacattt atagtatgaa    5118
cataattgtg cctgttatat gtgagaacaa acttacataa agaatagag gagggaggcc    5178 tatatacatg tagaaagaca taaaagtcta aactaaaaac ttatgaagaa tctttgataa    5238
atagccatta ttataaattt tataggtact ttcatgtctt aataacagga catgaaagtc    5298
taaaactttt gaacacagga caagaaactc taaactactt agccagtaat atctgcaact    5358
tatattatta taataggtga aaataatgag aaaatcatac cttttgccta attgtacgtg    5418
tgaatattct gatacaatag aattaaataa atttaaagtt agggtgaagc gtaatgtggg    5478
atagtcattt ccatggtcct ccgagtaaag tgaaagttga agaggttttt tcggaaaaca    5538
atagtgataa aacttttaaa gttggacaaa tatattcaca tccattatat gtttataagc    5598
tagagatttc taaaattgaa gcgtataaag gcgaaagtta tagttatata aatgcttcta    5658
tatttgtaaa gccttgcttt cttaataggg aaaatgaaat tgttaaatta gatgagtatg    5718
agatgactac agaagaattg aacgcagaca atggtggat tgaatcagaa aagtagaggt    5778
gagaatacta tgattaattt acttataaat acagatcttt ctaaaaagct gttaagtgaa    5838
tggcatccta ccaagaatgg tcgcttgaat cctgaaggta ttacatatgg aagttacgaa    5898
tatatttggt gggaatgctc tgaggggcat gtttggggat caactccaag tgataggctg    5958
aaagttgaag atgagctttg tccaaagtgt atgaagaaaa agcagcagct agataaatta    6018
cacaatgtta ataaaataga agctaaatca cttagaaata ttgatccagg tttatctaag    6078
caatggaatt tcaaaagaaa tgcagatgta acacctgata atgagatgat tgacgaagaa    6138
aattggaatg ttaggtggtg gatatgtggt aggggtcatg agtggaagga gtctgttaga    6198
```

```
agtagacttc atgataaaac tgtgtgtcca tactgttcaa ataagaaagt ttgtaaagac    6258
aactcattag caacaatgta tccagagata gcaaggagt  tttgtatctt tgacacatgt    6318
tatcggcaga aagtccgaaa tccatatgag gcaatttata cttcaaatga agaagtaatg    6378
tgggtttgta aagaaggtca tatgtggaga gaaaaaataa atttaagagt gaaaaacggt    6438
aagggatgta gagcatgtga aaagtatcaa cagtcaattg ctcttaataa cccagaaata    6498
gcaaaagaat ggcatcctac aaagaataaa gaagtatatg gtgtaacaac acctgaggag    6558
acatctacca gatgtaacga agagcatggg tgggtttgtg gtaagtgtgg acatgaatat    6618
aaagcaatgg tcaaagctag acatgaaggg gctgccaaat gtccgtcatg ttatcctcca    6678
gaaccaaggg taagaaaaaa gaaagagaa  gctttatttc aaacttataa taagatggaa    6738
gataataggg ttatctttga gaagaattta agaggaaaat ttaaagatag tgaaggatag    6798
attgattttt tacatgttat tttgtggaaa tgactttaaa taaaagtacc tataaggggg    6858
acggcaacga ttccttcttt ttggggccac tcataaaacc agatcaaata tcattttaaa    6918
tttgatctgg ttttttattt acagaagatg tcttccgtaa acttatcgga tttattataa    6978
taggtattgt ttacggaaca cattttaaat tggtattaaa ttaagtttac ggaacacttt    7038
tgaagagagg aagataataa tggattttaa gatgtggtta aaaatgacg  gaaaacgaga    7098 acaaaccatt caagtatata ctcgttcagt ccgtcaattt atggaatggt tacacatatc    7158
ccatggacaa aattggaatc cggatgaaat aagtgcaaaa gttattcatg aatggattca    7218
tcatatgcaa accattgaaa aagtggcaaa acctacaata aataaacgaa ttgcctcatt    7278
aaaagtatat tggtcatatc ttattgaaca acagattgca atatatgatc ctacaaagaa    7338
aataaagata aaacgtattt ctaggttaga agataccccct cgctggttga atgaaatcga    7398
acaagtaaaa ttacttaact tgatccgacg agaagaaaat gaatggaaac gaaaacgaaa    7458
tatggccatg gttcgtttaa tgttacaagc aggccttcga attggtgaag ttgcaaatct    7518
agatttagag gattatagaa aaattggtag tgtaggtact attacaattc gtgaaggtaa    7578
aggtggt                                                              7585
```

<210> SEQ ID NO 30
<211> LENGTH: 608
<212> TYPE: PRT
<213> ORGANISM: Bacillus thuringiensis

<400> SEQUENCE: 30

```
Met Asn Ser Lys Glu His Asp Tyr Leu Lys Val Cys Asn Asp Leu Ser
1               5                   10                  15

Asp Ala Asn Ile Asn Met Glu Arg Phe Asp Lys Asn Asp Ala Leu Glu
            20                  25                  30

Ile Gly Met Ser Ile Val Ser Glu Leu Leu Gly Met Ile Pro Gly Gly
        35                  40                  45

Lys Ala Leu Gln Phe Val Phe Asp Gln Leu Trp Ser Arg Leu Gly Asp
    50                  55                  60

Ser Gly Trp Ser Ala Phe Met Glu His Val Glu Leu Ile Asp Thr
65                  70                  75                  80

Lys Ile Glu Gly Tyr Ala Lys Asn Lys Ala Leu Ser Glu Leu Ala Gly
                85                  90                  95

Ile Gln Arg Asn Leu Glu Thr Tyr Ile Gln Leu Arg Asn Glu Trp Glu
            100                 105                 110

Asn Asp Ile Glu Asn Ser Lys Ala Gln Val Lys Val Ala Asn Tyr Tyr
        115                 120                 125
```

-continued

```
Glu Ser Leu Glu Gln Ala Val Glu Arg Ser Met Pro Gln Phe Ala Val
    130                 135                 140
Gly Asn Phe Glu Val Pro Leu Leu Thr Val Tyr Val Gln Ala Ala Asn
145                 150                 155                 160
Leu His Ile Leu Leu Leu Arg Asp Val Leu Ile Tyr Gly Lys Arg Trp
                165                 170                 175
Gly Trp Ser Glu Gln Lys Ile Lys Ile Tyr Tyr Asp Arg Gln Ile Lys
            180                 185                 190
Tyr Thr His Glu Tyr Thr Asn His Cys Val Asn Trp Tyr Asn Lys Gly
        195                 200                 205
Leu Glu Arg Leu Lys Asn Lys Gly Ser Ser Tyr Gln Asp Trp Tyr Asn
    210                 215                 220
Tyr Asn Arg Phe Arg Arg Glu Met Thr Leu Thr Val Leu Asp Ile Val
225                 230                 235                 240
Ala Leu Phe Pro His Tyr Asp Val Gln Thr Tyr Pro Ile Thr Thr Val
                245                 250                 255
Ala Gln Leu Thr Arg Glu Val Tyr Thr Asp Pro Leu Leu Asn Phe Asn
            260                 265                 270
Pro Lys Leu His Ser Val Ser Gln Leu Pro Ser Phe Ser Asp Met Glu
        275                 280                 285
Asn Ala Thr Ile Arg Thr Pro His Leu Met Glu Phe Leu Arg Met Leu
    290                 295                 300
Thr Ile Tyr Thr Asp Trp Tyr Ser Val Gly Arg Asn Tyr Tyr Trp Gly
305                 310                 315                 320
Gly His Arg Val Thr Ser Tyr His Val Gly Gly Glu Asn Ile Arg Ser
                325                 330                 335
Pro Leu Tyr Gly Arg Glu Ala Asn Gln Glu Val Pro Arg Asp Phe Tyr
            340                 345                 350
Phe Tyr Gly Pro Val Phe Lys Thr Leu Ser Lys Pro Thr Leu Arg Pro
        355                 360                 365
Leu Gln Gln Pro Ala Pro Ala Pro Pro Phe Asn Leu Arg Ser Leu Glu
    370                 375                 380
Gly Val Glu Phe His Thr Pro Thr Gly Ser Phe Leu Tyr Arg Glu Arg
385                 390                 395                 400
Gly Ser Val Asp Ser Phe Asn Glu Leu Pro Pro Phe Asn Leu Val Gly
                405                 410                 415
Leu Pro His Lys Val Tyr Ser His Arg Leu Cys His Ala Thr Phe Val
            420                 425                 430
Arg Lys Ser Gly Thr Pro Tyr Leu Thr Thr Gly Ala Ile Phe Ser Trp
        435                 440                 445
Thr His Arg Ser Ala Glu Glu Thr Asn Thr Ile Glu Ser Asn Ile Ile
    450                 455                 460
Thr Gln Ile Pro Leu Val Lys Ala Tyr Gln Ile Gly Ser Gly Thr Thr
465                 470                 475                 480
Val Arg Lys Gly Pro Gly Phe Thr Gly Gly Asp Ile Leu Arg Arg Thr
                485                 490                 495
Gly Pro Gly Thr Phe Gly Asp Met Arg Ile Asn Ile Asn Ala Pro Leu
            500                 505                 510
Ser Gln Arg Tyr Arg Val Arg Ile Arg Tyr Ala Ser Thr Thr Asp Leu
        515                 520                 525
Gln Phe Phe Thr Ser Ile Asn Gly Thr Thr Ile Asn Ile Gly Asn Phe
    530                 535                 540
Pro Lys Thr Ile Asn Asn Val Asn Pro Leu Ser Ser Glu Ser Tyr Arg
```

```
             545                 550                 555                 560
        Thr Val Ser Phe Ser Thr Pro Phe Ser Phe Ser Asp Ala Gln Ser Ile
                        565                 570                 575

Phe Arg Leu Gly Ile Gln Ala Phe Ser Gly Val Gln Glu Val Tyr Val
                        580                 585                 590

Asp Lys Ile Glu Phe Ile Pro Phe Glu Val Gly Phe Asn Asn Thr Ile
                        595                 600                 605

<210> SEQ ID NO 31
<211> LENGTH: 3525
<212> TYPE: DNA
<213> ORGANISM: Artificial Sequence
<220> FEATURE:
<223> OTHER INFORMATION: synthetic sequence
<220> FEATURE:
<221> NAME/KEY: CDS
<222> LOCATION: (1)..(3525)
<223> OTHER INFORMATION: TIC435 CDS; 1-1825 corresponds to TIC434 CDS;
      1826-3525 corresponds to Cry1 protoxin

<400> SEQUENCE: 31 atg aat tca aag gaa cat gat tat cta aaa gtt tgt aat gat tta agt          48
Met Asn Ser Lys Glu His Asp Tyr Leu Lys Val Cys Asn Asp Leu Ser
1               5                   10                  15 gac gcc aat att aat atg gag cgg ttt gat aag aat gat gca ctg gaa          96
Asp Ala Asn Ile Asn Met Glu Arg Phe Asp Lys Asn Asp Ala Leu Glu
            20                  25                  30 att ggt atg tct att gta tct gag ctc ctt ggt atg att cca ggt gga        144
Ile Gly Met Ser Ile Val Ser Glu Leu Leu Gly Met Ile Pro Gly Gly
        35                  40                  45 aaa gcc ttg caa ttt gtg ttt gat caa ttg tgg tct cgt ttg ggt gat        192
Lys Ala Leu Gln Phe Val Phe Asp Gln Leu Trp Ser Arg Leu Gly Asp
50                  55                  60 tct gga tgg agt gcg ttc atg gaa cat gtg gag gaa tta att gat act        240
Ser Gly Trp Ser Ala Phe Met Glu His Val Glu Glu Leu Ile Asp Thr
65                  70                  75                  80 aaa ata gaa ggg tat gca aaa aat aaa gcc tta tct gaa tta gca ggt        288
Lys Ile Glu Gly Tyr Ala Lys Asn Lys Ala Leu Ser Glu Leu Ala Gly
                85                  90                  95 ata caa aga aac ctt gaa aca tat ata caa tta cgt aat gaa tgg gaa        336
Ile Gln Arg Asn Leu Glu Thr Tyr Ile Gln Leu Arg Asn Glu Trp Glu
            100                 105                 110 aat gat atc gaa aac tca aag gct caa gtt aag gta gct aat tac tat        384
Asn Asp Ile Glu Asn Ser Lys Ala Gln Val Lys Val Ala Asn Tyr Tyr
        115                 120                 125 gaa agt ctt gag cag gcg gtt gaa agg agt atg cct caa ttt gca gtg        432
Glu Ser Leu Glu Gln Ala Val Glu Arg Ser Met Pro Gln Phe Ala Val
    130                 135                 140 ggg aat ttt gaa gta cca ctt tta act gtt tat gtg caa gct gct aat        480
Gly Asn Phe Glu Val Pro Leu Leu Thr Val Tyr Val Gln Ala Ala Asn
145                 150                 155                 160 ctt cat ata tta tta tta aga gat gtt cta att tat gga aag cgt tgg        528
Leu His Ile Leu Leu Leu Arg Asp Val Leu Ile Tyr Gly Lys Arg Trp
                165                 170                 175 gga tgg tcg gag cag aaa att aaa att tat tat gat aga cag att aag        576
Gly Trp Ser Glu Gln Lys Ile Lys Ile Tyr Tyr Asp Arg Gln Ile Lys
            180                 185                 190 tat acc cat gaa tac aca aat cat tgt gta aat tgg tat aat aaa gga        624
Tyr Thr His Glu Tyr Thr Asn His Cys Val Asn Trp Tyr Asn Lys Gly
        195                 200                 205 ctt gag aga tta aaa aat aaa ggt tct tct tat caa gat tgg tac aat        672
Leu Glu Arg Leu Lys Asn Lys Gly Ser Ser Tyr Gln Asp Trp Tyr Asn
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 210 |     |     |     | 215 |     |     |     |     | 220 |     |     |     |     |      |
| tat | aat | cgt | ttc | cgt | aga | gaa | atg | act | ctt | act | gtt | tta | gat | atc | gtt | 720  |
| Tyr | Asn | Arg | Phe | Arg | Arg | Glu | Met | Thr | Leu | Thr | Val | Leu | Asp | Ile | Val |      |
| 225 |     |     |     |     | 230 |     |     |     |     | 235 |     |     |     |     | 240 |      |
| gct | tta | ttc | ccg | cac | tat | gat | gta | caa | act | tat | cca | ata | aca | acc | gtt | 768  |
| Ala | Leu | Phe | Pro | His | Tyr | Asp | Val | Gln | Thr | Tyr | Pro | Ile | Thr | Thr | Val |      |
|     |     |     |     | 245 |     |     |     |     | 250 |     |     |     |     | 255 |     |      |
| gct | cag | cta | aca | agg | gaa | gtt | tat | acg | gat | cct | tta | ctt | aat | ttt | aat | 816  |
| Ala | Gln | Leu | Thr | Arg | Glu | Val | Tyr | Thr | Asp | Pro | Leu | Leu | Asn | Phe | Asn |      |
|     |     |     | 260 |     |     |     |     | 265 |     |     |     |     | 270 |     |     |      |
| cct | aaa | tta | cat | tct | gtg | tct | caa | tta | cct | agt | ttt | agt | gac | atg | gaa | 864  |
| Pro | Lys | Leu | His | Ser | Val | Ser | Gln | Leu | Pro | Ser | Phe | Ser | Asp | Met | Glu |      |
|     |     | 275 |     |     |     |     | 280 |     |     |     |     | 285 |     |     |     |      |
| aat | gca | aca | att | aga | acc | cca | cat | cta | atg | gaa | ttt | tta | aga | atg | cta | 912  |
| Asn | Ala | Thr | Ile | Arg | Thr | Pro | His | Leu | Met | Glu | Phe | Leu | Arg | Met | Leu |      |
|     | 290 |     |     |     |     | 295 |     |     |     |     | 300 |     |     |     |     |      |
| aca | att | tat | aca | gat | tgg | tat | agt | gtg | gga | aga | aac | tat | tat | tgg | gga | 960  |
| Thr | Ile | Tyr | Thr | Asp | Trp | Tyr | Ser | Val | Gly | Arg | Asn | Tyr | Tyr | Trp | Gly |      |
| 305 |     |     |     |     | 310 |     |     |     |     | 315 |     |     |     |     | 320 |      |
| gga | cat | cgc | gtg | acg | tct | tac | cat | gta | gga | gga | gag | aat | ata | aga | tca | 1008 |
| Gly | His | Arg | Val | Thr | Ser | Tyr | His | Val | Gly | Gly | Glu | Asn | Ile | Arg | Ser |      |
|     |     |     |     | 325 |     |     |     |     | 330 |     |     |     |     | 335 |     |      |
| cct | cta | tat | ggt | aga | gag | gca | aat | caa | gag | gtt | cct | aga | gat | ttt | tat | 1056 |
| Pro | Leu | Tyr | Gly | Arg | Glu | Ala | Asn | Gln | Glu | Val | Pro | Arg | Asp | Phe | Tyr |      |
|     |     |     | 340 |     |     |     |     | 345 |     |     |     |     | 350 |     |     |      |
| ttt | tat | gga | ccc | gtt | ttt | aag | acg | tta | tca | aag | ccg | act | cta | aga | cca | 1104 |
| Phe | Tyr | Gly | Pro | Val | Phe | Lys | Thr | Leu | Ser | Lys | Pro | Thr | Leu | Arg | Pro |      |
|     |     | 355 |     |     |     |     | 360 |     |     |     |     | 365 |     |     |     |      |
| tta | cag | cag | cct | gca | cca | gct | cct | ccc | ttt | aat | tta | cgt | agc | tta | gag | 1152 |
| Leu | Gln | Gln | Pro | Ala | Pro | Ala | Pro | Pro | Phe | Asn | Leu | Arg | Ser | Leu | Glu |      |
|     | 370 |     |     |     |     | 375 |     |     |     |     | 380 |     |     |     |     |      |
| gga | gta | gaa | ttc | cac | act | cct | aca | ggt | agt | ttt | ttg | tat | cgt | gaa | aga | 1200 |
| Gly | Val | Glu | Phe | His | Thr | Pro | Thr | Gly | Ser | Phe | Leu | Tyr | Arg | Glu | Arg |      |
| 385 |     |     |     |     | 390 |     |     |     |     | 395 |     |     |     |     | 400 |      |
| gga | tcg | gta | gat | tct | ttt | aat | gag | tta | ccg | cct | ttt | aat | cta | gtt | ggg | 1248 |
| Gly | Ser | Val | Asp | Ser | Phe | Asn | Glu | Leu | Pro | Pro | Phe | Asn | Leu | Val | Gly |      |
|     |     |     |     | 405 |     |     |     |     | 410 |     |     |     |     | 415 |     |      |
| tta | cct | cat | aag | gta | tac | agt | cac | cgt | tta | tgt | cat | gca | acg | ttt | gtt | 1296 |
| Leu | Pro | His | Lys | Val | Tyr | Ser | His | Arg | Leu | Cys | His | Ala | Thr | Phe | Val |      |
|     |     |     | 420 |     |     |     |     | 425 |     |     |     |     | 430 |     |     |      |
| cgt | aaa | tct | ggg | acc | cct | tat | tta | aca | aca | ggt | gcc | atc | ttt | tct | tgg | 1344 |
| Arg | Lys | Ser | Gly | Thr | Pro | Tyr | Leu | Thr | Thr | Gly | Ala | Ile | Phe | Ser | Trp |      |
|     |     | 435 |     |     |     |     | 440 |     |     |     |     | 445 |     |     |     |      |
| aca | cat | cgt | agt | gct | gaa | gaa | acc | aat | aca | att | gaa | tca | aat | atc | att | 1392 |
| Thr | His | Arg | Ser | Ala | Glu | Glu | Thr | Asn | Thr | Ile | Glu | Ser | Asn | Ile | Ile |      |
|     | 450 |     |     |     |     | 455 |     |     |     |     | 460 |     |     |     |     |      |
| acg | caa | atc | ccg | tta | gta | aaa | gca | tat | caa | att | gga | tcg | ggc | act | act | 1440 |
| Thr | Gln | Ile | Pro | Leu | Val | Lys | Ala | Tyr | Gln | Ile | Gly | Ser | Gly | Thr | Thr |      |
| 465 |     |     |     |     | 470 |     |     |     |     | 475 |     |     |     |     | 480 |      |
| gta | agg | aaa | gga | cca | gga | ttc | aca | gga | ggg | gat | ata | ctt | cga | aga | aca | 1488 |
| Val | Arg | Lys | Gly | Pro | Gly | Phe | Thr | Gly | Gly | Asp | Ile | Leu | Arg | Arg | Thr |      |
|     |     |     |     | 485 |     |     |     |     | 490 |     |     |     |     | 495 |     |      |
| ggt | cct | gga | aca | ttt | gga | gat | atg | aga | ata | aat | att | aat | gca | cca | tta | 1536 |
| Gly | Pro | Gly | Thr | Phe | Gly | Asp | Met | Arg | Ile | Asn | Ile | Asn | Ala | Pro | Leu |      |
|     |     |     | 500 |     |     |     |     | 505 |     |     |     |     | 510 |     |     |      |
| tct | caa | aga | tat | cgt | gta | agg | att | cgt | tat | gct | tct | acg | aca | gat | tta | 1584 |
| Ser | Gln | Arg | Tyr | Arg | Val | Arg | Ile | Arg | Tyr | Ala | Ser | Thr | Thr | Asp | Leu |      |
|     |     | 515 |     |     |     |     | 520 |     |     |     |     | 525 |     |     |     |      |
| caa | ttt | ttc | acg | agc | att | aat | gga | acc | act | att | aat | atc | ggc | aat | ttc | 1632 |
| Gln | Phe | Phe | Thr | Ser | Ile | Asn | Gly | Thr | Thr | Ile | Asn | Ile | Gly | Asn | Phe |      |

```
                    530                 535                 540
ccc aaa act att aat aat gtg aat cct tta agt tct gag agc tat aga       1680
Pro Lys Thr Ile Asn Asn Val Asn Pro Leu Ser Ser Glu Ser Tyr Arg
545                 550                 555                 560 aca gta tct ttt agt acg cca ttt agt ttt tca gat gca caa agt ata       1728
Thr Val Ser Phe Ser Thr Pro Phe Ser Phe Ser Asp Ala Gln Ser Ile
                565                 570                 575 ttt aga tta ggt ata caa gct ttt tct gga gtt caa gaa gtt tat gtg       1776
Phe Arg Leu Gly Ile Gln Ala Phe Ser Gly Val Gln Glu Val Tyr Val
            580                 585                 590 gat aaa att gaa ttt atc cct ttt gaa gta gga ttc aat aat aca atc       1824
Asp Lys Ile Glu Phe Ile Pro Phe Glu Val Gly Phe Asn Asn Thr Ile
        595                 600                 605 ctc gag gct gaa tat aat ctg gaa aga gcg cag aag gcg gtg aat gcg       1872
Leu Glu Ala Glu Tyr Asn Leu Glu Arg Ala Gln Lys Ala Val Asn Ala
    610                 615                 620 ctg ttt acg tct aca aac caa cta ggg cta aaa aca aat gta acg gat       1920
Leu Phe Thr Ser Thr Asn Gln Leu Gly Leu Lys Thr Asn Val Thr Asp
625                 630                 635                 640 tat cat att gat caa gtg tcc aat tta gtt acg tat tta tcg gat gaa       1968
Tyr His Ile Asp Gln Val Ser Asn Leu Val Thr Tyr Leu Ser Asp Glu
                645                 650                 655 ttt tgt ctg gat gaa aag cga gaa ttg tcc gag aaa gtc aaa cat gcg       2016
Phe Cys Leu Asp Glu Lys Arg Glu Leu Ser Glu Lys Val Lys His Ala
            660                 665                 670 aag cga ctc agt gat gaa cgc aat tta ctc caa gat tca aat ttc aaa       2064
Lys Arg Leu Ser Asp Glu Arg Asn Leu Leu Gln Asp Ser Asn Phe Lys
        675                 680                 685 gac att aat agg caa cca gaa cgt ggg tgg ggc gga agt aca ggg att       2112
Asp Ile Asn Arg Gln Pro Glu Arg Gly Trp Gly Gly Ser Thr Gly Ile
    690                 695                 700 acc atc caa gga ggg gat gac gta ttt aaa gaa aat tac gtc aca cta       2160
Thr Ile Gln Gly Gly Asp Asp Val Phe Lys Glu Asn Tyr Val Thr Leu
705                 710                 715                 720 tca ggt acc ttt gat gag tgc tat cca aca tat ttg tat caa aaa atc       2208
Ser Gly Thr Phe Asp Glu Cys Tyr Pro Thr Tyr Leu Tyr Gln Lys Ile
                725                 730                 735 gat gaa tca aaa tta aaa gcc ttt acc cgt tat caa tta aga ggg tat       2256
Asp Glu Ser Lys Leu Lys Ala Phe Thr Arg Tyr Gln Leu Arg Gly Tyr
            740                 745                 750 atc gaa gat agt caa gac tta gaa atc tat tta att cgc tac aat gca       2304
Ile Glu Asp Ser Gln Asp Leu Glu Ile Tyr Leu Ile Arg Tyr Asn Ala
        755                 760                 765 aaa cat gaa aca gta aat gtg cca ggt acg ggt tcc tta tgg ccg ctt       2352
Lys His Glu Thr Val Asn Val Pro Gly Thr Gly Ser Leu Trp Pro Leu
    770                 775                 780 tca gcc caa agt cca atc gga aag tgt gga gag ccg aat cga tgc gcg       2400
Ser Ala Gln Ser Pro Ile Gly Lys Cys Gly Glu Pro Asn Arg Cys Ala
785                 790                 795                 800 cca cac ctt gaa tgg aat cct gac tta gat tgt tcg tgt agg gat gga       2448
Pro His Leu Glu Trp Asn Pro Asp Leu Asp Cys Ser Cys Arg Asp Gly
                805                 810                 815 gaa aag tgt gcc cat cat tcg cat cat ttc tcc tta gac att gat gta       2496
Glu Lys Cys Ala His His Ser His His Phe Ser Leu Asp Ile Asp Val
            820                 825                 830 gga tgt aca gac tta aat gag gac cta ggt gta tgg gtg atc ttt aag       2544
Gly Cys Thr Asp Leu Asn Glu Asp Leu Gly Val Trp Val Ile Phe Lys
        835                 840                 845 att aag acg caa gat ggg cac gca aga cta ggg aat cta gag ttt ctc       2592
Ile Lys Thr Gln Asp Gly His Ala Arg Leu Gly Asn Leu Glu Phe Leu
```

```
              850               855              860
gaa gag aaa cca tta gta gga gaa gcg cta gct cgt gtg aaa aga gcg    2640
Glu Glu Lys Pro Leu Val Gly Glu Ala Leu Ala Arg Val Lys Arg Ala
865                 870                 875                 880 gag aaa aaa tgg aga gac aaa cgt gaa aaa ttg gaa tgg gaa aca aat    2688
Glu Lys Lys Trp Arg Asp Lys Arg Glu Lys Leu Glu Trp Glu Thr Asn
                885                 890                 895 atc gtt tat aaa gag gca aaa gaa tct gta gat gct tta ttt gta aac    2736
Ile Val Tyr Lys Glu Ala Lys Glu Ser Val Asp Ala Leu Phe Val Asn
                900                 905                 910 tct caa tat gat caa tta caa gcg gat acg aat att gcc atg att cat    2784
Ser Gln Tyr Asp Gln Leu Gln Ala Asp Thr Asn Ile Ala Met Ile His
            915                 920                 925 gcg gca gat aaa cgt gtt cat agc att cga gaa gct tat ctg cct gag    2832
Ala Ala Asp Lys Arg Val His Ser Ile Arg Glu Ala Tyr Leu Pro Glu
930                 935                 940 ctg tct gtg att ccg ggt gtc aat gcg gct att ttt gaa gaa tta gaa    2880
Leu Ser Val Ile Pro Gly Val Asn Ala Ala Ile Phe Glu Glu Leu Glu
945                 950                 955                 960 ggg cgt att ttc act gca ttc tcc cta tat gat gcg aga aat gtc att    2928
Gly Arg Ile Phe Thr Ala Phe Ser Leu Tyr Asp Ala Arg Asn Val Ile
                965                 970                 975 aaa aat ggt gat ttt aat aat ggc tta tcc tgc tgg aac gtg aaa ggg    2976
Lys Asn Gly Asp Phe Asn Asn Gly Leu Ser Cys Trp Asn Val Lys Gly
                980                 985                 990 cat gta gat gta gaa gaa caa aac aac caa cgt tcg gtc ctt gtt gtt    3024
His Val Asp Val Glu Glu Gln Asn Asn Gln Arg Ser Val Leu Val Val
            995                 1000                1005 ccg gaa tgg gaa gca gaa gtg tca caa gaa gtt cgt gtc tgt ccg        3069
Pro Glu Trp Glu Ala Glu Val Ser Gln Glu Val Arg Val Cys Pro
1010                1015                1020 ggt cgt ggc tat atc ctt cgt gtc aca gcg tac aag gag gga tat        3114
Gly Arg Gly Tyr Ile Leu Arg Val Thr Ala Tyr Lys Glu Gly Tyr
1025                1030                1035 gga gaa ggt tgc gta acc att cat gag atc gag aac aat aca gac        3159
Gly Glu Gly Cys Val Thr Ile His Glu Ile Glu Asn Asn Thr Asp
1040                1045                1050 gaa ctg aag ttt agc aac tgc gta gaa gag gaa atc tat cca aat        3204
Glu Leu Lys Phe Ser Asn Cys Val Glu Glu Glu Ile Tyr Pro Asn
1055                1060                1065 aac acg gta acg tgt aat gat tat act gta aat caa gaa gaa tac        3249
Asn Thr Val Thr Cys Asn Asp Tyr Thr Val Asn Gln Glu Glu Tyr
1070                1075                1080 gga ggt gcg tac act tct cgt aat cga gga tat aac gaa gct cct        3294
Gly Gly Ala Tyr Thr Ser Arg Asn Arg Gly Tyr Asn Glu Ala Pro
1085                1090                1095 tcc gta cca gct gat tat gcg tca gtc tat gaa gaa aaa tcg tat        3339
Ser Val Pro Ala Asp Tyr Ala Ser Val Tyr Glu Glu Lys Ser Tyr
1100                1105                1110 aca gat gga cga aga gag aat cct tgt gaa ttt aac aga ggg tat        3384
Thr Asp Gly Arg Arg Glu Asn Pro Cys Glu Phe Asn Arg Gly Tyr
1115                1120                1125 agg gat tac acg cca cta cca gtt ggt tat gtg aca aaa gaa tta        3429
Arg Asp Tyr Thr Pro Leu Pro Val Gly Tyr Val Thr Lys Glu Leu
1130                1135                1140 gaa tac ttc cca gaa acc gat aag gta tgg att gag att gga gaa        3474
Glu Tyr Phe Pro Glu Thr Asp Lys Val Trp Ile Glu Ile Gly Glu
1145                1150                1155 acg gaa gga aca ttt atc gtg gac agc gtg gaa tta ctc ctt atg        3519
Thr Glu Gly Thr Phe Ile Val Asp Ser Val Glu Leu Leu Leu Met
```

-continued

```
              1160              1165              1170
gag gaa                                                              3525
Glu Glu
    1175

<210> SEQ ID NO 32
<211> LENGTH: 1175
<212> TYPE: PRT
<213> ORGANISM: Artificial Sequence
<220> FEATURE:
<223> OTHER INFORMATION: Synthetic Construct

<400> SEQUENCE: 32

Met Asn Ser Lys Glu His Asp Tyr Leu Lys Val Cys Asn Asp Leu Ser
1               5                   10                  15

Asp Ala Asn Ile Asn Met Glu Arg Phe Asp Lys Asn Asp Ala Leu Glu
            20                  25                  30

Ile Gly Met Ser Ile Val Ser Glu Leu Leu Gly Met Ile Pro Gly Gly
        35                  40                  45

Lys Ala Leu Gln Phe Val Phe Asp Gln Leu Trp Ser Arg Leu Gly Asp
    50                  55                  60

Ser Gly Trp Ser Ala Phe Met Glu His Val Glu Leu Ile Asp Thr
65              70                  75                  80

Lys Ile Glu Gly Tyr Ala Lys Asn Lys Ala Leu Ser Glu Leu Ala Gly
                85                  90                  95

Ile Gln Arg Asn Leu Glu Thr Tyr Ile Gln Leu Arg Asn Glu Trp Glu
            100                 105                 110

Asn Asp Ile Glu Asn Ser Lys Ala Gln Val Lys Val Ala Asn Tyr Tyr
        115                 120                 125

Glu Ser Leu Glu Gln Ala Val Glu Arg Ser Met Pro Gln Phe Ala Val
    130                 135                 140

Gly Asn Phe Glu Val Pro Leu Leu Thr Val Tyr Val Gln Ala Ala Asn
145                 150                 155                 160

Leu His Ile Leu Leu Leu Arg Asp Val Leu Ile Tyr Gly Lys Arg Trp
                165                 170                 175

Gly Trp Ser Glu Gln Lys Ile Lys Ile Tyr Tyr Asp Arg Gln Ile Lys
            180                 185                 190

Tyr Thr His Glu Tyr Thr Asn His Cys Val Asn Trp Tyr Asn Lys Gly
        195                 200                 205

Leu Glu Arg Leu Lys Asn Lys Gly Ser Ser Tyr Gln Asp Trp Tyr Asn
    210                 215                 220

Tyr Asn Arg Phe Arg Arg Glu Met Thr Leu Thr Val Leu Asp Ile Val
225                 230                 235                 240

Ala Leu Phe Pro His Tyr Asp Val Gln Thr Tyr Pro Ile Thr Thr Val
                245                 250                 255

Ala Gln Leu Thr Arg Glu Val Tyr Thr Asp Pro Leu Leu Asn Phe Asn
            260                 265                 270

Pro Lys Leu His Ser Val Ser Gln Leu Pro Ser Phe Ser Asp Met Glu
        275                 280                 285

Asn Ala Thr Ile Arg Thr Pro His Leu Met Glu Phe Leu Arg Met Leu
    290                 295                 300

Thr Ile Tyr Thr Asp Trp Tyr Ser Val Gly Arg Asn Tyr Tyr Trp Gly
305                 310                 315                 320

Gly His Arg Val Thr Ser Tyr His Val Gly Gly Glu Asn Ile Arg Ser
                325                 330                 335

Pro Leu Tyr Gly Arg Glu Ala Asn Gln Glu Val Pro Arg Asp Phe Tyr
```

-continued

```
                340                 345                 350
Phe Tyr Gly Pro Val Phe Lys Thr Leu Ser Lys Pro Thr Leu Arg Pro
            355                 360                 365
Leu Gln Gln Pro Ala Pro Ala Pro Pro Phe Asn Leu Arg Ser Leu Glu
        370                 375                 380
Gly Val Glu Phe His Thr Pro Thr Gly Ser Phe Leu Tyr Arg Glu Arg
385                 390                 395                 400
Gly Ser Val Asp Ser Phe Asn Glu Leu Pro Pro Phe Asn Leu Val Gly
                405                 410                 415
Leu Pro His Lys Val Tyr Ser His Arg Leu Cys His Ala Thr Phe Val
            420                 425                 430
Arg Lys Ser Gly Thr Pro Tyr Leu Thr Thr Gly Ala Ile Phe Ser Trp
        435                 440                 445
Thr His Arg Ser Ala Glu Glu Thr Asn Thr Ile Glu Ser Asn Ile Ile
            450                 455                 460
Thr Gln Ile Pro Leu Val Lys Ala Tyr Gln Ile Gly Ser Gly Thr Thr
465                 470                 475                 480
Val Arg Lys Gly Pro Gly Phe Thr Gly Gly Asp Ile Leu Arg Arg Thr
                485                 490                 495
Gly Pro Gly Thr Phe Gly Asp Met Arg Ile Asn Ile Asn Ala Pro Leu
            500                 505                 510
Ser Gln Arg Tyr Arg Val Arg Ile Arg Tyr Ala Ser Thr Thr Asp Leu
        515                 520                 525
Gln Phe Phe Thr Ser Ile Asn Gly Thr Thr Ile Asn Ile Gly Asn Phe
            530                 535                 540
Pro Lys Thr Ile Asn Asn Val Asn Pro Leu Ser Ser Glu Ser Tyr Arg
545                 550                 555                 560
Thr Val Ser Phe Ser Thr Pro Phe Ser Phe Ser Asp Ala Gln Ser Ile
                565                 570                 575
Phe Arg Leu Gly Ile Gln Ala Phe Ser Gly Val Gln Glu Val Tyr Val
            580                 585                 590
Asp Lys Ile Glu Phe Ile Pro Phe Glu Val Gly Phe Asn Asn Thr Ile
        595                 600                 605
Leu Glu Ala Glu Tyr Asn Leu Glu Arg Ala Gln Lys Ala Val Asn Ala
    610                 615                 620
Leu Phe Thr Ser Thr Asn Gln Leu Gly Leu Lys Thr Asn Val Thr Asp
625                 630                 635                 640
Tyr His Ile Asp Gln Val Ser Asn Leu Val Thr Tyr Leu Ser Asp Glu
                645                 650                 655
Phe Cys Leu Asp Glu Lys Arg Glu Leu Ser Glu Lys Val Lys His Ala
            660                 665                 670
Lys Arg Leu Ser Asp Glu Arg Asn Leu Leu Gln Asp Ser Asn Phe Lys
        675                 680                 685
Asp Ile Asn Arg Gln Pro Glu Arg Gly Trp Gly Gly Ser Thr Gly Ile
    690                 695                 700
Thr Ile Gln Gly Gly Asp Asp Val Phe Lys Glu Asn Tyr Val Thr Leu
705                 710                 715                 720
Ser Gly Thr Phe Asp Glu Cys Tyr Pro Thr Tyr Leu Tyr Gln Lys Ile
                725                 730                 735
Asp Glu Ser Lys Leu Lys Ala Phe Thr Arg Tyr Gln Leu Arg Gly Tyr
            740                 745                 750
Ile Glu Asp Ser Gln Asp Leu Glu Ile Tyr Leu Ile Arg Tyr Asn Ala
        755                 760                 765
```

-continued

```
Lys His Glu Thr Val Asn Val Pro Gly Thr Gly Ser Leu Trp Pro Leu
770                 775                 780

Ser Ala Gln Ser Pro Ile Gly Lys Cys Gly Glu Pro Asn Arg Cys Ala
785                 790                 795                 800

Pro His Leu Glu Trp Asn Pro Asp Leu Asp Cys Ser Cys Arg Asp Gly
            805                 810                 815

Glu Lys Cys Ala His His Ser His Phe Ser Leu Asp Ile Asp Val
        820                 825                 830

Gly Cys Thr Asp Leu Asn Glu Asp Leu Gly Val Trp Val Ile Phe Lys
        835                 840                 845

Ile Lys Thr Gln Asp Gly His Ala Arg Leu Gly Asn Leu Glu Phe Leu
    850                 855                 860

Glu Glu Lys Pro Leu Val Gly Glu Ala Leu Ala Arg Val Lys Arg Ala
865                 870                 875                 880

Glu Lys Lys Trp Arg Asp Lys Arg Glu Lys Leu Glu Trp Glu Thr Asn
                885                 890                 895

Ile Val Tyr Lys Glu Ala Lys Glu Ser Val Asp Ala Leu Phe Val Asn
            900                 905                 910

Ser Gln Tyr Asp Gln Leu Gln Ala Asp Thr Asn Ile Ala Met Ile His
        915                 920                 925

Ala Ala Asp Lys Arg Val His Ser Ile Arg Glu Ala Tyr Leu Pro Glu
930                 935                 940

Leu Ser Val Ile Pro Gly Val Asn Ala Ala Ile Phe Glu Glu Leu Glu
945                 950                 955                 960

Gly Arg Ile Phe Thr Ala Phe Ser Leu Tyr Asp Ala Arg Asn Val Ile
                965                 970                 975

Lys Asn Gly Asp Phe Asn Asn Gly Leu Ser Cys Trp Asn Val Lys Gly
            980                 985                 990

His Val Asp Val Glu Glu Gln Asn Asn Gln Arg Ser Val Leu Val Val
        995                 1000                1005

Pro Glu Trp Glu Ala Glu Val Ser Gln Glu Val Arg Val Cys Pro
    1010                1015                1020

Gly Arg Gly Tyr Ile Leu Arg Val Thr Ala Tyr Lys Glu Gly Tyr
    1025                1030                1035

Gly Glu Gly Cys Val Thr Ile His Glu Ile Glu Asn Asn Thr Asp
    1040                1045                1050

Glu Leu Lys Phe Ser Asn Cys Val Glu Glu Glu Ile Tyr Pro Asn
    1055                1060                1065

Asn Thr Val Thr Cys Asn Asp Tyr Thr Val Asn Gln Glu Glu Tyr
    1070                1075                1080

Gly Gly Ala Tyr Thr Ser Arg Asn Arg Gly Tyr Asn Glu Ala Pro
    1085                1090                1095

Ser Val Pro Ala Asp Tyr Ala Ser Val Tyr Glu Glu Lys Ser Tyr
    1100                1105                1110

Thr Asp Gly Arg Arg Glu Asn Pro Cys Glu Phe Asn Arg Gly Tyr
    1115                1120                1125

Arg Asp Tyr Thr Pro Leu Pro Val Gly Tyr Val Thr Lys Glu Leu
    1130                1135                1140

Glu Tyr Phe Pro Glu Thr Asp Lys Val Trp Ile Glu Ile Gly Glu
    1145                1150                1155
```

-continued

```
Thr Glu  Gly Thr Phe Ile Val  Asp Ser Val Glu Leu  Leu Leu Met
    1160              1165                 1170

Glu Glu
    1175
```